US009228015B2

(12) United States Patent
Lee et al.

(10) Patent No.: US 9,228,015 B2
(45) **Date of Patent: *Jan. 5, 2016**

(54) NOGO RECEPTOR ANTAGONISTS AND METHODS OF INCREASING NEURITE OUTGROWTH

(71) Applicant: Biogen Idec MA Inc., Cambridge, MA (US)

(72) Inventors: Daniel H. S. Lee, Sudbury, MA (US); Dingyi Wen, Waltham, MA (US); R. Blake Pepinsky, Arlington, MA (US); Jane K. Relton, Belmont, MA (US); Xinzhong Wang, Framingham, MA (US); Alexey Lugovskoy, Woburn, MA (US); Werner Meier, Burlington, MA (US); Ellen A. Garber, Cambridge, MA (US); Laura Silvian, Waban, MA (US); Paul H. Weinreb, Andover, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/146,345

(22) Filed: Jan. 2, 2014

(65) Prior Publication Data

US 2014/0227266 A1 Aug. 14, 2014

Related U.S. Application Data

(63) Continuation of application No. 12/162,256, filed as application No. PCT/US2007/002199 on Jan. 26, 2007, now Pat. No. 8,669,345.

(60) Provisional application No. 60/762,487, filed on Jan. 27, 2006, provisional application No. 60/831,659, filed on Jul. 19, 2006.

(51) Int. Cl.

| | |
|---|---|
| ***C07K 16/28*** | (2006.01) |
| ***A01K 67/027*** | (2006.01) |
| ***C07K 14/705*** | (2006.01) |
| ***C12N 15/113*** | (2010.01) |
| ***C12N 15/85*** | (2006.01) |
| ***A61K 38/17*** | (2006.01) |
| ***A61K 39/395*** | (2006.01) |
| *A61K 48/00* | (2006.01) |
| *A61K 39/00* | (2006.01) |

(52) U.S. Cl.

CPC ........... *C07K 16/2863* (2013.01); *A01K 67/027* (2013.01); *A01K 67/0275* (2013.01); *A61K 38/179* (2013.01); *A61K 39/3955* (2013.01); *C07K 14/705* (2013.01); *C07K 16/28* (2013.01); *C12N 15/1136* (2013.01); *C12N 15/1138* (2013.01); *C12N 15/8509* (2013.01); *A01K 2217/058* (2013.01); *A01K 2227/105* (2013.01); *A01K 2267/0356* (2013.01); *A61K 48/00* (2013.01); *A61K 2039/505* (2013.01); *C07K 2316/96* (2013.01); *C07K 2317/34* (2013.01); *C07K 2317/55* (2013.01); *C07K 2317/56* (2013.01); *C07K 2319/30* (2013.01); *C07K 2319/33* (2013.01); *C07K 2319/74* (2013.01); *C12N 2310/111* (2013.01); *C12N 2310/14* (2013.01); *C12N 2310/53* (2013.01)

(58) Field of Classification Search

None

See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,399,216 | A | 8/1983 | Axel et al. |
| 4,510,245 | A | 4/1985 | Cousens et al. |
| 4,634,665 | A | 1/1987 | Axel et al. |
| 4,816,567 | A | 3/1989 | Cabilly et al. |
| 4,968,615 | A | 11/1990 | Koszinowski et al. |
| 5,168,062 | A | 12/1992 | Stinski |

(Continued)

FOREIGN PATENT DOCUMENTS

| | | | |
|---|---|---|---|
| EP | 0216846 | A1 | 4/1987 |
| EP | 0256055 | A1 | 2/1988 |

(Continued)

OTHER PUBLICATIONS

Ahmed et al., Disinhibition of neurotrophin-induced dorsal root ganglion cell neurite outgrowth on CNS myelin by siRNA-mediated knockdown of NgR, p75 NTR and Rho-A, Mol. Cell. Neurosci., 28:509-523 (2005).

(Continued)

*Primary Examiner* — Maury Audet

(74) *Attorney, Agent, or Firm* — Choate, Hall & Stewart LLP; Brenda Herschbach Jarrell, JD; Nishat A. Shaikh, JD

(57) ABSTRACT

Disclosed are immunogenic Nogo receptor-1 polypeptides, Nogo receptor-1 antibodies, antigen-binding fragments thereof, soluble Nogo receptors and fusion proteins thereof and nucleic acids encoding the same. Also disclosed are Nogo receptor antagonist polynucleotides. Also disclosed are compositions comprising, and methods for making and using, such Nogo receptor antibodies, antigen-binding fragments thereof, soluble Nogo receptors and fusion proteins thereof, nucleic acids encoding the same and antagonist polynucleotides.

5 Claims, 36 Drawing Sheets

(56) References Cited

U.S. PATENT DOCUMENTS

| | | | | |
|---|---|---|---|---|
| 5,179,017 | A | 1/1993 | Axel et al. | |
| 5,223,409 | A | 6/1993 | Ladner et al. | |
| 5,877,293 | A | 3/1999 | Adair et al. | |
| 5,886,152 | A | 3/1999 | Nakatani et al. | |
| 6,054,297 | A | 4/2000 | Carter et al. | |
| 6,475,753 | B1 | 11/2002 | Ruben et al. | |
| 6,627,741 | B2 | 9/2003 | Ruben et al. | |
| 6,774,216 | B2 | 8/2004 | Ruben et al. | |
| 7,041,474 | B2 | 5/2006 | Kingsbury | |
| 7,119,165 | B2 | 10/2006 | Strittmatter | |
| 7,173,118 | B2 | 2/2007 | Strittmatter et al. | |
| 7,309,485 | B2 | 12/2007 | He et al. | |
| 8,669,345 | B2 * | 3/2014 | Lee et al. | 530/300 |
| 2002/0012965 | A1 | 1/2002 | Strittmatter | |
| 2003/0113325 | A1 | 6/2003 | He et al. | |
| 2003/0124704 | A1 | 7/2003 | Strittmatter et al. | |
| 2003/0186267 | A1 * | 10/2003 | Feder et al. | 435/6 |
| 2004/0029169 | A1 | 2/2004 | He et al. | |
| 2005/0221420 | A1 | 10/2005 | Barske et al. | |
| 2005/0271655 | A1 | 12/2005 | Lee et al. | |

FOREIGN PATENT DOCUMENTS

| | | | |
|---|---|---|---|
| EP | 0323997 | A1 | 7/1989 |
| JP | 2009-505665 | A | 2/2009 |
| WO | WO-9117271 | A1 | 11/1991 |
| WO | WO-9201047 | A1 | 1/1992 |
| WO | WO-9209690 | A2 | 6/1992 |
| WO | WO-9215679 | A1 | 9/1992 |
| WO | WO-9218619 | A1 | 10/1992 |
| WO | WO-9220791 | A1 | 11/1992 |
| WO | WO-9301288 | A1 | 1/1993 |
| WO | WO-0151520 | A2 | 7/2001 |
| WO | WO-0229059 | A2 | 4/2002 |
| WO | WO-03002602 | A2 | 1/2003 |
| WO | WO-03018631 | A2 | 3/2003 |
| WO | WO-03031462 | A2 | 4/2003 |
| WO | WO-03035687 | A1 | 5/2003 |
| WO | WO-03089470 | A1 | 10/2003 |
| WO | WO-2004014311 | A2 | 2/2004 |
| WO | WO-2004093893 | A2 | 11/2004 |
| WO | WO-2005016955 | A2 | 2/2005 |
| WO | WO-2005045035 | A2 | 5/2005 |
| WO | WO-2005059515 | A2 | 6/2005 |
| WO | WO-2006124627 | A2 | 11/2006 |
| WO | WO-2007/025219 | A2 | 3/2007 |

OTHER PUBLICATIONS

Barton et al., Structure and axon outgrowth inhibitor binding of the Nogo-66 receptor and related proteins, EMBO J., 22:3291-3302 (2003).

Basso et al., MASCIS Evaluation of Open Field Locomotor Scores: Effects of Experience and Teamwork on Reliability, J. Neurotrauma, 13:343-359 (1996).

Beck et al., Therapeutic Fc-fusion proteins and peptides as successful alternatives to antibodies, mAbs, 3(5):415-416 (2011).

Brittis et al., Nogo Domains and a Nogo Receptor: Implications for Axon Regeneration, Neuron, 30:11-14 (2001).

Chen et al., Nogo-A is a myelin-associated neurite outgrowth inhibitor and an antigen for monoclonal antibody IN-1, Nature, 403:434-439 (2000).

Domeniconi et al., Myelin-Associated Glycoprotein Interacts with the Nogo66 Receptor to Inhibit Neurite Outgrowth, Neuron, 35:283-290 (2002).

Fournier et al., Characterization of the neuronal receptor mediating Nogo-66 inhibition of axonal regeneration, J. Neurochem., Abstract No. S08-01, 78(Suppl 1):105 (2001).

Fournier et al., Identification of a receptor mediating Nogo-66 inhibition of axonal regeneration, Nature, 409:341-346 (2001).

Fournier et al., Nogo Receptor Domain Analysis, Society for Neuroscience Abstracts 27:670, Society for Neuroscience, Abstract No. 258.3, presented at the Society for Neuroscience's 31st Annual Meeting, San Diego, CA (Nov. 12, 2001).

Fournier et al., Truncated Soluble Nogo Receptor Binds Nogo-66 and Blocks Inhibition of Axon Growth by Myelin, J. Neurosci., 22:8876-8883 (2002).

GrandPre et al., Functional Analysis of Nogo-66 and Nogo Receptor Domains, Society for Neuroscience Abstracts 27:670, Society for Neuroscience, Abstract No. 258.4, presented at the Society for Neuroscience's 31st Annual Meeting, San Diego, CA (Nov. 12, 2001).

Grandpré et al., Identification of the Nogo inhibitor of axon regeneration as a Reticulon protein, Nature, 403:439-444 (2000).

Grandpreé et al., Nogo-66 receptor antagonist peptide promotes axonal regeneration, Nature 417:547-551 (2002).

Grandprë et al., Nogo: A Molecular Determinant of Axonal Growth and Regeneration, The Neuroscientist, 7:377-386 (2001).

Grimpe et al., The Critical Role of Basement Membrane-Independent Laminin γ1 Chain during Axon Regeneration in the CNS, J. Neurosci., 22:3144-3160 (2002).

http://en.wikipedia.org/wiki/Heterologous.

International Search Report for International Application No. PCT/US2004/02702, mailed Apr. 20, 2006.

International Search Report for International Application No. PCT/US2005/002535, mailed Oct. 24, 2005.

International Search Report for International Application No. PCT/US2005/035719, mailed Apr. 13, 2006.

International Search Report for International Application No. PCT/US2007/002199, mailed Jul. 21, 2008.

Ji et al., Effect of combined treatment with methylprednisolone and soluble Nogo-66 receptor after rat spinal cord injury, Eur. J. Neurosci., 22:587-594 (2005).

Jones et al., NG2 Is a Major Chondroitin Sulfate Proteoglycan Produced after Spinal Cord Injury and Is Expressed by Macrophages and Oligodendrocyte Progenitors, J. Neurosci., 22:2792-2803 (2002).

Lee et al., Nogo Receptor Antagonism Promotes Stroke Recovery by Enhancing Axonal Plasticity, J. Neurosci., 24(27):6209-6217 (2004).

Lee et al., Nogo receptor antagonism promotes stroke recovery by enhancing axonal plasticity, Journal of Neuroscience, 24(27):6209-6219 (2004).

Li et al, Effect of soluble Nogo receptor treatment on functional and histological outcome after spinal cord injury in the rat, Biosis Database, Accession No. PREV200400194121, Abstract No. 80.22, Presented at the 33rd Annual Meeting of the Society of Neuroscience, New Orleans, LA (Nov. 8-12, 2003).

Li et al, Neutralization of NGR1 May Be Sufficient to Promote Rat DRG Neurite Outgrowth in the Presence of CNS Myeline, SFN 2003 Abstract Viewer & Itinerary Planner, Program No. 678.3, Presented at the 33rd Annual Meeting of the Society of Neuroscience, New Orleans, LA (Nov. 8-12, 2003).

Li et al., A Neutralizing Anti-Nogo66 Receptor Monoclonal Antibody Reverses Inhibition of Neurite Outgrowth by Central Nervous System Myelin, J. Biol. Chem., 42:43780-43788 (2004).

Li et al., Blockade of Nogo-66, Myelin-associated Glycoprotein, and Oligodendrocyte Myelin Glycoprotein by Soluble Nogo-66 Receptor Promotes Axonal Sprouting and Recovery after Spinal Injury, J. Neurosci., 24(46):10511-10520 (2004).

Li et al., Blockade of Nogo-66, myelin-associated glycoprotein, and oligodendrocyte myelin glycoprotein by soluble Nogo-66 receptor promotes axonal sprouting and recovery after spinal injury, Journal of Neuroscience, 24(46):10511-10520 (2004).

Li et al., Delayed Systematic Nogo-66 Receptor Antagonists Promotes Recovery from Spinal Cord Injury, J. Neurosci., 23:4219-4227 (2003).

Li et al., Functional Role and Therapeutic Implications of Neuronal Caspase-1 and -3 in a Mouse Model of Traumatic Spinal Cord Injury, Neurosci., 99:333-342 (2000).

Liu et al., Myelin-Associated Glycoprotein as a Functional Ligand for the Nogo-66 Receptor, Science, 297:1190-1193 (2002).

Liu et al., Transplants of Fibroblasts Genetically Modified to Express BDNF Promote Regeneration of Adult Rat Rubrospinal Axons and Recovery for Forelimb Function, J. Neurosci., 19:4370-4387 (1999).

(56) References Cited

OTHER PUBLICATIONS

MacDermid et al., A soluble Nogo receptor differentially affects plasticity of spinally projecting axons, European Journal of Neuroscience, 20(10):2567-2579 (2004).
McGee et al., The Nogo-66 receptor: focusing myelin inhibition of axon regeneration, Trends Neurosci., 26:193-198 (2003).
McKerracher et al., Identification of Myelin-Associated Glycoprotein as a Major Myelin-Derived Inhibitor of Neurite Growth, Neuron, 13:805-811 (1994).
Metz et al., Efficient testing of motor function in a spinal cord injured rats, Brain Res., 883:165-177 (2000).
Mikol et al., A Phosphatidylinositol-linked Peanut Agglutinin-binding Glycoprotein in Central Nervous System Myelin and on Oligodendrocytes, J. Cell. Biol., 106:1273-1279 (1988).
Mukhopadhyay et al., A Novel Role for Myelin-Associated Glycoprotein as an Inhibitor of Axonal Regeneration, Neuron, 13:757-767 (1994).
Noël et al., High In Vivo Production of a Model Monoclonal Antibody on Adenoviral Gene Transfer, Human Gene Therapy, 13:1483-1493 (2002).
Oertle et al., Nogo-A Inhibits Neurite Outgrowth and Cell Spreading with Three Discrete Regions, J. Neurosci., 23:5393-5406 (2003).
Partial European Search Report of EP 12 16 2911, dated Sep. 27, 2012, 4 pages.
Ramón-Cueto et al., Functional Recovery of Paraplegic Rats and Motor Axon Regeneration in Their Spinal Cords by Olfactory Ensheathing Glia, Neuron, 25:425-435 (2000).
Rutishauser et al., Cell Adhesion Molecules in Vertebrate Neural Development, Physiol. Rev., 68:819-857 (1988).
Supplementary European Search Report for European Application No. 07 76 2730, dated Nov. 9, 2009 (8 pages).
Supplementary Partial European Search Report for European Patent Application No. 03785123.5, dated Oct. 5, 2006.
Supplementary Partial European Search Report for European Patent Application No. 04707073.5, dated Sep. 5, 2006.
Wang et al., Amyloid Peptide Aβ1-42 Binds Selectively and with Picomolar Affinity to α7 Nicotinic Acetylcholine Receptors, J. Neurochem., 75:1155-1161 (2000).
Wang et al., Localization of Nogo-A and Nogo-66 Receptor Proteins at Sites of Axon-Myelin and Synaptic Contact, J. Neurosci., 22:5505-5515 (2002).
Wang et al., Oligodendrocyte-myelin glycoprotein is a Nogo receptor ligand that inhibits neurite outgrowth, Nature, 417:941-944 (2002).
Weidner et al., Spontaneous corticospinal axonal plasticity and functional recovery after adult central nervous system injury, Proc. Natl. Acad. Sci. USA, 98:3513-3518 (2001).
Weinreb et al., Resolution of Disulfide Heterogeneity in Nogo Receptor I Fusion Proteins by Molecular Engineering, Biotechnology Applied Biochemistry, 57:31-45 (2010).
Wen et al., Disulfide Structure of the Leucine-Rich Repeat C-Terminal Cap and C-Terminal Stalk Region of Nogo-66 Receptor, Biochem., 44:16491-16501 (2005).
Brünger, A.T. et al., Crystallography & NMR system: A new software suite for macromolecular structure determination, Acta Crystallogr. D. Biol. Crystallogr., 54(Pt 5):905-21 (1998).
Extended European Search Report for EP 12162911.7, 10 pages (Apr. 19, 2013).
Fischer, D. et al., Counteracting the Nogo receptor enhances optic nerve regeneration if retinal ganglion cells are in an active growth state, J. Neurosci., 24(7):1646-51 (2004).
Fu, Q.L. et al., Soluble Nogo-66 receptor prevents synaptic dysfunction and rescues retinal ganglion cell loss in chronic glaucoma, Invest. Ophthalmol. Vis. Sci., 52(11):8374-80 (2011).
He, X.L. et al., Structure of the Nogo receptor ectodomain: a recognition module implicated in myelin inhibition, Neuron., 38(2):177-85 (2003).
Schwede, T.F. et al., Homogenization and crystallization of histidine ammonia-lyase by exchange of a surface cysteine residue, Protein Engineering, 12(2):151-153 (1999).
Vagin, A. and Teplyakov, A., MOLREP: an Automated Program for Molecular Replacement, J. Appl. Cryst., 30:1022-1025 (1997).
Wang, X. et al., Intravitreal delivery of human NgR-Fc decoy protein regenerates axons after optic nerve crush and protects ganglion cells in glaucoma models, Invest. Ophthalmol. Vis. Sci., 56(2):1357-66 (2015).

* cited by examiner

RNAi-1# (HUMAN)

RNAi-2# (HUMAN, MOUSE, RAT)

ccaacccctac*gatgaagagggcgtccgct*ggagggagccggctgctggcatgggtgctgtggctgcaggcctggcaggtggcagccccatgcccag
gtgcctgcgtatgctacaatgagcccaaggtgacgacaagctgcccccagcagggcctgcaggctgtgcccgtgggcatccctgctgccagccagcgcat
cttcctgcacggcaaccgcatctcgcatgtgccagctgccagcttccgtgcctgccgcaacctcaccatcctgtggctgcactcgaatgtgctggcccgaattg
atgcggctgccttcactggcctggccctcctggagcagctggacctcagcgataatgcacagctccggtctgtggaccctgccacattccacggcctgggcc
gcctacacacgctgcacctggaccgctgcggcctgcaggagctgggcccggggctgttccgcggcctggctgccctgcagtacctctacctgcaggacaa
cgcgctgcaggcactgcctgatgacaccttccgcgacctgggcaacctcacacacctcttcctgcacggcaaccgcatctccagcgtgcccgagcgcgcct
tccgtgggctgcacagcctcgaccgtctcctactgcaccagaaccgcgtggcccatgtgcacccgcatgccttccgtgaccttggccgcctcatgacactcta
tctgtttgccaacaatctatcagcgctgcccactgaggccctggccccctgcgtgccctgcagtacctgaggctcaacgacaaccccctgggtgtgtgactgc
cgggcacgcccactc*tgggcctggctgcagaagtt*ccgcggctcctcctccgaggtgccctgcagcctcccgcaacgcctggctggccgtgacctcaaa
cgcctagctgccaatgacctgcagggctgcgctgtggccaccggcccttaccatcccatctggaccggcagggccaccgatgaggagccgctggggcttc
ccaagtgctgccagccagatgccgctgacaaggcctcagtactggagcctggaagaccagcttcggcaggcaatgcgctgaagggacgcgtgccgccc
ggtgacagcccgccgggcaacggctctggcccacggcacatcaatgactcaccctttgggactctgcctggctctgctgagcccccgctcactgcagtgcg
gcccgagggctccgagccaccagggttccccacctcgggccctcgccggaggccaggctgttcacgcaagaaccgcacccgcagccactgccgtctgg
gccaggcaggcagcgggggtggcgg*gactggtgactcagaagg*ctcaggtgccctacccagcctcacctgcagcctcacccccctgggcctggcgct
ggtgctgtggacagtgcttgggccctgctgacccccag RNAi-3# (HUMAN)

FIG. 16A nogor1
top
accgatgaagagggcgtccgctttctagagaagcggacgccctcttcatctttttg
bot
gatccaaaaagatgaagagggcgtccgcttctctagaaagcggacgccctcttcat nogor2
top
accgggcctggctgcagaagttttctagagaaacttctgcagccaggccctttttg
bot
gatccaaaaagggcctggctgcagaagtttctctagaaaacttctgcagccaggcc nogor3
top
accgactggtgactcagaaggcttctagagagccttctgagtcaccagtctttttg
bot
gatccaaaaagactggtgactcagaaggctctctagaagccttctgagtcaccagt nogor2m
top
accgggcctggcaccagaagttttctagagaaacttctggtgccaggccctttttg
bot
gatccaaaaagggcctggcaccagaagtttctctagaaaacttctggtgccaggcc

FIG. 16B

BIOGEN POLYCLONAL R150, RABBIT

7E11, BIOGEN mAb

7E11, BIOGEN mAb

BIOGEN POLYCLONAL R150, RABBIT (1:1000)

NOGO RECEPTOR ANTAGONISTS AND METHODS OF INCREASING NEURITE OUTGROWTH

CROSS-REFERENCE TO RELATED APPLICATIONS

This is a Continuation of co-pending U.S. patent application Ser. No. 12/162,256, filed Nov. 25, 2008, which is a 35 U.S.C. §371 National Stage of International Application No. PCT/US2007/002199, entitled "NOGO RECEPTOR ANTAGONISTS" filed Jan. 26, 2007, which claims the benefit of and priority to U.S. Provisional Application No. 60/831,659, filed Jul. 19, 2006, and U.S. Provisional Application No. 60/762,487, filed Jan. 27, 2006, the contents of each of which are hereby incorporated by reference in their entirety.

FIELD OF THE INVENTION

This invention relates to neurobiology and molecular biology. More particularly, this invention relates to immunogenic Nogo receptor-1 (NgR1) polypeptides, Nogo receptor-1 antibodies, antigen-binding fragments thereof soluble Nogo receptors and fusion proteins thereof and nucleic acids encoding the same. This invention further relates to Nogo receptor-1 antagonist polynucleotides. This invention further relates to compositions comprising, and methods for making and using, such Nogo receptor antibodies, antigen-binding fragments thereof immunogenic Nogo receptor-1 polypeptides, soluble Nogo receptors and fusion proteins thereof, nucleic acids encoding the same and antagonist polynucleotides.

BACKGROUND OF THE INVENTION

Axons and dendrites of neurons are long cellular extensions from neurons. The distal tip of an extending axon or neurite comprises a specialized region, known as the growth cone. Growth cones sense the local environment and guide axonal growth toward the neuron's target cell. Growth cones respond to several environmental cues, for example, surface adhesiveness, growth factors, neurotransmitters and electric fields. The guidance of growth at the cone involves various classes of adhesion molecules, intercellular signals, as well as factors that stimulate and inhibit growth cones. The growth cone of a growing neurite advances at various rates, but typically at the speed of one to two millimeters per day.

Growth cones are hand shaped, with broad flat expansion (microspikes or filopodia) that differentially adhere to surfaces in the embryo. The filopodia are continually active, some filopodia retract back into the growth cone, while others continue to elongate through the substratum. The elongations between different filopodia form lamellipodia.

The growth cone explores the area that is ahead of it and on either side with its lamellipodia and filopodia. When an elongation contacts a surface that is unfavorable to growth, it withdraws. When an elongation contacts a favorable growth surface, it continues to extend and guides the growth cone in that direction. The growth cone can be guided by small variations in surface properties of the substrata. When the growth cone reaches an appropriate target cell a synaptic connection is created.

Nerve cell function is greatly influenced by the contact between the neuron and other cells in its immediate environment (U. Rutishauser, T. M. Jessell, *Physiol. Rev.* 68:819 (1988)). These cells include specialized glial cells, oligodendrocytes in the central nervous system (CNS), and Schwann cells in the peripheral nervous system (PNS), which ensheathe the neuronal axon with myelin (an insulating structure of multi-layered membranes) (G. Lemke, in *An Introduction to Molecular Neurobiology*, Z. Hall, Ed. (Sinauer, Sunderland, Mass.), p. 281 (1992)).

While CNS neurons have the capacity to regenerate after injury, they are inhibited from doing so because of the presence of inhibitory proteins present in myelin and possibly also by other types of molecules normally found in their local environment (Brittis and Flanagan, *Neuron* 30:11-14 (2001); Jones et al., *J. Neurosc.* 22:2792-2803 (2002); Grimpe et al., *J. Neurosci.* 22:3144-3160 (2002)).

Several myelin inhibitory proteins that are found on oligodendrocytes have been characterized, e.g., NogoA (Chen et al., *Nature* 403:434-439 (2000); Grandpre et al., *Nature* 403:439-444 (2000)), myelin associated glycoprotein (MAO, McKerracher et al., *Neuron* 13:805-811 (1994); Mukhopadhyay et al., *Neuron* 13:757-767 (1994)) and oligodendrocyte glycoprotein (OM-gp, Mikol and Stefansson, *J. Cell. Biol.* 106:1273-1279 (1988)). Each of these proteins has been separately shown to be a ligand for the neuronal Nogo receptor-1 (Wang et al., *Nature* 417:941-944 (2002); Liu et al., *Science* 297:1190-93 (2002); Grandpre et al., *Nature* 403:439-444 (2000); Chen et al., *Nature* 403:434-439 (2000); Domeniconi et al., *Neuron* 35:283-90 (2002)).

Nogo receptor-1 is a GPI-anchored membrane protein that contains 8 leucine rich repeats (Fournier et al., *Nature* 409:341-346 (2001)). Upon interaction with an inhibitory protein (e.g., NogoA, MAG and OM-gp), the Nogo receptor-1 complex transduces signals that lead to growth cone collapse and inhibition of neurite outgrowth.

There is an urgent need for molecules that inhibit Nogo receptor-1 binding to its ligands and attenuate myelin-mediated growth cone collapse and inhibition of neurite outgrowth.

SUMMARY OF THE INVENTION

The present invention is directed to the use of Nogo receptor-1 antagonists for promoting neurite outgrowth, neuronal survival, and axonal regeneration in CNS neurons. The invention features molecules and methods useful for inhibiting neurite outgrowth inhibition, promoting neuronal survival, and/or promoting axonal regeneration in CNS neurons.

The invention also relates to soluble Nogo receptor-1 polypeptides and fusion proteins comprising them, and antibodies and antigenic fragments thereof directed against specific immunogenic regions of Nogo receptor-1. The invention also relates to immunogenic Nogo receptor-1 polypeptides that bind to the antibodies of the invention. The invention also relates to Nogo receptor-1 polypeptides that are bound by a monoclonal antibody that binds to Nogo receptor-1. Such polypeptides may be used, inter alia, as immunogens or to screen antibodies to identify those with similar specificity to an antibody of the invention. The invention further relates to nucleic acids encoding the polypeptides of this invention, vectors and host cells comprising such nucleic acids and methods of making the peptides. The antibodies, soluble receptors and receptor fusion proteins of this invention antagonize or block Nogo receptor-1 and are useful for inhibiting binding of Nogo receptor-1 to its ligands, inhibiting growth cone collapse in a neuron and decreasing the inhibition of neurite outgrowth or sprouting in a neuron.

In some embodiments, the invention provides a polypeptide selected from the group consisting of AAAFTGLTLLEQLDLSDNAQLR (SEQ ID NO: 26); LDLSD- NAQLR (SEQ ID NO: 27); LDLSDDAELR (SEQ ID NO: 29); LDLASDNAQLR (SEQ ID NO: 30); LDLASDDAELR (SEQ ID NO: 31); LDALSDNAQLR (SEQ ID NO: 32); LDALSDDAELR (SEQ ID NO: 33); LDLSSDNAQLR (SEQ ID NO: 34); LDLSSDEAELR (SEQ ID NO: 35); DNAQLRVVDPTT (SEQ ID NO: 36); DNAQLR (SEQ ID NO: 37); ADLSDNAQLRVVDPIT (SEQ ID NO: 41); LALSDNAQLRVVDITT (SEQ ID NO: 42); LDLSDNAALRVVDPTT (SEQ ID NO: 43); LDLSDNAQLHVVDPTT (SEQ ID NO: 44); and LDLSDNAQLAVVDPITT (SEQ ID NO: 45).

In some embodiments, the invention provides a nucleic acid encoding a polypeptide of the invention. In some embodiments, the nucleic acid is operably linked to an expression control sequence. In some embodiments, the invention provides a vector comprising a nucleic acid of the invention.

In some embodiments, the invention provides a host cell comprising a nucleic acid or comprising the vector of the invention. In some embodiments, the invention provides a method of producing a polypeptide of the invention comprising culturing a host cell comprising a nucleic acid or vector of the invention and recovering the polypeptide from the host cell or culture medium.

In some embodiments, the invention provides a method of producing an antibody comprising the steps of immunizing a host with a polypeptide of the invention or a host cell comprising a nucleic acid or comprising the vector of the invention and recovering the antibody. The invention also provides an antibody produced by the method or an antigen-binding fragment thereof.

In some embodiments, the invention provides an antibody or an antigen-binding fragment thereof that specifically binds to a polypeptide of the invention, wherein the antibody is not the monoclonal antibody produced by hybridoma cell line HB 7E11 (ATCC® accession No. PTA-4587).

In some embodiments of the invention, the antibody or antigen-binding fragment (a) inhibits growth cone collapse of a neuron; (b) decreases the inhibition of neurite outgrowth and sprouting in a neuron; and (c) inhibits Nogo receptor-1 binding to a ligand. In some embodiments, the neurite outgrowth and sprouting is axonal growth. In some embodiments, the neuron is a central nervous system neuron.

In some embodiments, an antibody of the invention is monoclonal. In some embodiments, an antibody of the invention is a murine antibody. In some embodiments, an antibody of the invention is selected from the group consisting of a humanized antibody, a chimeric antibody and a single chain antibody.

In some embodiments, the invention provides a method of inhibiting Nogo receptor-1 binding to a ligand, comprising the step of contacting Nogo receptor-1 with an antibody of the invention or antigen-binding fragment thereof. In some embodiments the ligand is selected from the group consisting of NogoA, NogoB, NogoC, MAG and OM-gp.

In some embodiments, the invention provides a method for inhibiting growth cone collapse in a neuron, comprising the step of contacting the neuron with an antibody of the invention or antigen-binding fragment thereof.

In some embodiments, the invention provides a method for decreasing the inhibition of neurite outgrowth or sprouting in a neuron, comprising the step of contacting the neuron with an antibody of the invention or antigen-binding fragment thereof. In some embodiments, the neurite outgrowth or sprouting is axonal growth. In some embodiments, the neuron is a central nervous system neuron.

In some embodiments, the invention provides a composition comprising a pharmaceutically acceptable carrier and an antibody of the invention or an antigen-binding fragment thereof. In some embodiments, the composition further comprises one or more additional therapeutic agents.

In some embodiments, the invention provides a method of promoting survival of a neuron at risk of dying, comprising contacting the neuron with an effective amount of an anti-Nogo receptor-1 antibody of the invention or antigen-binding fragment thereof. In some embodiments, the neuron is in vitro. In some embodiments, the neuron is in a mammal. In some embodiments, the mammal displays signs or symptoms of multiple sclerosis, ALS, Huntington's disease, Alzheimer's disease, Parkinson's disease, diabetic neuropathy, stroke, traumatic brain injuries or spinal cord injury.

In some embodiments, the invention provides a method of promoting survival of a neuron in a mammal, which neuron is at risk of dying, comprising (a) providing a cultured host cell expressing an anti-Nogo receptor-1 antibody of the invention or antigen-binding fragment thereof and (b) introducing the host cell into the mammal at or near the site of the neuron.

In some embodiments, the invention provides a gene therapy method of promoting survival of a neuron at risk of dying, which neuron is in a mammal, comprising administering at or near the site of the neuron a viral vector comprising a nucleotide sequence that encodes an anti-Nogo receptor-1 antibody of the invention or an antigen-binding fragment thereof, wherein the anti-Nogo receptor-1 antibody or antigen-binding fragment is expressed from the nucleotide sequence in the mammal in an amount sufficient to promote survival of the neuron.

In some embodiments, the invention provides an isolated polypeptide of 60 residues or less comprising an amino acid sequence selected from the group consisting of: amino acids 309 to 335 of SEQ ID NO:49; amino acids 309 to 336 of SEQ ID NO:49; amino acids 309 to 337 of SEQ ID NO:49; amino acids 309 to 338 of SEQ ID NO:49; amino acids 309 to 339 of SEQ ID NO:49; amino acids 309 to 340 of SEQ ID NO:49; amino acids 309 to 341 of SEQ ID NO:49; amino acids 309 to 342 of SEQ ID NO:49; amino acids 309 to 343 of SEQ ID NO:49; amino acids 309 to 344 of SEQ ID NO:49; amino acids 309 to 345 of SEQ ID NO:49; amino acids 309 to 346 of SEQ ID NO:49; amino acids 309 to 347 of SEQ ID NO:49; amino acids 309 to 348 of SEQ ID NO:49; amino acids 309 to 349 of SEQ ID NO:49; amino acids 309 to 350 of SEQ ID NO:49; amino acids 300 to 344 of SEQ ID NO:49; amino acids 301 to 344 of SEQ ID NO:49; amino acids 302 to 344 of SEQ ID NO:49; amino acids 303 to 344 of SEQ ID NO:49; amino acids 304 to 344 of SEQ ID NO:49; amino acids 305 to 344 of SEQ ID NO:49; amino acids 306 to 344 of SEQ ID NO:49; amino acids 307 to 344 of SEQ ID NO:49; amino acids 308 to 344 of SEQ ID NO:49; amino acids 336 to 344 of SEQ ID NO:49; amino acids 335 to 344 of SEQ ID NO:49; amino acids 334 to 344 of SEQ ID NO:49; amino acids 333 to 344 of SEQ ID NO:49; amino acids 332 to 344 of SEQ ID NO:49; amino acids 331 to 344 of SEQ ID NO:49; amino acids 330 to 344 of SEQ ID NO:49; amino acids 329 to 344 of SEQ ID NO:49; amino acids 328 to 344 of SEQ ID NO:49; amino acids 327 to 344 of SEQ ID NO:49; amino acids 326 to 344 of SEQ ID NO:49; amino acids 325 to 344 of SEQ ID NO:49; amino acids 324 to 344 of SEQ ID NO:49; amino acids 323 to 344 of SEQ ID NO:49; amino acids 322 to 344 of SEQ ID NO:49; amino acids 321 to 344 of SEQ ID NO:49; amino acids 320 to 344 of SEQ ID NO:49; amino acids 319 to 344 of SEQ ID NO:49; amino acids 318 to 344 of SEQ ID NO:49; amino acids 317 to 344 of SEQ ID NO:49; amino acids 316 to 344 of SEQ ID NO:49; amino acids 315 to 344 of SEQ ID NO:49; amino acids 314 to 344 of SEQ ID NO:49; amino acids 313 to 344 of SEQ ID NO:49; amino acids 312 to 344 of SEQ ID NO:49; amino acids 311 to 344 of SEQ ID NO:49; amino acids 310 to 344 of SEQ ID NO:49; amino acids 336 to 344 of SEQ ID NO:49; amino acids 336 to 345 of SEQ ID NO:49; amino acids 336 to 346 of SEQ ID NO:49; amino acids 336 to 347 of SEQ ID NO:49; amino acids 336 to 348 of SEQ ID NO:49; amino acids 336 to 349 of SEQ ID NO:49; amino acids 336 to 350 of SEQ ID NO:49; variants or derivatives of any of said polypeptide fragments, and a combination of at least two of any of said polypeptide fragments; except for up to three amino acid substitutions.

In some embodiments, the invention provides an isolated polypeptide of 60 residues or less comprising an amino acid sequence selected from the group consisting of: amino acids 311-344 of SEQ ID NO:49; amino acids 310-348 of SEQ ID NO:49; amino acids 323-328 of SEQ ID NO:49; amino acids 339-348 of SEQ ID NO:49; amino acids 378-414 of SEQ ID NO:49; amino acids 27-38 of SEQ ID NO:49; amino acids 39-61 of SEQ ID NO:49; amino acids 257-267 of SEQ ID NO:49; amino acids 280-292 of SEQ ID NO:49; amino acids 301-323 of SEQ ID NO:49; amino acids 335-343 of SEQ ID NO:49; amino acids 310-335 of SEQ ID NO:49; amino acids 326-328 of SEQ ID NO:49; variants or derivatives of any of said polypeptide fragments, and a combination of at least two of any of said polypeptide fragments.

In some embodiments, the invention provides an isolated polypeptide fragment of 60 residues or less, comprising an amino acid sequence identical to a reference amino acid sequence, except for up to three individual amino acid substitutions, wherein said reference amino acid sequence is selected from the group consisting of: (a) amino acids x to 344 of SEQ ID NO:49, (b) amino acids 309 to y of SEQ ID NO:49, and (c) amino acids x to y of SEQ ID NO:49, wherein x is any integer from 305 to 326, and y is any integer from 328 to 350; and wherein said polypeptide fragment inhibits Nogo-receptor-mediated neurite outgrowth inhibition. In some embodiments, the invention provides an isolated polypeptide fragment of 60 residues or less, comprising an amino acid sequence identical to a reference amino acid sequence, except for up to three individual amino acid substitutions, wherein said reference amino acid sequence is selected from the group consisting of: (a) amino acids x' to 344 of SEQ ID NO:49, (b) amino acids 309 to y' of SEQ ID NO:49, and (c) amino acids x' to y' of SEQ ID NO:49, where x' is any integer from 300 to 326, and y' is any integer from 328 to 360, and wherein said polypeptide fragment inhibits Nogo-receptor-mediated neurite outgrowth inhibition. In some embodiments, the invention provides an isolated polypeptide fragment of 60 residues or less, comprising an amino acid sequence identical to a reference amino acid sequence, except for up to three individual amino acid substitutions, wherein said reference amino acid sequence is selected from the group consisting of: amino acids 309 to 335 of SEQ ID NO:49; amino acids 309 to 344 of SEQ ID NO:49; amino acids 310 to 335 of SEQ ID NO:49; amino acids 310 to 344 of SEQ ID NO:49; amino acids 309 to 350 of SEQ ID NO:49; amino acids 300 to 344 of SEQ ID NO:49; and amino acids 315 to 344 of SEQ ID NO:49. In some embodiments, the invention provides an isolated polypeptide fragment of 60 residues or less, comprising an amino acid sequence identical to a reference amino acid sequence, except for up to three individual amino acid substitutions, wherein said reference amino acid sequence is amino acids 309 to 344 of SEQ ID NO:49. In some embodiments, the invention provides an isolated polypeptide fragment of 60 residues or less, comprising an amino acid sequence identical to a reference amino acid sequence, except for up to three individual amino acid substitutions, wherein said reference amino acid sequence is amino acids 309 to 335 of SEQ ID NO:49.

In some embodiments, the invention provides a polypeptide of the invention that is cyclic. In some embodiments, the cyclic polypeptide further comprises a first molecule linked at the N-terminus and a second molecule linked at the C-terminus; wherein the first molecule and the second molecule are joined to each other to form said cyclic molecule. In some embodiments, the first and second molecules are selected from the group consisting of: a biotin molecule, a cysteine residue, and an acetylated cysteine residue. In some embodiments, the first molecule is a biotin molecule attached to the N-terminus and the second molecule is a cysteine residue attached to the C-terminus of the polypeptide of the invention. In some embodiments, the first molecule is an acetylated cysteine residue attached to the N-terminus and the second molecule is a cysteine residue attached to the C-terminus of the polypeptide of the invention. In some embodiments, the first molecule is an acetylated cysteine residue attached to the N-terminus and the second molecule is a cysteine residue attached to the C-terminus of the polypeptide of the invention. In some embodiments, the C-terminal cysteine has an NH2 moiety attached.

In some embodiments, the invention provides an isolated polypeptide comprising a first polypeptide fragment and a second polypeptide fragment, wherein said first polypeptide fragment comprises an amino acid sequence identical to a first reference amino acid sequence, except for up to twenty individual amino acid substitutions, wherein said first reference amino acid sequence is selected from the group consisting of: (a) amino acids a to 445 of SEQ ID NO:49, (b) amino acids 27 to b of SEQ ID NO:49, and (c) amino acids a to b of SEQ ID NO:49, wherein a is any integer from 25 to 35, and b is any integer from 300 to 450; wherein said second polypeptide fragment comprises an amino acid sequence identical to a second reference amino acid sequence, except for up to twenty individual amino acid substitutions, wherein said second reference amino acid sequence is selected from the group consisting of (a) amino acids c to 445 of SEQ ID NO:49, (b) amino acids 27 to d of SEQ ID NO:49, and (c) amino acids c to d of SEQ ID NO:49, wherein c is any integer from 25 to 35, and d is any integer from 300 to 450; and wherein said polypeptide inhibits Nogo-receptor-mediated neurite outgrowth inhibition. In some embodiments, the invention further provides an isolated polypeptide comprising a first polypeptide fragment and a second polypeptide fragment, wherein the first polypeptide fragment comprises an amino acid sequence identical to a first reference amino acid sequence, except for up to twenty individual amino acid substitutions, wherein the first reference amino acid sequence is selected from the group consisting of: (a) amino acids 27 to 310 of SEQ ID NO:49 and (b) amino acids 27 to 344 of SEQ ID NO:49. In some embodiments, the invention further provides an isolated polypeptide comprising a first polypeptide fragment and a second polypeptide fragment, wherein the second polypeptide fragment comprises an amino acid sequence identical to a first reference amino acid sequence, except for up to twenty individual amino acid substitutions, wherein the second reference amino acid sequence is selected from the group consisting of (a) amino acids 27 to 310 of SEQ ID NO:49 and (b) amino acids 27 to 344 of SEQ ID NO:49. In some embodiments, the invention further provides an isolated polypeptide comprising a first polypeptide fragment and a second polypeptide fragment, wherein the second polypeptide fragment comprises an amino acid sequence identical to a first reference amino acid sequence, except for up to twenty individual amino acid substitutions, wherein the first polypeptide fragment comprises amino acids 27 to 310 of SEQ ID NO:49 and the second polypeptide fragment comprises amino acids 27 to 310 of SEQ ID NO:49 or wherein the first polypeptide fragment comprises amino acids 27 to 344 of SEQ ID NO:49 and the second polypeptide fragment comprises amino acids 27 to 310 of SEQ ID NO:49 or wherein the first polypeptide fragment comprises amino acids 27 to 344 of SEQ ID NO:49 and the second polypeptide fragment comprises amino acids 27 to 344 of SEQ ID NO:49. In some embodiments, the invention further provides that the first polypeptide fragment is situated upstream of the second polypeptide fragment. In some embodiments, the invention further provides a peptide linker situated between the first polypeptide fragment and the second polypeptide fragment. In some embodiments, the invention further provides that the peptide linker comprises SEQ ID NO:65 $(G4S)_3$. In some embodiments, the invention further provides that the peptide linker comprises SEQ ID NO:66 $(G4S)_2$.

In some embodiments, the invention provides a polypeptide of the invention wherein at least one cysteine residue is substituted with a heterologous amino acid. In some embodiments, the at least one cysteine residue is C266. In some embodiments, the at least one cysteine residue is C309. In some embodiments, the at least one cysteine residue is C335. In some embodiments, the at least one cysteine residue is at C336. In some embodiments, the at least one cysteine residue is substituted with a replacement amino acid selected from the group consisting of alanine, serine and threonine. In some embodiments, the replacement amino acid is alanine.

In some embodiments, the invention provides an isolated polypeptide comprising: (a) an amino acid sequence identical to a reference amino acid sequence except that at least one cysteine residue of said reference amino acid sequence is substituted with a different amino acid, wherein said reference amino acid sequence is selected from the group consisting of: (i) amino acids a to 445 of SEQ ID NO:49, (iii) amino acids 27 to b of SEQ ID NO:49, and (iii) amino acids a to b of SEQ ID NO:49, wherein a is any integer from 25 to 35, and b is any integer from 300 to 450; and (b) a heterologous polypeptide; wherein said polypeptide inhibits nogo-receptor-mediated neurite outgrowth inhibition. In some embodiments, the invention further provides that C266 of said reference amino acid sequence is substituted with a different amino acid. In some embodiments, the invention further provides that C309 of said reference amino acid sequence is substituted with a different amino acid. In some embodiments, the invention further provides that C335 of said reference amino acid sequence is substituted with a different amino acid. In some embodiments, the invention further provides that C266 and C309 of said reference amino acid sequence are substituted with different amino acids. In some embodiments, the invention further provides that C309 and C335 of said reference amino acid sequence are substituted with different amino acids. In some embodiments, the invention further provides that the different amino acid is alanine.

In some embodiments, the invention provides an isolated polypeptide comprising: (a) an amino acid sequence identical to a reference amino acid sequence, except for up to twenty individual amino acid substitutions, wherein said reference amino acid sequence is selected from the group consisting of: (i) amino acids a to 445 of SEQ ID NO:49, (ii) amino acids 27 to b of SEQ ID NO:49, and (iii) amino acids a to b of SEQ ID NO:49, wherein a is any integer from 25 to 35, and b is any integer from 300 to 450; and (b) a heterologous polypeptide; wherein said polypeptide inhibits nogo-receptor-mediated neurite outgrowth inhibition.

In some embodiments, the invention provides an isolated polypeptide comprising a first polypeptide fragment and a second polypeptide fragment, wherein said first polypeptide fragment comprises an amino acid sequence identical to a first reference amino acid sequence, except for up to twenty individual amino acid substitutions, wherein said first reference amino acid sequence is selected from the group consisting of: (a) amino acids a to 305 of SEQ ID NO:49, (b) amino acids 1 to b of SEQ ID NO:49, and (c) amino acids a to b of SEQ ID NO:49, wherein a is any integer from 1 to 27, and b is any integer from 264 to 309; and wherein said second polypeptide fragment comprises an amino acid sequence identical to a second reference amino acid sequence, except for up to twenty individual amino acid substitutions, wherein said second reference amino acid sequence is selected from the group consisting of: (a) amino acids c to 332 of SEQ ID NO:60, (b) amino acids 275 to d of SEQ ID NO:60, and (c) amino acids c to d of SEQ ID NO:60, wherein c is any integer from 265 to 306, and d is any integer from 308 to 340; and wherein said polypeptide inhibits nogo-receptor-mediated neurite outgrowth inhibition. In certain embodiments, the first reference amino acid sequence is selected from the group consisting of: (a) amino acids 1-274 of SEQ ID NO:49; and (b) amino acids 1-305 of SEQ ID NO:49. In certain embodiments, the second reference amino acid sequence is selected from the group consisting of: (a) amino acids 275-311 of SEQ ID NO:60; (b) amino acids 275-332 of SEQ ID NO:60; (c) amino acids 306-311 of SEQ ID NO:60; (d) amino acids 306-308 of SEQ ID NO:60; and (e) amino acids 306-309 of SEQ ID NO:60. In one embodiment, the first polypeptide fragment comprises amino acids 1-274 of SEQ ID NO:49 and the second polypeptide fragment comprises amino acids amino acids 275-311 of SEQ ID NO:60. In some embodiments, the first polypeptide fragment comprises amino acids 1-274 of SEQ ID NO:49 and the second polypeptide fragment comprises amino acids 275-332 of SEQ ID NO:60. In some embodiments, the first polypeptide fragment comprises amino acids 1-305 of SEQ ID NO:49 and the second polypeptide fragment comprises amino acids 306-311 of SEQ ID NO:60. In some embodiments, the first polypeptide fragment comprises amino acids 1-305 of SEQ ID NO:49 and the second polypeptide fragment comprises amino acids 306-308 of SEQ ID NO:60. In some embodiments, the first polypeptide fragment comprises amino acids 1-305 of SEQ ID NO:49 and the second polypeptide fragment comprises amino acids 306-309 of SEQ ID NO:60. In some embodiments at least one additional amino acid is added to the C-terminus of the second polypeptide fragment. In one embodiment, the at least one additional amino acid is tryptophan. In some embodiments, A269 of the first polypeptide fragment is substituted with a different amino acid. In one embodiment, the different amino acid is tryptophan.

In some embodiments the invention provides an isolated polypeptide comprising a first polypeptide fragment and a second polypeptide fragment, wherein said first polypeptide fragment consists of amino acids 1-310 of SEQ ID NO:49, except for up to twenty individual amino acid substitutions; and wherein said second polypeptide fragment consists of amino acids 311 to 318 of SEQ ID NO:60, except for up to five individual amino acid substitutions; and wherein said polypeptide inhibits nogo-receptor-mediated neurite outgrowth inhibition.

In some embodiments the invention further provides that the heterologous polypeptide is selected from the group consisting of: (a) serum albumin, (b) an Fc region, (c) a signal peptide, (d) a polypeptide tag, and (e) a combination of two or more of said heterologous polypeptides. In some embodiments, the invention further provides that the Fc region is selected from the group consisting of: an IgA Fc region; an IgD Fc region; an IgG Fc region, an IgEFc region; and an IgM Fc region. In one embodiment, the Fc region is an IgG Fc region. In some embodiments, the invention further provides that a peptide linker is situated between the amino acid sequence and the IgG Fc region. In one embodiment, the peptide linker comprises SEQ ID NO:66 $(G4S)_2$ In some embodiments, the invention further provides that the polypeptide tag is selected from the group consisting of: FLAG tag; Strep tag; poly-histidine tag; VSV-G tag; influenza virus hemagglutinin (HA) tag; and c-Myc tag.

In some embodiments, the invention provides a polypeptide of the invention attached to one or more polyalkylene glycol moieties. In some embodiments, the invention further provides that the one or more polyalkylene glycol moieties is a polyethylene glycol (PEG) moiety. In some embodiments, the invention further provides a polypeptide of the invention attached to 1 to 5 PEG moieties.

In some embodiments, the invention provides an isolated polynucleotide encoding a polypeptide of the invention. In some embodiments, the invention further provides that the nucleotide sequence is operably linked to an expression control element (e.g. an inducible promoter, a constitutive promoter, or a secretion signal). Additional embodiments include a vector comprising an isolated polynucleotide of the invention and a host cell comprising said vector.

In some embodiments, the invention provides an isolated polynucleotide selected from the group consisting of: (i) an antisense polynucleotide; (ii) a ribozyme; (iii) a small interfering RNA (siRNA); and (iv) a small-hairpin RNA (shRNA).

In some embodiments, the isolated polynucleotide is an antisense polynucleotide comprising at least 10 bases complementary to the coding portion of the NgR1 mRNA. In some embodiments, the polynucleotide is a ribozyme.

In further embodiments, the polynucleotide is a siRNA or a shRNA. In some embodiments, the invention provides that that siRNA or the shRNA inhibits NgR1 expression. In some embodiments, the invention further provides that the siRNA or shRNA is at least 90% identical to the nucleotide sequence comprising: CUACUUCUCCCGCAGGCG or CCCGGACCGACGUCUUCAA or CUGACCACUGAGUCUUCCG. In other embodiments, the siRNA or shRNA nucleotide sequence is CUACUUCUCCCGCAGGCG or CCCGGACCGACGUCUUCAA or CUGACCACUGAGUCUUCCG.

In some embodiments, the invention further provides that the siRNA or shRNA nucleotide sequence is complementary to the mRNA produced by the polynucleotide sequence GATGAAGAGGGCGTCCGCT or GGGCCTGGCTGCAGAAGTT or GACTGGTGACTCAGAG AAGGC.

Additional embodiments of the invention include pharmaceutical compositions comprising the polypeptides, polynucleotides, vectors or host cells of the invention and in certain embodiments a pharmaceutically acceptable carrier. In certain embodiments, the composition comprises amino acids 27-310 of SEQ ID NO: 7 and an anti-inflammatory agent. In other embodiments, the composition comprises amino acids 27-310 of SEQ ID NO: 9 and an anti-inflammatory agent. In some embodiments, the invention further provides that the inflammatory agent is selected from the group consisting of a steroidal anti-inflammatory agent and a non-steroidal anti-inflammatory agent. In certain embodiments, the steroidal anti-inflammatory agent is selected from the group consisting of hydrocortisone, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone, acetonide, triamcinolone benetonide and triamcinolone hexacetonide. In a particular embodiment, the steroidal anti-inflammatory agent is methylprednisolone. In other embodiments, the non-steroidal anti-inflammatory agent is selected from the group consisting of alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, tioxaprofen, indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, zomepirac, flufenamic acid, meclofenamic acid, mefenamic acid, niflumic acid, tolfenamic acid, diflunisal, flufenisal, isoxicam, piroxicam, sudoxicam, tenoxicam, acetyl salicylic acid, sulfasalazine, apazone, bezpiperylon, feprazone, mofebutazone, oxyphenbutazone and phenylbutazone.

Additional embodiments include compositions where amino acids 27-310 of SEQ ID NO: 7 or 9 are fused to a heterologous polypeptide. In some embodiments, the heterologous polypeptide is Fc.

Embodiments of the invention also include methods for promoting neurite outgrowth, comprising contacting a neuron with an agent which includes polypeptides, polynucleotides or compositions of the invention, wherein said agent inhibits Nogo receptor 1-mediated neurite outgrowth inhibition.

Additional embodiments include a method for inhibiting signal transduction by the NgR1 signaling complex, comprising contacting a neuron with an effective amount of an agent which includes polypeptide, polynucleotides, or compositions of the invention, wherein said agent inhibits signal transduction by the NgR1 signaling complex.

Other embodiments include a method for treating a central nervous system (CNS) disease, disorder, or injury in a mammal, comprising administering to a mammal in need of treatment an effective amount of an agent which includes polypeptides, polynucleotides, or compositions of the invention, wherein said agent inhibits Nogo Receptor 1-mediated neurite outgrowth inhibition. In certain embodiments, the disease, disorder or injury is selected from the group consisting of multiple sclerosis, ALS, Huntington's disease, Alzheimers disease, Parkinson's disease, diabetic neuropathy, stroke, traumatic brain injuries, spinal cord injury, optic neuritis, glaucoma, hearing loss, and adrenal leukodystrophy.

In some embodiments the invention further provides that the polypeptide is fused to a heterologous polypeptide. In some embodiments, the heterologous polypeptide is serum albumin. In some embodiments, the heterologous polypeptide is an Fc region. In some embodiments, the heterologous polypeptide is a signal peptide. In some embodiments, the heterologous polypeptide is a polypeptide tag. In some embodiments, the invention further provides that the Fc region is selected from the group consisting of an IgA Fc region; an IgD Fc region; an IgG Fc region, an IgEFc region; and an IgM Fc region. In some embodiments, the invention further provides that the polypeptide tag is selected from the group consisting of: FLAG tag; Strep tag; poly-histidine tag; VSV-G tag; influenza virus hemagglutinin (HA) tag; and c-Myc tag.

BRIEF DESCRIPTION OF THE DRAWINGS

FIG. 16A shows the nucleotide sequence of human Nogo receptor cDNA. The start and stop codons are underlined. The selected RNAi target regions are italicized. RNAi-1 and RNAi-3 target the human NgR gene specifically, RNAi-2 was designed to target human, mouse and rat NgR genes. FIG. 16 B shows the nucleotide sequences of the DNA oligonucleotides used for construction of NgR RNAi into expression vector pU6.

DETAILED DESCRIPTION OF THE INVENTION

Definitions and General Techniques

Figure 1:
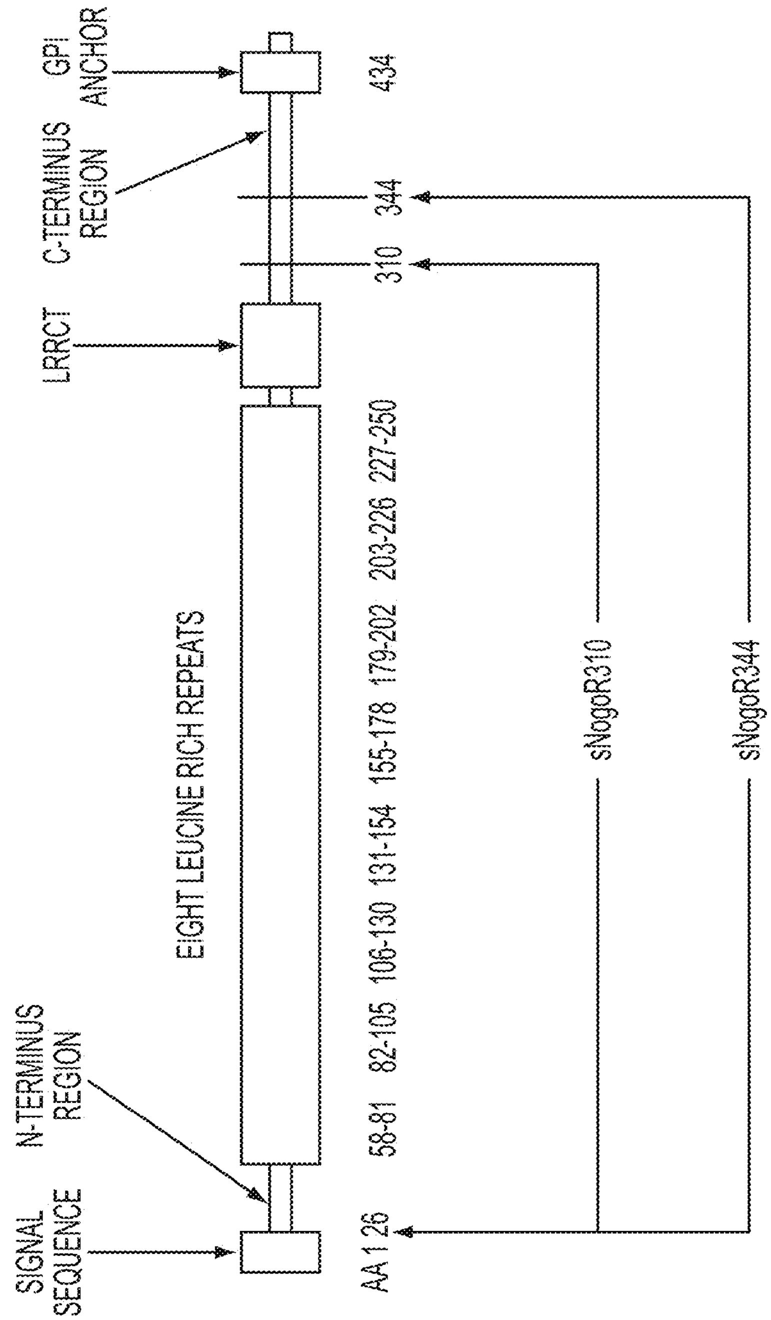
FIG. 1 is a schematic representation of the structure of Nogo receptor-1. Human sNogoR310 contains residues 26-310 of SEQ ID NO:7 and sNogoR344 contains residues 26-344 of SEQ ID NO:6. Rat sNogoR310 contains residues 27-310 of SEQ ID NO:9 and sNogoR344 contains residues 27-344 of SEQ ID NO:8.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

Although methods and materials similar or equivalent to those described herein can be used in practice or testing of the present invention, suitable methods and materials are described below. The materials, methods and examples are illustrative only, and are not intended to be limiting. Other features and advantages of the invention will be apparent from the detailed description and from the claims.

Throughout this specification and claims, the word "comprise," or variations such as "comprises" or "comprising." will be understood to imply the inclusion of a stated integer or group of integers but not the exclusion of any other integer or group of integers.

In order to further define this invention, the following terms and definitions are herein provided.

It is to be noted that the term "a" or "an" entity, refers to one or more of that entity, for example, "an immunoglobulin molecule," is understood to represent one or more immunoglobulin molecules. As such, the terms "a" (or "an"), "one or more," and "at least one" can be used interchangeably herein.

As used herein, the term "consists of," or variations such as "consist of" or "consisting of," as used throughout the specification and claims, indicate the inclusion of any recited integer or group of integers, but that no additional integer or group of integers may be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, "antibody" means an intact immunoglobulin, or an antigen-binding fragment thereof. Antibodies of this invention can be of any isotype or class (e.g., M, D, G, E and A) or any subclass (e.g., G1-4, A1-2) and can have either a kappa (κ) or lambda (λ) light chain.

As used herein, "Fc" means a portion of an immunoglobulin heavy chain that comprises one or more heavy chain constant region domains, CH1, CH2 and CH3. For example, a portion of the heavy chain constant region of an antibody that is obtainable by papain digestion.

As used herein, "NogoR fusion protein" means a protein comprising a soluble Nogo receptor-1 moiety fused to a heterologous polypeptide.

As used herein, "humanized antibody" means an antibody in which at least a portion of the non-human sequences are replaced with human sequences. Examples of how to make humanized antibodies may be found in U.S. Pat. Nos. 6,054,297, 5,886,152 and 5,877,293.

As used herein, "chimeric antibody" means an antibody, that contains one or more regions from a first antibody and one or more regions from at least one other antibody. The first antibody and the additional antibodies can be from the same or different species.

As used herein and in U.S. patent application 60/402,866, "Nogo receptor," "NogoR," "NogoR-1," "NgR," "NgR-1," "NgR1" and "NGR1" each means Nogo receptor-1.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

In the present invention, a "polypeptide fragment" refers to a short amino acid sequence of a larger polypeptide. Protein fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids or more in length.

The terms "fragment," "variant," "derivative" and "analog" when referring to a polypeptide of the present invention include any polypeptide which retains at least some biological activity. Polypeptides as described herein may include fragment, variant, or derivative molecules therein without limitation, so long as the polypeptide still serves its function. NgR1 polypeptides and polypeptide fragments of the present invention may include proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. NgR1 polypeptides and polypeptide fragments of the present invention may comprise variant regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. NgR1 polypeptides and polypeptide fragments of the invention may comprise conservative or non-conservative amino acid substitutions, deletions or additions. NgR1 polypeptides and polypeptide fragments of the present invention may also include derivative molecules. Variant polypeptides may also be referred to herein as "polypeptide analogs." As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

As used herein the term "disulfide bond" includes the covalent bond formed between two sulfur atoms. The amino acid cysteine comprises a thiol group that can form a disulfide bond or bridge with a second thiol group.

As used herein, "fusion protein" means a protein comprising a first polypeptide linearly connected, via peptide bonds, to a second, polypeptide. The first polypeptide and the second polypeptide may be identical or different, and they may be directly connected, or connected via a peptide linker (see below).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can contain the nucleotide sequence of the full-length cDNA sequence, including the untranslated 5' and 3' sequences, the coding sequences. A polynucleotide may comprise a conventional phosphodiester bond or a non-conventional bond (e.g., an amide bond, such as found in peptide nucleic acids (PNA)). The polynucleotide can be composed of any polyribonucleotide or polydeoxyribonucleotide, which may be unmodified RNA or DNA or modified RNA or DNA. For example, polynucleotides can be composed of single- and double-stranded DNA. DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an NgR polypeptide or polypeptide fragment of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an NgR polypeptide or polypeptide fragment of the present invention. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" and "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

A "linker" sequence is a series of one or more amino acids separating two polypeptide coding regions in a fusion protein. A typical linker comprises at least 5 amino acids. Additional linkers comprise at least 10 or at least 15 amino acids. In certain embodiments, the amino acids of a peptide linker are selected so that the linker is hydrophilic. The linker (Gly-Gly-Gly-Gly-Ser)$_3$ (G4S)$_3$ (SEQ ID NO:65) is a preferred linker that is widely applicable to many antibodies as it provides sufficient flexibility. Other linkers include (Gly-Gly-Gly-Gly-Ser)$_2$ (G4S)$_2$ (SEQ ID NO:66), Glu Ser Gly Arg Ser Gly Gly Gly Gly Ser Gly Gly Gly Gly Ser (SEQ ID NO:67), Glu Gly Lys Ser Ser Gly Ser Gly Ser Glu Ser Lys Ser Thr (SEQ ID NO:68), Glu Gly Lys Ser Ser Gly Ser Gly Ser Glu Set Lys Ser Thr Gln (SEQ ID NO:69), Glu Gly Lys Ser Ser Gly Ser Gly Ser Glu Ser Lys Val Asp (SEQ ID NO:70), Gly Ser Thr Ser Gly Ser Gly Lys Ser Ser Glu Gly Lys Gly (SEQ ID NO:71), Lys Glu Ser Gly Ser Val Ser Ser Glu Gln Leu Ala Gln Phe Arg Ser Leu Asp (SEQ ID NO:72), and Glu Ser Gly Ser Val Ser Ser Glu Glu Leu Ala Phe Arg Ser Leu Asp (SEQ ID NO:73). Examples of shorter linkers include fragments of the above linkers, and examples of longer linkers include combinations of the linkers above, combinations of fragments of the linkers above, and combinations of the linkers above with fragments of the linkers above.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA) or any other RNA product, and the translation of such mRNA into polypeptide(s), as well as any processes which regulate either transcription or translation. If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The invention is directed to certain NgR1 antagonists that promote neuronal survival, neurite outgrowth and axonal regeneration of neurons, for example, CNS neurons. For example, the present invention provides NgR1 polypeptides and polypeptide fragments, antibodies and fragments thereof, and polynucleotides which stimulate axonal growth under conditions in which axonal growth is normally inhibited. Thus, NgR1 antagonists of the invention are useful in treating injuries, diseases or disorders that can be alleviated by promoting neuronal survival, or by the stimulation of axonal growth or regeneration in the CNS.

Exemplary CNS diseases, disorders or injuries include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. Among these diseases, MS is the most widespread, affecting approximately 2.5 million people worldwide.

Nogo Receptor-1 Polypeptides

In one aspect, the present invention relates to Nogo receptor-1 polypeptides that are immunogenic. In some embodiments of the invention, the immunogenic polypeptide consists essentially of an amino acid sequence selected from the group consisting of: LDLSDNAQLRVVDPTT (rat) (SEQ ID NO: 1); LDLSDNAQLRSVDPAT (human) (SEQ ID NO: 2); AVASGPFRPFQTNQLTDEELLGLPKCCQPDAADKA (rat) (SEQ ID NO: 3); AVATGPYHPIWTGRATDEEPLGLPKCCQPDAADKA (human) (SEQ ID NO: 4); and CRLGQAGSGA (mouse) (SEQ ID NO: 5).

In some embodiments, the invention relates to Nogo receptor 1 polypeptides that are bound by a monoclonal antibody that binds to Nogo receptor-1. In some embodiments, the polypeptide is recognized by the 7E11 monoclonal antibody. In some embodiments, the polypeptide is selected from the group consisting of: LDLSDNAQLR (SEQ ID NO: 27); LDLSDDAELR (SEQ ID NO: 29); LDLASDNAQLR (SEQ ID NO: 30); LDLASDDAELR (SEQ ID NO: 31); LDALSDNAQLR (SEQ ID NO: 32); LDALSDDAELR (SEQ ID NO: 33); LDLSSDNAQLR (SEQ ID NO: 34); LDLSSDEAELR (SEQ ID NO: 35); DNAQLRVVDPTT (SEQ ID NO: 36); DNAQLR (SEQ ID NO: 37); ADLSDNAQLRVVDPTT (SEQ ID NO: 41); LALSDNAQLRVVDPTT (SEQ ID NO: 42); LDLSDNAALRVVDPT (SEQ ID NO: 43); LDLSDNAQLHVVDPTT (SEQ ID NO: 44); and LDLSDNAQLAVVDPTT (SEQ ID NO: 46).

In some embodiments, the invention relates to a nucleic acid encoding a polypeptide of SEQ ID NOs: 1-5, 26-27, 29-37 and 41-45. In some embodiments of the invention, the nucleic acid molecule is linked to an expression control sequence (e.g. pCDNA(I)).

The present invention also relates to a vector comprising a nucleic acid coding for a polypeptide of the invention. In some embodiments of the invention, the vector is a cloning vector. In some embodiments of the invention, the vector is an expression vector. In some embodiments of the invention, the vector contains at least one selectable marker.

The present invention also relates to host cells comprising the above-described nucleic acid or vector.

The present invention also relates to a method of producing an immunogenic polypeptide of the invention comprising the step of culturing a host cell. In some embodiments, the host cell is prokaryotic. In some embodiments, the host cell is eukaryotic. In some embodiments, the host cell is yeast.

The present invention is also directed to certain Nogo receptor-1 polypeptides and polypeptide fragments useful, e.g., for promoting neurite outgrowth, promoting neuronal survival, promoting axonal survival, or inhibiting signal transduction by the NgR1 signaling complex. Typically, the polypeptides and polypeptide fragments of the invention act to block NgR1-mediated inhibition of neuronal survival, neurite outgrowth or axonal regeneration of central nervous system (CNS) neurons.

The human NgR1 polypeptide is shown below as SEQ ID NO:49.

Full-Length Human NgR1 (SEQ ID NO:49:

```
MKRASAGGSRLLAWVLWLQAWQVAAPCPGACVCYNEPKVTTSCPQQGLQA

VPVGIPAASQRIFLHGNRISHVPAASFRACRNLTILWLHSNVLARIDAAA

FTGLALLEQLDLSDNAQLRSVDPATFHGLGRLHTLHLDRCGLQELGPGLF

RGLAALQYLYLQDNALQALPDDTFRDLGNLTHLFLHGNRISSVPERAFRG

LHSLDRLLLHQNRVAHVHPHAFRDLGRLMTLYLFANNLSALPTEALAPLR

ALQYLRLNDNPWVCDCRARPLWAWLQKFRGSSSEVPCSLPQRLAGRDLKR

LAANDLQGCAVATGPYHPIWTGRATDEEPLGLPKCCQPDAADKASVLEPG

RPASAGNALKGRVPPGDSPPGNGSGPRHINDSPFGTLPGSAEPPLTAVRP

EGSEPPGFPTSGPRRRPGCSRKNRTRSHCRLGQAGSGGGGTGDSEGSGAL

PSLTCSLTPLGLALVLWTVLGPC
```

The rat NgR1 polypeptide is shown below as SEQ ID NO:50.

Full-Length Rat NgR1 (SEQ ID NO:50):

```
MKRASSGGSRLLAWVLWLQAWRVATPCPGACVCYNEPKVTTSCPQQGLQA

VPTGIPASSQRIFLHGNRISHVPAASFQSCRNLTILWLHSNALARIDAAA

FTGLTLLEQLDLSDNAQLHVVDPTTFHGLGHLHTLHLDRCGLRELGPGLF

RGLAALQYLYLQDNNLQALPDNTFRDLGNLTHLFLHGNRIPSVPEHAFRG

LHSLDRLLLHQNHVARVHPHAFRDLGRLMTLYLFANNLSMLPAEVLMPLR

SLQYLRLNDNPWVCDCRARPLWAWLQKFRGSSSEVPCNLPQRLADRDLKR

LAASDLEGCAVASGPFRPIQTSQLTDEELLSLPKCCQPDAADKASVLEPG

RPASAGNALKGRVPPGDTPPGNGSGPRHINDSPFGTLPSSAEPPLTALRP

GGSEPPGLPTTGPRRRPGCSRKNRTRSHCRLGQAGSGASGTGDAEGSGAL

PALACSLAPLGLALVLWTVLGPC
```

The mouse NgR1 polypeptide is shown below as SEQ ID NO:51.

Full-Length Mouse NgR1 (SEQ ID NO:51):

```
MKRASSGGSRLLAWVLWLQAWRVATPCPGACVCYNEPKVTTSCPQQGLQA

VPTGIPASSQRIFLHGNRISHVPAASFQSCRNLTILWLHSNALARIDAAA

FTGLTLLEQLDLSDNAQLHVVDPTTFHGLGHLHTLHLDRCGLRELGPGLF

RGLAALQYLYLQDNNLQALPDNTFRDLGNLTHLFLHGNRIPSVPEHAFRG

LHSLDRLLLHQNHVARVHPHAFRDLGRLMTLYLFANNLSMLPAEVLMPLR

SLQYLRLNDNPWVCDCRARPLWAWLQKFRGSSSEVPCNLPQRLADRDLKR

LAASDLEGCAVASGPFRPIQTSQLTDEELLSLPKCCQPDAADKASVLEPG

RPASAGNALKGRVPPGDTPPGNGSGPRHINDSPFGTLPSSAEPPLTALRP

GGSEPPGLPTTGPRRRPGCSRKNRTRSHCRLGQAGSGASGTGDAEGSGAL

PALACSLAPLGLALVLWTVLGPC
```

Antibodies

The present invention further relates to an antibody or an antigen-binding fragment thereof that specifically binds a Nogo receptor-1 polypeptide of the invention. In some embodiments the antibody or antigen-binding fragment binds a polypeptide consisting essentially of an amino acid sequence selected from the group consisting of SEQ ID NOs: 1-5, 26-27, 29-37 and 41-45. The antibody or antigen-binding fragment of the present invention may be produced in vivo or in vitro. Production of the antibody or antigen-binding fragment is discussed below.

An antibody or an antigen-binding fragment thereof of the invention inhibits the binding of Nogo receptor-1 to a ligand (e.g., NogoA, NogoB, NogoC, MAG, OM-gp) and decreases myelin-mediated inhibition of neurite outgrowth and sprouting, particularly axonal growth, and attenuates myelin mediated growth cone collapse.

In some embodiments, the anti-Nogo receptor-1 antibody or antigen-binding fragment thereof is murine. In some embodiments, the Nogo receptor-1 is from rat. In other embodiments, the Nogo receptor-1 is human. In some embodiments the anti-Nogo receptor-1 antibody or antigen-binding fragment thereof is recombinant, engineered, humanized and/or chimeric.

In some embodiments, the antibody is selected from the group consisting of monoclonal 7E11 (ATCC® accession No. PTA-4587); monoclonal 1H2 (ATCC® accession No. PTA-4584); monoclonal 2F7 (ATCC® accession No. PTA-4585); monoclonal 3G5 (ATCC® accession No. PTA-4586); and monoclonal 5B10 (ATCC® accession No. PTA-4588). In some embodiments, the antibody is polyclonal antibody 46.

Exemplary antigen-binding fragments are, Fab, Fab', $F(ab')_2$. Fv, Fd, dAb, and fragments containing complementarity determining region (CDR) fragments, single-chain antibodies (scFv), chimeric antibodies, diabodies and polypeptides that contain at least a portion of an immunoglobulin that is sufficient to confer specific antigen-binding to the polypeptide (e.g., immunoadhesins).

As used herein, Fd means a fragment that consists of the $V_H$ and $C_{H1}$ domains; Fv means a fragment that consists of the $V_L$ and Vu domains of a single arm of an antibody; and dAb means a fragment that consists of a $V_H$ domain (Ward et al., *Nature* 341:544-546 (1989)). As used herein, single-chain antibody (scFv) means an antibody in which a $V_L$ region and a $V_H$ region are paired to form a monovalent molecules via a synthetic linker that enables them to be made as a single protein chain (Bird et al., *Science* 242:423-426 (1988) and Huston et al., *Proc. Natl. Acad. Sci. USA* 85:5879-5883 (1988)). As used herein, diabody means a bispecific antibody in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al., *Proc. Natl. Acad. Sci. USA* 90:6444-6448 (1993) and Poljak, R. J., et al., *Structure* 2:1121-1123 (1994)). As used herein, immunoadhesin that specifically binds an antigen of interest, means a molecule in which one or more CDRs may be incorporated, either covalently or noncovalently.

In some embodiments, the invention provides a subunit polypeptide of a Nogo receptor-1 antibody of the invention, wherein the subunit polypeptide is selected from the group consisting of: (a) a heavy chain or a variable region thereof and (b) a light chain or a variable region thereof.

In some embodiments, the invention provides a nucleic acid encoding the heavy chain or the variable region thereof, or the light chain and the variable region thereof of a subunit polypeptide of a Nogo receptor-1 antibody of the invention.

In some embodiments, the invention provides a hypervariable region (CDR) of a Nogo receptor-1 antibody of the invention or a nucleic acid encoding a CDR.

Immunization

Antibodies of the invention can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies may be polyclonal or monoclonal.

In some embodiments, the host is immunized with an immunogenic Nogo receptor-1 polypeptide of the invention. In other embodiments, the host is immunized with Nogo receptor-1 associated with the cell membrane of an intact or disrupted cell and antibodies of the invention are identified by binding to a Nogo receptor-1 polypeptide of the invention.

In some embodiments, the Nogo receptor-1 antigen is administered with an adjuvant to stimulate the immune response. Adjuvants often need to be administered in addition to antigen in order to elicit an immune response to the antigen. These adjuvants are usually insoluble or undegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see e.g., Harlow and Lane, *Antibodies, A Laboratory Manual* (1988); Yelton, D. E. et al., *Ann. Rev. of Biochem.* 50:657-80. (1981); and Ausubel et al., *Current Protocols in Molecular Biology* (New York: John Wiley & Sons) (1989). Determination of immunoreactivity with an immunogenic Nogo receptor-1 polypeptide of the invention may be made by any of several methods well known in the art, including, e.g., immunoblot assay and ELISA.

Production of Antibodies and Antibody Producing Cell Lines

Monoclonal antibodies of the invention can made by standard procedures as described, e.g., in Harlow and Lane, *Antibodies, A Laboratory Manual* (1988), supra.

Briefly, at an appropriate period of time the animal is sacrificed and lymph node and/or splenic B-cells are immortalized by any one of several techniques that are well-known in the art, including but not limited to transformation, such as with EBV or fusion with an immortalized cell line, such as myeloma cells. Thereafter, the cells are clonally separated and the supernatants of each clone tested for production of an antibody specific for an immunogenic Nogo receptor-1 polypeptide of the invention. Methods of selecting, cloning and expanding hybridomas are well known in the art. Similarly, methods for identifying the nucleotide and amino acid sequence of the immunoglobulin genes are known in the art.

Other suitable techniques for producing an antibody of the invention involve in vitro exposure of lymphocytes to the Nogo receptor-1 or to an immunogenic polypeptide of the invention, or alternatively, selection of libraries of antibodies in phage or similar vectors. See Huse et al., *Science,* 246:1275-81 (1989). Antibodies useful in the present invention may be employed with or without modification.

Antigens (in this case Nogo receptor-1 or an immunogenic polypeptide of the invention) and antibodies can be labeled by joining, either covalently or non-covalently, a substance that provides for a detectable signal. Various labels and conjugation techniques are known in the art and can be employed in practicing the invention. Suitable labels include, but are not limited to, radionucleotides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

In some embodiments of the invention, an antibody has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth (see below for more detailed discussion).

The antibodies of this invention may also be human monoclonal antibodies, for example those produced by immortalized human cells, by SCID-hu mice or other non-human animals capable of producing "human" antibodies.

Phage Display Libraries

Anti-Nogo receptor-1 antibodies of this invention can be isolated by screening a recombinant combinatorial antibody library. Exemplary combinatorial libraries are for binding to an immunogenic Nogo receptor-1 polypeptide of the invention, such as a scFv phage display library, prepared using $V_L$ and $V_H$ cDNAs prepared from mRNA derived an animal immunized with an immunogenic Nogo receptor-1 polypeptide of the invention. Methodologies for preparing and screening such libraries are known in the art. There are commercially available methods and materials for generating phage display libraries (e.g., the Pharmacia Recombinant Phage Antibody System, catalog no. 27-9400-01; the Stratagene SurfZAP™ phage display kit, catalog no. 240612; and others from MorphoSys). There are also other methods and reagents that can be used in generating and screening antibody display libraries (see e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al., *Bio/Technology* 9:1370-1372 (1991); Hay et al., *Hum. Antibod. Hybridomas* 3:81-85; (1992) Huse et al., *Science* 246:1275-1281 (1989); McCafferty et al., *Nature* 348:552-554 (1990); Griffiths et al., *EMBO J.* 12:725-

734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nucl. Acids Res.* 19:4133-4137 (1991); and Barbas et al., *Proc. Natl. Acad. Sci. USA* 88:7978-7982 (1991).

Following screening and isolation of an anti-Nogo receptor-1 antibody of the invention from a recombinant immunoglobulin display library, the nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express an antibody isolated by screening a combinatorial library, DNA encoding the antibody heavy chain and light chain or the variable regions thereof is cloned into a recombinant expression vector and introduced into a mammalian host cell, as described above.

Class Switching

Anti-Nogo receptor-1 antibodies of the invention can be of any isotype. An antibody of any desired isotype can be produced by class switching. For class switching, nucleic acids encoding $V_L$ or $V_H$, that do not include any nucleotide sequences encoding $C_L$ or $C_H$, are isolated using methods well known in the art. The nucleic acids encoding $V_L$ or $V_H$ are then operatively linked to a nucleotide sequence encoding a $C_L$ or $C_H$ from a desired class of immunoglobulin molecule. This may be achieved using a vector or nucleic acid that comprises a $C_L$ or $C_H$ chain, as described above. For example, an anti-Nogo receptor-1 antibody of the invention that was originally IgM may be class switched to an IgG. Further, the class switching may be used to convert one IgG subclass to another, e.g., from IgG1 to IgG2.

Mutated Antibodies

In other embodiments, antibodies or antigen-binding fragments of the invention may be mutated in the variable domains of the heavy and/or light chains to alter a binding property of the antibody. For example, a mutation may be made in one or more of the CDR regions to increase or decrease the $K_d$ of the antibody for Nogo receptor-1, to increase or decrease $K_{off}$, or to alter the binding specificity of the antibody. Techniques in site-directed mutagenesis are well known in the art. See e.g., Sambrook et al., *Molecular Cloning—A Laboratory Manual*, Cold Spring Harbor Laboratory Press (1989) and Ausubel et al., *Current Protocols in Molecular Biology* (New York John Wiley & Sons) (1989). In a preferred embodiment, mutations are made at an amino acid residue that is known to be changed compared to germline in a variable region of an anti-Nogo receptor-1 antibody of the invention. In some embodiments, mutations are made at one or more amino acid residues that are known to be changed compared to the germline in a variable region of an anti-Nogo receptor-1 antibody of the invention. In another embodiment, a nucleic acid encoding an antibody heavy chain or light chain variable region is mutated in one or more of the framework regions. A mutation may be made in a framework region or constant domain to increase the half-life. A mutation in a framework region or constant domain also may be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

Fusion Antibodies and Immunoadhesins

In another embodiment, a fusion antibody or immunoadhesin may be made which comprises all or a portion of an anti-Nogo receptor-1 antibody of the invention linked to another polypeptide. In some embodiments, only the variable region of the anti-Nogo receptor-1 antibody is linked to the polypeptide. In other embodiments, the Vu domain of an anti-Nogo receptor-1 antibody of this invention is linked to a first polypeptide, while the $V_L$ domain of the antibody is linked to a second polypeptide that associates with the first polypeptide in a manner that permits the $V_H$ and $V_L$ domains to interact with one another to form an antibody binding site. In other embodiments, the $V_H$ domain is separated from the $V_L$ domain by a linker that permits the $V_H$ and $V_L$ domains to interact with one another (see below under Single Chain Antibodies). The $V_H$-linker-$V_L$ antibody is then linked to a polypeptide of interest. The fusion antibody is useful to directing a polypeptide to a cell or tissue that expresses a Nogo receptor-1 ligand. The polypeptide of interest may be a therapeutic agent, such as a toxin, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

Single Chain Antibodies

The present invention includes a single chain antibody (scFv) that binds a Nogo receptor-1 polypeptide of the invention. To produce the ScFv, $V_H$- and $V_L$-encoding DNA is operatively linked to DNA encoding a flexible linker, e.g., encoding the amino acid sequence $(Gly_4\text{-}Ser)_3$ (SEQ ID NO: 10), such that the $V_H$ and $V_L$ sequences can be expressed as a contiguous single-chain protein, with the $V_L$ and $V_H$ regions joined by the flexible linker (see e.g., Bird et al., *Science* 242:423-426 (1988); Huston et al., *Proc. Natl. Acad. Sci. USA* 85:5879-5883 (1988); McCafferty et al., *Nature* 348:552-554 (1990)). The single chain antibody may be monovalent, if only a single $V_H$ and $V_L$ are used, bivalent, if two $V_H$ and $V_L$ are used, or polyvalent, if more than two $V_H$ and VL are used.

Chimeric Antibodies

The present invention further included a bispecific antibody or antigen-binding fragment thereof in which one specificity is for a Nogo receptor-1 polypeptide of the invention. In one embodiment, a chimeric antibody can be generated that specifically binds to a Nogo receptor-1 polypeptide of the invention through one binding domain and to a second molecule through a second binding domain. The chimeric antibody can be produced through recombinant molecular biological techniques, or may be physically conjugated together. In addition, a single chain antibody containing more than one $V_H$ and $V_L$ may be generated that binds specifically to a polypeptide of the invention and to another molecule that is associated with attenuating myelin mediated growth cone collapse and inhibition of neurite outgrowth and sprouting. Such bispecific antibodies can be generated using techniques that are well known for example, Fanger et al., *Immunol Methods* 4: 72-81 (1994) and Wright and Harris, supra and in connection with (iii) see e.g., Traunecker et al. *Int. J. Cancer* (Suppl.) 7: 51-52 (1992).

In some embodiments, the chimeric antibodies are prepared using one or more of the variable regions from an antibody of the invention. In another embodiment, the chimeric antibody is prepared using one or more CDR regions from said antibody.

Derivatized and Labeled Antibodies

An antibody or an antigen-binding fragment of the invention can be derivatized or linked to another molecule (e.g., another peptide or protein). In general, the antibody or antigen-binding fragment is derivatized such that binding to a polypeptide of the invention is not affected adversely by the derivatization or labeling. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antigen-binding fragment with another molecule (such as a streptavidin core region or a polyhistidine tag).

In some embodiments, a derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

In some embodiments, the derivatized antibody is a labeled antibody. Exemplary, detection agents with which an antibody or antibody portion of the invention may be derivatized are fluorescent compounds, including fluorescein, fluorescein isothiocyanate, rhodamine, 5-dimethylamine-1-naphthalenesulfonyl chloride, phycoerythrin, lanthanide phosphors and the like. An antibody also may be labeled with enzymes that are useful for detection, such as horseradish peroxidase, β-galactosidase, luciferase, alkaline phosphatase, glucose oxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitopes recognized by a secondary reporter (e.g., leucine zipper pair sequences, binding sites for secondary antibodies, metal binding domains, epitope tags).

An anti-Nogo receptor-1 antibody or an antigen-fragment thereof also may be labeled with a radio-labeled amino acid. The radiolabel may be used for both diagnostic and therapeutic purposes. The radio-labeled anti-Nogo receptor-1 antibody may be used diagnostically, for example, for determining Nogo receptor-1 levels in a subject. Further, the radio-labeled anti-Nogo receptor-1 antibody may be used therapeutically for treating spinal cord injury. Examples of labels for polypeptides include, but are not limited to, the following radioisotopes or radionucleotides—$^{3}H$, $^{14}C$, $^{15}N$, $^{35}S$, $^{90}Y$, $^{99}Tc$, $^{111}I$, $^{125}I$, $^{131}I$.

An anti-Nogo receptor-1 antibody or an antigen-fragment thereof may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Characterization of Anti-Nogo Receptor-1 Antibodies

Class and Subclass of Anti-Nogo Receptor-1 Antibodies

The class and subclass of anti-Nogo receptor-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

Binding Affinity of Anti-Nogo Receptor-1 Antibody to Nogo Receptor-1

The binding affinity and dissociation rate of an anti-Nogo receptor-1 antibody of the invention to a Nogo receptor-1 polypeptide of the invention may be determined by any method known in the art. For example, the binding affinity can be measured by competitive ELISAs, RIAs, BIAcore or KinExA technology. The dissociation rate also can be measured by BIAcore or KinExA technology. The binding affinity and dissociation rate are measured by surface plasmon resonance using, e.g., a BIAcore. The $K_d$ of 7E11 and 1H2 were determined to be $1\times10^{-7}$ M and $2\times10^{-8}$ M, respectively.

Inhibition of Nogo Receptor-1 Activity by Anti-Nogo Receptor-1 Antibody

In some embodiments, an anti-Nogo receptor-1 antibody or an antigen-binding fragment of the invention thereof inhibits the binding of Nogo receptor-1 to a ligand. The $IC_{50}$ of such inhibition can be measured by any method known in the art, e.g., by ELISA, RIA, or Functional Antagonism. In some embodiments, the $IC_{50}$ is between 0.1 and 500 nM. In some embodiments, the $IC_{50}$ is between 10 and 400 nM. In yet other embodiments, the antibody or portion thereof has an $IC_{50}$ of between 60 nM and 400 nM. The $IC_{50}$ of 7E11 and 1H2 were determined to be 400 nM and 60 nM, respectively, in a binding assay. See also Table 3, infra.

In some embodiments, the present invention also include NgR1-specific antibodies or antigen-binding fragments, variants, or derivatives which are antagonists of NgR1 activity. For example, the binding of certain NgR1 antibodies to NgR1 blocks NgR1-mediated inhibition of neuronal survival, neurite outgrowth or axonal regeneration of central nervous system (CNS) neurons.

In other embodiments, the present invention includes an antibody, or antigen-binding fragment, variant, or derivative thereof which specifically or preferentially binds to at least one epitope of NgR1, where the epitope comprises, consists essentially of or consists of at least about four to five amino acids of SEQ ID NO:49, at least seven, at least nine, or between at least about 15 to about 30 amino acids of SEQ ID NO:49. The amino acids of a given epitope of SEQ ID NO:49 as described may be, but need not be contiguous or linear. In certain embodiments, the at least one epitope of NgR1 comprises, consists essentially of, or consists of a non-linear epitope formed by the extracellular domain of NgR1 as expressed on the surface of a cell or as a soluble fragment, e.g., fused to an IgG Fc region. Thus, in certain embodiments the at least one epitope of NgR1 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:49, where non-contiguous amino acids form an epitope through protein folding.

In other embodiments, the present invention includes an antibody, or antigen-binding fragment, variant, or derivative thereof which specifically or preferentially binds to at least one epitope of NgR1, where the epitope comprises, consists essentially of, or consists of, in addition to one, two, three, four, five, six or more contiguous or non-contiguous amino acids of SEQ ID NO:49 as described above, and an additional moiety which modifies the protein, e.g., a carbohydrate moiety may be included such that the NgR1 antibody binds with higher affinity to modified target protein than it does to an unmodified version of the protein. Alternatively, the NgR1 antibody does not bind the unmodified version of the target protein at all.

In certain embodiments, an antibody, or antigen-binding fragment, variant, or derivative thereof of the invention binds specifically to at least one epitope of NgR1 or fragment or variant described above, i.e., binds to such an epitope more readily than it would bind to an unrelated, or random epitope; binds preferentially to at least one epitope of NgR1 or fragment or variant described above, i.e., binds to such an epitope more readily than it would bind to a related, similar, homologous, or analogous epitope; competitively inhibits binding of a reference antibody which itself binds specifically or preferentially to a certain epitope of NgR1 or fragment or variant described above; or binds to at least one epitope of NgR1 or fragment or variant described above with an affinity characterized by a dissociation constant KD of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human NgR1 polypeptide or fragment thereof, relative to a murine NgR1 polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds NgR1 polypeptides or fragments or variants thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. Alternatively, an antibody, or antigen-binding fragment, variant, or derivative thereof of the invention binds NgR1 polypeptides or fragments or variants thereof with an off rate (k(off)) of less than or equal to $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$ or $10^{-7}$ $sec^{-1}$.

In other embodiments, an antibody, or antigen-binding fragment, variant, or derivative thereof of the invention binds NgR1 polypeptides or fragments or variants thereof with an on rate (k(on)) of greater than or equal to $10^{3}$ $M^{-1}$ $sec^{-1}$, $5\times10^{3}$ $M^{-1}$ $sec^{-1}$, $10^{4}M^{-1}$ $sec^{-1}$ or $5\times10^{4}$ $M^{-1}$ $sec^{-1}$. Alternatively, an antibody, or antigen-binding fragment, variant, or derivative thereof of the invention binds NgR1 polypeptides or fragments or variants thereof with an on rate (k(on)) greater than or equal to $10^{5}$ $M^{-1}$ $sec^{-1}$, $5\times10^{5}$ $M^{-1}$ $sec^{-1}$, $10^{6}$ $M^{-1}$ $sec^{-1}$, or $5\times10^{6}$ $M^{-1}$ $sec^{-1}$ or $10^{7}$ $M^{-1}$ $sec^{-1}$.

In one embodiment, a NgR1 antagonist for use in the methods of the invention is an antibody molecule, or immunospecific fragment thereof. Unless it is specifically noted, as used herein a "fragment thereof" in reference to an antibody refers to an immunospecific fragment, i.e., an antigen-specific fragment. In one embodiment, an antibody of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on NgR1. A bispecific antibody may be a tetravalent antibody that has two target binding domains specific for an epitope of NgR1 and two target binding domains specific for a second target. Thus, a tetravalent bispecific antibody may be bivalent for each specificity.

In certain embodiments of the present invention comprise administration of an NgR1 antagonist antibody, or immunospecific fragment thereof in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain NgR1 antagonist antibodies or immunospecific fragments thereof for use in the therapeutic methods described herein, the Fc portion may be mutated to alter, e.g., increase, decrease or modulate effector function using techniques known in the art. For example, the deletion or inactivation (through point mutations or other means) of a constant region domain may reduce or alter Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

In certain embodiments both the variable and constant regions of NgR1 antagonist antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human anti bodies can likewise be produced by various display technologies, e.g., phage display or other viral display systems, as described in more detail elsewhere herein.

NgR1 antagonist antibodies or immunospecific fragments thereof for use in the diagnostic and treatment methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

NgR1 antagonist antibodies or immunospecific fragments thereof for use in the treatment methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In preferred embodiments, an NgR1 antagonist antibody or immunospecific fragment thereof for use in the treatment methods disclosed herein will not elicit a deleterious immune response in the animal to be treated, e.g., in a human. In one embodiment, NgR1 antagonist antibodies or immunospecific fragments thereof for use in the treatment methods disclosed herein may be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each. V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and those sequences are subsequently incorporated into a range of binding polypeptides, e.g., NgR1 antagonist antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

NgR1 antagonist antibodies or fragments thereof for use in the methods of the present invention may be generated by any suitable method known in the art. Polyclonal antibodies can be produced by various procedures well known in the art. For example, a NgR1 immunospecific fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified NgR1 antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Those skilled in the art will also appreciate that DNA encoding antibodies or antibody fragments (e.g., antigen binding sites) may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding VH and VL regions are amplified from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH or VL regions are usually recombinantly fused to either the phage gene III or gene VIII. Phage expressing an antigen binding domain that binds to an antigen of interest (i.e., a NgR1 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgB antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., NgR1. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

NgR1 antagonist antibodies may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibodies for use in the therapeutic methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Recombinant expression of an antibody, or fragment, derivative or analog thereof, e.g., a heavy or light chain of an antibody which is an NgR1 antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa calfornica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or B3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hsprt- or aprt-cells, respectively. Also, antimetabolite resistance can be used as the basis of selection for the following genes: dhfr, which confers resistance to methotrexate (Wigler et al., *Proc. Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260: 926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody.

In certain embodiments, modified antibodies for use in the methods disclosed herein are minibodies. Minibodies can be made using methods described in the art (see, e.g., U.S. Pat. No. 5,837,821 or WO 94/09817A1).

In another embodiment, modified antibodies for use in the methods disclosed herein are CH2 domain deleted antibodies which are known in the art. Domain deleted constructs can be derived using a vector (e.g., from Biogen IDEC Incorporated) encoding an IgG1 human constant domain (see, e.g., WO 02/060955A2 and WO 02/096948A2). This exemplary vector was engineered to delete the CH2 domain and provide a synthetic vector expressing a domain deleted IgG1 constant region.

In one embodiment, a NgR1 antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides the use of antibodies that comprise, consist essentially of, or consist of, variants (including derivatives) of antibody molecules (e.g., the VH regions and/or VL regions) described herein, which antibodies or fragments thereof immunospecifically bind to a NgR1 polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Compositions comprising, and uses of, the antibodies of the present invention are described below.

Soluble Nogo Receptor-1 Polypeptides

Protein

Full-length Nogo receptor-1 consists of a signal sequence, a N-terminus region (NT), eight leucine rich repeats (LRR), a LRRCT region (a leucine rich repeat domain C-terminal of the eight leucine rich repeats), a C-terminus region (CT) and a GPI anchor (see FIG. 1).

The NgR domain designations used herein are defined as follows:

TABLE 1

| Example NgR domains | | | |
|---|---|---|---|
| Domain | hNgR (SEQ ID: 49) | rNgR (SEQ ID NO: 50) | mNgR (SEQ ID NO: 51) |
| Signal Seq. | 1-26 | 1-26 | 1-26 |
| LRRNT | 27-56 | 27-56 | 27-56 |
| LRR1 | 57-81 | 57-81 | 57-81 |
| LRR2 | 82-105 | 82-105 | 82-105 |
| LRR3 | 106-130 | 106-130 | 106-130 |
| LRR4 | 131-154 | 131-154 | 131-154 |
| LRR5 | 155-178 | 155-178 | 155-178 |
| LRR6 | 179-202 | 179-202 | 179-202 |
| LRR7 | 203-226 | 203-226 | 203-226 |
| LRR8 | 227-250 | 227-250 | 227-250 |
| LRRCT | 260-309 | 260-309 | 260-309 |
| CTS (CT Signaling) | 310-445 | 310-445 | 310-445 |
| GPI | 446-473 | 446-473 | 446-473 |

Some embodiments of the invention provide a soluble Nogo receptor-1 polypeptide. Soluble Nogo receptor-1 polypeptides of the invention comprise an NT domain; 8 LRRs and an LRRCT domain and lack a signal sequence and a functional GPI anchor (i.e., no GPT anchor or a GPI anchor that lacks the ability to efficiently associate to a cell membrane).

In some embodiments, a soluble Nogo receptor-1 polypeptide comprises a heterologous LRR. In some embodiments a soluble Nogo receptor-1 polypeptide comprises 2, 3, 4, 5, 6, 7, or 8 heterologous LRRs. A heterologous LRR means an LRR obtained from a protein other than Nogo receptor-1. Exemplary proteins from which a heterologous LRR can be obtained are toll-like receptor (TLR1.2); T-cell activation leucine repeat rich protein; deceorin; OM-gp; insulin-like growth factor binding protein acidic labile subunit slit and robo; and toll-like receptor 4.

In some embodiments, the invention provides a soluble Nogo receptor-1 polypeptide of 319 amino acids (soluble Nogo receptor-1 344, sNogoR1-344, or sNogoR344) (residues 26-344 of SEQ ID NOs: 6 and 8 or residues 27-344 of SEQ ID NO: 8). In some embodiments, the invention provides a soluble Nogo receptor-1 polypeptide of 285 amino acids (soluble Nogo receptor-1 310, sNogoR1-310, or sNogoR310) (residues 26-310 of SEQ ID NOs: 7 and 9 or residues 27-310 of SEQ ID NO: 9). See FIG. 1.

TABLE 1

| Sequences of Human and Rat Nogo receptor-1 Polypeptides | |
|---|---|
| SEQ ID NO: 6 (human 1-344) | MKRASAGGSRLLAWVLWLQAWQVAAPCPGACVCYNEPKVTTS<br>CPQQGLQAVPVGIPAASQRIFLHGNRISHVPAASFRACRNLTIL<br>WLHSNVLARIDAAAFTGLALLEQLDLSDNAQLRSVDPATFHGLGR<br>LHTLHLDRCGLQELGPGLFRGLAALQYLYLQDNALQALPDDTFRD<br>LGNLTHLFLHGNRISSVPERAFRGLHSLDRLLLHQNRVAHVHPHA<br>FRDLGRLMTLYLFANNLSALPTEALAPLRALQYLRLNDNPWVCDC |

TABLE 1-continued

| Sequences of Human and Rat Nogo receptor-1 Polypeptides | |
|---|---|
| | RARPLWAWLQKFRGSSSEVPCSLPQRLAGRDLKRLAANDLQGCA<br>VATGPYHPIWTGRATDEEPLGLPKCCQPDAADKA |
| SEQ ID NO: 7<br>(human 1-310) | MKRASAGGSRLLAWVLWLQAWQVAAPCPGACVCYNEPKVTTS<br>CPQQGLQAVPVGIPAASQRIFLHGNRISHVPAASFRACRNLTIL<br>WLHSNVLARIDAAAFTGLALLEQLDLSDNAQLRSVDPATFHGLGR<br>LHTLHLDRCGLQELGPGLFRGLAALQYLYLQDNALQALPDDTFRD<br>LGNLTHLFLHGNRISSVPERAFRGLHSLDRLLLHQNRVAHVHPHA<br>FRDLGRLMTLYLFANNLSALPTEALAPLRALQYLRLNDNPWVCDC<br>RARPLWAWLQKFRGSSSEVPCSLPQRLAGRDLKRLAANDLQGCA |
| SEQ ID NO: 8<br>(rat 1-344) | MKRASSGGSRLPTWVLWLQAWRVATPCPGACVCYNEPKVTTSR<br>PQQGLQAVPAGIPASSQRIFLHGNRISYVPAASFQSCRNLTILW<br>LHSNALAGIDAAAFTGLTLLEQLDLSDNAQLRVVDPTTFRGLGHL<br>HTLHLDRCGLQELGPGLFRGLAALQYLYLQDNNLQALPDNTFRDL<br>GNLTHLFLHGNRIPSVPEHAFRGLHSLDRLLLHQNHVARVHPHAF<br>RDLGRLMTLYLFANNLSMLPAEVLVPLRSLQYLRLNDNPWVCDCR<br>ARPLWAWLQKFRGSSSGVPSNLPQRLAGRDLKRLATSDLEGCAV<br>ASGPFRPFQTNQLTDEELLGLPKCCQPDAADKA |
| SEQ ID NO: 9<br>(rat 1-310) | MKRASSGGSRLPTWVLWLQAWRVATPCPGACVCYNEPKVTTSR<br>PQQGLQAVPAGIPASSQRIFLHGNRISYVPAASFQSCRNLTILW<br>LHSNALAGIDAAAFTGLTLLEQLDLSDNAQLRVVDPTTFRGLGHL<br>HTLHLDRCGLQELGPGLFRGLAALQYLYLQDNNLQALPDNTFRDL<br>GNLTHLFLHGNRIPSVPEHAFRGLHSLDRLLLHQNHVARVHPHAF<br>RDLGRLMTLYLFANNLSMLPAEVLVPLRSLQYLRLNDNPWVCDCR<br>ARPLWAWLQKFRGSSSGVPSNLPQRLAGRDLKRLATSDLEGCA |
| SEQ ID NO: 58<br>(human 1-310<br>with ala<br>substitutions<br>at amino<br>acid<br>positions<br>266 and 309) | MKRASAGGSRLLAWVLWLQAWQVAAPCPGACVCYNEPKVTTS<br>CPQQGLQAVPVGIPAASQRIFLHGNRISHVPAASFRACRNLTIL<br>WLHSNVLARIDAAAFTGLALLEQLDLSDNAQLRSVDPATFHGLGR<br>LHTLHLDRCGLQELGPGLFRGLAALQYLYLQDNALQALPDDTFRD<br>LGNLTHLFLHGNRISSVPERAFRGLHSLDRLLLHQNRVAHVHPHA<br>FRDLGRLMTLYLFANNLSALPTEALAPLRALQYLRLNDNPWVCDA<br>RARPLWAWLQKFRGSSSEVPCSLPQRLAGRDLKRLAANDLQGAA |
| SEQ ID NO: 59<br>(rat 1-310<br>with ala<br>substitutions<br>at amino<br>acid<br>positions<br>266 and 309) | MKRASSGGSRLPTWVLWLQAWRVATPCPGACVCYNEPKVTTSR<br>PQQGLQAVPAGIPASSQRIFLHGNRISYVPAASFQSCRNLTILW<br>LHSNALAGIDAAAFTGLTLLEQLDLSDNAQLRVVDPTTFRGLGHL<br>HTLHLDRCGLQELGPGLFRGLAALQYLYLQDNNLQALPDNTFRDL<br>GNLTHLFLHGNRIPSVPEHAFRGLHSLDRLLLHQNHVARVHPHAF<br>RDLGRLMTLYLFANNLSMLPAEVLVPLRSLQYLRLNDNPWVCDAR<br>ARPLWAWLQKFRGSSSGVPSNLPQRLAGRDLKRLATSDLEGAA |
| SEQ ID NO: 64<br>(human 1-344<br>with ala<br>substitutions<br>at amino<br>acid<br>positions<br>266 and 309) | MKRASAGGSRLLAWVLWLQAWQVAAPCPGACVCYNEPKVTTS<br>CPQQGLQAVPVGIPAASQRIFLHGNRISHVPAASFRACRNLTIL<br>WLHSNLARIDAAAFTGLALLEQLDLSDNAQLRSVDPATFHGLGR<br>LHTLHLDRCGLQELGPGLFRGLAALQYLYLQDNALQALPDDTFR<br>DLGNLTHLFLHGNRISSVPERAFRGLHSLDRLLLHQNRVAHVHPH<br>AFRDLGRLMTLYLFANNLSALPTEALAPLRALQYLRLNDNPWVC<br>DARARPLWAWLQKFRGSSSEVPCSLPQRLAGRDLKRLAANDLQG<br>AAVATGPYHPIWTGRATDEEPLGLPKCCQPDAADKA |

In some embodiments of the invention, the soluble Nogo receptor-1 polypeptides of the invention are used to inhibit the binding of a ligand to Nogo receptor-1 and act as an antagonist of Nogo receptor-1 ligands. In some embodiments of the invention, the soluble Nogo receptor-1 polypeptides of the invention are used to decrease inhibition of neurite outgrowth and sprouting in a neuron, such as axonal growth and to inhibit myelin mediated growth cone collapse in a neuron. In some embodiments, the neuron is a CNS neuron.

sNogoR310 and sNogoR344, surprisingly, block the binding of NogoA, NogoB, NogoC, MAG and OM-gp to Nogo receptor-1.

In another embodiment, the present invention provides an isolated polypeptide fragment of 60 residues or less, comprising an amino acid sequence identical to a reference amino acid sequence, except for up to one, two, three, four, ten, or twenty individual amino acid substitutions, wherein said reference amino acid sequence is selected from the group consisting of: (a) amino acids x to 344 of SEQ ID NO:49, (b) amino acids 309 to y of SEQ ID NO:49, and (c) amino acids x to y of SEQ ID NO:49, wherein x is any integer from 305 to 326, and y is any integer from 328 to 350; and wherein said polypeptide fragment inhibits Nogo-receptor-mediated neurite outgrowth inhibition. In some embodiments, the invention provides an isolated polypeptide fragment of 60 residues or less, comprising an amino acid sequence identical to a reference amino acid sequence, except for up to one, two, three, four, ten or twenty individual amino acid substitutions, wherein said reference amino acid sequence is selected from the group consisting of: (a) amino acids x' to 344 of SEQ ID NO:49, (b) amino acids 309 to y' of SEQ ID NO:49, and (c) amino acids x' to y' of SEQ ID NO:49, where x' is any integer from 300 to 326, and y' is any integer from 328 to 360, and wherein said polypeptide fragment inhibits Nogo-receptor-mediated neurite outgrowth inhibition.

By "an NgR1 reference amino acid sequence," or "reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

In some embodiments, the invention provides an isolated polypeptide fragment of 60 residues or less, comprising an amino acid sequence identical to a reference amino acid sequence, except for up to one, two, or three individual amino acid substitutions, wherein said reference amino acid sequence is selected from the group consisting of: amino acids 309 to 335 of SEQ ID NO:49; amino acids 309 to 344 of SEQ ID NO:49; amino acids 310 to 335 of SEQ ID NO:49; amino acids 310 to 344 of SEQ ID NO:49; amino acids 309 to 350 of SEQ ID NO:49; amino acids 300 to 344 of SEQ ID NO:49; and amino acids 315 to 344 of SEQ ID NO:49.

In one embodiment, the invention provides an isolated polypeptide fragment of 60 residues or less, comprising an amino acid sequence identical to a reference amino acid sequence, except for up to three individual amino acid substitutions, wherein said reference amino acid sequence is amino acids 309 to 344 of SEQ ID NO:49.

In one embodiment, the invention provides an isolated polypeptide fragment of 60 residues or less, comprising an amino acid sequence identical to a reference amino acid sequence, except for up to three individual amino acid substitutions, wherein said reference amino acid sequence is amino acids 309 to 335 of SEQ ID NO:49.

In one embodiment, the invention provides an isolated polypeptide comprising: (a) an amino acid sequence identical to a reference amino acid sequence except that at least one cysteine residue of said reference amino acid sequence is substituted with a different amino acid, wherein said reference amino acid sequence is selected from the group consisting of: (i) amino acids a to 445 of SEQ ID NO:49, (ii) amino acids 27 to b of SEQ ID NO:49, and (i) amino acids a to b of SEQ ID NO:49, wherein a is any integer from 25 to 35, and b is any integer from 300 to 450; and (b) a heterologous polypeptide; wherein said polypeptide inhibits nogo-receptor-mediated neurite outgrowth inhibition.

Exemplary amino acid substitutions for polypeptide fragments according to this embodiment include substitutions of individual cysteine residues in the polypeptides of the invention with different amino acids. Any different amino acid may be substituted for a cysteine in the polypeptides of the invention. Which different amino acid is used depends on a number of criteria, for example, the effect of the substitution on the conformation of the polypeptide fragment, the charge of the polypeptide fragment, or the hydrophilicity of the polypeptide fragment. Amino acid substitutions for the amino acids of the polypeptides of the invention and the reference amino acid sequence can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Typical amino acids to substitute for cysteines in the reference amino acid include alanine, serine, threonine, in particular, alanine. Making such substitutions through engineering of a polynucleotide encoding the polypeptide fragment is well within the routine expertise of one of ordinary skill in the art.

In another embodiment, the present invention provides an isolated polypeptide of the invention wherein at least one cysteine residue is substituted with a different amino acid. Cysteine residues that can substituted in human NgR1 include C27, C31, C33, C43, C80, C140, C264, C266, C287, C309, C335, C336, C419, C429, C455 and C473. Cysteine residues that can substituted in rat NgR1 include C27, C31, C33, C80, C140, C264, C266, C287, C309, C335, C336, C419, C429, C455 and C473. Cysteine residues that can substituted in mouse NgR1 include C27, C31, C33, C43, C80, C140, C264, C266, C287, C309, C335, C336, C419, C429, C455 and C473.

The present invention further provides an isolated polypeptide fragment of 40 residues or less, where the polypeptide fragment comprises an amino acid sequence identical to amino acids 309 to 344 of SEQ ID NO:49, except that: C309 is substituted, C335 is substituted, C336 is substituted, C309 and C335 are substituted, C309 and C336 are substituted, C335 and C336 are substituted, or C309, C335, and C336 are substituted.

The cysteine residues in the polypeptides of the invention may be substituted with any heterologous amino acid. In certain embodiments, the cysteine is substituted with a small uncharged amino acid which is least likely to alter the three dimensional conformation of the polypeptide, e.g., alanine, serine, threonine, preferably alanine.

In some embodiments, the soluble Nogo receptor-1 polypeptide of the invention is a component of a fusion protein that further comprises a heterologous polypeptide. In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments the Fc is joined to the C-terminal end of the soluble Nogo receptor-1 polypeptide of the invention. In some embodiments the fusion Nogo receptor-1 protein is a dimer. The invention further encompasses variants, analogs, or derivatives of polypeptide fragments as described above.

In some embodiments, the invention provides an isolated polypeptide comprising: (a) an amino acid sequence identical to a reference amino acid sequence, except for up to twenty individual amino acid substitutions, wherein said reference amino acid sequence is selected from the group consisting of (i) amino acids a to 445 of SEQ ID NO:49, (ii) amino acids 27 to b of SEQ ID NO:49, and (iii) amino acids a to b of SEQ ID NO:49, wherein a is any integer from 1 to 35, and b is any integer from 300 to 450, and (b) a heterologous polypeptide; wherein said polypeptide inhibits nogo-receptor-mediated neurite outgrowth inhibition. In some embodiments, the isolated polypeptide is amino acids 1 to 310 of SEQ ID NO:49, wherein R269 and A310 are substituted with a different amino acid. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In one embodiment, the different amino acid is tryptophan.

An exemplary soluble NgR-Fc fusion protein is human NgR1(319)-Fc which comprises Fc joined to the C-terminal end of amino acids 1 to 319 of SEQ ID NO:49.

Exemplary soluble NgR-Fc fusion proteins with cysteine substitutions are Ala-Ala-human(h)NgR1(310)-Fc which comprises Fc joined to the C-terminal end of a soluble polypeptide with the amino acid sequence of SEQ ID NO:58, Ala-Ala-rat(r)NgR1(310)-Fc which comprises Fc joined to the C-terminal end of a soluble polypeptide with the amino acid sequence of SEQ ID NO:59 and Ala-Ala-human(h) NgR1(344)-Fc which comprises Fc joined to the C-terminal end of a soluble polypeptide with the amino acid sequence of SEQ ID NO:64.

In the present invention, a polypeptide can be composed of amino acids joined to each other by peptide bonds or modified peptide bonds, i.e., peptide isosteres, and may contain amino acids other than the 20 gene-encoded amino acids (e.g., non-naturally occurring amino acids). The polypeptides of the present invention may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from natural processes or may be made by synthetic methods. Modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).).

Polypeptides described herein may be cyclic. Cyclization of the polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two α-thio amino acid residues (e.g., cysteine, homocysteine). Certain peptides of the present invention include modifications on the N- and C-terminus of the peptide to form a cyclic polypeptide. Such modifications include, but are not limited, to cysteine residues, acetylated cysteine residues, cysteine residues with a NH2 moiety and biotin. Other methods of peptide cyclization are described in Li & Roller, *Curr. Top. Med. Chem.* 3:325-341 (2002) and U.S Patent Publication No. U.S. 2005-0260626 A1, which are incorporated by reference herein in their entirety.

In methods of the present invention, an NgR1 polypeptide or polypeptide fragment of the invention can be administered directly as a preformed polypeptide, or indirectly through a nucleic acid vector. In some embodiments of the invention, an NgR1 polypeptide or polypeptide fragment of the invention is administered in a treatment method that includes: (1) transforming or transfecting an implantable host cell with a nucleic acid, e.g., a vector, that expresses an NgR1 polypeptide or polypeptide fragment of the invention; and (2) implanting the transformed host cell into a mammal, at the site of a disease, disorder or injury. For example, the transformed host cell can be implanted at the site of a chronic lesion of MS. In some embodiments of the invention, the implantable host cell is removed from a mammal, temporarily cultured, transformed or transfected with an isolated nucleic acid encoding an NgR1 polypeptide or polypeptide fragment of the invention, and implanted back into the same mammal from which it was removed. The cell can be, but is not required to be, removed from the same site at which it is implanted. Such embodiments, sometimes known as ex vivo gene therapy, can provide a continuous supply of the NgR1 polypeptide or polypeptide fragment of the invention, localized at the site of action, for a limited period of time.

Additional exemplary NgR polypeptides of the invention and methods and materials for obtaining these molecules for practicing the present invention are described below.

Fusion Proteins and Conjugated Polypeptides

Some embodiments of the invention involve the use of an NgR1 polypeptide that is not the full-length NgR1 protein, e.g., polypeptide fragments of NgR1, fused to a heterologous polypeptide moiety to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the NgR1 polypeptide moiety of the invention or to be cleavable, in vitro or in vivo. Heterologous moieties to accomplish these other objectives are known in the art.

In some embodiments of the invention, an NgR1 polypeptide fragment can be fused to another NgR polypeptide fragment, e.g., an NgR2 or NgR3 polypeptide fragment along with Fc.

The human NgR2 polypeptide is shown below as SEQ ID NO:60.

Full-Length Human NgR2 (SEQ ID NO:60):

```
MLPGLRRLLQ APASACLLLM LLALPLAAPS CPMLCTCYSS
PPTVSCQANN FSSVPLSLPP STQRLFLQNN LIRTLRPGTF
GSNLLTLWLF SNNLSTIYPG TFRHLQALEE LDLGDNRHLR
SLEPDTFQGL ERLQSLHLYR CQLSSLPGNI FRGLVSLQYL
YLQENSLLHL QDDLFADLAN LSHLFLHGNR LRLLTEHVFR
GLGSLDRLLL HGNRLQGVHR AAFRGLSRLT ILYLFNNSLA
SLPGEALADL PSLEFLRLNA NPWACDCRAR PLWAWFQRAR
VSSSDVTCAT PPERQGRDLR ALREADFQAC PPAAPTRPGS
RARGNSSSNH LYGVAEAGAP PADPSTLYRD LPAEDSRGRQ
```

-continued

```
GGDAPTEDDY WGGYGGEDQR GEQMCPGAAC QAPPDSRGPA

LSAGLPSPLL CLLLLVPHHL
```

The mouse NgR2 polypeptide is shown below as SEQ ID NO:61.

Full-Length Mouse NgR2 (SEQ ID NO:61):

```
MLPGLRRLLQ GPASACLLLT LLALPSVTPS CPMLCTCYSS

PPTVSCQANN FSSVPLSLPP STQRLFLQNN LIRSLRPGTF

GPNLLTLWLF SNNLSTIHPG TFRHLQALEE LDLGDNRHLR

SLEPDTFQGL ERLQSLHLYR CQLSSLPGNI FRGLVSLQYL

YLQENSLLHL QDDLFADLAN LSHLFLHGNR LRLLTEHVFR

GLGSLDRLLL HGNRLQGVHR AAFHGLSRLT ILYLFNNSLA

SLPGEALADL PALEFLRLNA NPWACDCRAR PLWAWFQRAR

VSSSDVTCAT PPERQGRDLR ALRDSDFQAC PPPTPTRPGS

RARGNSSSNH LYGVAEAGAP PADPSTLYRD LPAEDSRGRQ

GGDAPTEDDY WGGYGGEDQR GEQTCPGAAC QAPADSRGPA

LSAGLRTPLL CLLPLALHHL
```

The human NgR3 polypeptide is shown below as SEQ ID NO:62.

Full-Length Human NgR3 (SEQ ID NO:62):

```
MLRKGCCVEL LLLLVAAELP LGGGCPRDCV CYPAPMTVSC

QAHNFAAIPE GIPVDSERVF LQNNRIGLLQ PGHFSPAMVT

LWIYSNNITY IHPSTFEGFV HLEELDLGDN RQLRTLAPET

FQGLVKLHAL YLYKCGLSAL PAGVFGGLHS LQYLYLQDNH

IEYLQDDIFV DLVNLSHLFL HGNKLWSLGP GTFRGLVNLD

RLLLHENQLQ WVHHKAFHDL RRLTTLFLFN NSLSELQGEC

LAPLGALEFL RLNGNPWDCG CRARSLWEWL QRFRGSSSAV

PCVSPGLRHG QDLKLLRAED FRNCTGPASP HQIKSHTLTT

TDRAARKEHH SPHGPTRSKG HPHGPRPGHR KPGKNCTNPR

NRNQISKAGA GKQAPELPDY APDYQHKFSF DIMPTARPKR

KGKCARRTPI RAPSGVQQAS SASSLGASLL AWTLGLAVTL R
```

The mouse NgR3 polypeptide is shown below as SEQ ID NO:63.

Full-Length Mouse NgR3 (SEQ ID NO:63):

```
MLRKGCCVEL LLLLLAGELP LGGGCPRDCV CYPAPMTVSC

QAHNFAAIPE GIPEDSERIF LQNNRITFLQ QGHFSPAMVT

LWIYSNNITF IAPNTFEGFV HLEELDLGDN RQLRTLAPET

FQGLVKLHAL YLYKCGLSAL PAGIFGGLHS LQYLYLQDNH

IEYLQDDIFV DLVNLSHLFL HGNKLWSLGQ GIFRGLVNLD

RLLLHENQLQ WVHHKAFHDL HRLTTLFLFN NSLTELQGDC

LAPLVALEFL RLNGNAWDCG CRARSLWEWL RRFRGSSSAV
```

-continued

```
PCATPELRQG QDLKLLRVED FRNCTGPVSP HQIKSHTLTT

SDRAARKEHH PSHGASRDKG HPHGHPPGSR SGYKKAGKNC

TSHRNRNQIS KVSSGKELTE LQDYAPDYQH KFSFDIMPTA

RPKRKGKCAR RTPIRAPSGV QQASSGTALG APLLAWILGL AVTLR
```

In some embodiments, the invention provides an isolated polypeptide comprising a first polypeptide figment and a second polypeptide fragment, wherein said first polypeptide fragment comprises an amino acid sequence identical to a first reference amino acid sequence, except for up to one, two, three, four, ten, or twenty individual amino acid substitutions, wherein said first reference amino acid sequence is selected from the group consisting of (a) amino acids a to 305 of SEQ ID NO:49, (b) amino acids 1 to b of SEQ ID NO:49, and (c) amino acids a to b of SEQ ID NO:49, wherein a is any integer from 1 to 27, and b is any integer from 264 to 309; and wherein said second polypeptide fragment comprises an amino acid sequence identical to a second reference amino acid sequence, except for up to one, two, three, four, ten, or twenty individual amino acid substitutions, wherein said second reference amino acid sequence is selected from the group consisting of (a) amino acids c to 332 of SEQ ID NO:60, (b) amino acids 275 to d of SEQ ID NO:60, and (c) amino acids c to d of SEQ ID NO:60, wherein c is any integer from 265 to 306, and d is any integer from 308 to 340; and; wherein said polypeptide inhibits nogo-receptor-mediated neurite outgrowth inhibition.

In one embodiment, the invention provides an isolated polypeptide comprising a first polypeptide fragment and a second polypeptide fragment, wherein said first polypeptide fragment comprises an amino acid sequence identical to a first reference amino acid sequence, except for up to one, two, three, four, ten, or twenty individual amino acid substitutions, wherein said first reference amino acid sequence is amino acids 1-274 of SEQ ID NO:49 and wherein said second polypeptide fragment comprises an amino acid sequence identical to a second reference amino acid sequence, except for up to one, two, three, four, ten, or twenty individual amino acid substitutions, wherein said second reference amino acid sequence is amino acids 275-311 of SEQ ID NO:60 and; wherein said polypeptide inhibits nogo-receptor-mediated neurite outgrowth inhibition.

In one embodiment, the invention provides an isolated polypeptide comprising a first polypeptide fragment and a second polypeptide fragment, wherein said first polypeptide fragment comprises an amino acid sequence identical to a first reference amino acid sequence, except for up to one, two, three, four, ten, or twenty individual amino acid substitutions, wherein said first reference amino acid sequence is amino acids 1-274 of SEQ ID NO:49 and wherein said second polypeptide fragment comprises an amino acid sequence identical to a second reference amino acid sequence, except for up to one, two, three, four, ten, or twenty individual amino acid substitutions, wherein said second reference amino acid sequence is amino acids 275-332 of SEQ ID NO:60 and; wherein said polypeptide inhibits nogo-receptor-mediated neurite outgrowth inhibition.

In one embodiment, the invention provides an isolated polypeptide comprising a first polypeptide fragment and a second polypeptide fragment, wherein said first polypeptide fragment comprises an amino acid sequence identical to a first reference amino acid sequence, except for up to one, two, three, four, ten, or twenty individual amino acid substitutions, wherein said first reference amino acid sequence is amino acids 1-305 of SEQ ID NO:49 and wherein said second polypeptide fragment comprises an amino acid sequence identical to a second reference amino acid sequence, except for up to one, two, three, four, ten, or twenty individual amino acid substitutions, wherein said second reference amino acid sequence is amino acids 306-311 of SEQ ID NO:60 and; wherein said polypeptide inhibits nogo-receptor-mediated neurite outgrowth inhibition.

In one embodiment, the invention provides an isolated polypeptide comprising a first polypeptide fragment and a second polypeptide fragment, wherein said first polypeptide fragment comprises an amino acid sequence identical to a first reference amino acid sequence, except for up to one, two, three, four, ten, or twenty individual amino acid substitutions, wherein said first reference amino acid sequence is amino acids 1-305 of SEQ ID NO:49 and wherein said second polypeptide fragment comprises an amino acid sequence identical to a second reference amino acid sequence, except for up to one, two, three, four, ten, or twenty individual amino acid substitutions, wherein said second reference amino acid sequence is amino acids 306-309 of SEQ ID NO:60 and; wherein said polypeptide inhibits nogo-receptor-mediated neurite outgrowth inhibition. In another embodiment, at least one additional amino acid is added to the C-terminus of the second polypeptide fragment. Exemplary amino acids that can be added to the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In one embodiment, the added amino acid is tryptophan. In an additional embodiment, the arginine at position 269 of SEQ ID NO:49 is substituted with tryptophan.

In one embodiment, the invention provides an isolated polypeptide comprising a first polypeptide fragment and a second polypeptide fragment, wherein said first polypeptide fragment consists of amino acids 1-310 of SEQ ID NO:49, except for up to one, two, three, four, ten, or twenty individual amino acid substitutions; and wherein said second polypeptide fragment consists of amino acids 311-318 of SEQ ID NO:60 except for up to one, two, three, four, or five individual amino acid substitutions; and wherein said polypeptide inhibits nogo-receptor-mediated neurite outgrowth inhibition.

In some embodiments, the polypeptides of the invention further comprise a heterologous polypeptide. In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments the Fc is joined to the C-terminal end of the polypeptides of the invention. In some embodiments the fusion is a dimer. The invention further encompasses variants, analogs, or derivatives of polypeptide fragments as described above.

As an alternative to expression of a fusion protein, a chosen heterologous moiety can be preformed and chemically conjugated to the NgR polypeptide moiety of the invention. In most cases, a chosen heterologous moiety will function similarly, whether fused or conjugated to the NgR polypeptide moiety. Therefore, in the following discussion of heterologous amino acid sequences, unless otherwise noted, it is to be understood that the heterologous sequence can be joined to the NgR polypeptide moiety in the form of a fusion protein or as a chemical conjugate.

NgR1 aptamers and antibodies and fragments thereof for use in the treatment methods disclosed herein may also be recombinantly fused to a heterologous polypeptide at the N- or C-terminus or chemically conjugated (including covalent and non-covalent conjugations) to polypeptides or other compositions. For example, NgR1 antagonist aptamers and antibodies and fragments thereof may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

NgR1 antagonist polypeptides, aptamers, and antibodies and fragments thereof for use in the treatment methods disclosed herein include derivatives that are modified, i.e., by the covalent attachment of any type of molecule such that covalent attachment does not prevent the NgR1 antagonist polypeptide, aptamer, or antibody from inhibiting the biological function of NgR1. For example, but not by way of limitation, the NgR1 antagonist polypeptides, aptamers and antibodies and fragments thereof of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

NgR1 antagonist polypeptides, aptamers and antibodies and fragments thereof for use in the treatment methods disclosed herein can be composed of amino acids joined to each other by peptide bonds or modified peptide bonds, i.e., peptide isosteres, and may contain amino acids other than the 20 gene-encoded amino acids. NgR1 antagonist polypeptides, aptamers and antibodies and fragments thereof may be modified by natural processes, such as posttranslational processing, or by chemical modification techniques which are well known in the art. Such modifications are well described in basic texts and in more detailed monographs, as well as in a voluminous research literature. Modifications can occur anywhere in the NgR1 antagonist polypeptide, aptamer or antibody or fragments thereof, including the peptide backbone, the amino acid side-chains and the amino or carboxyl termini, or on moieties such as carbohydrates. It will be appreciated that the same type of modification may be present in the same or varying degrees at several sites in a given NgR1 antagonist polypeptide, aptamer or antibody or fragments thereof. Also, a given NgR1 antagonist polypeptide, aptamer or antibody or fragments thereof may contain many types of modifications. NgR1 antagonist polypeptides, aptamers or antibodies or fragments thereof may be branched, for example, as a result of ubiquitination, and they may be cyclic, with or without branching. Cyclic, branched, and branched cyclic NgR1 antagonist polypeptides, aptamers and antibodies or fragments thereof may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enymol* 182:626-646 (1990); Rattan et al., *Ann NY Acad Sci* 663:48-62 (1992)).

The heterologous polypeptide to which the NgR1 antagonist polypeptide, aptamer or antibody or fragments thereof is fused is useful therapeutically or is useful to target the NgR1 antagonist polypeptide, aptamer or antibody or fragments thereof. NgR1 antagonist fusion proteins, aptamers and antibodies or fragments thereof can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the NgR antagonist polypeptide, aptamer or antibody or fragments thereof or to be cleavable, in vitro or in vivo. Heterologous moieties to accomplish these other objectives are known in the art.

As an alternative to expression of an NgR1 antagonist fusion polypeptide, aptamer or antibody or fragments thereof, a chosen heterologous moiety can be preformed and chemically conjugated to the antagonist polypeptide, aptamer or antibody. In most cases, a chosen heterologous moiety will function similarly, whether fused or conjugated to the NgR1 antagonist polypeptide, aptamer or antibody or fragments thereof. Therefore, in the following discussion of heterologous amino acid sequences, unless otherwise noted, it is to be understood that the heterologous sequence can be joined to the NgR1 antagonist polypeptide, aptamer or antibody or fragments thereof in the form of a fusion protein or as a chemical conjugate.

Pharmacologically active polypeptides such as NgR1 antagonist polypeptides, aptamers or antibodies or fragments thereof may exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as polypeptide fragments of the NgR signaling domain can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known. Examples include serum albumins such as, e.g., bovine serum albumin (BSA) or human serum albumin (HSA).

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA,* 89:1904-08 (1992) and Syed et al., *Blood* 89:3243-52 (1997), HSA can be used to form a fusion protein or polypeptide conjugate that displays pharmacological activity by virtue of the NgR polypeptide moiety while displaying significantly increased in vivo stability, e.g., 10-fold to 100-fold higher. The C-terminus of the HSA can be fused to the N-terminus of the NgR polypeptide moiety. Since HSA is a naturally secreted protein, the HSA signal sequence can be exploited to obtain secretion of the fusion protein into the cell culture medium when the fusion protein is produced in a eukaryotic, e.g., mammalian, expression system.

In certain embodiments, NgR1 antagonist polypeptides, aptamers, antibodies and antibody fragments thereof for use in the methods of the present invention further comprise a targeting moiety. Targeting moieties include a protein or a peptide which directs localization to a certain part of the body, for example, to the brain or compartments therein. In certain embodiments, NgR1 antagonist polypeptides, aptamers, antibodies or antibody fragments thereof for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin:biotin, protein A:IgG, etc.). In other embodiments, the NgR1 antagonist polypeptides, aptamers, antibodies or antibody fragments thereof for use in the methods of the present invention thereof are attached to one more brain targeting moieties. In additional embodiments, the brain targeting moiety is attached to a plurality of NgR1 antagonist polypeptides, aptamers, antibodies or antibody fragments thereof for use in the methods of the present invention.

A brain targeting moiety associated with an NgR1 antagonist polypeptide, aptamer, antibody or antibody fragment thereof enhances brain delivery of such an NgR1 antagonist polypeptide, antibody or antibody fragment thereof. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); diptheria toxin conjugates (see, for e.g., Gaillard et al., *International Congress Series* 1277:185-198 (2005); and SEQ ID NOs: 1-18 of U.S. Pat. No. 6,306,365. The contents of the above references are incorporated herein by reference in their entirety.

Enhanced brain delivery of an NgR composition is determined by a number of means well established in the art. For example, administering to an animal a radioactively labelled NgR1 antagonist polypeptide, aptamer, antibody or antibody fragment thereof linked to a brain targeting moiety, determining brain localization; and comparing localization with an equivalent radioactively labelled NgR1 antagonist polypeptide, aptamer, antibody or antibody fragment thereof that is not associated with a brain targeting moiety. Other means of determining enhanced targeting are described in the above references.

Some embodiments of the invention employ an NgR polypeptide moiety fused to a hinge and Fc region, i.e., the C-terminal portion of an Ig heavy chain constant region. In some embodiments, amino acids in the hinge region may be substituted with different amino acids. Exemplary amino acid substitutions for the hinge region according to these embodiments include substitutions of individual cysteine residues in the hinge region with different amino acids. Any different amino acid may be substituted for a cysteine in the hinge region. Amino acid substitutions for the amino acids of the polypeptides of the invention and the reference amino acid sequence can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Typical amino acids to substitute for cysteines in the reference amino acid include alanine, serine, threonine, in particular, serine and alanine. Making such substitutions through engineering of a polynucleotide encoding the polypeptide fragment is well within the routine expertise of one of ordinary skill in the art.

Potential advantages of an NgR-polypeptide-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is generally used, e.g., an IgG1 Fc region or IgG4 Fc region. Materials and methods for constructing and expressing DNA encoding Fc fusions are known in the art and can be applied to obtain fusions without undue experimentation. Some embodiments of the invention employ a fusion protein such as those described in Capon et al., U.S. Pat. Nos. 5,428,130 and 5,565,335.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.,* 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. Se e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the NgR polypeptide moiety.

In some embodiments, the DNA sequence may encode a proteolytic cleavage site between the secretion cassette and the NgR polypeptide moiety. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes an NgR1 polypeptide or polypeptide fragment of the invention and used for the expression and secretion of the polypeptide. Host cells that are typically used include immortal hybridoma cells, myeloma cells, 293 cells, Chinese hamster ovary (CHO) cells, Hela cells, and COS cells.

Fully intact, wild-type Fc regions display effector functions that normally are unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the CH2 domain of the Fc region of IgE, such that this site does not interfere with the efficient secretion of the immunofusin. Transmembrane domain sequences, such as those present in IgM, also are generally deleted.

The IgG1 Fc region is most often used. Alternatively, the Fc region of the other subclasses of immunoglobulin gamma (gamma-2, gamma-3 and gamma-4) can be used in the secretion cassette. The IgG1 Fc region of immunoglobulin gamma-1 is generally used in the secretion cassette and includes at least part of the hinge region, the CH2 region, and the CH3 region. In some embodiments, the Fc region of immunoglobulin gamma-1 is a CH2-deleted-Fc, which includes part of the hinge region and the CH3 region, but not the CH2 region. A CH2-deleted-Fc has been described by Gillies et al., *Hum. Antibod. Hybridomas* 1:47 (1990). In some embodiments, the Fc region of one of IgA, IgD, IgE, or IgM, is used.

NgR-polypeptide-moiety-Fc fusion proteins can be constructed in several different configurations. In one configuration the C-terminus of the NgR polypeptide moiety is fused directly to the N-terminus of the Fc hinge moiety. In a slightly different configuration, a short polypeptide, e.g., 2-10 amino acids, is incorporated into the fusion between the N-terminus of the NgR polypeptide moiety and the C-terminus of the Fc moiety. In the alternative configuration, the short polypeptide is incorporated into the fusion between the C-terminus of the NgR polypeptide moiety and the N-terminus of the Fc moiety. An exemplary embodiment of this configuration is NgR1 (310)-2XG4S-Fc, which is amino acids 26-310 of SEQ ID NO:49 linked to $(Gly-Gly-Gly-Gly-Ser)_2$ (SEQ ID NO:66) which is linked to Fc. Such a linker provides conformational flexibility, which may improve biological activity in some circumstances. If a sufficient portion of the hinge region is retained in the Fc moiety, the NgR-polypeptide-moiety-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link an NgR1 polypeptide or polypeptide fragment of the invention to serum albumin. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, SIAB. Linkers that provide a protected or non-protected thiol for reaction with sulfhydryl groups to product a reducible linkage include SPDP, SMPT, SATA, and SATP. Such reagents are commercially available (e.g., Pierce Chemical Company, Rockford, Ill.).

Conjugation does not have to involve the N-terminus of an NgR1 polypeptide or polypeptide fragment of the invention or the thiol moiety on serum albumin. For example, NgR-polypeptide-albumin fusions can be obtained using genetic engineering techniques, wherein the NgR polypeptide moiety is fused to the serum albumin gene at its N-terminus, C-terminus, or both.

NgR polypeptides of the invention can be fused to a polypeptide tag. The term "polypeptide tag," as used herein, is intended to mean any sequence of amino acids that can be attached to, connected to, or linked to an NgR polypeptide and that can be used to identify, purify, concentrate or isolate the NgR polypeptide. The attachment of the polypeptide tag to the NgR polypeptide may occur, e.g., by constructing a nucleic acid molecule that comprises: (a) a nucleic acid sequence that encodes the polypeptide tag, and (b) a nucleic acid sequence that encodes an NgR polypeptide. Exemplary polypeptide tags include, e.g., amino acid sequences that are capable of being post-translationally modified, e.g., amino acid sequences that are biotinylated. Other exemplary polypeptide tags include, e.g., amino acid sequences that are capable of being recognized and/or bound by an antibody (or fragment thereof) or other specific binding reagent. Polypeptide tags that are capable of being recognized by an antibody (or fragment thereof) or other specific binding reagent include, e.g., those that are known in the art as "epitope tags." An epitope tag may be a natural or an artificial epitope tag. Natural and artificial epitope tags are known in the art, including, e.g., artificial epitopes such as FLAG, Strep, or poly-histidine peptides. FLAG peptides include the sequence Asp-Tyr-Lys-Asp-Asp-Asp-Asp-Lys (SEQ ID NO:74) or Asp-Tyr-Lys-Asp-Glu-Asp-Asp-Lys (SEQ ID NO:75) (Einhauer, A. and Jungbauer, A., *J. Biochem. Biophys. Methods* 49:1-3: 455-465 (2001)). The Strep epitope has the sequence Ala-Trp-Arg-His-Pro-Gln-Phe-Gly-Gly (SEQ ID NO:76). The VSV-G epitope can also be used and has the sequence Tyr-Thr-Asp-Ile-Glu-Met-Asn-Arg-Leu-Gly-Lys (SEQ ID NO:77). Another artificial epitope is a poly-His sequence having six histidine residues (His-His-His-His-His-His (SEQ ID NO:78). Naturally-occurring epitopes include the influenza virus hemagglutinin (HA) sequence Tyr-Pro-Tyr-Asp-Val-Pro-Asp-Tyr-Ala-Ile-Glu-Gly-Arg (SEQ ID NO:79) recognized by the monoclonal antibody 12CA5 (Murray et al., *Anal. Biochem.* 229:170-179 (1995)) and the eleven amino acid sequence from human c-myc (Myc) recognized by the monoclonal antibody 9E10 (Glu-Gln-Lys-Leu-Leu-Ser-Glu-Glu-Asp-Leu-Asn (SEQ ID NO:80) (Manstein et al., *Gene* 162:129-134 (1995)). Another useful epitope is the tripeptide Glu-Glu-Phe which is recognized by the monoclonal antibody YL 1/2. (Stammers et al. *FEBS Let.* 283:298-302 (1991)).

In certain embodiments, the NgR polypeptide and the polypeptide tag may be connected via a linking amino acid sequence. As used herein, a "linking amino acid sequence" may be an amino acid sequence that is capable of being recognized and/or cleaved by one or more proteases. Amino acid sequences that can be recognized and/or cleaved by one or more proteases are known in the art. Exemplary amino acid sequences are those that are recognized by the following proteases: factor VIIa, factor IXa, factor Xa, APC, t-PA, u-PA, trypsin, chymotrypsin, enterokinase, pepsin, cathepsin B,H, L,S,D, cathepsin G, renin, angiotensin converting enzyme, matrix metalloproteases (collagenases, stromelysins, gelatinases), macrophage elastase, Cir, and C is. The amino acid sequences that are recognized by the aforementioned proteases are known in the art. Exemplary sequences recognized by certain proteases can be found, e.g., in U.S. Pat. No. 5,811,252.

Polypeptide tags can facilitate purification using commercially available chromatography media.

In some embodiments of the invention, an NgR polypeptide fusion construct is used to enhance the production of an NgR polypeptide moiety in bacteria. In such constructs a bacterial protein normally expressed and/or secreted at a high level is employed as the N-terminal fusion partner of an NgR1 polypeptide or polypeptide fragment of the invention. See e.g., Smith et al., *Gene* 67:31 (1988); Hopp et al., *Biotechnology* 6:1204 (1988); La Vallie et al., *Biotechnology* 11:187 (1993).

By fusing an NgR polypeptide moiety at the amino and carboxy termini of a suitable fusion partner, bivalent or tetravalent forms of an NgR1 polypeptide or polypeptide fragment of the invention can be obtained. For example, an NgR polypeptide moiety can be fused to the amino and carboxy termini of an Ig moiety to produce a bivalent monomeric polypeptide containing two NgR polypeptide moieties. Upon dimerization of two of these monomers, by virtue of the Ig moiety, a tetravalent form of an NgR polypeptide is obtained. Such multivalent forms can be used to achieve increased binding affinity for the target. Multivalent forms of an NgR1 polypeptide or polypeptide fragment of the invention also can be obtained by placing NgR polypeptide moieties in tandem to form concatamers, which can be employed alone or fused to a fusion partner such as Ig or HSA.

Conjugated Polymers (Other than Polypeptides)

Some embodiments of the invention involve an NgR1 polypeptide or polypeptide fragment of the invention wherein one or more polymers are conjugated (covalently linked) to the NgR polypeptide. Examples of polymers suitable for such conjugation include polypeptides (discussed above), sugar polymers and polyalkylene glycol chains. Typically, but not necessarily, a polymer is conjugated to the NgR1 polypeptide or polypeptide fragment of the invention for the purpose of improving one or more of the following: solubility, stability, or bioavailability.

The class of polymer generally used for conjugation to an NgR1 polypeptide or polypeptide fragment of the invention is a polyalkylene glycol. Polyethylene glycol (PEG) is most frequently used. PEG moieties, e.g., 1, 2, 3, 4 or 5 PEG polymers, can be conjugated to each NgR polypeptide to increase serum half life, as compared to the NgR polypeptide alone. PEG moieties are non-antigenic and essentially biologically inert. PEG moieties used in the practice of the invention may be branched or unbranched.

The number of PEG moieties attached to the NgR polypeptide and the molecular weight of the individual PEG chains can vary. In general, the higher the molecular weight of the polymer, the fewer polymer chains attached to the polypeptide. Usually, the total polymer mass attached to an NgR polypeptide or polypeptide fragment is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the NgR polypeptide through any suitable, exposed reactive group on the polypeptide. The exposed reactive group(s) can be, e.g., an N-terminal amino group at the epsilon amino group of an internal lysine residue, or both. An activated polymer can react and covalently link at any fee amino group on the NgR polypeptide. Free carboxylic groups, suitably activated carbonyl groups, hydroxyl, guanidyl, imidazole, oxidized carbohydrate moieties and mercapto groups of the NgR polypeptide (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific)

that can impair the desired pharmacological activity of the NgR polypeptide moiety. Preferably, at least 50% of the biological activity (as demonstrated, e.g., in any of the assays described herein or known in the art) of the NgR polypeptide is retained, and most preferably nearly 100% is retained.

The polymer can be conjugated to the NgR polypeptide using conventional chemistry. For example, a polyalkylene glycol moiety can be coupled to a lysine epsilon amino group of the NgR polypeptide. Linkage to the lysine side chain can be performed with an N-hydroxysuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors,* 3: 4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5: 133-140, 1994. Reaction parameters are generally selected to avoid temperature, solvent, and pH conditions that would damage or inactivate the NgR polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with an NgR1 polypeptide or polypeptide fragment of the invention in the presence of a reducing agent. In addition, one can manipulate the reaction conditions to favor PEGylation substantially only at the N-terminal amino group of the NgR polypeptide, i.e. a mono-PEGylated protein. In either case of mono-PEGylation or poly-PEGylation, the PEG groups are typically attached to the protein via a —CH2-NH— group. With particular reference to the —CH2- group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated NgR polypeptides of the invention generally includes the steps of (a) reacting an NgR1 polypeptide or polypeptide fragment of the invention with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/NgR polypeptide generally includes the steps of: (a) reacting an NgR1 polypeptide or polypeptide fragment of the invention with a reactive PEG molecule under reductive alkylation conditions, at a pH suitable to permit selective modification of the N-terminal amino group of NgR; and (b) obtaining the reaction product(s).

For a substantially homogeneous population of mono-polymer/NgR polypeptide, the reductive alkylation reaction conditions are those that permit the selective attachment of the water-soluble polymer moiety to the N-terminus of an NgR1 polypeptide or polypeptide fragment of the invention. Such reaction conditions generally provide for pKa differences between the lysine side chain amino groups and the N-terminal amino group. For purposes of the present invention, the pH is generally in the range of 3-9, typically 3-6.

NgR polypeptides of the invention can include a tag e.g., a moiety that can be subsequently released by proteolysis. Thus, the lysine moiety can be selectively modified by first reacting a His-tag modified with a low-molecular-weight linker such as Traut's reagent (Pierce Chemical Company, Rockford, Ill.) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce Chemical Company, Rockford, Ill.). Similarly one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the NgR polypeptide. Coupling can be effected using, e.g., a maleimide group, a vinylsulfone group, a haloacetate group, or a thiol group.

Optionally, the NgR polypeptide is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

The NgR polypeptides of the invention, in certain embodiments, are soluble polypeptides. Methods for making a polypeptide soluble or improving the solubility of a polypeptide are well known in the art.

Nucleic Acid Molecules of the Present Invention

The present invention provide a nucleic acid that encodes a polypeptide of the invention, including the polypeptides of any one of SEQ ID NOs: 1-9, 26-27, 29-37 and 41-45. In some embodiments, the nucleic acid encodes a polypeptide selected from the group consisting of amino acid residues 26-344 of Nogo receptor-1 as shown in SEQ ID NOs: 6 and 8 or amino acid residues 27-344 of Nogo receptor-1 as shown in SEQ ID NO: 8. In some embodiments, the nucleic acid molecule encodes a polypeptide selected from the group consisting of amino acid residues 26-310 of Nogo receptor-1 as shown in SEQ ID NOs: 7 and 9 or amino acid residues 27-310 of Nogo receptor-1 as shown in SEQ ID NO: 9. As used herein, "nucleic acid" means genomic DNA, cDNA, mRNA and antisense molecules, as well as nucleic acids based on alternative backbones or including alternative bases whether derived from natural sources or synthesized. In some embodiments, the nucleic acid further comprises a transcriptional promoter and optionally a signal sequence each of which is operably linked to the nucleotide sequence encoding the polypeptides of the invention.

In some embodiments, the invention provides a nucleic acid encoding a Nogo receptor-1 fusion protein of the invention, including a fusion protein comprising a polypeptide selected from the group consisting of amino acid residues 26-344 of Nogo receptor-1 as shown in SEQ ID NOs: 6 and 8 or amino acid residues 27-344 of SEQ ID NO: 8 and amino acid residues 26-310 of Nogo receptor-1 as shown in SEQ ID NOs: 7 and 9 or amino acid residues 27-310 of SEQ ID NO: 9. In some embodiments, the nucleic acid encodes a Nogo receptor-1 fusion protein comprising a polypeptides selected from the group consisting of SEQ ID NOs: 26-27, 29-37 and 41-45. In some embodiments, the nucleic acid encoding a Nogo receptor-1 fusion protein further comprises a transcriptional promoter and optionally a signal sequence. In some embodiments, the nucleotide sequence further encodes an immunoglobulin constant region. In some embodiments, the immunoglobulin constant region is a heavy chain constant region. In some embodiments, the nucleotide sequence further encodes an immunoglobulin heavy chain constant region joined to a hinge region. In some embodiments the nucleic acid further encodes Fc. In some embodiments the Nogo receptor-1 fusion proteins comprise an Fc fragment.

The encoding nucleic acids of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

The present invention also includes polynucleotides that hybridize under moderately stringent or high stringency conditions to the noncoding strand, or complement, of a polynucleotide that encodes any one of the polypeptides of the invention. Stringent conditions are known to those skilled in the art and can be found in CURRENT PROTOCOLS IN MOLECULAR BIOLOGY, John Wiley & Sons, N.Y. (1989) 6.3.1-6.3.6.

The human Nogo receptor-1 polynucleotide is shown below as SEQ ID NO:81.

Full-Length Human Nogo Receptor-1 is encoded by nucleotide 166 to nucleotide 1587 of SEQ ID NO:81:

```
agcccagcca gagccgggcg gagcggagcg cgccgagcct
cgtcccgcgg ccgggccggg gccgggccgt agcggcggcg
cctggatgcg gacccggccg cggggagacg ggcgcccgcc
ccgaaacgac tttcagtccc cgacgcgccc cgcccaaccc
ctacgatgaa gagggcgtcc gctggaggga gccggctgct
ggcatgggtg ctgtggctgc aggcctggca ggtggcagcc
ccatgcccag gtgcctgcgt atgctacaat gagcccaagg
tgacgacaag ctgcccccag cagggcctgc aggctgtgcc
cgtgggcatc cctgctgcca gccagcgcat cttcctgcac
ggcaaccgca tctcgcatgt gccagctgcc agcttccgtg
cctgccgcaa cctcaccatc ctgtggctgc actcgaatgt
gctggcccga attgatgcgg ctgccttcac tggcctggcc
ctcctggagc agctggacct cagcgataat gcacagctcc
ggtctgtgga ccctgccaca ttccacggcc tgggccgcct
acacacgctg cacctggacc gctgcggcct gcaggagctg
ggcccggggc tgttccgcgg cctggctgcc ctgcagtacc
tctacctgca ggacaacgcg ctgcaggcac tgcctgatga
caccttccgc gacctgggca acctcacaca cctcttcctg
cacggcaacc gcatctccag cgtgcccgag cgcgccttcc
gtgggctgca cagcctcgac cgtctcctac tgcaccagaa
ccgcgtggcc catgtgcacc cgcatgcctt ccgtgacctt
ggccgcctca tgacactcta tctgtttgcc aacaatctat
cagcgctgcc cactgaggcc ctggcccccc tgcgtgccct
gcagtacctg aggctcaacg acaacccctg ggtgtgtgac
tgccgggcac gcccactctg ggcctggctg cagaagttcc
gcggctcctc ctccgaggtg ccctgcagcc tcccgcaacg
```

-continued

```
cctggctggc cgtgacctca aacgcctagc tgccaatgac
ctgcagggct gcgctgtggc caccggccct taccatccca
tctggaccgg cagggccacc gatgaggagc cgctggggct
tcccaagtgc tgccagccag atgccgctga caaggcctca
gtactggagc ctggaagacc agcttcggca ggcaatgcgc
tgaagggacg cgtgccgccc ggtgacagcc cgccgggcaa
cggctctggc ccacggcaca tcaatgactc accctttggg
actctgcctg gctctgctga gccccgctc actgcagtgc
ggcccgaggg ctccgagcca ccagggttcc ccacctcggg
ccctcgccgg aggccaggct gttcacgcaa gaaccgcacc
cgcagccact gccgtctggg ccaggcaggc agcgggggtg
gcgggactgg tgactcagaa ggctcaggtg ccctacccag
cctcacctgc agcctcaccc ccctgggcct ggcgctggtg
ctgtggacag tgcttgggcc ctgctgaccc ccagcggaca
caagagcgtg ctcagcagcc aggtgtgtgt acatacgggg
tctctctcca cgccgccaag ccagccgggc ggccgacccg
tggggcaggc caggccaggt cctccctgat ggacgcctg
```

The rat Nogo receptor-1 polynucleotide is shown below as SEQ ID NO:82 and is accession number NM_053613 in Genbank.

```
atgaagaggg cgtcctccgg aggaagccgg ctgccgacat
gggtgttatg gctacaggcc tggagggtag caacgccctg
ccctggtgcc tgtgtgtgct acaatgagcc caaggtcaca
acaagccgcc cccagcaggg cctgcaggct gtacccgctg
gcatcccagc ctccagccag agaatcttcc tgcacggcaa
ccgaatctct tacgtgccag ccgccagctt ccagtcatgc
cggaatctca ccatcctgtg cgtgcactca aatgcgctgg
ccgggattga tgccgcggcc ttcactggtc tgaccctcct
ggagcaacta gatcttagtg acaatgcaca gctccgtgtc
gtggacccca ccacgttccg tggcctgggc cacctgcaca
cgctgcacct agaccgatgc ggcctgcagg agctggggcc
tggcctattc cgtgggctgg cagctctgca gtacctctac
ctacaagaca acaacctgca ggcacttccc gacaacacct
tccgagacct gggcaacctc acgcatctct ttctgcatgg
caaccgtatc cccagtgttc ctgagcacgc tttccgtggc
ttgcacagtc ttgaccgtct cctcttgcac cagaaccatg
tggctcgtgt gcacccacat gccttccggg accttggccg
actcatgacc ctctacctgt ttgccaacaa cctctccatg
ctccccgcag aggtcctagt gcccctgagg tctctgcagt
acctgcgact caatgacaac ccctgggtgt gtgactgcag
```

-continued

```
ggcacgtccg ctctgggcct ggctgcagaa gttccgaggt
tcctcatccg gggtgcccag caacctaccc caacgcctgg
caggccgtga tctgaagcgc ctggctacca gtgacttaga
gggttgtgct gtggcttcgg ggcccttccg tcccttccag
accaatcagc tcactgatga ggagctgctg ggcctcccca
agtgctgcca gccggatgct gcagacaagg cctcagtact
ggaacccggg aggccggcgt ctgttggaaa tgcactcaag
ggacgtgtgc ctcccggtga cactccacca ggcaatggct
caggcccacg gcacatcaat gactctccat ttgggacttt
gcccggctct gcagagcccc cactgactgc cctgcggcct
gggggttccg agcccccggg actgcccacc acgggccccc
gcaggaggcc aggttgttcc agaaagaacc gcacccgtag
ccactgccgt ctgggccagg caggaagtgg gagcagtgga
actggggatg cagaaggttc gggggccctg cctgccctgg
cctgcagcct tgctcctctg ggccttgcac tggtactttg
gacagtgctt gggccctgct ga
```

The mouse Nogo receptor-1 polynucleotide is shown below as SEQ ID NO:83 and is accession number NM_022982 in Genbank.

```
agccgcagcc cgcgagccca gcccggcccg gtagagcgga
gcgccggagc ctcgtcccgc ggccgggccg ggaccgggcc
ggagcagcgg cgcctggatg cggacccggc cgcgcgcaga
cgggcgcccg ccccgaagcc gcttccagtg cccgacgcgc
cccgctcgac cccgaagatg aagagggcgt cctccggagg
aagcaggctg ctggcatggg tgttatggct acaggcctgg
agggtagcaa caccatgccc tggtgcttgt gtgtgctaca
atgagcccaa ggtaacaaca agctgccccc agcagggtct
gcaggctgtg cccactggca tcccagcctc tagccagcga
atcttcctgc atggcaaccg aatctctcac gtgccagctg
cgagcttcca gtcatgccga aatctcacta tcctgtggct
gcactctaat gcgctggctc ggatcgatgc tgctgccttc
actggtctga ccctcctgga gcaactagat cttagtgata
atgcacagct tcatgtcgtg gaccctacca cgttccacgg
cctgggccac ctgcacacac tgcacctaga ccgatgtggc
ctgcgggagc tgggtcccgg cctattccgt ggactagcag
ctctgcagta cctctaccta caagacaaca atctgcaggc
actccctgac aacacctttc gagacctggg caacctcacg
catctctttc tgcatggcaa ccgtatcccc agtgtgcctg
agcacgcttt ccgtggcctg cacagtcttg accgcctcct
cttgcaccag aaccatgtgg ctcgtgtgca cccacatgcc
ttccgggacc ttggccgcct catgaccctc tacctgtttg
```

-continued

```
ccaacaacct ctccatgctg cctgcagagg tcctaatgcc
cctgaggtct ctgcagtacc tgcgactcaa tgacaacccc
tgggtgtgtg actgccgggc acgtccactc tgggcctggc
tgcagaagtt ccgaggttcc tcatcagagg tgccctgcaa
cctgccccaa cgcctggcag accgtgatct taagcgcctc
gctgccagtg acctagaggg ctgtgctgtg gcttcaggac
ccttccgtcc catccagacc agtcagctca ctgatgagga
gctgctgagc ctccccaagt gctgccagcc agatgctgca
gacaaagcct cagtactgga acccgggagg ccagcttctg
ccggaaacgc cctcaaggga cgtgtgcctc ccggtgacac
tccaccaggc aatggctcag gccctcggca catcaatgac
tctccatttg gaactttgcc cagctctgca gagcccccac
tgactgccct gcggcctggg ggttccgagc caccaggact
tcccaccact ggtccccgca ggaggccagg ttgttcccgg
aagaatcgca cccgcagcca ctgccgtctg ggccaggcgg
gaagtggggc cagtggaaca ggggacgcag agggttcagg
ggctctgcct gctctggcct gcagccttgc tcctctgggc
cttgcactgg tactttggac agtgcttggg ccctgctgac
cagccaccag ccaccaggtg tgtgtacata tggggtctcc
ctccacgccg ccagccagag ccagggacag gctctgaggg
gcaggccagg ccctccctga cagatgcctc cccaccagcc
cacccccatc tccaccccat catgtttaca gggttccggg
ggtggcgttt gttccagaac gccacctccc acccggatcg
cggtatatag agatatgaat tttattttac ttgtgtaaaa
tatcggatga cgtggaataa agagctcttt tcttaaaaaa
aaaaaaaaaa aa
```

The human Nogo receptor-2 polynucleotide is shown below as SEQ ID NO:84 and is accession number BK001302 in Genbank.

```
atgctgcccg ggctcaggcg cctgctgcaa gctcccgcct
cggcctgcct cctgctgatg ctcctggccc tgcccctggc
ggcccccagc tgccccatgc tctgcacctg ctactcatcc
ccgcccaccg tgagctgcca ggccaacaac ttctcctctg
tgccgctgtc cctgccaccc agcactcagc gactcttcct
gcagaacaac ctcatccgca cgctgcggcc aggcaccttt
gggtccaacc tgctcaccct gtggctcttc tccaacaacc
tctccaccat ctacccgggc actttccgcc acttgcaagc
cctggaggag ctggacctcg gtgacaaccg gcacctgcgc
tcgctggagc ccgacacctt ccagggcctg gagcggctgc
agtcgctgca tttgtaccgc tgccagctca gcagcctgcc
```

-continued

```
cggcaacatc ttccgaggcc tggtcagcct gcagtacctc
tacctccagg agaacagcct gctccaccta caggatgact
tgttcgcgga cctggccaac ctgagccacc tcttcctcca
cgggaaccgc ctgcggctgc tcacagagca cgtgtttcgc
ggcctgggca gcctggaccg gctgctgctg cacgggaacc
ggctgcaggg cgtgcaccgc gcggccttcc gcggcctcag
ccgcctcacc atcctctacc tgttcaacaa cagcctggcc
tcgctgcccg gcgaggcgct cgccgacctg ccctcgctcg
agttcctgcg gctcaacgct aacccctggg cgtgcgactg
ccgcgcgcgg ccgctctggg cctggttcca gcgcgcgcgc
gtgtccagct ccgacgtgac ctgcgccacc cccccggagc
gccagggccg agacctgcgc gcgctccgcg aggccgactt
ccaggcgtgt ccgcccgcgg cacccacgcg gccgggcagc
cgcgcccgcg gcaacagctc ctccaaccac ctgtacgggg
tggccgaggc cggggcgccc ccagccgatc cctccaccct
ctaccgagat ctgcctgccg aagactcgcg ggggcgccag
ggcggggacg cgcctactga ggacgactac tggggggggct
acgggggtga ggaccagcga ggggagcaga tgtgccccgg
cgctgcctgc caggcgcccc cggactcccg aggccctgcg
ctctcggccg ggctccccag ccctctgctt tgcctcctgc
tcctggtgcc ccaccacctc tga
```

The mouse Nogo receptor-2 polynucleotide is shown below as SEQ ID NO:85 and is accession number NM_199223 in Genbank.

```
atgctgcccg ggctccggcg cctgctgcaa ggtcctgcct
cagcctgcct actgctgaca ctcctggccc ttccttccgt
gacccccagc tgtcctatgc tctgcacctg ctactcctcc
ccgcccaccg tgagctgcca ggccaacaac ttctcctcag
tgccgctgtc cttgccaccc agtacacaga gactcttctt
gcagaacaac ctcatccgct cactgcggcc aggcaccttt
gggcccaacc tgctcaccct gtggctcttc tccaacaacc
tctccaccat ccaccctggc accttccgcc acctgcaggc
cctagaagaa ctggacctcg gtgacaaccg gcacctgcgc
tccctggagc ccgacacctt ccagggtctg gagaggctgc
agtcactaca cctgtatcgt tgccagctca gcagcctgcc
tggcaacatt ttccgaggct tggtcagcct acagtacctc
tacctccagg agaacagcct gctccatcta caggatgact
tgttcgcgga cctggccaac ctgagccacc tcttcctcca
cgggaaccgc ctgcggctgc tcacggagca cgtgttccgc
ggcttgggca gcctggaccg gctgttgctg cacgggaacc
ggctgcaggg cgtgcaccgc gcggctttcc acggcctcag
```

-continued

```
ccgcctcacc atcctctacc tgttcaacaa cagcctggcc
tcgctgccgg gagaggcgct ggccgacctg ccggcgctcg
agttcctgcg gctcaacgcc aacccctggg cgtgcgactg
ccgcgctcgg ccgctctggg cttggttcca gcgcgcgcgg
gtgtccagct ccgacgtgac ctgcgccacc ccgcccgagc
gccagggccg ggacctgcgc gcgctgcgcg actccgattt
ccaagcgtgc ccgccgccca cgcccacgcg gccgggcagc
cgcgcccgcg gcaacagctc ttccaaccac ctgtacggcg
tggccgaggc tggcgctccc cccgcagacc cgtccacgct
ctaccgagat ctgcccgccg aggactcgcg ggggcgccag
ggcggggacg cgcccaccga ggacgactac tggggggggct
acggcggcga ggatcagcgg ggcgagcaga cgtgtcccgg
ggccgcgtgc caggcgcccg cagactcgcg tggccccgcg
ctctcggccg ggctgcgcac ccctctgctc tgcctcttgc
ccctggcgct ccatcacctctga
```

The human Nogo receptor-3 polynucleotide is shown below as SEQ ID NO:86 and is accession number BK001305 in Genbank.

```
atgcttcgca aagggtgctg tgtggagttg ctgctgctgt
tggtagctgc ggagctgccc ctgggtggtg gctgcccacg
ggactgtgtg tgctacccgg cgcccatgac ggtcagctgc
caggcgcaca actttgcagc catcccggag ggcatccccg
tggacagcga gcgcgtcttc ctgcagaaca accgcatcgg
cctcctccag cccggccact tcagccccgc catggtcacc
ctgtggatct actcgaacaa catcacctac atccacccca
gcaccttcga gggcttcgtg cacctggagg agctggacct
cggcgacaac cggcagctgc ggacgctggc acccgagacc
ttccagggcc tggtgaagct tcacgccctc tacctctaca
agtgtgggct cagcgccttg ccggccggcg tctttggcgg
cctgcacagc ctgcagtacc tctacctgca ggacaaccac
atcgagtacc tccaggacga catcttcgtg gacctggtca
acctcagcca cctgtttctc cacggcaaca agctgtggag
tctgggcccg ggcaccttcc ggggcctggt gaacctggac
cgtcttttgc tgcacgagaa ccagctgcag tgggtccacc
acaaggcatt ccacgacctc cgcaggctga ccaccctctt
cctcttcaac aacagcctct cggagctgca gggtgagtgc
ctggccccgc tgggggccct ggagttcctc cgcctcaatg
gcaacccctg ggactgtggt tgtcgcgcgc gctccctgtg
ggaatggctg cagaggttcc ggggctccag ctccgctgtc
ccctgtgtgt cccctgggct gcggcacggc caggacctga
```

-continued

```
agctgctgag ggccgaggac ttccggaact gcacgggacc
agcgtccccg caccagatca agtcacacac gctcaccacc
accgacaggg ccgcccgcaa ggaacaccac tcaccccacg
gcccccaccag gagcaagggc cacccgcacg gccccggcc
cggccacagg aagccgggga agaactgcac caaccccagg
aaccgcaatc agatctctaa ggcgggcgcc gggaaacagg
cccccgagct gccagactat gccccagact accagcacaa
gttcagtttt gacatcatgc ctacggcccg gcccaagagg
aagggcaagt gtgcccgcag gacccccatc cgtgccccca
gcggggtgca gcaggcctcc tcggccagtt ccctgggggc
ctccctcctg gcctggacac tggggctggc ggtcactctc cgctga
```

The mouse Nogo receptor-3 polynucleotide is shown below as SEQ ID NO:8 and is accession number BK001304 in Genbank.

```
atgcttcgca aagggtgctg tgtggaattg ctgctgttgc
tgctcgctgg agagctacct ctgggtggtg gttgtcctcg
agactgtgtg tgctaccctg cgcccatgac tgtcagctgc
caggcacaca actttgctgc catcccggag ggcatcccag
aggacagtga gcgcatcttc ctgcagaaca atcgcatcac
cttcctccag cagggccact tcagccccgc catggtcacc
ctctggatct actccaacaa catcactttc attgctccca
acaccttcga gggctttgtg catctggagg agctagacct
tggagacaac cgacagctgc gaacgctggc acccgagacc
ttccaaggcc tggtgaagct tcacgccctc tacctctata
agtgtggact gagcgccctg cccgcaggca tctttggtgg
cctgcacagc ctgcagtatc tctacttgca ggacaaccat
atcgagtacc tccaagatga catctttgtg gacctggtca
atctcagtca cttgtttctc catggtaaca agctatggag
cctgggccaa ggcatcttcc ggggcctggt gaacctggac
cggttgctgc tgcatgagaa ccagctacag tgggttcacc
acaaggcttt ccatgacctc cacaggctaa ccaccctctt
tctcttcaac aacagcctca ctgagctgca gggtgactgt
ctggcccccc tggtggcctt ggagttcctt cgcctcaatg
ggaatgcttg ggactgtggc tgccgggcac gttccctgtg
ggaatggctg cgaaggttcc gtggctctag ctctgctgtc
ccctgcgcga cccccgagct gcggcaaggc caggatctga
agctgctgag ggtggaggac ttccggaact gcacaggacc
agtgtctcct caccagatca agtctcacac gcttaccacc
tctgacaggg ctgcccgcaa ggagcaccat ccgtcccatg
gggcctccag ggacaaaggc cacccacatg gccatccgcc
tggctccagg tcaggttaca agaaggcagg caagaactgc
```

-continued

```
accagccaca ggaaccggaa ccagatctct aaggtgagct

ctgggaaaga gcttaccgaa ctgcaggact atgcccccga

ctatcagcac aagttcagct ttgacatcat gcccaccgca

cgacccaaga ggaagggcaa gtgtgctcgc aggaccccca

tccgtgcccc cagtggggtg cagcaggcat cctcaggcac

ggcccttggg gccccactcc tggcctggat actggggctg

gcagtcactc tccgctga
```

NgR1 Polynucleotide Antagonists

Specific embodiments comprise NgR1 polynucleotide antagonists which prevent expression of NgR1 (knockdown). NgR1 polynucleotide antagonists include, but are not limited to antisense molecules, ribozymes, siRNA, shRNA and RNAi. Typically, such binding molecules are separately administered to the animal (see, for example, O'Connor, *J. Neurochem.* 56:560 (1991), but such binding molecules may also be expressed in vivo from polynucleotides taken up by a host cell and expressed in vivo. See also Oligodeoxynucleotides as Antisense Inhibitors of Gene Expression, CRC Press, Boca Raton, Fla. (1988).

Expression of the NgR gene can, in some embodiments, be inhibited using RNA interference ("RNAi"). RNAi refers to the expression of an RNA which interferes with the expression of the targeted mRNA. RNAi is a phenomenon in which the introduction of double-stranded RNA (dsRNA) into a cell causes degradation of the homologous mRNA. First discovered in the nematode *Caenorhabditis elegans*, RNAi has since been found to operate in a wide range of organisms. An "RNAi nucleic acid" as used herein is a nucleic acid sequence generally shorter than 50 nucleotides in length, that causes gene silencing at the mRNA level.

For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNA targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

Specifically, the RNAi silences a targeted gene via interacting with the specific mRNA (e.g. NgR1) through a siRNA (short interfering RNA). The ds RNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi. A sequence capable of inhibiting gene expression by RNA interference can have any length. For instance, the sequence can have at least 10, 15, 20, 25, 30, 35, 40, 45, 50, 100 or more consecutive nucleotides. The sequence can be dsRNA or any other type of polynucleotide, provided that the sequence can form a functional silencing complex to degrade the target mRNA transcript.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 18-25 nucleotide "small interfering" RNA duplexes (siRNAs). Accordingly, siRNA molecules are advantageously used in the methods of the present invention. siRNAs can be produced endogenously by degradation of longer dsRNA molecules by an RNase III-related nuclease called Dicer. (Bernstein et al., *Nature* 409:363-366, 2001). sIRNAs can also be introduced into a cell exogenously, or by transcription of an expression construct Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing. Without wishing to be bound by any particular theory, it is believed that a RISC is guided to a target mRNA, where the siRNA duplex interacts sequence-specifically to mediate cleavage in a catalytic fashion. (Bernstein et al., *Nature* 409:363-366, 2001; Boutla et al., *Curr Biol* 11:1776-1780, 2001). Cleavage of the mRNA takes place near the middle of the region bound by the siRNA strand. This sequence specific mRNA degradation results in gene silencing.

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., Nature 418:379-380, 2002) and HIV (Capodici et al., *J Immunol* 169:5196-5201, 2002), and reducing expression of oncogenes (e.g., the bar-abl gene; Scherr et al., *Blood* September 26 epub ahead of print, 2002). RNAi has been used to modulate gene expression in mammalian (mouse) and amphibian (*Xenopus*) embryos (respectively, Calegari et al., *Proc Natl Acad. Sci. USA* 99:14236-14240, 2002; and Zhou, et al., *Nucleic Acids Res* 30:1664-1669, 2002), and in postnatal mice (Lewis et al., *Nat Genet.* 32:107-108, 2002), and to reduce transgene expression in adult transgenic mice (McCaffrey et al., *Nature* 418:38-39, 2002). Methods have been described for determining the efficacy and specificity of siRNAs in cell culture and in vivo (see e.g., Bertrand et al., *Biochem Biophys Res Commun* 296:1000-1004, 2002; Lassus et al., *Sci STKE* 2002 (147):PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded

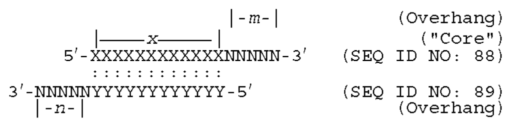

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n>1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al., *Proc. Natl. Acad. Sci. USA* 94:3279-3283, 1997). In addition, it has long been known that dsRNA activates the interferon cascade in mammalian cells, which can also lead to altered cell physiology (Colby et al., *Annu. Rev. Microbiol.* 25:333, 1971; Kleinschmidt et al., *Annu. Rev. Biochem.* 41:517, 1972; Lampson et al., *Proc. Natl. Acad. Sci. USA* 58:L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat. Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

In some embodiments, the invention provides that that siRNA or the shRNA inhibits NgR1 expression. In some embodiments, the invention further provides that the siRNA or shRNA is at least 80%, 90%, or 95% identical to the nucleotide sequence comprising: CUACUUCUCCCGCAGGCG (SEQ ID NO:52) or CCCGGACCGACGUCUUCAA (SEQ ID NO:54) or CUGACCACUGAGUCUUCCG (SEQ ID NO:56). In other embodiments, the siRNA or shRNA nucleotide sequence is CUACUUCUCCCGCAGGCG (SEQ ID NO:52) or CCCGGACCGACGUCUUCAA (SEQ ID NO:54) or CUGACCACUGAGUCUUCCG (SEQ ID NO:56).

In some embodiments, the invention further provides that the siRNA or shRNA nucleotide sequence is complementary to the mRNA produced by the polynucleotide sequence GATGAAGAGGGCGTCC GCT (SEQ ID NO:53) or GGGCCTGGCTGCAGAAGTT (SEQ ID NO:55) or GACTGGTGACTCAGAG AAGGC (SEQ ID NO:57).

In some embodiments of the invention, the shRNA is expressed from a lentiviral vector as described in Example 26.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., *Nature* 344:565 (1990); Picken et al., *Science* 253:314 (1991); Usman and Cedergren, *Trends in Biochem. Sci.* 17:334 (1992); Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, *TIBS.* 17:34 (1992); Usman et al., *Nucleic Acids Symp. Ser.* 31:163 (1994); Burgin et al., *Biochemistry* 35:14090 (1996)). Sugar modification of nucleic acid molecules have been extensively described in the art (see Eckstein et al., International Publication PCT No. WO 92/07065; Perrault et al., *Nature* 344: 565-568 (1990); Pieken et al., *Science* 253: 314-317 (1991); Usman and Cedergren, *Trends in Biochem. Sci.* 17: 334-339 (1992); Usman et al., International Publication PCT No. WO 93/15187; Sproat, U.S. Pat. No. 5,334,711 and Beigelman et al., *J. Biol. Chem.* 270:25702 (1995); Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Karpeisky et al., 1998, *Tetrahedron Lett.* 39:1131 (1998); Earnshaw and Gait, *Biopolymers* (*Nucleic Acid Sciences*) 48:39-55 (1998); Verma and Eckstein, *Annu. Rev. Biochem.* 67:99-134 (1998);

and Burlina et al., *Bioorg. Med. Chem.* 5:1999-2010 (1997); all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siRNA nucleic acid molecules of the instant invention so long as the ability of siRNA to promote RNAi is cells is not significantly inhibited.

The invention features modified siRNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, Nucleic Acid Analogues: Synthesis and Properties, in Modern Synthetic Methods, VCH, 331-417 (1995), and Mesmaeker et al., Novel Backbone Replacements for Oligonucleotides, in Carbohydrate Modifications in Antisense Research, ACS, 24-39 (1994).

While chemical modification of oligonucleotide internucleotide linkages with phosphorothioate, phosphorothioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

siRNA molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., *Nucleic Acids Res.* 23:2677 (1995); Caruthers et al., *Methods in Enzymology* 211:3-19 (1992) (incorporated by reference herein)) have expanded the ability to modify nucleic acid molecules by introducing nucleotide modifications to enhance their nuclease stability, as described above.

Polynucleotides of the present invention can include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see, e.g., Lin and Matteucci, *J. Am. Chem. Soc.* 120:8531-8532 (1998). A single G-clamp analog substitution within an oligonucleotide can result in substantially enhanced helical thermal stability and mismatch discrimination when hybridized to complementary oligonucleotides. The inclusion of such nucleotides in polynucleotides of the invention results in both enhanced affinity and specificity to nucleic acid targets, complementary sequences, or template strands. Polynucleotides of the present invention can also include one or more (e.g., about 1, 2, 3, 4, 5, 6, 7, 8, 9, 10, or more) LNA "locked nucleic acid" nucleotides such as a 2,4'-C methylene bicyclo nucleotide (see, e.g., Wengel et al., International PCT Publication No. WO 00/66604 and WO 99/14226).

The present invention also features conjugates and/or complexes of siRNA molecules of the invention. Such conjugates and/or complexes can be used to facilitate delivery of siRNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

Therapeutic polynucleotides (e.g., siRNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

The present invention also provides for siRNA molecules having chemical modifications that maintain or enhance enzymatic activity of proteins involved in RNAi. Such nucleic acids are also generally more resistant to nucleases than unmodified nucleic acids. Thus, in vitro and/or in vivo the activity should not be significantly lowered.

Use of the polynucleotide-based molecules of the invention will lead to better treatment of the disease progression by affording the possibility of combination therapies (e.g., multiple siRNA molecules targeted to different genes; nucleic acid molecules coupled with known small molecule modulators; or intermittent treatment with combinations of molecules, including different motifs and/or other chemical or biological molecules). The treatment of subjects with siRNA molecules can also include combinations of different types of nucleic acid molecules, such as enzymatic nucleic acid molecules (ribozymes), allozymes, antisense, 2,5-A oligoadenylate, decoys, aptamers etc.

In another aspect, a siRNA molecule of the invention can comprise one or more 5' and/or a 3'-cap structures, for example on only the sense siRNA strand, antisense siRNA strand, or both siRNA strands.

By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moeity.

The 3'-cap can be selected from a group comprising, 4',5'-methylene nucleotide; 1-(beta-D-erythrofuranosyl) nucleotide; 4'-thio nucleotide, carbocyclic nucleotide; 5'-aminoalkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, *Tetrahedron* 49:1925 (1993); incorporated by reference herein).

Various modifications to nucleic acid siRNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes NgR1 may be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the NgR1 gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding NgR1, means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of NgR1. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Polynucleotides for use in the therapeutic methods disclosed herein, including aptamers described below, can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

An antisense oligonucleotide for use in the therapeutic methods disclosed herein may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydrohydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl) uracil, (acp3)w, and 2,6-diaminopurine.

An antisense oligonucleotide for use in the therapeutic methods disclosed herein may also comprise at least one modified sugar moiety selected from the group including, but not limited to, arabinose, 2-fluoroarabinose, xylulose, and hexose.

In yet another embodiment, an antisense oligonucleotide for use in the therapeutic methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641 (1987)). The oligonucleotide is a 2'-0-methylribonucleotide (Inoue et al., *Nucl. Acids Res.* 15:6131-6148 (1987)), or a chimeric RNA-DNA analogue (Inone et al., *FEBS Lett* 215:327-330 (1987)).

Polynucleotides of the invention, including aptamers may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448-7451 (1988)), etc.

Polynucleotide compositions for use in the therapeutic methods disclosed herein further include catalytic RNA, or a ribozyme (See, e.g., PCT International Publication WO 90/11364, published Oct. 4, 1990; Sarver et al., *Science* 247: 1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). Preferably, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and may be delivered to cells which express NgR1 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous NgR1 messages and inhibit translation. Since ribozymes unlike antisense molecules, are catalytic, a lower intracellular concentration is required for efficiency.

Aptamers

In another embodiment, the NgR1 antagonist for use in the methods of the present invention is an aptamer. An aptamer can be a nucleotide or a polypeptide which has a unique sequence, has the property of binding specifically to a desired target (e.g., a polypeptide), and is a specific ligand of a given target. Nucleotide aptamers of the invention include double stranded DNA and single stranded RNA molecules that bind to NgR1.

Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in e.g. U.S. Pat. Nos. 5,475,096, 5,580,737, 5,567,588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Nucleotide aptamers may be used, for example, as diagnostic tools or as specific inhibitors to dissect intracellular signaling and transport pathways (James (2001) Curr. Opin. Pharmacol. 1:540-546). The high affinity and specificity of nucleotide aptamers makes them good candidates for drug discovery. For example, aptamer antagonists to the toxin ricin have been isolated and have IC50 values in the nanomolar range (Hesselberth J R et al. (2000) J Biol Chem 275:4937-4942). Nucleotide aptamers may also be used against infectious disease, malignancy and viral surface proteins to reduce cellular infectivity.

Nucleotide aptamers for use in the methods of the present invention may be modified (e.g., by modifying the backbone or bases or conjugated to peptides) as described herein for other polynucleotides.

Using the protein structure of NgR1, screening for aptamers that act on NgR1 using the SELEX process would allow for the identification of aptamers that inhibit NgR1-mediated processes (e.g., NgR1-mediated inhibition of axonal regeneration).

Polypeptide aptamers for use in the methods of the present invention are random peptides selected for their ability to bind to and thereby block the action of NgR1. Polypeptide aptamers may include a short variable peptide domain attached at both ends to a protein scaffold. This double structural constraint greatly increases the binding affinity of the peptide aptamer to levels comparable to an antibody's (nanomolar range). See, e.g., Hoppe-Seyler F et al. (2000) *J Mol Med* 78(8):426-430. The length of the short variable peptide is typically about 10 to 20 amino acids, and the scaffold may be any protein which has good solubility and compacity properties. One non-limiting example of a scaffold protein is the bacterial protein Thioredoxin-A. See, e.g., Cohen B A et al. (1998) *PNAS* 95(24): 14272-14277.

Polypeptide aptamers are peptides or small polypeptides that act as dominant inhibitors of protein function. Peptide aptamers specifically bind to target proteins, blocking their functional ability (Kolonin et al. (1998) *Proc. Natl. Acad. Sci.* 95: 14,266-14,271). Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Nat. Acad. Sci.* 94:12,473-12,478) or by ribosome display (Hanes et al. (1997) *Proc Natl. Acad. Sci.* 94:4937-4942). They can also be isolated from phage libraries (Hoogenboom, H. R., et al. (1998) *Immunotechnology* 4:1-20) or chemically generated peptide libraries. Additionally, polypeptide aptamers may be selected using the selection of Ligand Regulated Peptide Aptamers (LiRPAs). See, e.g., Binkowski B F et al., (2005) *Chem & Biol* 12(7): 847-855, incorporated herein by reference. Although the difficult means by which peptide aptamers are synthesized makes their use more complex than polynucleotide aptamers, they have unlimited chemical diversity. Polynucleotide aptamers are limited because they utilize only the four nucleotide bases, while peptide aptamers would have a much-expanded repertoire (i.e., 20 amino acids).

Peptide aptamers for use in the methods of the present invention may be modified (e.g., conjugated to polymers or fused to proteins) as described for other polypeptides elsewhere herein.

Compositions

In some embodiments, the invention provides compositions comprising a polypeptide selected from the group consisting of SEQ ID NOs: 1-5, 26-27, 29-37 and 41-45.

In some embodiments, the invention provides compositions comprising an anti-Nogo receptor-1 antibody or an antigen-binding fragment thereof, or a soluble Nogo receptor-1 polypeptide or fusion protein of the present invention.

In some embodiments, the invention provides a composition comprising a polynucleotide of the present invention.

In some embodiments, the invention provides compositions comprising a polypeptide of the present invention and an anti-inflammatory agent.

In some embodiments, the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the molecules of this invention for delivery into the cell. Exemplary "pharmaceutically acceptable carriers" are any and all solvents, dispersion media, coatings, antibacterial and antifungal agents, isotonic and absorption delaying agents, and the like that are physiologically compatible, water, saline, phosphate buffered saline, dextrose, glycerol, ethanol and the like, as well as combinations thereof. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the antibodies, antigen-binding fragments, soluble Nogo receptors or fusion proteins of the invention.

Compositions of the invention may be in a variety of forms, including, for example, liquid, semi-solid and solid dosage forms, such as liquid solutions (e.g., injectable and infusible solutions), dispersions or suspensions. The preferred form depends on the intended mode of administration and therapeutic application. In one embodiment, compositions are in the form of injectable or infusible solutions, such as compositions similar to those used for passive immunization of humans with other antibodies.

The composition can be formulated as a solution, micro emulsion, dispersion, liposome, or other ordered structure suitable to high drug concentration. Sterile injectable solutions can be prepared by incorporating an anti-Nogo receptor-1 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See e.g., *Sustained and Controlled Release Drug Delivery Systems*, J. R. Robinson, ed., Marcel Dekker, Inc., New York (1978).

Supplementary active compounds also can be incorporated into the compositions. In some embodiments, a Nogo receptor-1 antibody or an antigen-binding fragments thereof, or soluble Nogo receptor-1 polypeptides or fusion proteins of the invention are coformulated with and/or coadministered with one or more additional therapeutic agents, including, for example, an anti-inflammatory agent. In one embodiment, the anti-inflammatory agent is a non-steroidal anti-inflammatory agent. In another embodiment, the anti-inflammatory agent is a steroidal anti-inflammatory agent. In a particular embodiment, the anti-inflammatory agent is methylprednisolone.

In one embodiment, the present invention is directed to the use of a Nogo receptor antagonist in combination with a non-steroidal anti-inflammatory agent (NSAID), prodrug esters or pharmaceutically acceptable salts thereof. Examples of NSAIDs which are well-known in the art include propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxicam), salicylates (e.g., acetyl salicylic acid and sulfasalazine) and the pyrazolones (e.g., apazone, bezpiperylon, feprazone, mofebutazone, oxyphenbutazone and phenylbutazone); Structurally related NSAIDs having similar analgesic and anti-inflammatory properties to the NSAIDs are also intended to be encompassed by this group.

In another embodiment, the present invention is directed to the use of a Nogo receptor antagonist in combination with any of one or more steroidal anti-inflammatory agents such as corticosteroids, prodrug esters or pharmaceutically acceptable salts thereof. Non-limiting examples of such steroidal agents include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group. In one particular embodiment, the Nogo receptor antagonist is used in combination with methylprednisolone.

The pharmaceutical compositions of the invention may include a "therapeutically effective amount" or a "prophylactically effective amount" of an antibody, antigen-binding fragment, polypeptide(s), or fusion protein of the invention. A "therapeutically effective amount" refers to an amount effective, at dosages and for periods of time necessary, to achieve the desired therapeutic result. A therapeutically effective amount of the Nogo receptor-1 antibody or antigen-binding fragment thereof, soluble Nogo receptor-1 polypeptide or Nogo receptor fusion protein may vary according to factors such as the disease state, age, sex, and weight of the individual. A therapeutically effective amount is also one in which any toxic or detrimental effects of the antibody, antigen-binding fragment, soluble Nogo receptor-1 polypeptide or Nogo receptor fusion protein are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody, antigen-binding fragment, and soluble receptor-1 polypeptide or Nogo receptor fusion protein and the particular therapeutic or prophylactic effect to be achieved, and (b) the limitations inherent in the art of compounding such an antibody, antigen-binding fragment, and soluble receptor-1 polypeptide or Nogo receptor fusion protein for the treatment of sensitivity in individuals. In some embodiments a therapeutically effective dose range for Nogo receptor-1 antibodies or antigen-binding fragments thereof is 0.1-4 mg/Kg per day. In some embodiments a therapeutically effective dose range for Nogo receptor-1 antibodies or antigen-binding fragments thereof is 0.2-4 mg/Kg per day. In some embodiments a therapeutically effective dose range for Nogo receptor-1 antibodies or antigen-binding fragments thereof is 0.2 mg/Kg per day.

In the methods of the invention the NgR1 antagonists are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the NgR1 antagonist is administered. In some embodiments of the invention, the dosage is 0.01-1.0 mg/kg body weight per day. In some embodiments, the dosage is 0.001-0.5 mg/kg body weight per day.

For treatment with an NgR1 antagonist of the invention, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

In some methods, two or more NgR1 antagonists are administered simultaneously, in which case the dosage of each antagonist administered falls within the ranges indicated. Supplementary active compounds also can be incorporated into the compositions used in the methods of the invention. For example, an NgR1 antagonist may be coformulated with and/or coadministered with one or more additional therapeutic agents, such as an anti-inflammatory agent, for example, methylprednisolone.

The invention encompasses any suitable delivery method for an NgR1 antagonist to a selected target tissue, including bolus injection of an aqueous solution or implantation of a controlled-release system. Use of a controlled-release implant reduces the need for repeat injections.

The NgR1 antagonists used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-91 (1992); Gaspar et al., "Permanent 125I Implants for Recurrent Malignant Gliomas," *Int. J. Radiation Oncology Biol. Phys.* 43(5): 977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise an NgR1 antagonist of the invention dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments, an NgR1 antagonist of the invention is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer an NgR antagonist according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Uses of the Antibodies, Antigen-Binding Fragments, Soluble Receptors, Fusion Proteins, Polynucleotides and Compositions In some embodiments, the invention provides methods for inhibiting Nogo receptor-1 activity by administering anti-Nogo receptor-1 antibodies, antigen-binding fragments of such antibodies, soluble Nogo receptor-1 polypeptides, or fusion proteins comprising such polypeptides to a mammal in need thereof.

In some embodiments, the invention provides a method of inhibiting Nogo receptor-1 binding to a ligand, comprising the step of contacting Nogo receptor-1 with an antibody or antigen-binding fragment of this invention. In some embodiments, the ligand is selected from the group consisting of NogoA, NogoB, NogoC, MAG and OM-gp.

In some embodiments, the invention provides a method for inhibiting growth cone collapse in a neuron, comprising the step of contacting the neuron with the antibody or antigen-binding fragment thereof of this invention. In some embodiments, the invention provides a method for decreasing the inhibition of neurite outgrowth or sprouting in a neuron, comprising the step of contacting the neuron with the antibody or antigen-binding fragment of this invention. In some embodiments, the neuron is a CNS neuron. In some of these methods, the neurite outgrowth or sprouting is axonal growth.

In some embodiments, the invention provides a method of promoting survival of a neuron in a mammal, which neuron is at risk of dying, comprising (a) providing a cultured host cell expressing (i) an anti-Nogo receptor-1 antibody or antigen-binding fragment thereof; or (ii) a soluble Nogo receptor-1 polypeptide; and (b) introducing the host cell into the mammal at or near the site of the neuron. Almudena Ramon-Cueto, M Isabel Cordero, Fernando F Santos-Benito and Jesus Avila (2000) Functional recovery of paralegic rats and motor axon regeneration in their spinal cords by olfactory ensheathing cells. *Neuron* 25, 425-435.

In some embodiments, the invention provides a gene therapy method of promoting survival of a neuron at risk of dying, which neuron is in a mammal, comprising administering at or near the site of the neuron a viral vector comprising a nucleotide sequence that encodes (a) an anti-Nogo receptor-1 antibody or antigen-binding fragment thereof or (b) a soluble Nogo receptor-1 polypeptide, wherein the anti-Nogo receptor-1 antibody, antigen-binding fragment, or soluble Nogo receptor-1 polypeptide is expressed from the nucleotide sequence in the mammal in an amount sufficient to promote survival of the neuron. Viral vectors and methods useful for these embodiments are described in, e.g., Noël et al., *Human Gene Therapy,* 13:1483-93 (2002).

In some embodiments, the invention provides a method of inhibiting Nogo receptor-1 binding to a ligand, comprising the step of contacting the ligand with the soluble Nogo receptor-1 polypeptide or the Nogo receptor-1 fusion protein of this invention.

In some embodiments, the invention provides a method of modulating an activity of a Nogo receptor-1 ligand, comprising the step of contacting the Nogo receptor-1 ligand with a soluble Nogo receptor-1 polypeptide or a Nogo receptor-1 fusion protein of the invention.

In some embodiments, the invention provides a method for inhibiting growth cone collapse in a neuron, comprising the step of contacting a Nogo receptor-1 ligand with a soluble Nogo receptor-1 polypeptide or a Nogo receptor-1 fusion protein of this invention. In some embodiments, the invention provides a method for decreasing the inhibition of neurite outgrowth or sprouting in a neuron, comprising the step of contacting a Nogo receptor-1 ligand with the soluble Nogo receptor-1 polypeptide or the Nogo receptor-1 fusion protein of this invention. In some embodiments, the neuron is a CNS neuron. In some embodiments, the ligand is selected from the group consisting of NogoA, NogoB, NogoC, MAG and OM-gp. In some embodiments, the neurite outgrowth or sprouting is axonal growth.

In some embodiments, the invention provides a method for promoting neurite outgrowth comprising contacting a neuron with a polypeptide, a polynucleotide, or a composition of the invention. In some embodiments, the polypeptide, polynucleotide or composition inhibits neurite outgrowth inhibition. In some embodiments, the neuron is in a mammal. In some embodiments, the mammal is a human.

In some embodiments, the invention provides a method of inhibiting signal transduction by the NgR1 signaling complex, comprising contacting a neuron with an effective amount of a polypeptide, a polynucleotide, or a composition of the invention. In some embodiments, the neuron is in a mammal. In some embodiments, the mammal is a human.

In some embodiments, the invention provides a method of treating a central nervous system (CNS) disease, disorder, or injury in a mammal, comprising administering to a mammal in need of treatment an effective amount of a polypeptide, a polynucleotide, or a composition of the present invention. In some embodiments, the disease, disorder, or injury is multiple sclerosis, ALS, Huntington's disease, Alzheimer's disease, Parkinson's disease, diabetic neuropathy, stroke, traumatic brain injuries, spinal cord injury, optic neuritis, glaucoma, hearing loss, and adrenal leukodystrophy.

Any of the types of antibodies or receptors described herein may be used therapeutically. In some embodiments, the anti-Nogo receptor-1 antibody is a human antibody. In some embodiments, the mammal is a human patient. In some embodiments, the antibody or antigen-binding fragment thereof is administered to a non-human mammal expressing a Nogo receptor-1 with which the antibody cross-reacts (e.g., a primate, cynomologous or rhesus monkey) for veterinary purposes or as an animal model of human disease. Such animal models may be useful for evaluating the therapeutic efficacy of antibodies of this invention.

In some embodiments, administration of anti-Nogo receptor-1 antibody or antigen-binding fragment, or soluble Nogo receptor-1 polypeptide or fusion protein is used to treat a spinal cord injury to facilitate axonal growth throughout the injured site.

The anti-Nogo receptor-1 antibodies or antigen-binding fragments, or soluble Nogo receptor-1 polypeptides or fusion proteins of the present invention can be provided alone, or in combination, or in sequential combination with other agents that modulate a particular pathological process. For example, anti-inflammatory agents may be co-administered following stroke as a means for blocking further neuronal damage and inhibition of axonal regeneration. As used herein, the Nogo receptor-1 antibodies, antigen-binding fragments, soluble Nogo receptor-1 and Nogo receptor fusion proteins, are said to be administered in combination with one or more additional therapeutic agents when the two are administered simultaneously, consecutively or independently.

The anti-Nogo receptor-1 antibodies, antigen-binding fragments, soluble Nogo receptor-1 polypeptides, Nogo receptor-1 fusion proteins of the present invention can be administered via parenteral, subcutaneous, intravenous, intramuscular, intraperitoneal, transdermal, inhalational or buccal routes. For example, an agent may be administered locally to a site of injury via microinfusion. Typical sites include, but are not limited to, damaged areas of the spinal cord resulting from injury. The dosage administered will be dependent upon the age, health, and weight of the recipient, kind of concurrent treatment, if any, frequency of treatment, and the nature of the effect desired.

The compounds of this invention can be utilized in vivo, ordinarily in mammals, such as humans, sheep, horses, cattle, pigs, dogs, cats, rats and mice, or in vitro.

Vectors of the Invention

In some embodiments, the invention provides recombinant DNA molecules (rDNA) that contain a coding sequence. As used herein, a rDNA molecule is a DNA molecule that has been subjected to molecular manipulation. Methods for generating rDNA molecules are well known in the art, for example, see Sambrook et al., *Molecular Cloning—A Laboratory Manual*, Cold Spring Harbor Laboratory Press (1989). In some rDNA molecules, a coding DNA sequence is operably linked to expression control sequences and vector sequences.

In some embodiments, the invention provides vectors comprising the nucleic acids encoding the polypeptides of the invention. The choice of vector and expression control sequences to which the nucleic acids of this invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable or selectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Examples of such vector plasmids are pUC8, pUC9, pBR322 and pBR329 (Bio-Rad® Laboratories), pPL and pKK223 (Pharmacia). Any suitable prokaryotic host can be used to express a recombinant DNA molecule encoding a protein of the invention.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Examples of such vectors are pSVL and pKSV-10 (Pharmacia), pBPV-1, pML2d (International Biotechnologies), pTDT1 (ATCC® 31255) and other eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., *J. Mol. Anal. Genet.* 1:327-341 (1982)). Alternatively, the selectable marker can be present on a separate plasmid, the two vectors introduced by co-transfection of the host cell, and transfectants selected by culturing in the appropriate drug for the selectable marker.

To express the antibodies, or antibody portions of the invention, DNAs encoding partial or full-length light and heavy chains are inserted into expression vectors such that the genes are operatively linked to transcriptional and translational control sequences. Expression vectors include plasmids, retroviruses, cosmids, YACs, EBV-derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In some embodiments, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can be easily inserted and expressed, as described above. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the immunogenic polypeptides, Nogo receptor-1 antibodies, antigen-binding fragments, soluble Nogo receptor-1 polypeptides and soluble Nogo receptor-1 fusion proteins of the present invention, the recombinant expression vectors of the invention carry regulatory sequences that control their expression in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al.

In one embodiment, a proprietary expression vector of Biogen IDEC, Inc., referred to as NEOSPLA (U.S. Pat. No. 6,159,730) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

Other embodiments of the invention use a lentiviral vector for expression of the polynucleotides of the invention, e.g., NgR antagonist polynucleotides, e.g., siRNA molecules. Lentiviruses can infect noncycling and postmitotic cells, and also provide the advantage of not being silenced during development allowing generation of transgenic animals through infection of embryonic stem cells. Milhavet et al., *Pharmacological Rev.* 55:629-648 (2003). Other polynucleotide expressing viral vectors can be constructed based on, but not limited to, adeno-associated virus, retrovirus, adenovirus, or alphavirus.

Transcription of the polynucleotides of the invention, e.g., siRNA molecule sequences can be driven from a promoter for eukaryotic RNA polymerase I (pol I), RNA polymerase II (pol II), or RNA polymerase II (pol III). Transcripts from pol II or pol II promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, *Proc. Natl. Acad. Sci. USA* 87:6743-7 (1990); Gao and Huang, *Nucleic Acids Res.* 21:2867-72 (1993); Lieber et al., *Methods Enzymol.* 217:47-66 (1993); Zhou et al., *Mol. Cell. Biol.* 10:4529-37 (1990)). Several investigators have demonstrated that polynucleotides expressed from such promoters can function in mammalian cells (e.g. Kashani-Sabet et al., *Antisense Res. Dev.* 2:3-15 (1992); Ojwang et al., *Proc. Natl. Acad. Sci. USA* 89:10802-6 (1992); Chen et al., *Nucleic Acids Res.* 20:4581-9 (1992); Yu et al., *Proc. Natl. Acad. Sci. USA* 90:6340-4 (1993); L'Huillier et al., *EMBO J.* 11:4411-8 (1992); Lisziewicz et al., *Proc. Natl. Acad. Sci. U.S.A* 90:8000-4 (1993); Thompson et al., *Nucleic Acids Res.* 23:2259 (1995); Sullenger & Cech, *Science* 262:1566 (1993)). More specifically, transcription units such as the ones derived from genes encoding U6 small nuclear (snRNA), transfer RNA (tRNA) and adenovirus VA RNA are useful in generating high concentrations of desired RNA molecules such as siRNA in cells (Thompson et al., supra; Couture and Stinchcomb, 1996, supra; Noonberg et al., *Nucleic Acid Res.* 22:2830 (1994); Noonberg et al., U.S. Pat. No. 5,624,803; Good et al., *Gene Ther.* 4:45 (1997); Beigelman et al., International PCT Publication No. WO 96/18736. The siRNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In addition to the heterologous genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

Host Cells and Methods of Recombinantly Producing Protein of the Invention

Nucleic acid molecules encoding anti-Nogo receptor-1 antibodies, immunogenic peptides, soluble Nogo receptor-1 polypeptides, soluble Nogo receptor-1 fusion proteins of this invention and vectors comprising these nucleic acid molecules can be used for transformation of a suitable host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of appropriate cell hosts with a rDNA molecule of the present invention is accomplished by well known methods that typically depend on the type of vector used and host system employed. With regard to transformation of prokaryotic host cells, electroporation and salt treatment methods can be employed (see, for example, Sambrook et al., *Molecular Cloning—A Laboratory Manual*, Cold Spring Harbor Laboratory Press (1989); Cohen et al., *Proc. Natl. Acad. Sci. USA* 69:2110-2114 (1972)). With regard to transformation of vertebrate cells with vectors containing rDNA, electroporation, cationic lipid or salt treatment methods can be employed (see, for example, Graham et al., *Virology* 52:456-467 (1973); Wigler et al., *Proc. Natl. Acad. Sci. USA* 76:1373-1376 (1979)).

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503-517 (1975) or the proteins produced from the cell may be assayed by an immunological method.

Host cells for expression of a polypeptide or antibody of the invention for use in a method of the invention may be prokaryotic or eukaryotic. Mammalian cell lines available as hosts for expression are well known in the art and include many immortalized cell lines available from the American Type Culture Collection (ATCC®). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other useful eukaryotic host cells include plant cells. Other cell lines that may be used are insect cell lines, such as Sf9 cells. Exemplary prokaryotic host cells are *E. coli* and *Streptomyces.*

When recombinant expression vectors encoding the immunogenic polypeptides, Nogo receptor-1 antibodies or antigen-binding fragments, soluble Nogo receptor-1 polypeptides and soluble Nogo receptor-1 fusion proteins of the invention are introduced into mammalian host cells, they are produced by culturing the host cells for a period of time sufficient to allow for expression of the antibody, polypeptide and fusion polypeptide in the host cells or, more preferably, secretion of the immunogenic polypeptides, Nogo receptor-1 antibodies or antigen-binding fragments, soluble Nogo receptor-1 polypeptides and soluble Nogo receptor-1 fusion proteins of the invention into the culture medium in which the host cells are grown. Immunogenic polypeptides, Nogo receptor-1 antibodies or antigen-binding fragments, soluble Nogo receptor-1 polypeptides and soluble Nogo receptor-1 fusion proteins of the invention can be recovered from the culture medium using standard protein purification methods.

Further, expression of immunogenic polypeptides, Nogo receptor-1 antibodies or antigen-binding fragments, soluble Nogo receptor-1 polypeptides and soluble Nogo receptor-1 fusion proteins of the invention of the invention (or other moieties therefrom) from production cell lines can be enhanced using a number of known techniques. For example, the glutamine synthetase gene expression system (the OS system) is a common approach for enhancing expression under certain conditions. The GS system is discussed in whole or part in connection with European Patent Nos. 0 216 846, 0 256 055, and 0 323 997 and European Patent Application No. 89303964.4.

Host Cells

The present invention further provides host cells transformed with a nucleic acid molecule that encodes a Nogo receptor-1 antibody, antigen-binding fragment, soluble Nogo receptor-1 polypeptide and/or soluble Nogo receptor-1 fusion protein of the invention. The host cell can be either prokaryotic or eukaryotic. Eukaryotic cells useful for expression of a protein of the invention are not limited, so long as the cell line is compatible with cell culture, methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Examples of useful eukaryotic host cells include Chinese hamster ovary (CHO) cells available from the ATCC® as CCL61, NIH Swiss mouse embryo cells NIH-3T3 available from the ATCC as CRL1658, baby hamster kidney cells (BHK), and the like eukaryotic tissue culture cell lines.

Other useful eukaryotic host cells include plant cells. Other cell lines that may be used are insect cell lines, such as Sf9 cells. Exemplary prokaryotic host cells are *E. coli* and *Streptomyces*.

Production of Recombinant Proteins Using a rDNA Molecule

The present invention further provides methods for producing an a Nogo receptor-1 antibody or antigen-binding fragment, soluble Nogo receptor-1 polypeptide and/or soluble Nogo receptor-1 fusion protein of the invention using nucleic acid molecules herein described. In general terms, the production of a recombinant form of a protein typically involves the following steps:

First, a nucleic acid molecule is obtained that encodes a protein of the invention. If the encoding sequence is uninterrupted by introns, it is directly suitable for expression in any host.

The nucleic acid molecule is then optionally placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

It will be readily apparent to one of ordinary skill in the relevant arts that other suitable modifications and adaptations to the methods and applications described herein are obvious and may be made without departing from the scope of the invention or any embodiment thereof. In order that this invention may be better understood, the following examples are set forth. These examples are for purposes of illustration only and are not to be construed as limiting the scope of the invention in any manner.

EXAMPLE 1

Production of Murine Monoclonal Anti-Nogo Receptor-1 Antibodies

Anti-Nogo receptor-1 antibodies that specifically bind an immunogenic Nogo receptor-1 polypeptide of the invention were made using the following methods and procedures.

Immunizations

Two immunization approaches were used:

1. COS-7 Cells or Cell Membranes Containing Nogo Receptor-1 (NogoR-1) as the Immunogen The rat Nogo receptor-1 gene (GenBank™ No. AF 462390) was subcloned into the mammalian expression vector pEAG1256 (Biogen®) that contained the CMV promotor and geneticin resistance gene for drug selection. The recombinant plasmid was transfected into COS-7 cells using Superfect (Qiagen®). Transfectants were selected using geneticin (Gibco™, 2 mg/ml), cloned and verified for surface expression of Nogo receptor-1 protein by FACS. COS-7 membranes were prepared from these cells according to procedures as described [Wang et al., *J. Neurochem.* 75:1155-1161 (2000)] with two washings, and stored at 1 mg/ml [protein concentration] in 10% glycerol at −70° C.

Eight-week-old female RBF mice (Jackson Labs, Bar Harbor, Me.) were immunized intraperitoneally either with an emulsion containing 50 μg rat Nogo receptor-1-COS-7 membranes or whole COS-7 cells expressing Nogo receptor-1 on the surface and 50 μl RIBI MPL+TDM+CWS adjuvant (Sigma® Chemical Co., St. Louis, Mo.) once every two weeks (Lipman et al., 1992). Sera from the immunized mice were collected before the first immunization, 7 days after the second and third immunizations, and 38 days after the third immunization and the anti-Nogo receptor-1 antibody titers were measured by ELISA as described below.

2. Specific Nogo Receptor-1 Peptides as the Immunogen

Figure 2:
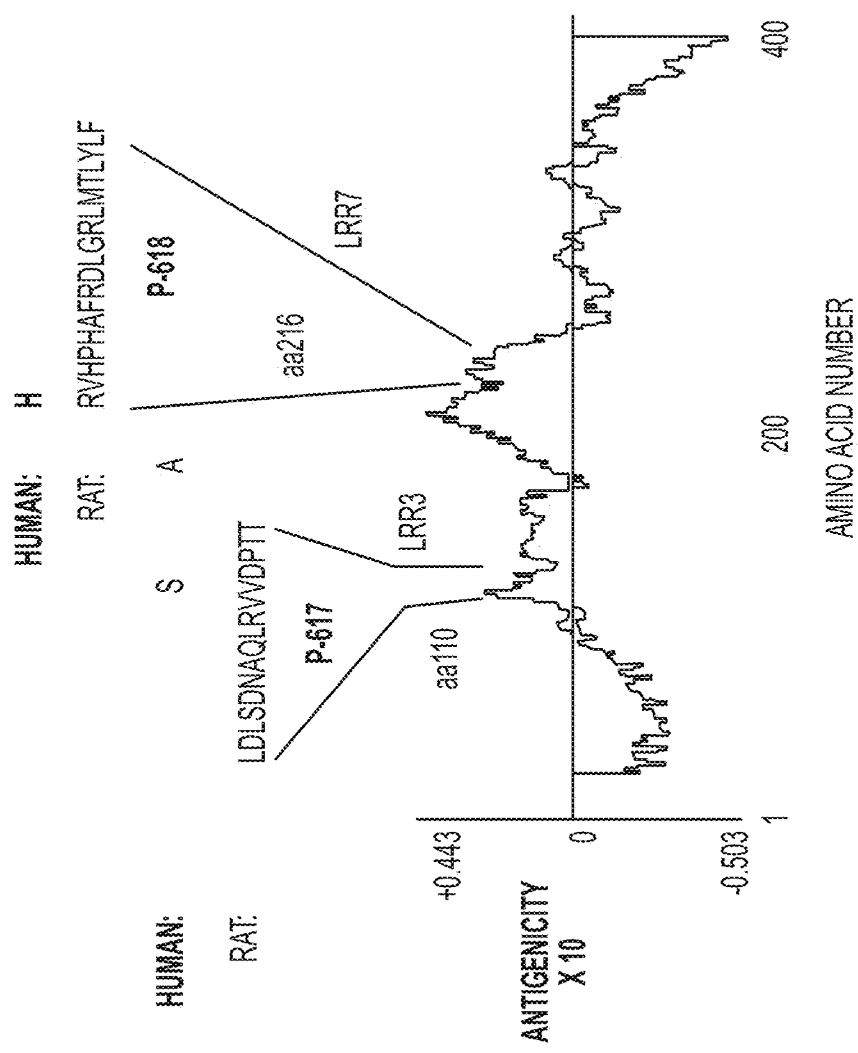
FIG. 2 depicts an antigenicity plot for the Nogo receptor-1 protein using the Vector Nti™ software. Rat P-617 is SEQ ID NO: 10 and rat P-618 is SEQ ID NO: 11. Human P-617 is SEQ ID NO:47 and human P-618 is SEQ ID NO:48.

The rat Nogo receptor-1 gene sequence was subjected to antigenicity analyses using Vector NTi™ software (FIG. 2). Antigenic peptides identified in the analyses were conjugated to Keyhole Limpet Hemocyanin (KLH) using standard glutaraldehyde procedures.

Eight-week-old female RBF mice (Jackson Labs, Bar Harbor, Me.) were immunized intraperitoneally with an emulsion containing 50 μg KLH-conjugated peptides and 50 μl complete Freund's adjuvant (Sigma® Chemical Co., St. Louis, Mo.) once every two weeks. Serum from the immunized mice was collected before the first immunization and 1 week after the second and third immunizations and anti-Nogo receptor-1 antibody titers were measured. A booster dose was given after the third immunization. Three days after this booster dose immunization, fusion experiments were initiated.

Hybridoma Production and Screening

Sera from mice immunized with antigenic Nogo receptor-1 peptides were screened by ELISA whereas sera from mice immunized with COS-7 cells expressing Nogo receptor-1 were screened by flow cytometry. Mice that were positive for antibodies that specifically bound Nogo receptor-1-COS-7 cells were identified by flow cytometry and were sacrificed. Splenocytes were isolated from the mice and fused to the FL653 myeloma (an APRT-derivative of a Ig-/HGPRT-Balb/c mouse myeloma, maintained in DMEM containing 10% FBS, 4500 mg/L glucose, 4 mM L-glutamine, and 20 mg/ml 8-azaguanine) as described (Kennett et al., *Monoclonal Antibodies: A New Dimension in Biological Analysis*, Plenum Press, New York (1993)). Fused cells were plated into 24- or 48-well plates (Corning Glass Works, Corning, N.Y.), and fed with adenine, aminopterin and thymidine containing culture media. AAT resistant cultures were screened by ELISA or flow cytometry for binding to either Nogo receptor-1-COS-7 cells or to a Nogo receptor-1 antigenic peptide as described below. Cells in the positive wells were further subcloned by limiting dilution.

To screen for antibody binding to a Nogo receptor-1 antigenic peptide, the peptides that were used as immunogens were conjugated to BSA. 0.5 μg of the conjugated peptide in 50 μl of 0.1 M sodium bicarbonate buffer, pH 9.0 was added to each well of a 96-well MaxiSorp™ plate (Nunc™). The plate was then incubated at 37° C. for 1 hour or 4° C. for 16 hours and non-specific binding sites were blocked using 25 mM HEPES, pH 7.4 containing 0.1% BSA, 0.1% ovalbumin, 0.1% blotto and 0.001% azide. Hybridoma supernatant was added and incubated at 25° C. for 1 hour. After washing three times with PBS, 50 d of a 1:10,000 dilution of horseradish peroxidase-conjugated goat anti-mouse secondary antibody (Jackson ImmunoResearch Inc.) was added to each well and incubated further for 1 hour. After three washings, color was developed by TMB (Pierce) and stopped with 2 M sulphuric acid. Color intensity was monitored in a spectrophotometer at 450 nm.

Antibodies were screened for binding to full length Nogo receptor-1 as follows. COS-7 cells were labeled with 0.1 uM CellTracker™ Green CMFDA (Molecular Probes, Eugene, Oreg.) as described by the vendor. Equal volumes of CellTracker™ labeled control cells were mixed with washed Nogo receptor-1-COS-7 cells before incubation with anti-Nogo receptor-1 test sera. Fifty microliters of the cell mixture was dispensed into each well of a 96-well V-bottom polystyrene plates (Costar 3877, Corning, N.Y.) and 100 μl of hybridoma supernatant or a control anti-Nogo receptor-1 antibody was added. After incubation at 4° C. for 30 minutes, the cells were washed and incubated with 50 μl of R-phycoerythrin-conjugated affinity pure F(ab')2 fragment goat anti-mouse IgG Fc gamma specific second antibody (1:200, Jackson ImmunoResearch Laboratory, West Grove, Pa.) in PBS. At the end of the incubation, the cells were washed twice with PBS and suspended in 200 μl of PBS containing 1% FBS, and subjected to FACS analyses. Alternately, Nogo receptor-1-COS-7 cells were mixed with hybridoma supernatant and then treated with R-phycoerythrin-conjugated goat anti-mouse secondary antibody and directly subjected to standard FACS analyses.

We generated 25 anti-Nogo receptor-1 antibodies using a variety of immunogens. We generated two antibodies, 7E11 and 5B10, using a peptide sequence corresponding to rat Nogo receptor-1 residues 110-125 as the immunogen. We generated three antibodies, 1H2, 3G5 and 2F7, using membranes prepared from COS7 cells transfected with full length rat Nogo receptor-1 as the immunogen. We generated 13 antibodies using sNogoR310-Fc as the immunogen (1D9.3, 1E4.7, 1B4.3, 2C4.3, 1F10.3, 2H1.4, 1H3.3, 1G4.1, 1E4.1, 2G7.1, 2C4.1, 2F11.1, and 1H4.1) and 7 antibodies using a peptide sequence corresponding to rat Nogo receptor-1 residues 423-434 as the immunogen (2E8.1, 2G11.2, and 1B5.1).

Sequence Analysis of Monoclonal Antibodies 7E11 and 5B10

We extracted total RNA using Qiagen® RNeasy® mini kit, and generated cDNA from the isolated RNA. We amplified the light chain sequence by PCR using primers 5'-TGAGGAGACGGTGACCGTGGTCCCTTGGCCCCAG-3' (SEQ ID NO: 12) and 5'-AGGTSMARCTGCAGSAGTCWGG-3' (SEQ ID NO: 25). We amplified the heavy chain sequence by PCR using primers 5'-GGGGATATCCACCATGAAGTTGCCTGTTAGGCTGTTG-3' (SEQ ID NO: 13) and 5'-GGGGGATATCCACCATGAGGKCCCCWGCTCAGYTYCTKGGA-3' (SEQ ID NO. 14). These primers comprise degenerate nucleotides as follows: S represents G or C; M represents A or C, R represents G or A; W represents A or T; K represents G or T; and Y represents T or C. We cloned the PCR fragments into a sequencing vector and determined the DNA sequence of the CDRs by dideoxychain termination using primers specific for the sequencing vector. We conceptually translated the DNA sequences and partial amino acid sequences of the CDR regions of the heavy of light chains of the monoclonal antibodies 7E11 and 5B10 are shown in Table 2. The 3 CDRs from the heavy and light chains of the mAbs are underlined in Table 2. The light chains of 7E11 and 5B10 have 94% amino acid sequence identity and the heavy chains have 91% amino acid sequence identity. mAbs 7E11, 5110, and 1H2 are of the IgG1 isotype and mAbs 3G5 and 2F7 are of the IgG2a isotype. Each of these five mAbs has a light chain of the kappa isotype. We analyze the sequence of the other monoclonal antibodies by this approach.

TABLE 2

AMINO ACID SEQUENCE OF MABS 7E11 AND 5B10

| | Sequence | SEQ ID NO: |
|---|---|---|
| 7E11 Light Chain | MKLPVRLLVLMFWIPASSSDVVMTQTPLSLPVSLGDQASISCR<br>SSQSLVHSNGNTYLHWYLQKPGQSPKLLIYKVSNRFSGVPDR<br>FSGSGSGTDFTLKISRVDAEDLGVYFCSQSTHVPFTFGGGTKL<br>EIKRADAAPTVSISHH | 15 |
| 5B 10 Light | MKLPVRLLVLMFWIPASSSDVVMTQTPLSLPVSLGDQASISCR<br>SSQSLVHSNGYTYLHWYLQRPGQSPKLLIYKVSNRFSGVPDR | 16 |

TABLE 2-continued

| AMINO ACID SEQUENCE OF MABS 7E11 AND 5B10 | | |
|---|---|---|
| | Sequence | SEQ ID NO: |
| Chain | FSGSGSGTDFTLKISRVDAEDLGVYFCSQSTHVPYTFGGGTKL EIKRADAAPTVSISHH | |
| 7E11 Heavy Chain | VQLQESGAELVMPGASVKMSCKASGYTFTDYWMHWVKQRP GQGLEWIGAIDPSDSYSSYNQNFKGKATLTVDGSSSTAYMQL SSLTSEDSAVYYCARRITEAGAWFAYWGQGTTVT | 17 |
| 5B 10 Heavy Chain | LQXSGAEIVMPGTAVTMSCKASGYTFTDFWMHWVKQRPGQ GLEWIGAIDPSDSYSRINQKFKGKATLTVDESSSTAYMQLSSL TSEDSAVYYCARRITEAGAWFAYWGQGTTVT | 18 |

Epitope Mapping of Monoclonal Antibody 7E11 mAb 7E11 binds both rat and human NgR1. To determine the epitope responsible for 7E11 binding, we generated fragments and synthetic peptides of rat NgR1 and tested them for 7E11 binding.

A recombinant fragment of the rat NgR1 that contains all 8 LRR domains and the N- and C-terminal caps (sNgR310) was treated with either acid or cyanogen bromide (CNBr) and separated the fragments by gel electrophoresis. Untreated sNgR310 migrates with an apparent molecular weight of 42 kDa. Acid treatment of sNgR310 produced two major cleavage products of 15 kDa (aa 27-aa 122) and 30 kDa (aa 123-aa 310). CNBr treatment generated three fragments, a 33/35 kDa doublet (aa 27-aa 229), which may represent fragments with heterogeneous glycosylation, a 10 kDa product (aa 241-aa 310), and an 11-amino-acid fragment (as 230-aa 240), which is not retained on the gel. A western blot of the gel was probed with 7E11 and demonstrated that it bound to intact rat NgR1 (aa 27-aa 310), the 15 kDa acid fragment (aa 27-aa 122) and the 35 kDa CNBr fragment (aa 27-aa 229). 7E11 did not bind to the 30 kDa acid fragment (aa 123-aa 310) or the 10 kDa CNBr fragment (aa 241-aa 310). Both the 15 kDa acid fragment and the 35 kDa CNBr fragment contained the sequence LDLSDNAQLRVVDYIT (SEQ ID NO: 1), consistent with 7E11 binding to a single epitope on NgR1.

The 7E11 binding site was further analyzed by testing tryptic peptide digests of sNgR310. HPLC analyses showed several fragments, indicating that there were several trypsin-sensitive lysine and arginine residues in the NgR1 sequence. 7E11 bound only a single tryptic digest peptide, providing additional evidence that 7E11 binds to a single epitope on NgR1. Subsequent mass spectroscopy (MS) and sequence analyses identified the bound peptide to be AAAFTGLTLLEQLDLSDNAQLR (SEQ ID NO: 26).

The LDLSDNAQLRVVDPTT peptide (SEQ ID NO: 1) was subjected to further mapping analysis. The peptide was digested with trypsin, which yielded two major fragments, LDLSDNAQLR (SEQ ID NO: 27) and VVDPTT (SEQ ID NO: 28), and the ability of 7E11 to bind them was tested. MS analysis revealed that the antibody bound peptide LDLSDNAQLR (SEQ ID NO: 27), and therefore this peptide contains the binding epitope for 7E11. Within this peptide fraction, detailed MS analysis identified several scrambled peptides that also bound 7E11, including peptides with deamination at Asn115 and Gln117, addition of Alanine at 112 or 113, or addition of Serine at 114 (Table 3). These data indicate that several amino acid residues located in this peptide fragment may not be critical for 7E11 binding.

TABLE 3

| MUTANT PEPTIDES BOUND BY 7E11. | |
|---|---|
| Peptides bound | Amino Acid Sequence |
| Wild-type Fragment | LDLSDNAQLR (SEQ ID NO: 27) |
| Deaminated | LDLSDDAELR (SEQ ID NO: 29) |
| Scrambled Fragment | LDLASDNAQLR (SEQ ID NO: 30) |
| #1 Deaminated | LDLASDDAELR (SEQ LD NO: 31) |
| Scrambled Fragment | LDALSDNAQLR (SEQ ID NO: 32) |
| #2 Deaminated | LDALSDDAELR (SEQ ID NO: 33) |
| Scrambled Fragment | LDLSSDNAQLR (SEQ ID NO: 34) |
| #3 Deaminated | LDLSSDEAELR (SEQ ID NO: 35) |

The LDLSDNAQLRVVDPIT (SEQ ID NO:1) peptide was also digested with the endoprotease Asp-N and 7E11 binding was tested. Endoprotease Asp-N cleaved the peptide into 3 peptide fragments, L, DLS and DNAQLRVVDPTT (SEQ ID NO: 36). Of these products, 7E11 bound the DNAQLRVVDPTT (SEQ ID NO:36) peptide. Taken together, the trypsin and Asp-N cleavage data further localize the 7E11 binding epitope to the sequence shared between them, DNAQLR (SEQ ID NO: 37).

The amino acid sequences of NgR1, NgR2, and NgR3 from various species were analyzed to predict critical residues in the 7E11 binding epitope based on the observation that 7E11 bound rat and human NgR1 but not mouse NgR1, human NgR2 or mouse NgR3. Sequence alignment revealed that amino acids 110-125 of rat NgR1 and the corresponding sequence of human NgR1 are identical and that the mouse NgR1 sequence differs only by one amino acid at position 119 (Arg119 in rat and human NgR1, and His119 in mouse NgR1; Table 4).

TABLE 4

| SEQUENCE ALIGNMENT OF NGRS FROM DIFFERENT SPECIES. | | |
|---|---|---|
| Protein(s) | Sequence of aa 110 to aa 119 | SEQ ID NO: |
| Rat & Human NgR1 | LDLSDNAQLR | 27 |
| Mouse NgR1 | LDLSDNAQLH | 38 |
| Rat & Human NgR2 | LDLGDNRHLR | 39 |
| Rat, Human & Mouse NgR3 | LDLGDNRQLR | 40 |

Arg119 on NgR1 contributes to 7E11 binding because it binds well to rat and human NgR1 but poorly to mouse NgR1.

Similarly, because 7E11 does not bind well to NgR3, Ala116 is involved in the epitope because within the DNAQLR sequence (SEQ ID NO:37) NgR3 only differs from NgR1 by an Arginine at the corresponding sequence. Within the DNAQLR (SEQ ID NO:37) sequence, 4 out of 6 of the residues in NgR2 are identical to rat NgR1. Ala116 and Gln117 are replaced with Arginine and Histidine, respectively. This confirms that Ala116 is an important amino acid residue contributing to 7E11 binding, but does not necessarily preclude the involvement of Gln117.

To verify these contact points, several peptides containing point mutations within the LDLSDNAQLR sequence (SEQ ID NO: 27) were generated and tested for 7E11 binding. The peptides were immobilized on a MaxiSorp™ plate (Nunc™) and serial dilutions of 7E11 were applied. The resulting $EC_{50}$ values are shown in Table 5. 7E11 bound to mutants Leu110Ala and Asp111Ala with similar $EC_{50}$ values as to the original peptide. When Gln117Ala was tested, the $EC_{50}$ increased 30-fold and when Arg119His was tested the $EC_{50}$ increased 25-fold. The most significant change in $EC_{50}$ was observed when Arg 119 was mutated to Alanine.

TABLE 5

7E11 BINDS TO MUTANT PEPTIDES WITH DIFFERENT $EC_{50}$

| Change in peptide | Sequence | $EC_{50}$ | SEQ ID NO: |
|---|---|---|---|
| No changes | LDLSDNAQLRVVDPTT | 0.55 | 1 |
| L110A | ADLSDNAQLRVVDPTT | 0.62 | 41 |
| D111A | LALSDNAQLRVVDPTT | 0.31 | 42 |
| Q117A | LDLSDNAALRVVDPTT | 16 | 43 |
| R119H | LDLSDNAQLHVVDPTT | 12 | 44 |
| R119A | LDLSDNAQLAVVDPTT | 88 | 45 |

The position of the 7E11 binding epitope was also determined in the recently resolved crystal structure of sNgR310. As expected, the structure shows that the 7E11 epitope is exposed on the surface of the molecule. Residues Arg119, Gln117, Ala116, and Asp114 protrude outward from the structure while Leu118 and Asn115 are located inward. The epitope falls an top of an acidic patch within the concave surface of the structure and a basic surface that faces one of the sides.

Inhibition of Ligand Binding to Soluble Nogo Receptor-1 by Monoclonal Anti-Nogo Receptor-1 Antibody The anti-Nogo receptor-1 monoclonal antibodies produced as described above were tested to determine whether they inhibited ligand binding to Nogo receptor-1.

Figure 3A:
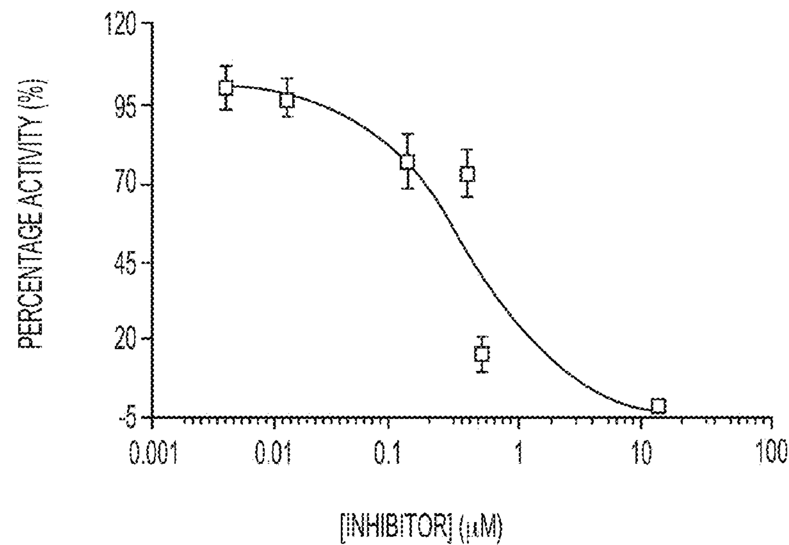
FIG. 3A is a graph depicting the binding activity of anti-Nogo receptor-1 antibody, 7E11. The graph presents the effect of 7E11 concentration on the binding of Nogo66 to Nogo receptor-1.
Figure 3B:
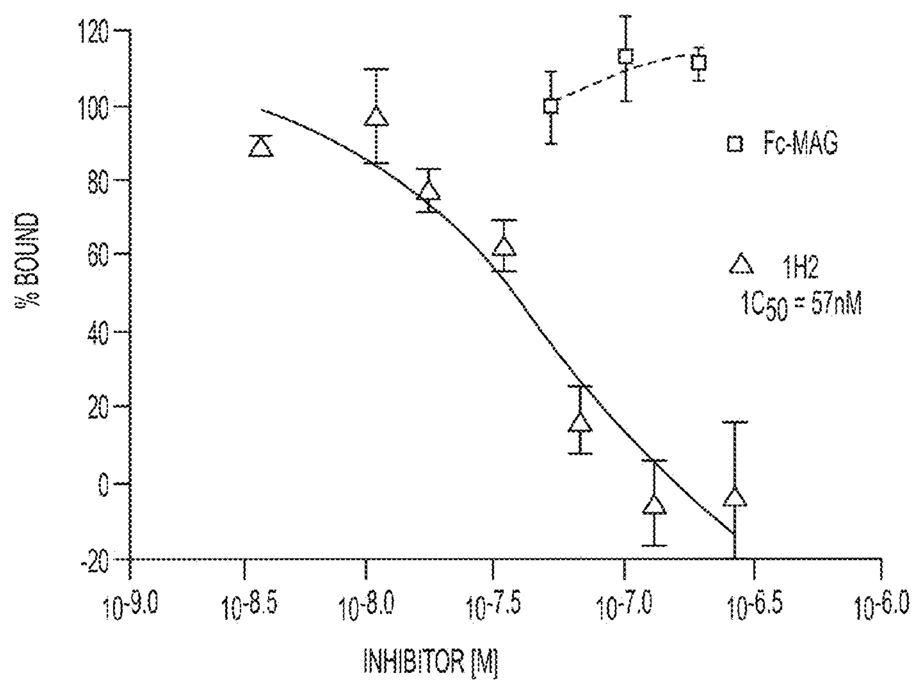
FIG. 3B depicts the binding activity of anti-Nogo receptor-1 antibody, 1H2. The graph presents the effect of 1H2 concentration on the binding of Nogo66 to sNogoR344-Fc (also referred to herein and in U.S. patent application 60/402,866 as Fc-sNogoR344 or Ig-sNogoR344). Fc-MAG did not compete with Nogo66 for binding to sNogoR344-Fc.

0.5 μg of a soluble Nogo receptor-1 fusion protein comprising amino acid residues 26-344 of rat Nogo receptor-1 and the hinge and Fc region of the rat IgG1 molecule (sNogoR344-Fc) produced as described below was immobilized on 250 g of protein-A- or wheatgerm agglutinin-conjugated SPA beads (Amersham Pharmacia Biotech) for 2 hours at 25° C. SPA beads coupled with Fc-sNogoR-1, anti-Nogo receptor-1 mAb and 1 μl $^{125}$I-Nogo66 (Amersham, 2000 Ci/mmol, 1 nM) in 501 of the HEPES-buffered incubation medium (10 mM HEPES, pH 7.4, 0.1% bovine serum albumin, 0.1% ovalbumin, 2 mM $MgCl_2$, 2 mM $CaCl_2$ and protease inhibitors) was added to each sample well. After 16 hours, radioactivity was measured in quadruplicate samples using a TopCount® (Packard). $IC_{50}$ values were calculated from a curve-fit analysis (FIG. 3) (PRISM, GraphPad Software, NJ). In some experiments, we also used AP-ligand conjugates (e.g. AP-Nogo66) and detected binding by monitoring alkaline phosphatase activity. We also assayed the ability of the mAbs to block binding of the ligands MAG-Fc and AP-OM-gp to Nogo receptor-1.

Monoclonal antibodies 7E11, 5B10, 1H2, 3G5 and 2F7 all inhibited binding of Nogo66, MAG and OM-gp to sNogoR344-Fc. The calculated $IC_{50}$ for Nogo66 for 7E11 and 1H2 were 400 nM and 60 nM, respectively. The data from ELISAs monitoring mAb-mediated inhibition of binding of the three ligands to Nogo receptor-1 are summarized in Table 6.

TABLE 6

MABS INHIBIT BINDING OF NOGO66, MAG AND OM-GP TO NOGO RECEPTOR-1.

| mAb | MAG + sNogoR344-Fc | Nogo66 + sNogoR344-Fc | OM-gp + sNogoR344-Fc |
|---|---|---|---|
| 7E11 | 30 nM (60%) $EC_{50}$ = 0.5 μM | $EC_{50}$ = 1.7 μM | $EC_{50}$ = 150 nM |
| 1H2 | 30 nM (60%) | ND | ND |
| 3G5 | 30 nM (60%) | $EC_{50}$ = 9 nM | ND |
| 2F7 | 30 nM (55%) | $EC_{50}$ = 10 nM | $EC_{50}$ = 5 nM |
| 1D9.3 | 30 nM (70%) $EC_{50}$ = 2.7 nM | $EC_{50}$ = 13 nM | $EC_{50}$ = 5.2 nM |
| 2G7.1 | 30 nM (84%) | $EC_{50}$ = 18 nM | $EC_{50}$ = 1 nM |
| 1E4.1 | 30 nM (75%) $EC_{50}$ = 2.8 nM | — | $EC_{50}$ = 9.1 nM |
| 1G4.1 | 30 nM (90%) $EC_{50}$ = 9.9 nM | — | $EC_{50}$ = 8.2 nM |
| 2C4.1 | 30 nM (50%) | — | ND |
| 2F11.1 | 30 nM (45%) | ND | ND |
| 1H4.1 | — | ND | ND |
| 2E8.1 | 30 nM (87%) $EC_{50}$ = 9.2 nM | $EC_{50}$ = 1.5 nM | $EC_{50}$ = 42.9 nM |
| 2G11.2 | 30 nM (80%) | ND | ND |
| 1B5.1 | 30 nM (0%) | ND | ND |

The percent displacement is shown at 30 nM antibody and the $EC_{50}$ for certain mAbs determined from curve-fit analysis as described. "-" indicates no detectable activity and "ND" indicates not determined.

EXAMPLE 2

Production of Fab-Phage Anti-Nogo Receptor-1 Antibodies

Anti-Nogo receptor-1 Fab-phage antibodies that specifically bind an immunogenic Nogo receptor-1 polypeptide of the invention were also made by screening a Fab-phage library as follows.

The MorphoSys Fab-phage library HuCAL® GOLD was screened against recombinant rat soluble sNogoR310-Fc protein and COS7 cells expressing rat Nogo receptor-1. Fab-phages that specifically bound to Nogo receptor-1 were purified and characterized. The heavy chain of 14D5 is derived from the $V_H2$ gene and the light chain is derived from the $V_K1$ gene. The amino acid sequences of the CDRs of the heavy chain and light chain of one of these Fab-phages, 14D5, are shown in Table 7.

TABLE 7

AMINO ACID SEQUENCE OF CDRS OF 14D5

| | Amino Acid Sequence | SEQ ID NO: |
|---|---|---|
| Heavy Chain CDR1 | GFSLSTSGGSVG | 19 |
| Heavy Chain CDR2 | LIYSNDTKYYSTSLKT | 20 |
| Heavy Chain CDR3 | SRFWTGEYDV | 21 |

TABLE 7-continued

| AMINO ACID SEQUENCE OF CDRS OF 14D5 | | |
|---|---|---|
| | Amino Acid Sequence | SEQ ID NO: |
| Light Chain CDR1 | RASQNIAITLN | 22 |
| Light Chain CDR2 | LASSLQS | 23 |
| Light Chain CDR3 | QQYDNYPL | 24 |

14D5 binds to rat Nogo receptor-1 in both monovalent and bivalent forms. In addition, 14D5 binds to mouse and human Nogo receptor-1 and human Nogo receptor-2 but not mouse Nogo receptor-3.

EXAMPLE 3

Immunoprecipitation of Nogo Receptor-1 by Anti-Nogo Receptor-1 Monoclonal Antibodies To perform the immunoprecipitation, 100 μl lysed cells or 50 μl PiPLC treated cells were mixed with 400 or 450 μl extraction buffer [10 mM Tris-HCl, pH 7.2, 0.5% Tween-20™, 0.2 mM PMSF] or RIPA buffer, respectively in the presence of 30 μl Protein A or G and 1-2 μg antibody. The mixture was incubated in a shaker at 4° C. for 16 hours.

Samples were spun gently to pellet the protein A or G coupled beads. The beads were washed three times with 1 ml wash buffer (10 mM Tris-HCl, pH 72, 0.1% Tween-20™). The final wash was performed using 10% of original wash buffer.

Beads were resuspended in 100 μl of 2×SDS with 10% beta-mercaptoethanol. Samples were incubated at room temperature before being run on a 4-20% Tris-Glycine gel for SDS-PAGE. As determined by SDS-PAGE gel analysis, monoclonal antibodies, 305 and 2F7, immunoprecipitate Nogo receptor-1.

EXAMPLE 4

Determining Antibody Specificity by ELISA

Figure 4:
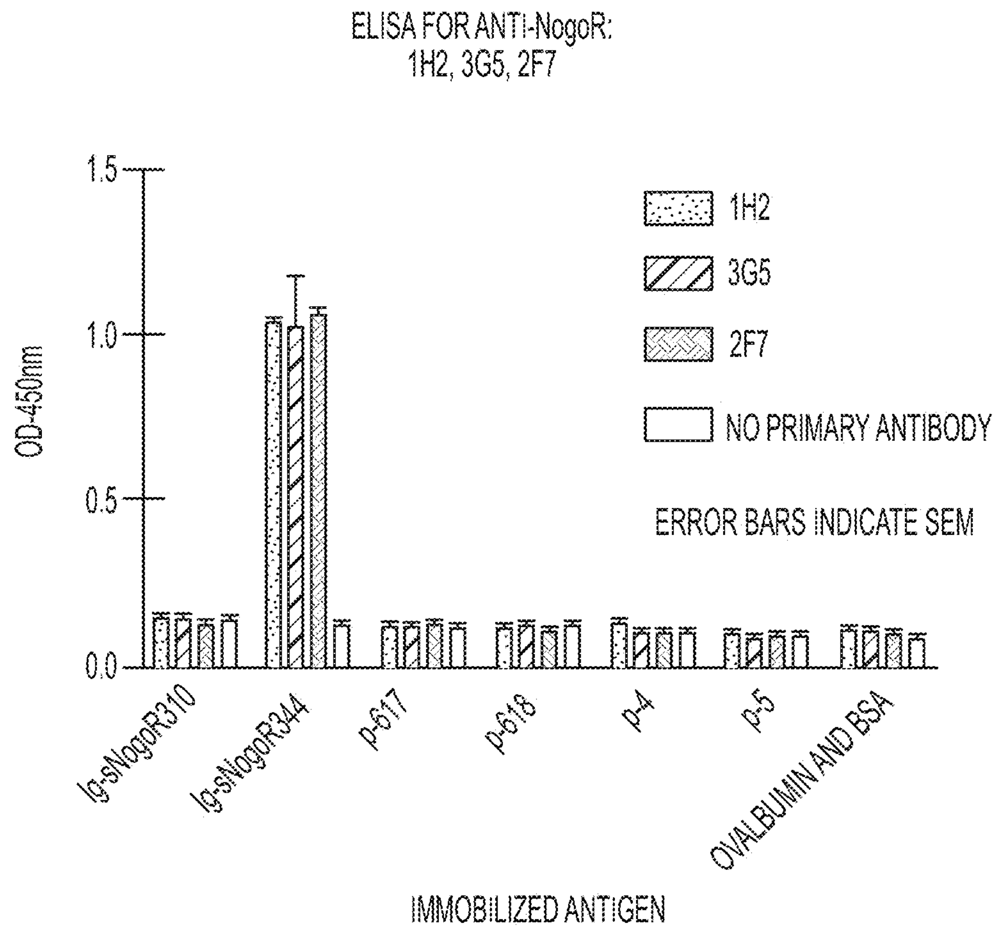
FIG. 4 depicts the results of an ELISA for anti-Nogo-R-1 antibodies 1H2, 3G5 and 2F7. The effect of the antibodies on $OD_{450}$ in the presence of immobilized antigens was determined. The immobilized antigens were sNogoR310-Fc (also referred to herein and in U.S. patent application 60/402,866 as Fc-sNogoR310 or Ig-sNogoR310), sNogoR344-Fc, p-617, p-618, p-4, p-5 and ovalbumin and BSA.

To determine the specificity of the monoclonal and Fab-phage antibodies produced in Examples 1 and 2, we performed an ELISA using a panel of Nogo receptor-1 polypeptides. The panel consisted of sNogoR310-Fc (a fusion protein comprising amino acids 26-310 of rat Nogo receptor-1 and a rat Fc fragment), sNogoR344-Fc (see supra), polypeptide p-617 (SEQ ID NO: 1), polypeptide p-618 (a 19-amino acid polypeptide from the LRR7 region of rat Nogo receptor-1; FIG. 2; SEQ ID NO: 11) and polypeptides p-4 and p-5 (polypeptides from the LRR5 and LRRCT regions of Nogo receptor-1, respectively). Ovalbumin and BSA were used as controls. As shown in FIG. 4, mAbs 1H2, 3G5 and 2F7 all specifically bound to sNogoR344-Fc. In similar experiments, those antibodies also specifically bound a polypeptide consisting of amino acids 310-344 of rat Nogo receptor-1 (SEQ ID NO: 3) and mAbs 7E11 and 5B10 specifically bound polypeptide p-617 (SEQ ID NO: 1).

Ten of the antibodies (1D9.3, 1E4.7, 1B4.3, 2C4.3, 1F10.3, 2H1.4, 1H3.3, 1G4.1, 1E4.1, and 2G7.1) from the sNogoR310-Fc immunization displaced each other for binding, indicating that they recognize a similar or overlapping epitopes on sNogoR310-Fc. The other three antibodies from the sNogoR310-Fc immunization (2C4.1, 2F11.1, and 1H4.1) recognize different epitopes located in amino acid residues 26-310.

We also performed ELISA binding assays using the Fab-phage $141)_5$. Where AP-Nogo66, AP-OM-gp and MAO-Fc ligands were allowed to bind to immobilized sNogoR344-Fc, 1 μM 14D5 completely inhibited Nogo and MAO binding. 10 μM of 14D5 was required to completely inhibit the binding of OM-gp to sNogoR344-Fc.

EXAMPLE 5

Neurite Outgrowth Assay

To test the ability of the monoclonal and Fab-phage antibodies produced above to lessen the inhibitory effect of CNS myelin on neurons, Lab-Tek® culture slides (4 wells) were coated with 0.1 mg/ml poly-D-lysine (Sigma®). CNS myelin or PBS was spotted as 3 μl drops. Fluorescent microspheres (Polysciences) were added to the myelin/PBS to allow later identification of the drops (Grandpre et al., *Nature* 403:439-444 (2000)). Lab-Tek® slides were then rinsed and coated with 10 μg/ml laminin (Gibco™). Dorsal root ganglions (DRG's) from P3-4 Sprague Dawley rat pups were dissociated with 1 mg/ml collagenase type 1 (Worthington), triturated with fire-polished Pasteur pipettes pre-plated to enrich in neuronal cells and finally plated at 23,000 cells/well on the pre-coated Lab-Tek® culture slides. The culture medium was F12 containing 5% heat inactivated donor horse serum, 5% heat inactivated fetal bovine serum and 50 ng/ml mNGF and incubated at 37° C. and 5% $CO_2$ for 6 hours. Fifteen jag/ml of mAb 7E11 was added immediately after plating.

Slides were fixed for 20 minutes with 4% paraformaldehyde containing 20% sucrose and stained for the neuronal marker anti beta-III-tubulin (Covance TUJ1) diluted 1:500. As secondary antibody anti-mouse Alexa Fluor® 594 (Molecular Probes) was diluted 1:300 and slides were coverslipped with Gel/Mount™ (Biømeda™). 5× digital images were acquired with OpenLab™ software and analysed by using the MetaMorph® software for quantification of neurite outgrowth.

Figure 5:
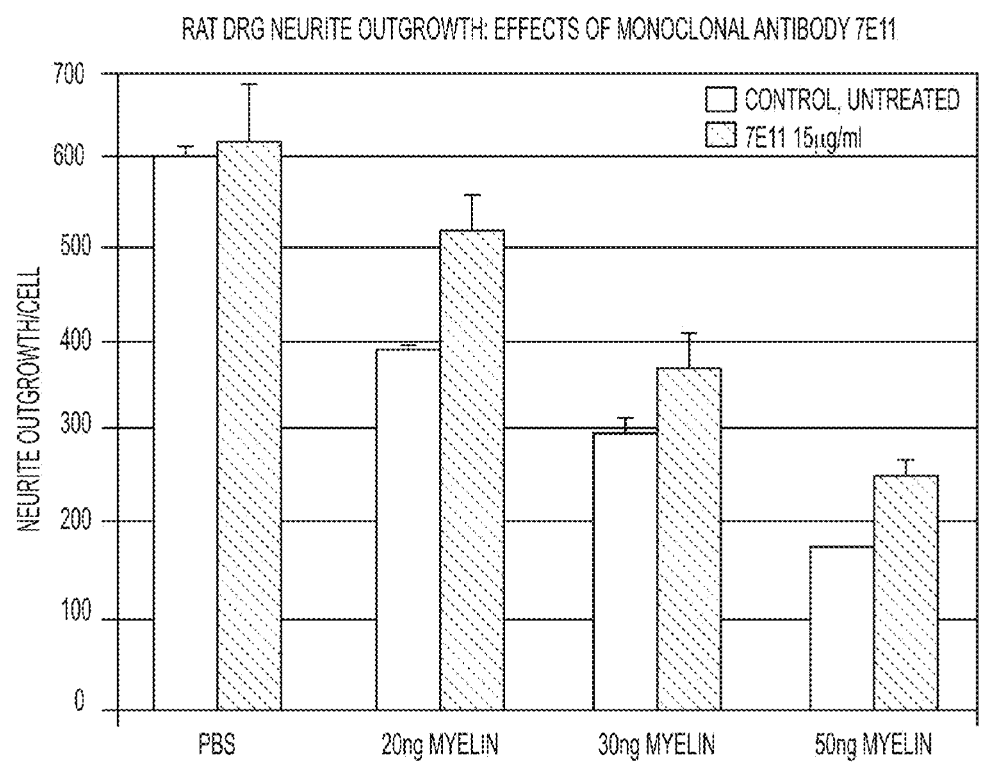
FIG. 5 is a graph depicting the effects of monoclonal antibody, 7E11, on rat DRG neurite outgrowth in the presence of varying amounts of myelin.

MAb 7E11 protected DRG neurons from myelin-mediated inhibition of neurite outgrowth. (FIG. 5). Similar results were observed with mAbs 1H2 and 3G5.

In a neurite outgrowth protection assay where rat P7 DRG neurons were cultured on a CNS myelin substrate, bivalent 14D5 also efficiently promoted neurite outgrowth.

EXAMPLE 6

Immunohistochemistry with 7E11 on Cells Transfected with Nogo Receptor-1

To further characterize the binding properties of anti-Nogo receptor-1 mAbs produced as described in Example 1, we compared binding to both fixed and live COS-7 or 293 cells expressing rat or human Nogo receptor-1.

Fixed Cells:

Nogo receptor-1 transfected and non-transfected cells were plated in 8-well Lab-Tek™ culture slides, fixed with 4% paraformaldehyde for 15 minutes, blocked with 10% normal goat serum, 0.1% Triton X-100 in PBS for 1 hour. Mab 7E11 was added at 15 μg/ml and 1.5 μg/ml in blocking solution and incubated for 2 hours at room temperature; Alexa®-conjugated secondary antibody anti-mouse (Molecular Probes)

was incubated at a 1:300 dilution in blocking solution for 1 hour; DAPI was added at 5 μg/ml to the secondary antibody to label all nuclei.

Live Cells:

Transfected and non-transfected cells were plated in 8 well Lab-Tek™ culture slides, blocked with FACS buffer (containing 4% donor horse serum) for 30 minutes at 4° C., incubated with 7E11 at 15 μg/ml and 1.5 μg/ml in FACS buffer for 1 hour at 4° C., rinsed and incubated with secondary antibody anti-mouse-Alexa® (1:300 in FACS buffer) for 30 minutes at 4° C.

Immunohistochemical staining experiments demonstrated that all of the mAbs bound cells expressing rat Nogo receptor-1. mAbs 7E11, 2G7.1 and 2C4.1 bound both fixed and live cells expressing human Nogo receptor-1.

EXAMPLE 7

Mouse Model of Spinal Cord Contusive Injury

To test the effect of anti-Nogo receptor-1 mAbs produced in Example 1 on neurons in vivo, we use a mouse spinal cord contusion injury model.

Female mice (18-22 g) are treated prophylactically with analgesic and antibiotic agents. Mice are anesthetized and placed in a stereotaxic apparatus with vertebral column fixation under a stereomicroscope. Trauma to the spinal cord is introduced by a modified version of the weight-drop method (M. Li et al., *Neuroscience* 99:333-342 (2000).

Briefly, a T9 and T10 laminectomy is made and the vertebral column is stabilized using a pair of mouse transverse clamps supporting the T9-T10 transverse processes bilaterally. A stainless steel impact rod with a diameter of 1.4 mm and weight of 2 g, is raised 2.5 cm above the dura and dropped onto the spinal cord at the T10 level. During the surgery, mice are kept on a 37° C. warming blanket and 1 ml of warmed sterile saline is administered subcutaneously to each mouse after surgery to avoid dehydration. The bladder is manually expressed once daily until reflexive bladder control is regained.

All animals receive post-operative analgesia every 8-12 hours after surgery and antibiotic treatment twice daily for 7 days thereafter. Animals have free access to food and water for the duration of the study. Anti-Nogo receptor-1 antibodies are delivered to the injury site via intrathecal injection for 28 days as described in the rat spinal cord transection model below.

EXAMPLE 8

Characterization of Soluble Nogo Receptor-1 Fusion Proteins

To characterize soluble Nogo receptor-1 polypeptides (sNogoR-1) and fusion proteins (Fc-sNogoR-1) we performed the following experiment.

Figure 6A:
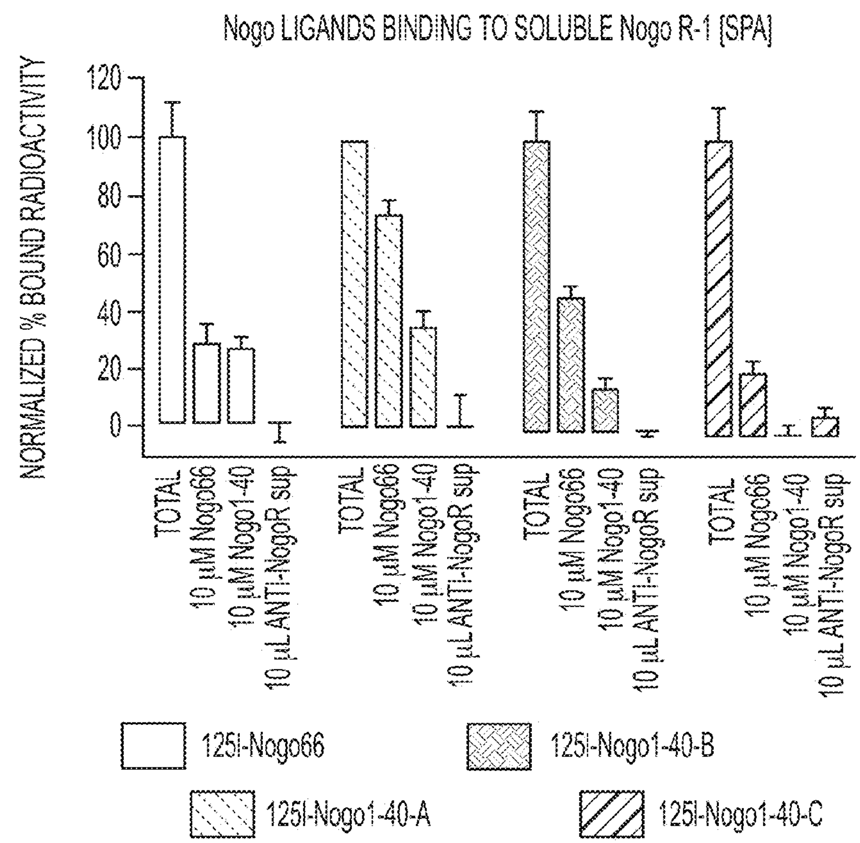
FIG. 6A is a graph depicting the effect of binding of sNogoR310 to $^{125}$I-Nogo66 and $^{125}$I-Nogo40 in the presence of the following competitors: Nogo66, Nogo40 and anti-Nogo receptor-1 monoclonal antibody supernatant.
Figure 6B:
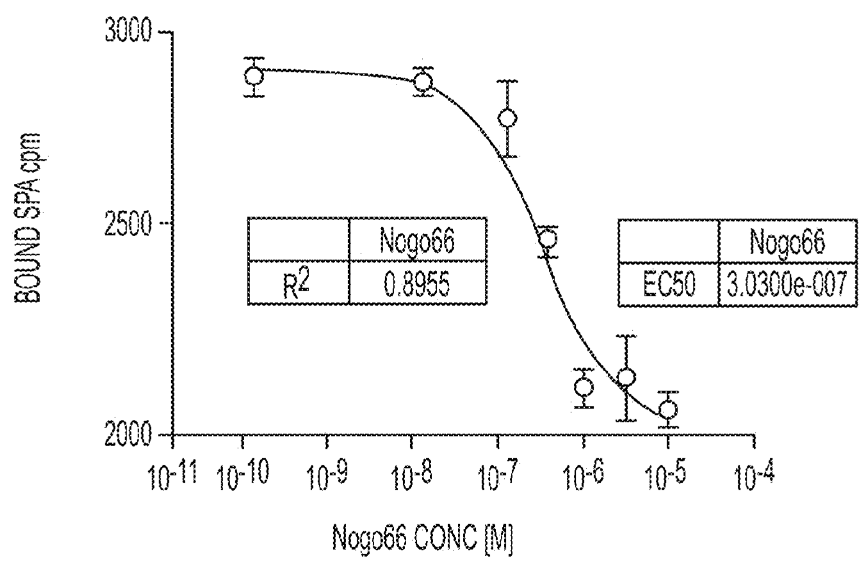
FIG. 6B depicts the binding activity of $^{125}$I-Nogo66 to sNogoR310.
Figure 7:
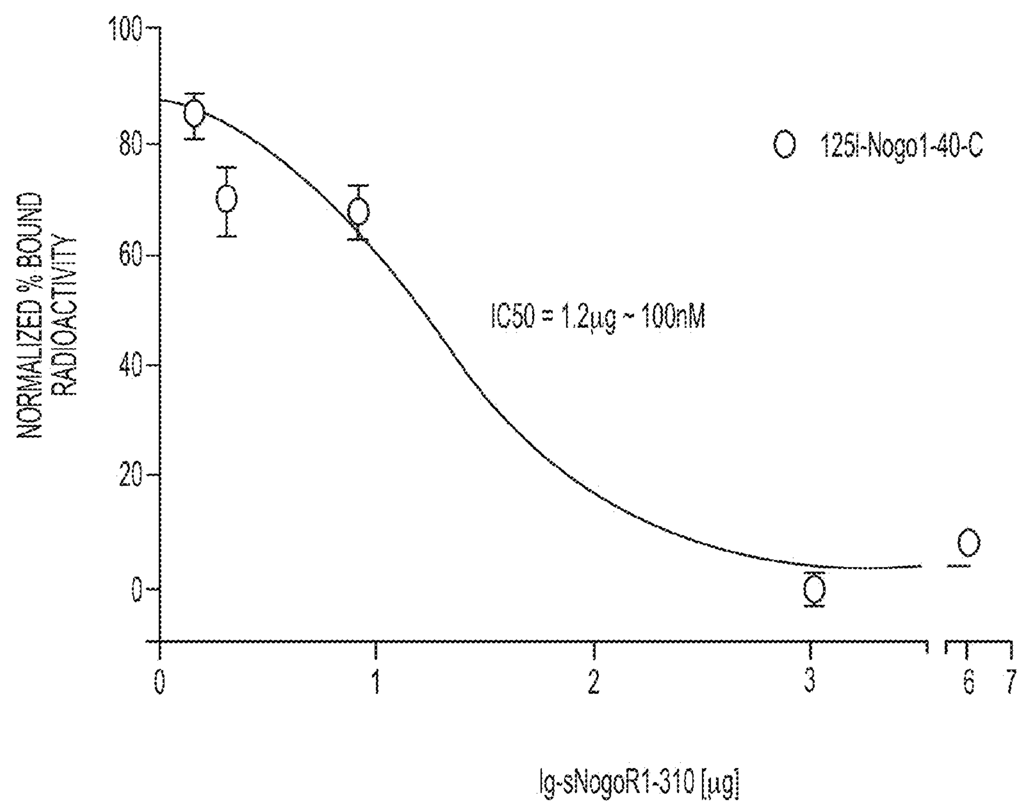
FIG. 7 is a graph depicting the effect of sNogoR310-Fc on $^{125}$I-Nogo40 binding to sNogoR310.
Figure 8:
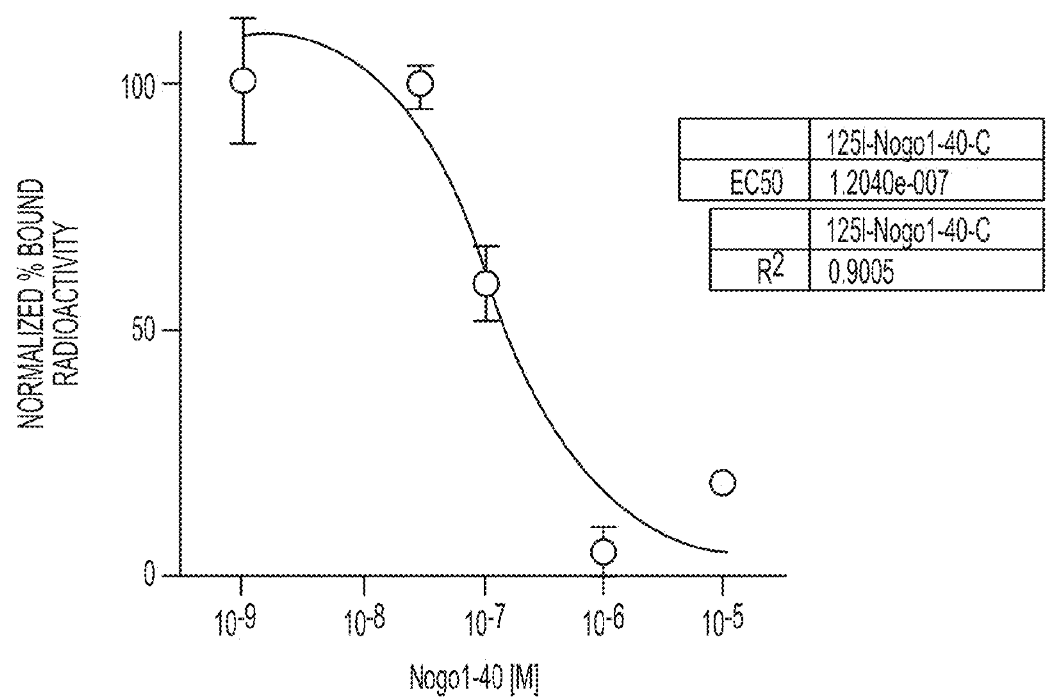
FIG. 8 is a graph depicting the binding activity of sNogoR310-Fc to $^{125}$I-Nogo40.

Three μg of soluble Nogo receptors (sNogoR310-Fc and sNogoR344-Fc) were immobilized on 250 μg WGA-SPA beads and received 0.5 μL of radioactive ligand (final concentration 0.5 nM) in a final volume of 100 μL of binding buffer (20 mM HEPES, pH 7.4, 2 mM Ca, 2 mM Mg, 0.1% BSA, 0.1% ovalbumin and protease inhibitors). Ligands included 10 μM Nogo66, 10 μM $^{125}$I-Nogo40 (amino acids 1-40 of NogoA) and 10 μL of anti-Nogo receptor-1 antibody supernatant for each ligand set. The three tyrosines on Nogo40 were separately iodinated and designated as Nogo40-A, -B and -C respectively. Mean values of triplicates are presented as normalized % bound radioactivity (FIGS. 6, 7 and 8). Error bars indicate SEM. Bound radioactivity in the absence of inhibitors was taken as 100% and the lowest bound radioactivity in the presence of 10 μM Nogo40 was taken as the 0% for data normalization.

EXAMPLE 9

Inhibition of Ligand Binding to Soluble Nogo Receptor-1 Fusion Protein

A binding assay similar to the binding assay of Example 8 was used to test the ability of two mAbs produced in Example 1 to inhibit $^{125}$I-Nogo66 binding to sNogoR344-Fc. Mabs 2F7 and 3G5 inhibited $^{125}$I-Nogo66 binding to sNogoR344-Fc.

EXAMPLE 10

Neurite Outgrowth Assay

Lab-Tek® culture slides (4 wells) were coated with 0.1 mg/ml poly-D-lysine (Sigma®). CNS myelin alone or mixed with sNogoR310, sNogoR310-Fc fusion protein, mAb 5B10 or control PBS were separately spotted as 3 μl drops. Fluorescent microspheres (Polysciences) were added to the myelin/PBS to allow later identification of the drops (Grandpre et al., *Nature* 403:439-444 (2000)). Lab-Tek® slides were then rinsed and coated with 10 μg/ml laminin (Gibco™).

Dorsal root ganglions (DRG's) from P3-4 Sprague Dawley rat pups were dissociated with 1 mg/ml collagenase type 1 (Worthington), triturated with fire-polished Pasteur pipettes pre-plated to enrich in neuronal cells and finally plated at 23,000 cells/well on the pre-coated Labtek culture slides. The culture medium was F12 containing 5% heat inactivated donor horse serum, 5% heat inactivated fetal bovine serum and 50 ng/ml mNGF and incubated at 37° C. and 5% $CO_2$ for 6 hours.

Figure 9A:
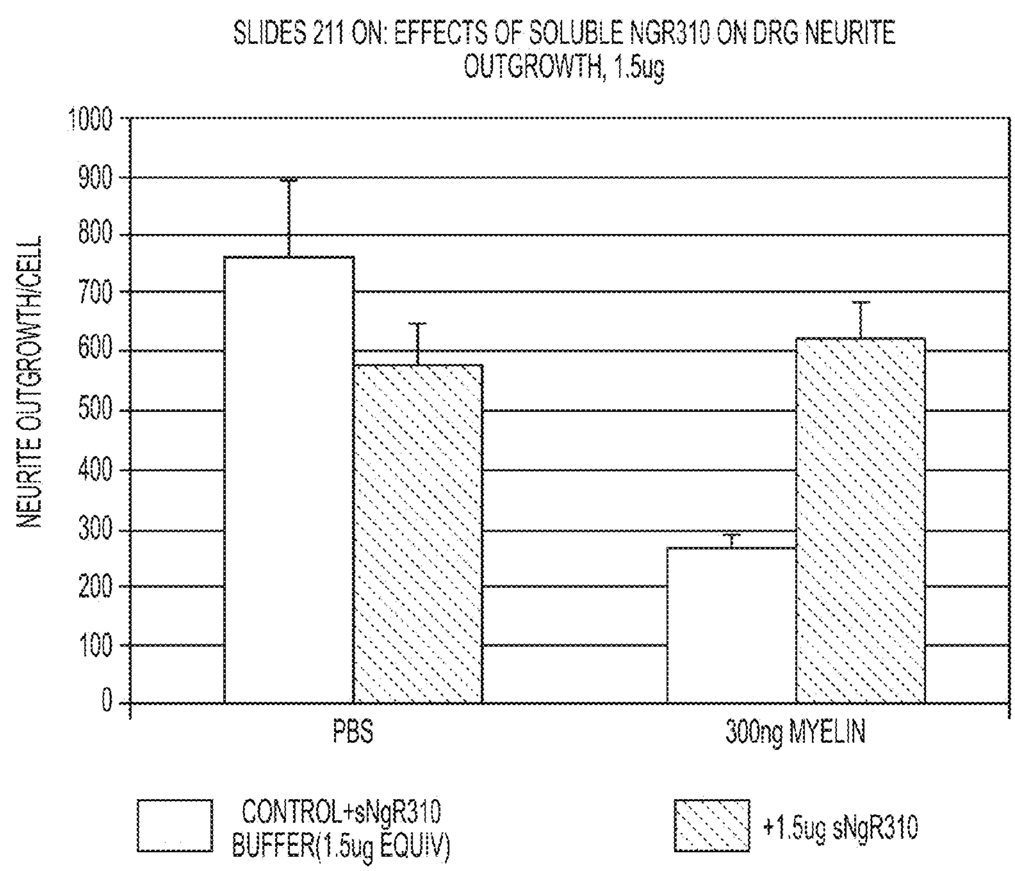
FIG. 9A is a graph of the effect of sNogoR310 on neurite outgrowth/cell in the presence or absence of myelin.
Figure 9B:
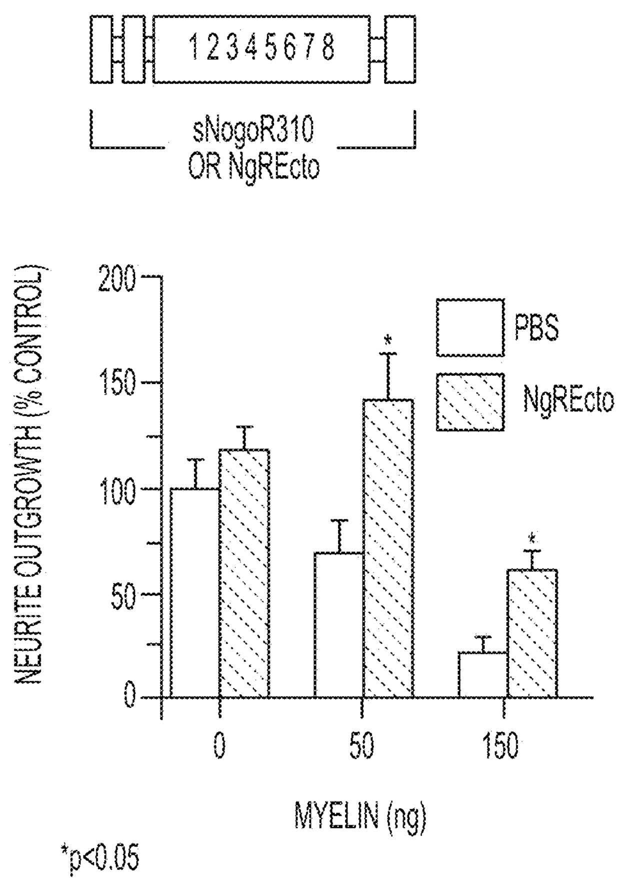
FIG. 9B is a graph of the effect of sNogoR310 on neurite outgrowth in the presence or absence of myelin.
Figure 10A:
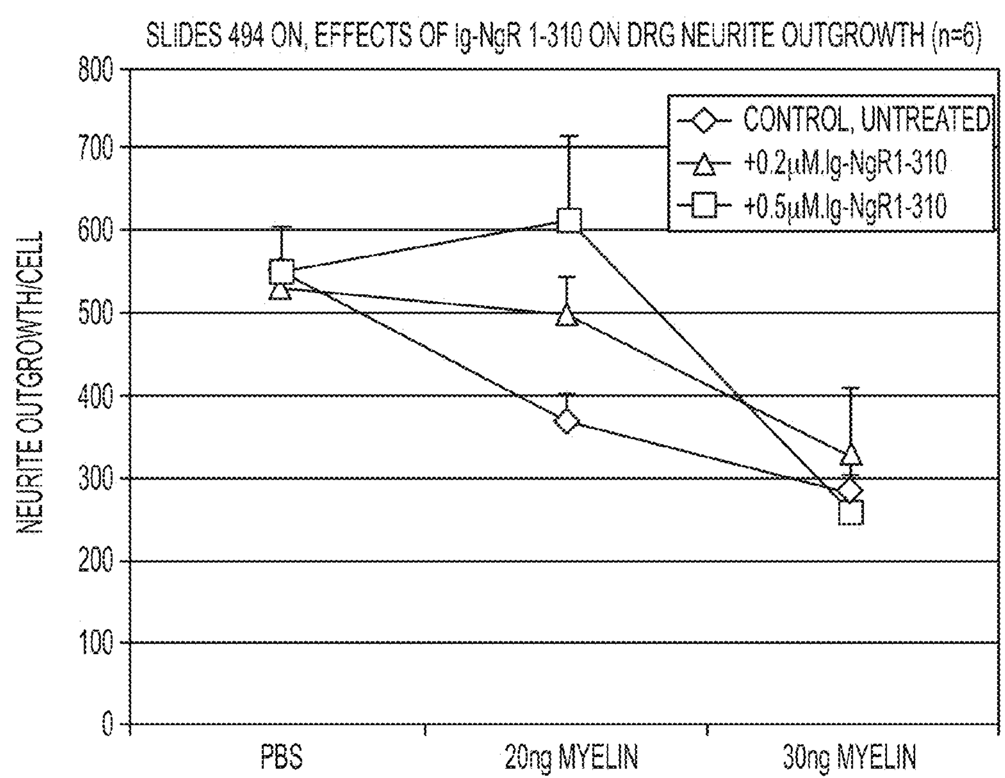
FIG. 10A is a graph depicting the effect of sNogoR310-Fc on P4 rat DRG neurite outgrowth in the presence or absence of increasing amounts of myelin.
Figure 10B:
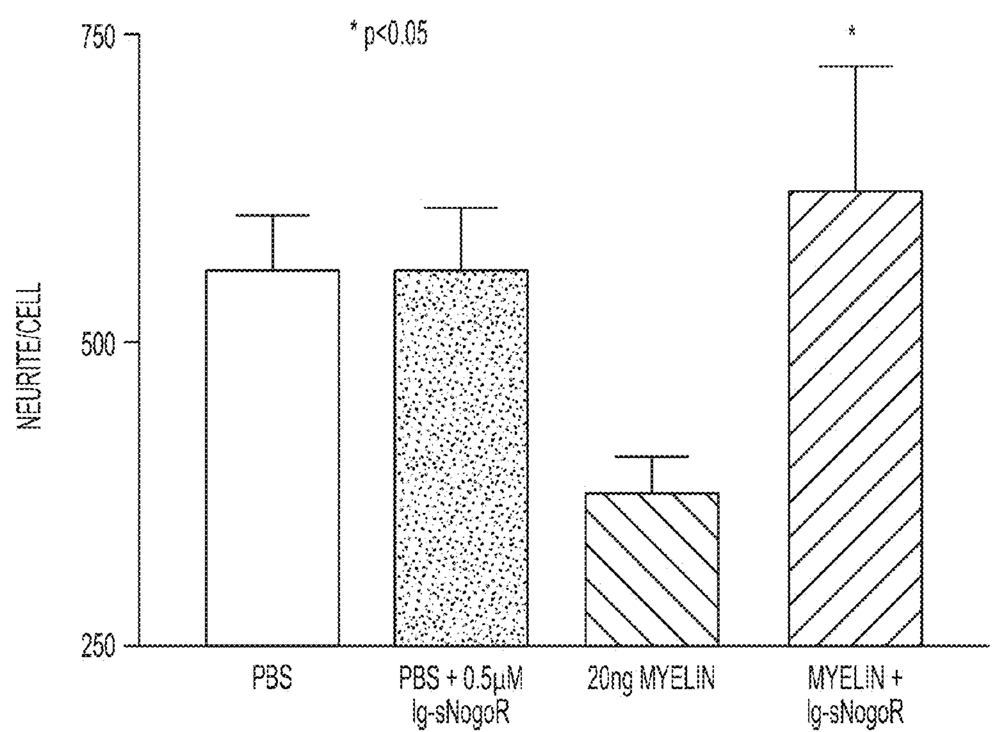
FIG. 10B depicts the number of neurites/cell following treatment with PBS, PBS+sNogoR310-Fc, 20 ng myelin and myelin+sNogoR310-Fc.
Figure 11:
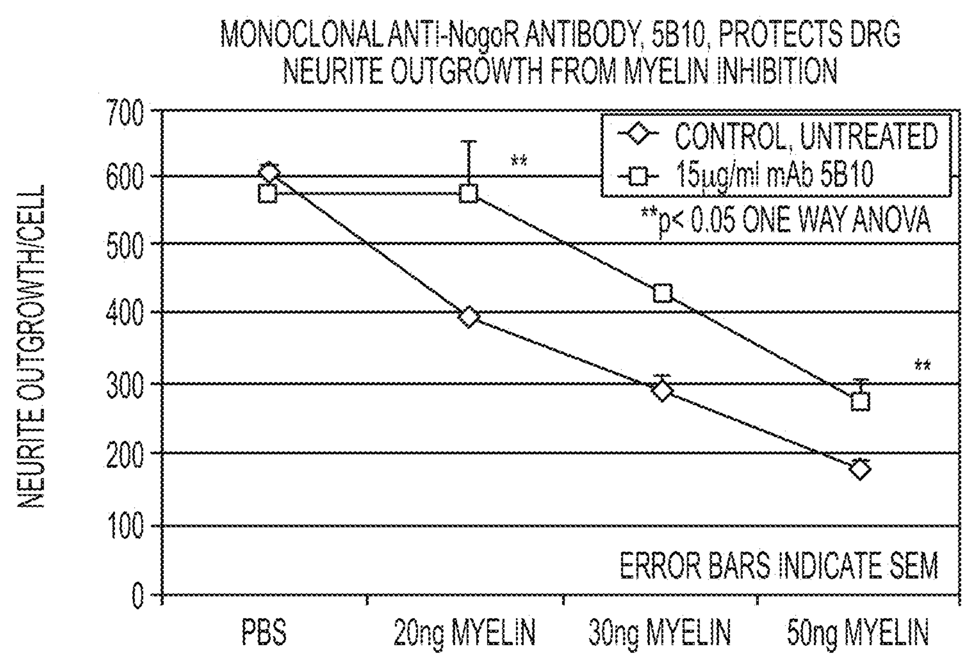
FIG. 11 is a graph depicting the effect of monoclonal antibody 5B10 on DRG neurite outgrowth/cell in the presence of increasing amounts of myelin.

Slides were fixed for 20 minutes with 4% paraformaldehyde containing 20% sucrose and stained for the neuronal marker anti beta-III-tubulin (Covance TUJ1) diluted 1:500. As secondary antibody anti-mouse Alexa Fluor® 594 (Molecular Probes) was diluted 1:300 and slides were coverslipped with Gel/Mount™ (Biømeda™). 5× digital images were acquired with OpenLab™ software and analyzed by using the MetaMorph® software for quantification of neurite outgrowth.

sNogoR310, sNogoR310-Fc and mAb 5B10 all protected DRG neurons from myelin-mediated inhibition of neurite outgrowth (FIGS. 9-11). sNogoR310 was used in a similar assay using chick neurons and was found to be protective.

We also tested the neuro-protective effect of soluble Nogo receptors by performing experiments with cells grown in the presence and absence of laminin. Neuronal cell growth in media without laminin is poor and models neuronal stress conditions.

DRG's were dissected from post-natal day 6-7 rat pups (P6-7), dissociated into single cells and plated on 96-well plates pre-coated with poly-D-lysine as described above. In some wells 2 μg/ml laminin was added for 2-3 hours and rinsed before the cells were plated. After an 18-20 h incubation the plates were fixed with 4% para-formaldehyde, stained with rabbit anti-Beta-III-tubulin antibody diluted 1:500 (Covance®) and anti-HuC/D diluted 1:100 (Molecular Probes), and fluorescent secondary antibodies (Molecular Probes) were added at 1:200 dilution. The ArrayScan® II (Cellomics®) was used to capture 5× digital images and to quantify neurite outgrowth as average neurite outgrowth/neuron per well, by using the Neurite outgrowth application. Nine 5× images from 3 wells/condition were analyzed.

In some experiments, a sub-clone of PC12 cells (Neuroscreen™) was used (Cellomics®). The Neuroscreen™ cells were pre-differentiated for 7 days with 200 ng/ml NGF, detached and replated on 96-well plates pre-coated with poly-D-lysine. In some wells 5 μg/ml laminin was added for 2-3 hours and rinsed before the cells were plated. After 2 days incubation the plates were fixed with 4% paraformaldehyde, stained with rabbit anti-Beta-III-tubulin antibody diluted 1:500 (Covance®) and Hoechst (nuclear stain). The ArrayScan® II was used to quantify neurite outgrowth as in the DRG cells.

sNogoR344-Fc or rat IgG were added in solution to P6-7 DRG neurons and to differentiated Neuroscreen™ cells at the time of plating.

The neuro-protective effect of sNogoR344-Fc was observed at 1 μM and 10 μM when P6 DRG neurons were grown in the absence of laminin. Quantification of neurite outgrowth showed a dose-dependent increase with the addition of sNogoR344-Fc. Addition of sNogoR344-Fc at the same concentrations to DRG neurons growing on a laminin substrate, did not produce any unusual effect, indicating that sNogoR344-Fc is only active on stressed cells. The neuro-protective effect of sNogoR344-Fc at the same concentrations in the absence of laminin also was seen with Neuroscreen™ cells.

EXAMPLE 11

Production and Purification of Fc-sNogoR-1 Fusion Protein

A cDNA construct encoding amino acids 1-310 of rat Nogo receptor-1 was fused to rat IgG1 Fc contained in a mammalian expression vector and this vector was electroporated into Chinese hamster ovary (CHO) (DG44) cells. Cells were maintained in alpha-MEM, supplemented with 10% dialyzed fetal bovine serum, 2 mM glutamine and antibiotic-antimycotic reagents. Two days after transfection, the conditioned media was collected and analyzed by Western blot under reducing conditions. A protein band about 60 kDa was detected using a polyclonal rabbit anti-Nogo receptor-1 antibody. Cells were expanded and sorted using a R-PE conjugated goat anti-rat IgG antibody. After the second sorting, cells were plated at a density of one cell/well in 96-well plates. Secreted soluble Nogo receptor-1 protein levels from individual wells was tested and compared using a Sandwich ELISA. ELISA plate was coated with goat anti-rat IgG Fc specific antibody. Conditioned media was applied. The bound soluble Nogo receptor-1 protein was detected by HRP conjugated donkey anti-rat IgG Fab, Fc-specific antibody. Clone 4C12 had the highest secretion level. 4C12 was expanded and grown in CHO-M7 media in spinner flask. The secretion level was about 10 mg/L at 37° C.

CHO cells expressing the sNogoR310-Fc fusion protein were cultured in large scale. 1.7 L of concentrated conditioned media was obtained from a 10 L bioreactor run. The pH was raised by addition of one-tenth volume 1.0 M Tris-HCl, pH 8.9. Solid sodium chloride and glycine were added to 3.0 M and 1.5 M respectively. A 60 mL protein A-Sepharose™ column equilibrated with 10 mM Tris-HC, 3 M sodium chloride, 1.5 M glycine, pH 8.9 was prepared. Concentrated conditioned media was applied to the column at 1.5 mL/min using a peristaltic pump. The column was washed with 300 mL of 10 mM Tris-HCl, 3 M sodium chloride, 1.5 M glycine, pH 8.9 followed with 120 mL 5 mM Tris-HCl, 3 M sodium chloride, pH 8.9. Protein was eluted with 25 mM sodium phosphate, 100 mM sodium chloride, pH 2.8. 10 mL fractions were collected in tubes containing 1.0 mL of 1.0 M HEPES, pH 8.5. Protein fractions were pooled and dialyzed against 3×2 L of 5 mM sodium phosphate, 300 mM NaCl, pH 7.4.

EXAMPLE 12

Spinal Cord Transection Assay

To test their ability to promote functional recovery in vivo, an sNogoR-1 fusion protein was tested in a rat spinal cord transection assay.

Alzet® osmotic pumps were loaded with test solution (sNogoR310-Fc in PBS) made up freshly on the day of use. The loading concentration was calculated to be 5 and 50 μM. Pumps were primed for >40 hours at 37° C. prior to implantation into animals. Female Long Evans rats were given pre-operative analgesia and tranquilizer and anesthetized using isoflurane (3% in $O_2$).

Rats were placed in a stereotaxic frame and the motor cortex exposed for infusion of the tract tracing agent BDA (10,000 MW) bilaterally. Rats then underwent dorsal hemisection of the spinal cord at TS-T6 followed by implantation of the intrathecal catheter and pump system to deliver test compound (n=1 per group).

Rats were allowed to recover and survive up to 28 days after surgery. Behavioral scoring using the BBB system was recorded up to 28 days after induction of injury, just prior to termination of the in-life phase of the study. Following perfusion and fixation, spinal cords were removed, cryoprotected, sectioned, stained and axonal counts performed.

Figure 12:
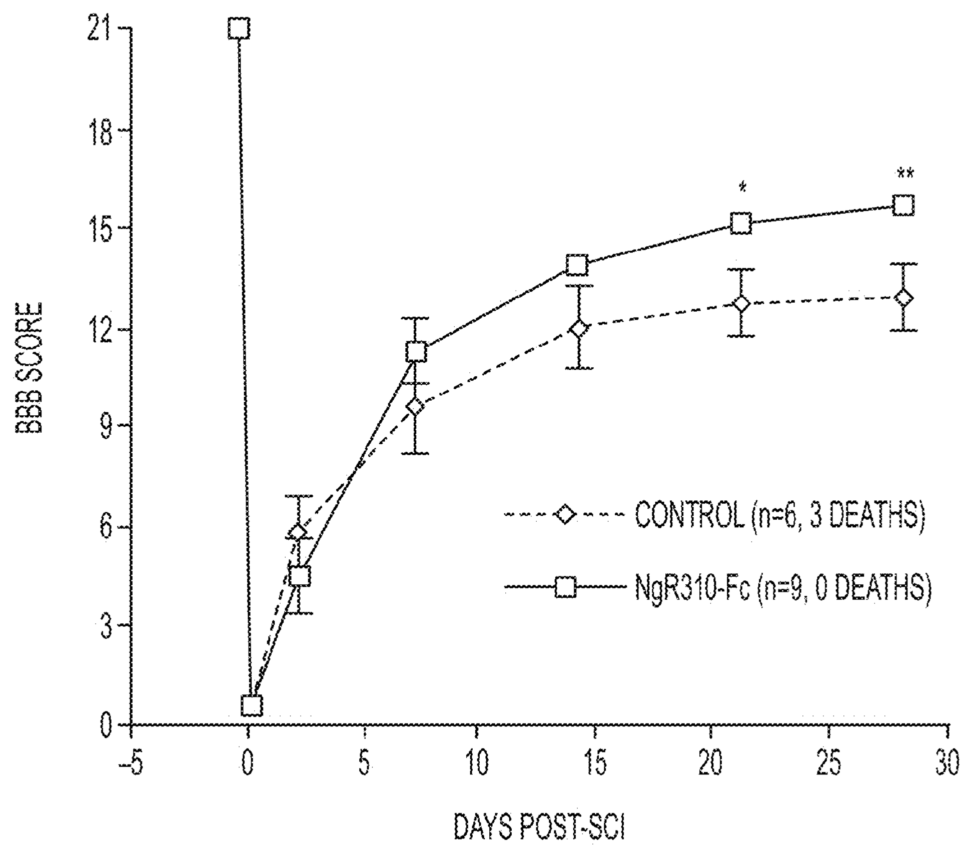
FIG. 12 is a graph depicting the effect of sNogoR310-Fc on the BBB score up to 30 days following induction of injury in a rat spinal cord transection model.

The Basso-Beattie-Bresnahan (BBB) locomotor rating scale (Basso et al., *Neurotrauma* 13:343-359 (1996)), the inclined plane test and the inclined grid walking test (Li and Strittmatter, *J Neurosci.* 23:4219-27 (2003)) were monitored in rats and mice after injury. For the inclined plane test, we measured the maximal angle to which a 50 cm×60 cm board could be angled for 5 sec without the mouse sliding off. For inclined grid walking, the mice were trained to climb a wire grid (35 cm long with 2.54 cm squares) at a slope of 45 degrees. The number of instances in which the hindpaw dropped below the grid plane was scored for each excursion from bottom to top. For the rat behavioral testing, BBB locomotor scale, grid walking and footprint analysis were performed. For grid walking, the rats were trained to walk on a wire grid (70 cm long with 2.54 an squares), and the number of instances in which the hindpaw dropped below the grid plane was counted. For footprint analysis, the walking patterns of rat hindpaws were recorded with ink during a continuous locomotion across a 90 cm runway, and stride length on each side and stride width were calculated (Metz et al., *Brain Res.* 883:165-177 (2000)). All of these behavioral tests were performed by at least two individuals. Throughout the surgery, behavioral testing and histologic analysis, researchers were blind to the identity of the compound in the minipump.

sNogoR310-Fc promoted functional recovery (FIG. 12).

EXAMPLE 13

Rat Spinal Cord Contusion Assay

The effect of soluble Nogo receptor-1 polypeptides and fusion proteins on neurons in vivo are tested in a rat spinal cord contusion assay.

Female hooded Long Evans rats (170-190 g) are treated prophylactically with analgesic and antibiotic agents. Ten minutes before surgery, animals are tranquilized with 2.5 mg/kg Midazolam i.p. and anesthetized in 2-3% isoflurane in $O_2$. Rats are then shaved, wiped down with alcohol and betadine, and ocular lubricant applied to their eyes. Next, an incision is made down the midline and the T1 to T12 vertebrae exposed.

A dorsal laminectomy is performed at T9½ and T10 to expose the cord. The rat is mounted on the Impactor. T7 and T8 segments are first clamped and then the T11 and T12 segments are attached to the caudal clamp. A soft material is placed underneath the chest of the rat. The Impactor rod is set to the zero position and the electrical ground clip is attached to the wound edge. The Impactor rod is then raised to 25.0 mm and appropriately adjusted to a position directly above the exposed spinal cord. Next, the Impactor rod is released to hit the exposed cord and the Impactor rod is immediately lifted.

The rat is then dismounted, and Gelfoam® placed on the wound. The muscle over the wound is sutured, and the incision is surgically stapled. Animals are placed in an incubator until they recover from anesthesia. Rats are given antibiotics, analgesics, and saline as required. Bladders are expressed every morning and evening thereafter until function is recovered.

Soluble Nogo receptor-1 fusion protein (e.g., sNogoR310-Fc) is administered intrathecally as described in the rat spinal cord transection model above. BBB scoring is performed one-day after surgery, then every week thereafter until 4 to 6 weeks.

EXAMPLE 14

Expression of sNogoR310 in Transgenic Mice

We produced transgenic mice expressing soluble Nogo receptor-1 protein to test its effect when expressed in vivo.

We cloned the mouse sNogoR310 cDNA (corresponding to amino acids 1-310 of the Nogo receptor-1) into the Nod site of the C-3123 vector. In this vector, sNogoR310 expression is under the control of the glial fibrillary acidic protein (gfap) gene regulatory elements, which allow high level expression with enhanced secretion from reactive astrocytes at site of injury. We digested the resulting vector sequentially with AatII and SfiI and isolated the gfap::sNogoR310 construct on a 3.4 kb fragment. We microinjected this fragment into embryos to generate transgenic mice. We verified by PCR that the transgene had integrated and identified five founder lines. We crossed heterozygous males of the two founder lines with the highest expression levels to female C57BL/6J mice. We confirmed that the GFAP-positive cells express and secrete sNogoR310 in heterozygous transgenic mice by Western blot analysis using antibody raised against Nogo receptor-1.

We homogenized the cortex and spinal cord in Tris-buffered saline supplemented with protease inhibitors (Roche) and centrifuged the homogenate at 40,000 rpm for 20 min at 4° C. We treated the supernatant with 4% paraformaldehyde for 20 min to enhance antibody specificity and dialyzed prior to immunoblotting. We homogenized the particulate fraction by sonication in RIPA buffer (1% Triton® X-100, 0.5% sodium deoxycholate, 0.1% SDS in PBS), centrifuged the resulting homogenate and treated this supernatant (detergent-soluble particulate fraction) as above. We analyzed 20 μg of brain or spinal cord protein by immunoblot using rabbit antiserum raised against Nogo receptor-1 at 1:2000 dilution. We visualized immunoreactivity by incubation with AP-conjugated anti-rabbit IgG and NBT/BCIP AP substrates.

We detected secreted 37 kDa sNogoR310 in detergent-free soluble extracts of cortex and spinal cord from the two transgenic lines Tg08 and Tg01, but little if any soluble Nogo receptor-1 protein at 37 or 81 kDa is present in littermate wild type (WT) mice. Examination of the particulate fractions demonstrated that there were comparable levels of endogenous Nogo receptor-1 in both WT and transgenic mice.

EXAMPLE 15

Expression of sNogoR310 in Transgenic Mice after Injury

We tested the effect of CNS injury on sNogoR310 expression in transgenic mice by performing a dorsal over-hemisection injury. We obtained sNogoR310 transgenic and non-transgenic control animals by mating heterozygous males with C57/BL6 females as described in Example 14.

We deeply anesthetized adult female heterozygous transgenic or littermate WT mice (10-16 weeks of age) and performed a complete laminectomy, fully exposing the dorsal part of spinal cord at T6 and T7 levels. We performed a dorsal over-hemisection at T6 with a 30-gauge needle and a pair of microscissors to completely sever the dorsal and dorsolateral corticospinal tracts (CSTs). We passed a marked needle across the dorsal part of the spinal cord several times to assure that the lesion was at a depth of 1.0 mm. We sutured the muscle layers over the laminectomies and closed the skin on the back with surgical staples. To trace the corticospinal tracts, we made a burr hole overlying cerebral cortex on the right side into the skull 14 days after spinal cord injury. We applied the tracer BDA (MW 10,000, 10% in PBS) (Molecular Probes, Eugene, Oreg.) to 4 injection sites at a depth of 0.7 mm from the cortical surface, Four weeks after injury, the mice were perfused transcardially with PBS, followed by 4% paraformaldehyde. Mice used for sNogoR310 expression experiments did not receive any tracer injection.

For the mice used for western blot analysis, the spinal cord at a level between T3 and L3 was collected without perfusion 14 days after injury. Mice used for Nogo receptor-1 immunohistochemical staining were perfused with 4% paraformaldehyde 10 days after hemisection, and the injured spinal cord was removed for sectioning. To examine sNogoR310 expression in the injured brain of transgenic and WT mice, a cortex stab injury was performed with a number 11 scalpel blade held in a stereotaxic apparatus (David Kopf, Tujunga, Calif.). A 4 mm parasagittal cut was made, 0.5 mm posterior to Bregma, 1.5 mm laterally from midline and 3.5 mm deep.

We detected increased levels of sNogoR310 in soluble extracts of spinal cords ten days after the injury in transgenic mice but not in WT mice, consistent with the upregulation after injury of GFAP around the lesion. To confirm that this was not due to compensatory upregulation of Nogo-A, we tested its expression and found that it was similar in either intact or injured cortex and spinal cord from either WT and transgenic mice.

We examined the cellular expression of sNogoR310 in injured CNS by immunostaining the injured brain and spinal cord containing the lesion area with antibodies against Nogo receptor-1 and GFAP. The general morphology of reactive astrocytic glia does not differ between WT and transgenic mice, but the density stained for Nogo receptor-1 in both intra- and extracellular space is remarkably higher in the gfap::sNogoR310 transgenic mice than in WT mice, indicating increased sNogoR310 expression around the lesion in transgenic mice. Nogo receptor-1 protein is co-localized with astrocytic marker GFAP only in the transgenic mice. There is also a greatly enhanced diffuse non-cellular staining in the transgenic samples, consistent with sNogoR310 in the extracellular space. Neuronal cell body Nogo receptor-1 staining is detected in both WT and transgenic mice.

EXAMPLE 16

Secreted sNogoR310 Induces CST Sprouting in Transgenic Mice

We tested whether increased expression of sNogoR310 around the lesion in transgenic mice results in the regeneration of injured axons.

We investigated the integrity of descending corticospinal tracts (CST) by injecting anterograde tracer biotin dextran amine (BDA) into the right motor cortex as described in Li and Strittmatter, *J. Neurosci.* 23:4219-27 (2003). In littermate WT mice, the prominent dorsal CST (dCST) is tightly bundled rostral to the lesion, and a few dorsolateral CST fibers are visible ipsilaterally. A small number of BDA-labeled short collateral sprouts project into gray matter, particularly in the ventral cord, but the sprouting is largely confined to the side of the cord contralateral to the tracer injection. However, the sections rostral to dorsal hemisection from injured sNogoR310 transgenic mice indicate a quite different BDA labeling pattern. A high density of BDA-labeled CST fibers are observed outside of prominent dCST in all the transgenic mice from line Tg08 or line Tg01. Ectopic fibers extend throughout the gray matter area, and some fibers reach into lateral and dorsolateral white matter. Several fibers (4-12 sprouts per transverse section) are seen on the opposite side of the spinal cord (ipsilateral to the tracer injection site). Micro densitometric measurement of the collateral sprouts indicates approximately a tenfold increase in sprouting density in sNogoR310 transgenic mice. Examination of parasagittal longitudinal sections from 1 to 4 mm rostral to the lesion reveals that dCST fibers extend a large number of branching sprouts into the ventral gray matter area in sNogoR310 transgenic mice, in contrast to the littermate WT animals. Generally, the pattern and extent of sprouting rostral to the lesion in transgenic mice are similar to those observed in the mice treated systemically with Nogo receptor-1 antagonist peptide NEP1-40 (Li and Strittmatter, *J. Neurosci,* 23:4219-27 (2003)).

These results demonstrate that secreted sNogoR310 induces CST sprouting in the transgenic mice.

EXAMPLE 17

Regenerating CST Axons Bypass the Lesion Site into Distal Spinal Cord in sNogoR310 Transgenic Mice We isolated spinal cord 4 mm rostral to and 4 mm caudal to the lesion site (8 mm long in total) from transgenic mice and embedded it in a glutaraldehyde-polymerized albumin matrix, and cut parasagittally on a vibratome (30 μm thick). We collected transverse sections (50 μm) from the spinal cord 5-7 mm rostral to and 5-7 mm caudal to the injury site. For sNogoR310-Fc injection experiments in rats, the spinal cord extending from 10 mm rostral to 10 mm caudal from the lesion site was cut parasaggitally (50 μm) on a vibrating microtome. Transverse sections were collected from the spinal cord 11-16 mm rostral to and 11-16 mm caudal to the injury site. We incubated the sections with avidin-biotin-peroxidase complex and visualized the BDA tracer by nickel-enhanced diaminobenzidine HRP reaction (Grandpre, *Nature* 417:547-551 (2002)). We processed some sections for serotonin immunohistochemistry (anti-5-HT antibody) by indirect immunofluorescence. To visualize the lesion area, we double-stained some sections with antibodies directed against GFAP (Sigma®, St. Louis, Mo.). We mounted, dehydrated and covered the sections with mounting medium.

We tested whether the fibers induced by sNogoR310 expressed in transgenic mice after injury (see Example 16) cross the lesion area into the caudal spinal cord to provide functional recovery.

Consecutive parasaggital sections across the injury site drawn in camera lucida display the overall distribution pattern of the regenerating CST fibers a few millimeters from the lesion. Sections from WT mice show no CST fibers extending beyond the injury site. Similar sections from sNogoR310 transgenic mice display numerous CST fibers that cross the transection area and project into the distal gray and white matter areas in a highly branched pattern. Immediately rostral to hemisection, a high density of BDA-labeled CST sprouting originated from prominent dCST projects into the lesion area, but most CST sprouts failed to pass the transection area where scar formation and tissue cavitation are prominent. A small but highly significant fraction of the regenerating axons bypass the lesion site through the remaining tissue bridges of the ventral and ventrolateral gray and white matter. In addition, a few CST fibers appear to cross the transection area itself via the lesioned dorsal and dorsolateral spinal cord into distal regions. In the vicinity of lesion, the course of regenerating fibers was typically tortuous and quite distinct from the normal straight fibers in the rostral CST. Collaterals and arborized fibers are most frequently seen in gray matter area of distal spinal cord. The reconstructions demonstrate 5-15 BDA-labeled regenerating fibers coursing in the rostral-caudal axis at any level 1-4 mm caudal to the lesion in each transgenic mouse. For transverse sections 5-7 mm caudal to dorsal hemisection, BDA-labeled CST axons are seen in both the gray matter and white matter areas in each transgenic mouse. The fiber counts for the transgenic mice indicate approximately a similar number of BDA-labeled CST fibers to the proximal levels in the sagittal sections.

In addition to CST fibers, the other descending tracts, such as raphespinal fibers, also contribute to locomotor function in mice. In this mouse dorsal over-hemisection model, the transection injures a majority of the serotonergic fibers, decreasing the density of these fibers by approximately 80% in the ventral horn. Analysis of total length of serotonin fibers in the ventral horn of caudal spinal card indicates a much greater number of these fibers in transgenic mice than WT group, indicating that the growth-promoting effects of sNogoR310 in transgenic mice are not limited to one axon descending pathway.

EXAMPLE 18

Transgenic Expression of sNogoR310 Improves Locomotor Recovery

The CST axon tracing and serotonergic fiber analysis indicate that the sNogoR310 released from astrocytes in transgenic mice stimulates extensive anatomical regeneration of injured descending axons in the spinal cord. We performed several behavioral tests as described in Example 12 to determine whether these regenerated fibers benefit functional recovery.

Figure 13A:
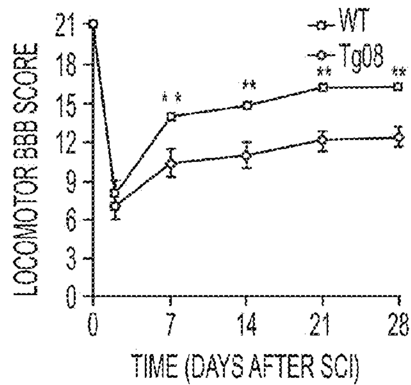
FIGS. 13A and 13B report the locomotor BBB score as a function of time after dorsal hemisection in the WT or transgenic mice from Line 08 or Line 01.
Figure 13B:
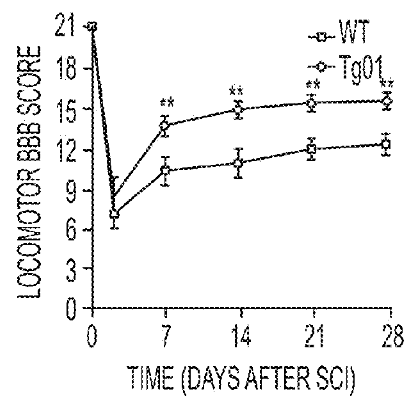

As assessed by the BBB test, the WT mice partially recover locomotor function during a 4-week period of survival. At 4 weeks post-injury, most WT mice recover a level characterized by consistent plantar stepping with consistent weight support, but they exhibit only occasional to frequent forelimb-hindlimb coordination, with a rotation of predominant paw position when making initial contact with surface. In contrast, the BBB scores of sNogoR310 transgenic mice from both lines Tg08 and Tg01 are significantly higher than control group throughout the 7-28 day observation period (FIGS. 13A and 13B). At 28 days after injury, most transgenic mice show consistent forelimb-hindlimb coordination, and the predominant paw position is parallel to the body.

Figure 13C:
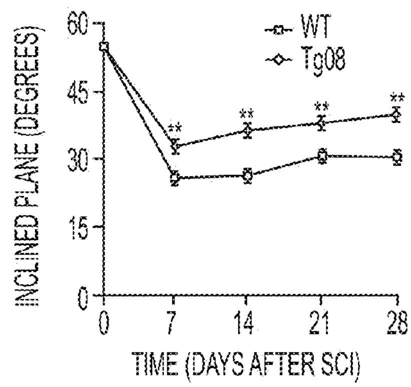
FIG. 13C graphs the maximal tolerated inclined plane angle as a function of time after injury for WT and transgenic mice.
Figure 13D:
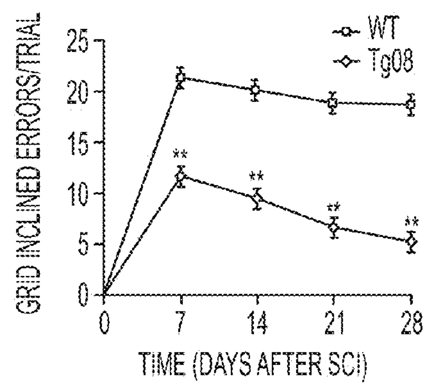
FIG. 13D shows hindlimb errors during inclined grid climbing as a function of post-injury time. In all the graphs, means±s.e.m. from 7-9 mice in each group are reported. The values from transgenic group are statistically different from the WT mice. (double asterisks, P<0.01; Student's t-test).

We employed two more behavioral tests to further characterize the performance of sNogoR310 transgenic mice. First, we measured the maximal angle to which a board would be tilted without a mouse losing its grip within 5 sec. Before dorsal hemisection injury, both transgenic and WT mice can sustain their posture on board angled at 55 degrees. On days 7-28 after injury, the sustainable angle is reduced in all mice, but the angles sustainable by the transgenic mice are significantly greater than those for the control group (FIG. 13C). In another behavioral test, mice climbed a grid placed at a 45 degree angle to vertical and excursions of the hindlimbs below the plane of the grid were counted (Metz et al., *Brain Res.* 883:165-177 (2000)). No mice made errors on this test during the pre-injury training. There are numerous foot fault errors with only minimal improvement in WT mice during the period 2-6 weeks post-injury. In contrast, the sNogoR310 transgenic mice exhibit a progressive improvement in grid climbing during this period, with the majority of improvement occurring between 1-3 weeks post-injury (FIG. 13D). Thus, transgenic mice secreting sNogoR310 from astrocytes exhibit CST regeneration, raphespinal sprouting and improved motor function after thoracic spinal hemisection.

EXAMPLE 19

Intrathecal Administration of sNogoR310-Fc Protein Induces CST Sprouting

As a second test of the growth-promoting benefit of soluble Nogo receptor-1 after spinal trauma, we administered the purified protein intrathecally.

We fused the ligand binding domain (27-310) of rat Nogo receptor-1 to the rat IgG1 Fc domain to promote stability and purification. We purified protein from stably transfected CHO cells. This protein blocks Nogo-66, MAG and myelin action in vitro, as shown previously for mouse sNogoR310-Myc His (Fournier et al., *J Neurosci.* 22:8876-8883 (2002); Liu et al., *Science* 297:1190-1193 (2002)). We delived sNogoR310-Fc protein intrathecally to rats with a mid-thoracic dorsal hemisection injury through an osmotic minipump. During a four-week survival period after injury, 1.2 mg sNogoR310-Fc protein was locally administered in each rat. In rats receiving the vehicle treatment (1.2 mg rat IgG), sections rostral to hemisection display the tightly bundled prominent dorsal CST and very few ectopic BDA-labeled CST fibers above the lesion site. Sections rostral to lesion from injured rats receiving sNogoR310-Fc protein exhibit a quite different pattern of labeling. Numerous ectopic fibers sprouting from the BDA-labeled CST are observed from transverse and parasagittal sections. In some cases, projections cross from the dCST area near the midline to the circumference of the cord, becoming intermingled with the dorsolateral CST. The sprouting axons extend though gray matter to a greater extent than white matter. A measure of ectopic sprouting fibers (≥100 μm in transverse sections, ≥200 μm in sagittal sections) adjacent to the dCST reveals a greater increase in the sNogoR310-Fc-treated rats.

EXAMPLE 20

CST Axons Regenerate into Distal Spinal Cord in sNogoR310-Fc Treated Rats

We deeply anaesthetized female Sprague-Dawley rats (190-250 g) and conducted laminectomies at spinal levels of T6-7, exposing the spinal cord. We cut the dorsal half of the spinal cord with a 30-gauge needle and a pair of microscissors to sever the dorsal parts of CSGT tracts, and assured the depth of the lesion (1.8 mm) by passing the sharp part of a number 11 blade across the dorsal half of the cord (Grandpre et al., *Nature* 417:547-551 (2002)). An osmotic minipump (Alzet® 2ML4, 2 ml volume, 2.5 μl/h, 28 day delivery), which was filled with 1.2 mg rat IgG in PBS or 1.2 mg sNogoR310-Fc fusion protein in PBS, was sutured to muscles under the skin on the back of the animals. A catheter connected to the outlet of the minipump was inserted into the intrathecal space of the spinal cord at the T7-8 level through a small hole in the dura.

Nogo receptor-1 antagonist protein infusion induced extensive sprouting rostral to a rat hemisection, but a more critical issue is whether the sprouting CST fibers project to distal spinal cord and contribute to locomotor recovery. Longitudinal sections across lesion site from vehicle-treated rats display no detectable or a very small number of BDA-labeled ventral CST fibers below the lesion level (Grandpre et al., *Nature* 417:547-551 (2002); Weidner et al., *Proc. Natl. Acad. Sci. USA* 98:3513-3518 (2001)). The similar sections from sNogoR310-Fc treated rats demonstrate many BDA-labeled fibers bypass the transection site and project to the caudal spinal cord largely through the bridging tissues of the ventral and ventrolateral spinal cord. Immunostaining for astrocytic marker GFAP display that the extent of transection reached deeper than central canal area. Unlike the linear profile of rostral fibers in prominent dorsal CST, the regenerated CST fibers usually follow a highly branching trajectory in the distal spinal cord, particularly in gray matter area. These fibers are detected in many regions of spinal cord, but they are more easily seen in the central part and dorsal half of spinal cord throughout the spinal cord. Counts of CST fibers from sagittal sections indicate approximately 20 BDA-labeled axons at 1-2 mm caudal to lesion and 15 traced axons at 7-8 mm distal to lesion from each sNogoR310-Fc-treated rat.

Generally, the branching pattern of these fibers is similar to that observed from local NEP 1-40 peptide treated animals, but more collateral branching in each sprout is seen from the sections treated with sNogoR310-Fc protein. A measure of the sprouts from distal spinal cord demonstrates that the total collateral length of each sprout in sNogoR310-Fc-treated rats is twice as great as that from NEP 1-40-treated animals. The number of sprouts (≥200 μm in length) at 1-10 mm caudal to spinal cord in both Nogo receptor-1 antagonist-treated groups is approximately 20-40 times greater than control groups. More sprouts are seen from sNogoR310-Fc treated rats than local NEP 1-40 treatment (~50 vs. 25 sprouts/rat), but this difference is not statistically significant ($p=0.1713$, t-test).

Regenerating CST axons are observed in transverse sections of spinal cord 11-15 mm caudal to hemisection in rats receiving sNogoR310-Fc treatment. These fibers are detected in both gray matter and white matter of the spinal cord. The fibers detected in gray matter often exhibit more collateral branching than in white matter area. In contrast, in transverse sections from vehicle-treated group, only occasional BDA-labeled are seen in the ventral white matter area, consistent with the uninjured ventral CST axons. At this level of distal spinal card, the average number of BDA-labeled CST fibers from both Nogo receptor-1 antagonist-treated groups [sNogoR310-Fc and NEP 1-40] are approximately 20-fold greater than vehicle-treated rats. Taken together, both Nogo receptor antagonists, sNogoR310-Fc protein and NEP 1-40 peptide, result in dramatic CST axon regeneration in distal spinal cord, but the sprouting induced by the former exhibits a more highly branched pattern.

EXAMPLE 21

Local sNogoR310-Fc Induces Sprouting of Rubropinal and Serotonergic Axons in Injured Rat Spinal Cord Fourteen days after hemisection, a burr hole was made on each side of the skull overlying the sensorimotor cortex of the lower limbs to trace CST fibers. The anterograde neuronal tracer BDA (10% in PBS, 3.5 μl per cortex) was applied at seven injection sites at a depth of 1.5 mm from dura on each side (Grandpre et al., *Nature* 417:547-551 (2002)). For rubrospinal tract tracing in rats, the tracer BDA (1 μl; MW 10,000; 10% in PBS) was injected into red nucleus on the left side (5.8 mm posterior to bregma, 0.7 mm lateral, 7.0 mm ventral to the skull surface). Two weeks after BDA injection, these animals were perfused with PBS, followed by 4% paraformaldehyde, and tissue was collected for histology.

Repair of injured rubrospinal tract (RST) fibers contribute to functional improvements after spinal cord injury (Liu et al., *J. Neurosci.,* 19:4370-4387 (1999)). The widespread distribution of Nogo receptor-1 in CNS neurons (Wang et al., *J. Neurosci.* 22:5505-5515 (2002)) makes it possible that inhibition of Nogo receptor-1 with its antagonist may result in regrowth of RST axons after injury. To test effects of sNogoR310-Fc on injured RST, the integrity of this pathway was traced by injecting BDA into left red nucleus. At the spinal cord level, RST fibers are normally located in dorsolateral white matter area of spinal cord, and are transected by the dorsal hemisections of this study. In transverse sections 11-15 mm rostral to lesion from control rats, a small number of short BDA-labeled fibers are seen between the prominent RST and dorsal horn gray matter. Sections at same level treated with sNogoR310-Fc exhibit many linking fibers between the main RST and dorsal horn gray matter. Transverse sections 11-15 mm distal to SCI, no BDA-labeled RST fibers in vehicle-treated rats. In contrast, sections at the same level receiving sNogoR310-Fc treatment display many BDA-labeled RST fibers in both gray and white matter contralateral to tracer injection. Some sprouts with a branching pattern are seen in the gray matter ipsilateral to BDA injection.

Ruphespinal spinal fibers were also examined in sNogoR310-Fc treated spinal injured rats. Immunostaining demonstrates the density of serotonergic fibers 11-15 mm rostral to lesion that is similar between vehicle and sNogoR310-Fc treated groups. In the sections 11-15 mm below the lesion, the seroton fibers in sNogoR310-Fc treated rats are twice as numerous as those in the control group. These results demonstrate that the responsiveness to Nogo receptor-1 inhibition by sNogoR310-Fc protein is not limited to CST fibers, and that the other descending tracts, such as rubrospinal and serotonergic axons, are also responsive to Nogo receptor-1 antagonism.

EXAMPLE 22

Local Treatment with sNogoR310-Fc Improves Functional Recovery in Rats

Intrathecal administration of sNogoR310-Fc protein stimulates axon regeneration in several descending pathways after traumatic spinal cord injury. We tested whether the protein also improves functional recovery in the injured spinal cord.

Figure 14A:
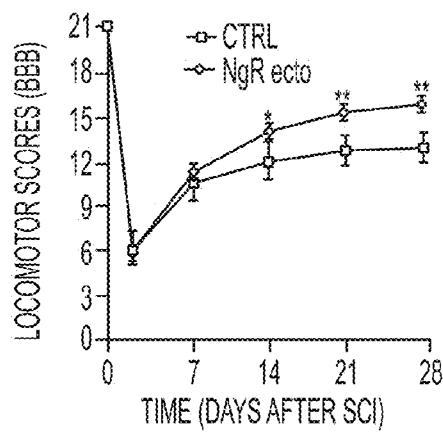
FIG. 14A shows the locomotor BBB score as a function of time after dorsal hemisection in vehicle or sNogoR310-Fc treated animals.
Figure 14B:
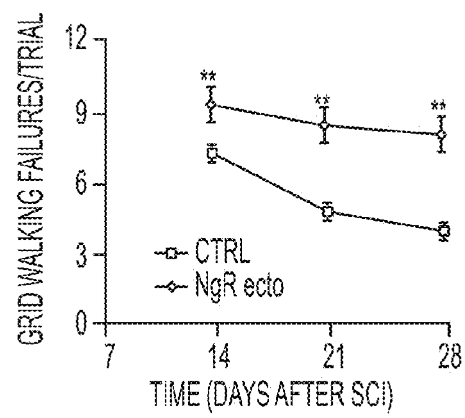
FIG. 14B shows hindlimb errors during grid walking as a function of time after injury.

At 2 weeks after the hemisection, the locomotor BBB score in vehicle-treated rats reaches a stable level of 12 (FIG. 14A). At 4 weeks after lesion, most of controls (6 out of 7) have frequent-consistent weight-supported plantar steps and frequent-consistent forelimb-hindlimb coordination, but they have a rotation of predominant paw position when making initial contact with surface. In contrast, in rats receiving sNogoR310-Fc protein treatment, the locomotor score continues to improve between 2-4 weeks post-trauma. At 4 weeks after injury, all 9 of the sNogoR310-Fc treated animals had consistent forelimb-hindlimb coordination and a parallel paw position at initial contact with the testing surface.

Figure 14C:
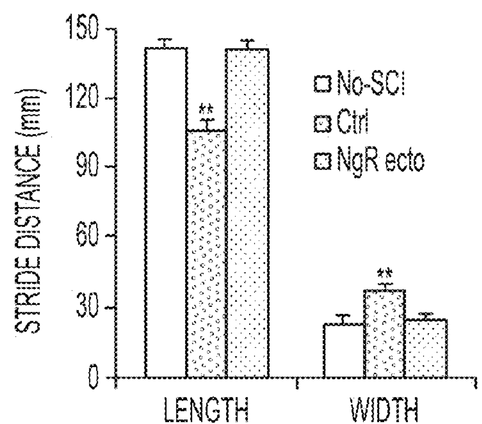
FIG. 14C shows footprint analysis revealing a shorter stride length and a greater stride width in control mice than uninjured or injured+sNogoR310-Fc rats. In all the graphs, means±s.e.m. from 7-9 rats in each group are reported. The values of sNogoR310-Fc group are statistically different from the control (FIGS. 14A-B). The control values are statistically different from no-SCI or SCI+sNogoR310-Fc rats in FIG. 14C. (asterisk, p<0.05; double asterisks, p<0.01; Student's t-test).

Grid walking has been used to assess the deficits in descending fine motor control after spinal cord injury (Metz et al., *Brain Res.* 883:165-177 (2000)). This performance requires forelimb-hindlimb coordination and voluntary movement control mediated by ventrolateral, corticospinal and rubrospinal fibers. During the pre-injury training, all the rats accurately place their hindlimbs on the grid bars. At 2-4 weeks post-injury, control rats make 8-9 errors per session with only minimal improvement over time. In contrast, the rats treated with sNogoR310-Fc exhibit a progressive improvement on grid walking and make significant fewer errors (4-7/session on average). The majority of the improvement occurs at 2-3 weeks after injury. Analysis of hindpaw footprints in control group displays that stride length is significantly decreased and stance width is increased at 4 weeks post-hemisection, compared with uninjured rats or injured animals receiving sNogoR310-Fc treatment (FIG. 14C). Therefore, these multiple behavioral tests demonstrate that blockade of Nogo receptor-1 function with local injection of antagonist protein improves locomotor recovery after injury.

EXAMPLE 23

Binding of a Monoclonal Anti-NgR1 Antibody, 1D9, to Soluble Rat Nogo Receptor 310 (sNgR310)

Figure 15:
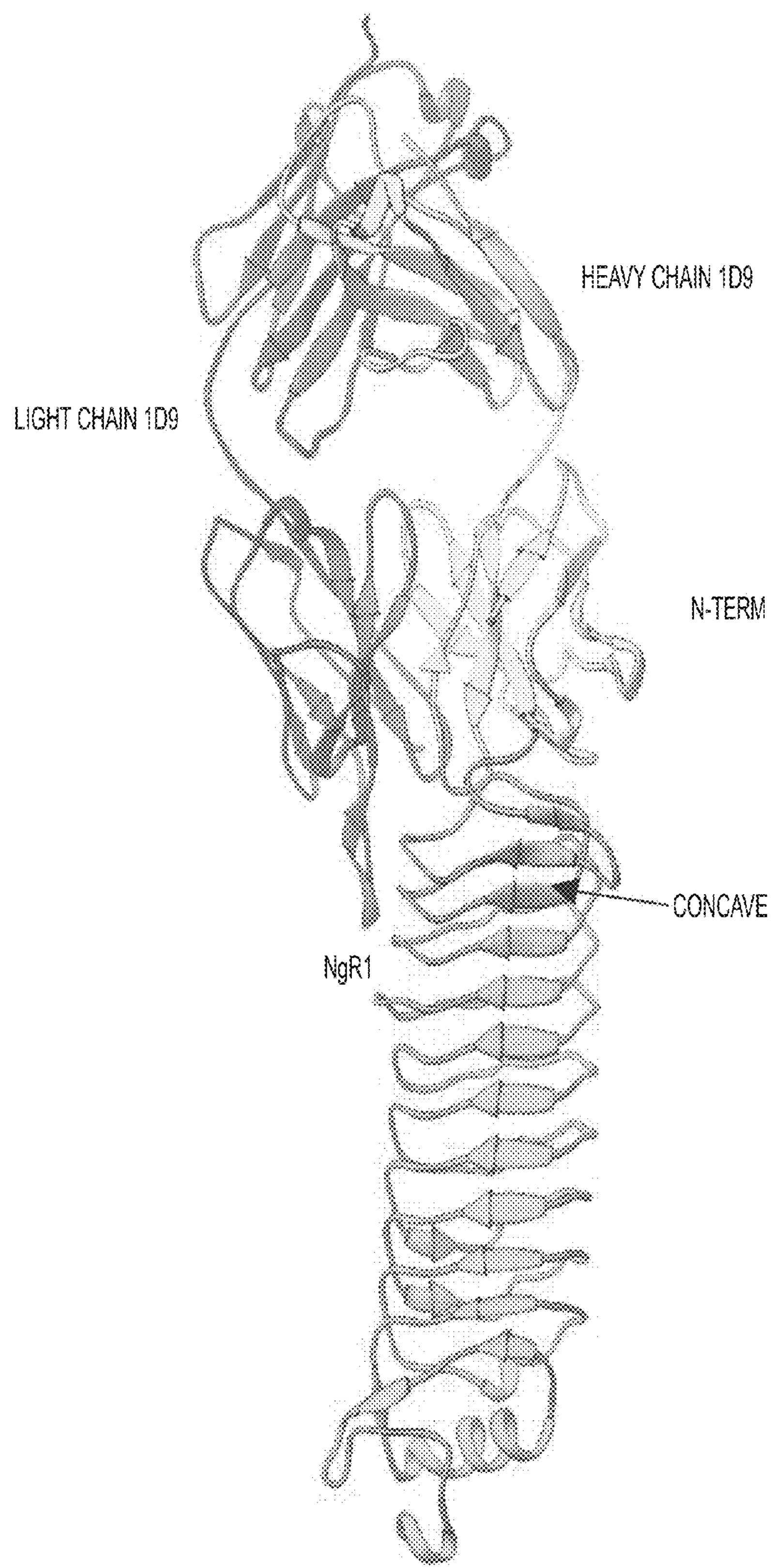
FIG. 15 shows a model of the binding of the anti-rNgR1 antibody, 1D9, to the soluble fragment of rat NgR1 (srNgR310).

Structural analyses performed on the co-crystal complex of the 1D9 Fab and a soluble fragment of rat NgR1 (srNgR310) shows that this antibody binds near the junction of the N-terminus cap and leucine rich repeat domain on rat NgR1. FIG. 15. 1D9 binds only to rat NgR1 and does not recognize human or mouse NgR1, nor NgR2 and NgR3. For crystallization of rat srNgR310-Fc with the 1D9 Fab, each macromolecule was cleaved with papain and purified from the Fc portion and stored in 10 mM Hopes pH 7, 50 mM NaCl. The complex was prepared at 80 μM each and mixed at a volumetric ratio of 2:1 with a reservoir solution consisting of 14% Peg3350, 0.4M Zinc Acetate, 0.1M Magnesium Chloride. The solution was incubated at 20 C for 1 hr and centrifuged at 12,000×g for 3 minutes to remove precipitate. Crystals were grown by placing 3-5 μL of the supernatant over wells containing 50% to 100% of the reservoir solution at 20 C. Thin plate-like crystals grew over a period of 1 week at 20 C. The crystals were cryoprotected by quickly transferring into 0.2M Zinc Acetate, 8% Peg3350, 25% Ethylene Glycol for 2 min and then frozen by quick transfer into liquid nitrogen.

Crystals approximately 10 μm thick diffracted to 3.2 Å at beamline X25 at the National Synchrotron Light Source (Upton, N.Y.). Data processing with the HKL program package v. 1.97 (Otwinowski, Z., and Minor, W., *Methods Enzymol* 276: 307-326 (1997)) revealed the crystals to belong to a P21212 space group and approximate cell dimensions a=90.6 Å, b=188.6 Å, c=125.5 Å, and α=β=γ=90, consistent with 2 Fab-NgR1 complexes per asymmetric unit.

The crystal structure was solved by utilizing information on multiple isomorphous replacement experiments on soaked crystals to identify common mercury sites bound to the NgR along with molecular replacement. The space group was identified by inspection of mercury and gold isomorphous difference patterson maps in which a consistent 5 sigma peak was identified at the w=0 harker section. Molecular replacement with MOLREP (Vagin, A., and Teplyakov, A., *J. Appl. Cryst.* 30:1022-1025 (1997)) utilizing a rat NgR homology model based on the human NgR1 structure (pdb code 1OZN) (He, X. L. et al., *Neuron* 38:177 (2003)) and a homology model for the 1D9 Fab led to placement of one NgR1, one Fab and a second NgR1 molecules with a resulting R-factor of 48% and clear density for the CDR regions of the Fab. The placement of the model was confirmed by mapping the mercury sites identified from difference patterson maps onto equivalent positions on both NgR1 molecules near Asp138 and His182. No additional Fab fragments have been clearly identified in the density. Refinement of the two NgR1 and 1 Fab using CNX (Brunger, A. T. et al., *Acta Crystallogr D Biol Crystallogr* 54:905-921 (1998)) to 3.2 Å resolution has proceeded with a current R-factor of 42% and Rfree of 46%.

Table 8 shows the contacts between the 1D9 Fab and rat NgR1. Contacts in which atoms from the Fab are within 3.9 Å distance from atoms in rat NgR1 are listed and those contacts that could form a hydrogen bond with either the main chain or side chain have an associated asterisk(*).

TABLE 8

| CDR L1 | CDR L2 | CDR L3 |
|---|---|---|
| KSSQSLLNSRNRKNYLA | WASTRES | MQSYNLFT |
| N31-1D9 | | |
| Y71-NgRI | | |
| R33-1D9 | | |
| Y71, D97*, A94-NgRI | | |
| N34-1D9 | | |
| S70*, Y71-NgRI | | |
| **CDR H1** | **CDR H2** | **CDR H3** |
| GFSLSSYGVH | VIWSGGNTHYNSALMS | VGIYYEGAWFAY |
| F27-1D9 | S53-1D9 | |
| P26-NgRI | S79*-NgRI | |
| S28-11D9 | G54-1D9 | Y101-1D9 |
| P26-NgRI | R81-NgRI | P73*, A74*, S76*, A50, V51*-NgRI |
| S30-1D9 | N56-1D9 | Y102-1D9 |
| A57*-NgRI | Q78*-NgRI | Y71, P73, A50, V51*, L36*-NgRI |
| S31-1D9 | | E103-1D9 |
| G54-NgRI | | Q49, A50, V51, P52, A53*-NgRI |
| Y32-1D9 | | G104-1D9 |
| P26, P28-NgRI | | A53-NgRI |

*indicates H-bond interactions

EXAMPLE 24

NgR RNAi Screening by Transient Transfection

Three RNAi constructs were designed against the human NogoR1 (FIG. 16A) transcript. RNAi-1 and RNAi-3 target the human NgR gene specifically. RNAi-2 was designed to target human, mouse, and rat NgR genes. Pairs of DNA oligonucleotides were synthesized and constructed into a PolIII promoter based RNAi expression vector, pU6 that contained the human U6 promotor, kar resistance gene, and a PacI cloning site. Nogor 2m was designed to carry two mismatches to the target sequence and serve as a negative control. The nucleotide sequences of these oligonucleotides are shown in FIG. 16B.

The RNAi constructs were screened initially by co-transfecting the human NgR expression vector together with the RNAi expression plasmids (phU6NgR-RNAi-1, 2 and 3) in mouse L cells. Mouse L cells were plated in 6 well culture plates and then transfected with control GFP reporter plasmid alone or with RNAi vector against GFP, pU6GFPRNAi (lanes 2 and 3). The expression of GFP was monitored as a control for GFP gene silencing. Mouse L cells were transfected with 0.5, 1 or 2 μg of hNgR expression vector (lanes 4-6). The DNA amount in each well was adjusted to a total of 4 μg DNA by adding pUC19 plasmid. The RNAi:target ratio was 4:1. Five micrograms of hNgR vector was co-transfected with 2 μg NgR RNAi-1, 2, 3, or 2m plasmid (lanes 7-10). Forty eight hours post transfection, cells were harvested in SDS loading buffer and subjected to SDS-PAGE. The expression of hNgR was analyzed by western blot using rabbit serum against polyclonal hNgR antibody R150 (panel A) or monoclonal antibody 7E11 (panel B).

Figure 17A:
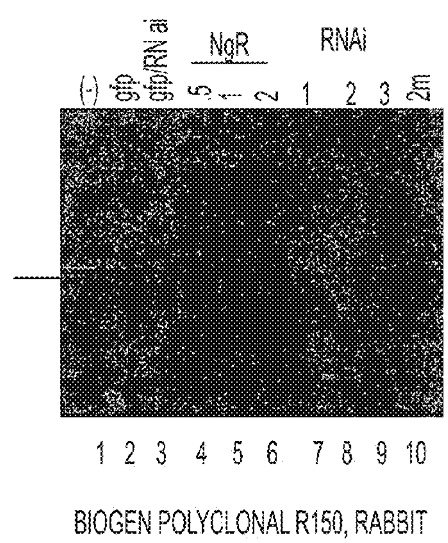
FIG. 17 depicts the results of the transient transfection test of RNAi knockdown in mouse L cells.
Figure 17B:
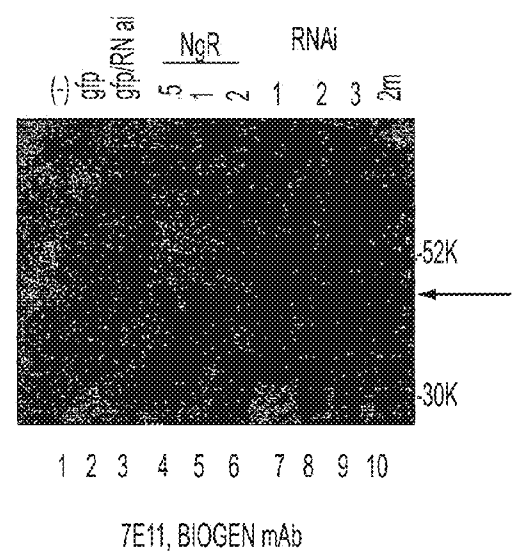

Effective NgR expression silencing was observed in phU6NgR-RNAi-1 and -2 transfected cells on Western blot using NgR antibodies 7E11 (monoclonal) and R150 (rabbit polyclonal). The results are shown in FIG. 17. The expression of NgR was reduced to basal levels in NgR RNAi-1 and -2 transfected cells. In contrast, NgR RNAi-3 did not show any significant reduction of NgR, which was similar to the control, mutant NgR RNAi-2m. Therefore, NgR RNAi-1 and -2 are effective in hNgR gene silencing. Transient transfection results demonstrated >90% inhibition of NgR expression.

EXAMPLE 25

Human NGR Silencing Confirmation

Figures 18A, 18B:
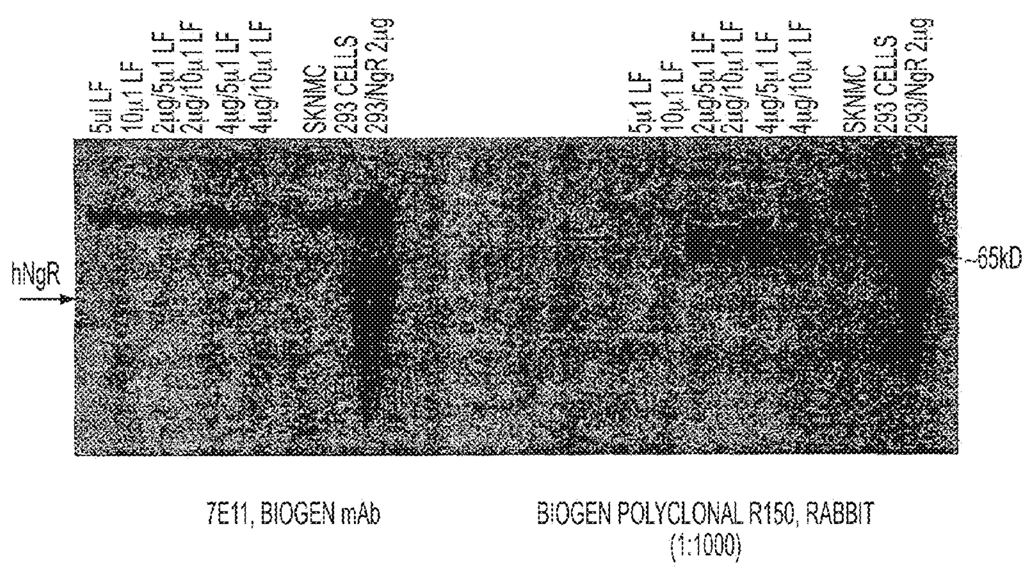
FIG. 18 shows the transfection of the human NgR expression vector into SKN and 293 cells.

Although the detected signals are specific to hNgR (only in hNgR cDNA transfected cells) with two types of antibodies (FIG. 17), the apparent MW of the detected bands (50 kD) was lower than expected. While not being bound by theory, this is probably due to the altered glycosylation of human NgR in mouse L cells. In order to confirm the observation on NgR MW discrepancy, hNgR cDNA transfection was carried out again in human SKN cells and 293 cells using Lipofectin. Forty-eight hours post transfection, cells were harvested in SDS loading buffer and subjected to SDS-PAGE. The expression of NgR was detected by Western blot using both 7E11 and R150 as described above. No hNgR specific signal was detected in parental SKN or 293 cells and the apparent MW of hNgR detected with R150 is of expected in both SKN and 293 cells, >65 kD (FIG. 18).

Figure 19:
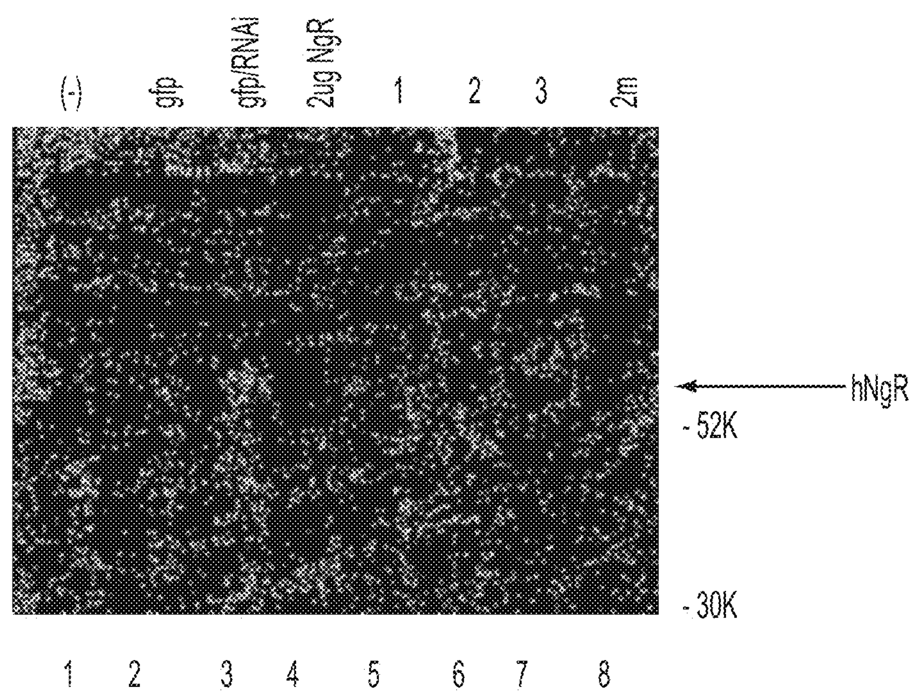
FIG. 19 depicts the transient transfection test of RNAi knockdown in human SKN cells.

The RNAi mediated hNgR silencing was confirmed in SKN cells. SKN cells were plated in 6 well culture plates and then transfected with control GFP reporter plasmid alone or with RNAi vector against GFP, pU6GFPRNAi (lanes 2 and 3). The expression of GFP was monitored as a control for GFP gene silencing. SKN cells were transfected 2 μg of hNgR expression vector (lane 4). DNA amount in each well was adjusted to total of 4 μg DNA by adding pUC19 plasmid DNA. 0.5 μg hNgR vector was co-transfected with 2 g NgR RNAi-1, 2, 3 or 2m plasmid (lanes 5-8). Forty-eight hours poet transfection, cells were harvested in SDS loading buffer and subjected to SDS-PAGE. The expression of hNgR was analyzed by western blot using rabbit serum against hNgR R150. Again, greater than 90%0/NgR knockdown was demonstrated in all NgR RNAi-1 and -2, but less efficient in NgR RNAi-3 and -2m (FIG. 19).

EXAMPLE 26

NgR Knockdown in Neuroscreen Cells

Figure 20:
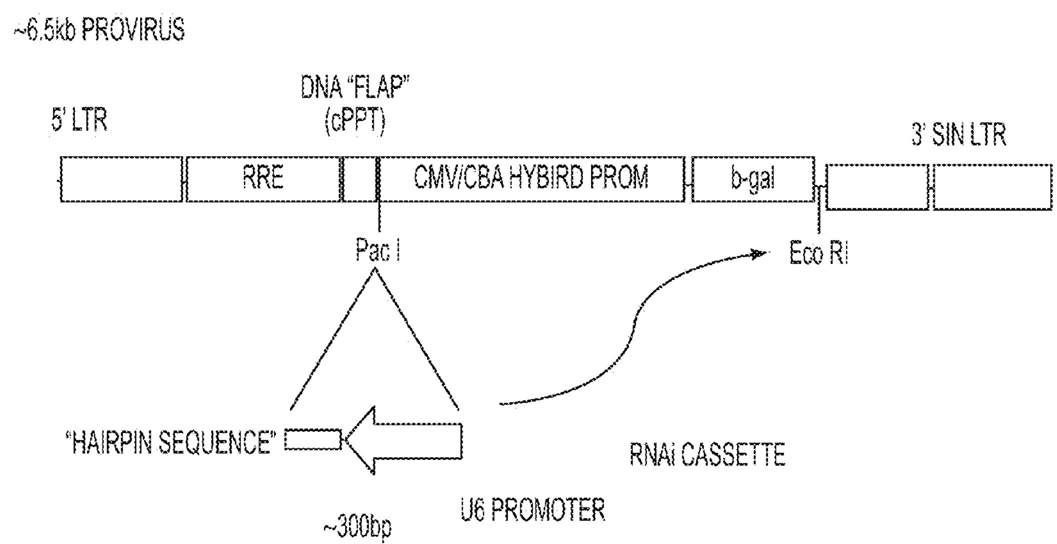
FIG. 20 shows a schematic representation of a RNAi lentiviral vector. The RNAi expression cassette can be inserted at the Pad site or EcoRI site. LTR-long terminal repeat; RRE-Rev response elements; cPPT-central polypurine tract; CBA-chicken beta actin; WPRE-Woodchuck Hepatitis virus post-transcriptional regulatory element; SIN LTR-seld inactivating LTR.

NeuroScreen cells expressing NgR were obtained from Cellomics Inc. for NgR function analysis. In order to achieve stable NgR knockdown in NeuroScreen cells, all RNAi constructs were converted into lentiviral vectors in either beta-gal or GFP backbones. A schematic representation of the lentiviral vector is shown in FIG. 20. Lentiviral vectors were generated by transfection of 293 cells with packaging plasmids (Invitrogen). To construct the lentiviral vector for stable expression of NgR1 RNAi, the RNAi cassettes consisting of the hU6 promoter that drives the expression of the hairpins (i.e., Nogo-1, Nogo-2, Nogo-2m, and Nogo-3) were excised from the phU6 vector (described in Example 24) by PacI digestion and cloned into the unique PacI site of SSM007 plasmids. See, for e.g., methods described in Robinson et al., *Nature Genetics* 33:401-406 (2003). To track lentiviral vector transduction, a CBA-GFP expression cassette or CMV-LacZ expression cassette were inserted into SSM007 plasmid at the XbaI site, and the resultant constructs were termed SSM007-BFGW and SSM007-BFZW, respectively.

After converting all NgR1 RNAi constructs into SSM007-BFGW and SSM007-BFZW backbone, the vectors were co-transfected with packaging plasmids, pLP1, pLP2 and pLP/VSVG into FT293 cells for lentiviral vector production (Viropower kit, Invitrogen). pLP1 is a 8889 bp construct that contains the HIV-1 gag/pol sequence and the rev response element (RRE) expressed from a CMV promoter and with a b-globin poly A; pLP2 is a 4180 bp construct that expresses Rev from the RSV promoter and with an HIV-1 poly A to terminate the transcript; pLP/VSVG is a 5821 bp plasmid and expresses Vesicular stomatitis virus glycoprotein 0 from the CMV promoter and beta-globin poly A.

Due to the self-limiting effect of RNAi interference to lentiviral titer, all viral stock titers appeared lower than regular lentiviral vectors, in the range of 4-5×$10^5$ transducing unit in the culture medium. NgR RNAi lentivectors (LV-NgR RNAi) were used to transduce NeuroScreen cells at moi (multiplicity of infection) of 1. The transduction efficiency was about 1% as indicated by GFP expression or beta-galactosidase staining.

Because NgR RNAi-2 was demonstrated to be effective in NgR silencing and it targets all human, mouse and rat NgR, LV-NgR RNAi-2 was chosen to transduce NeuroScreen cells. Transduced cells were cloned by limited dilution in 96 well plates. Beta-galactosidase positive or GFP positive clones were identified and expanded for further NgR expression analyses.

Figure 21:
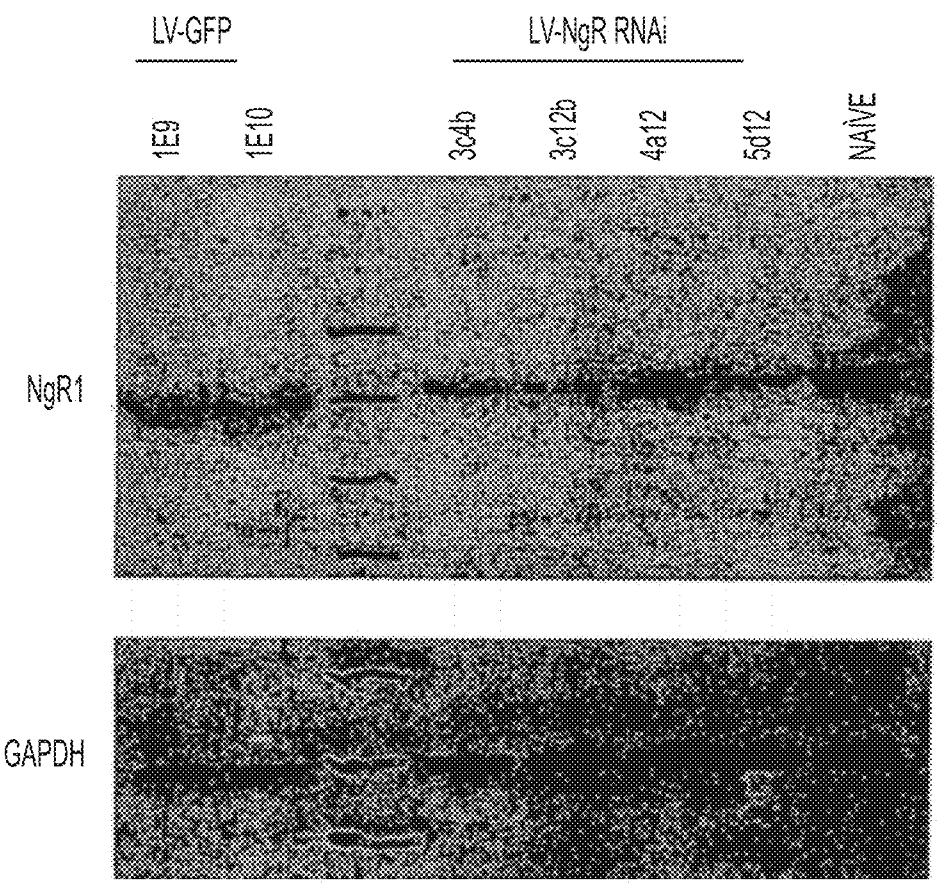
FIG. 21 shows a western blot analysis using 7E11 antibody to demonstrate NgR1 knockdown in cloned Neuroscreen cells.
Figure 22:
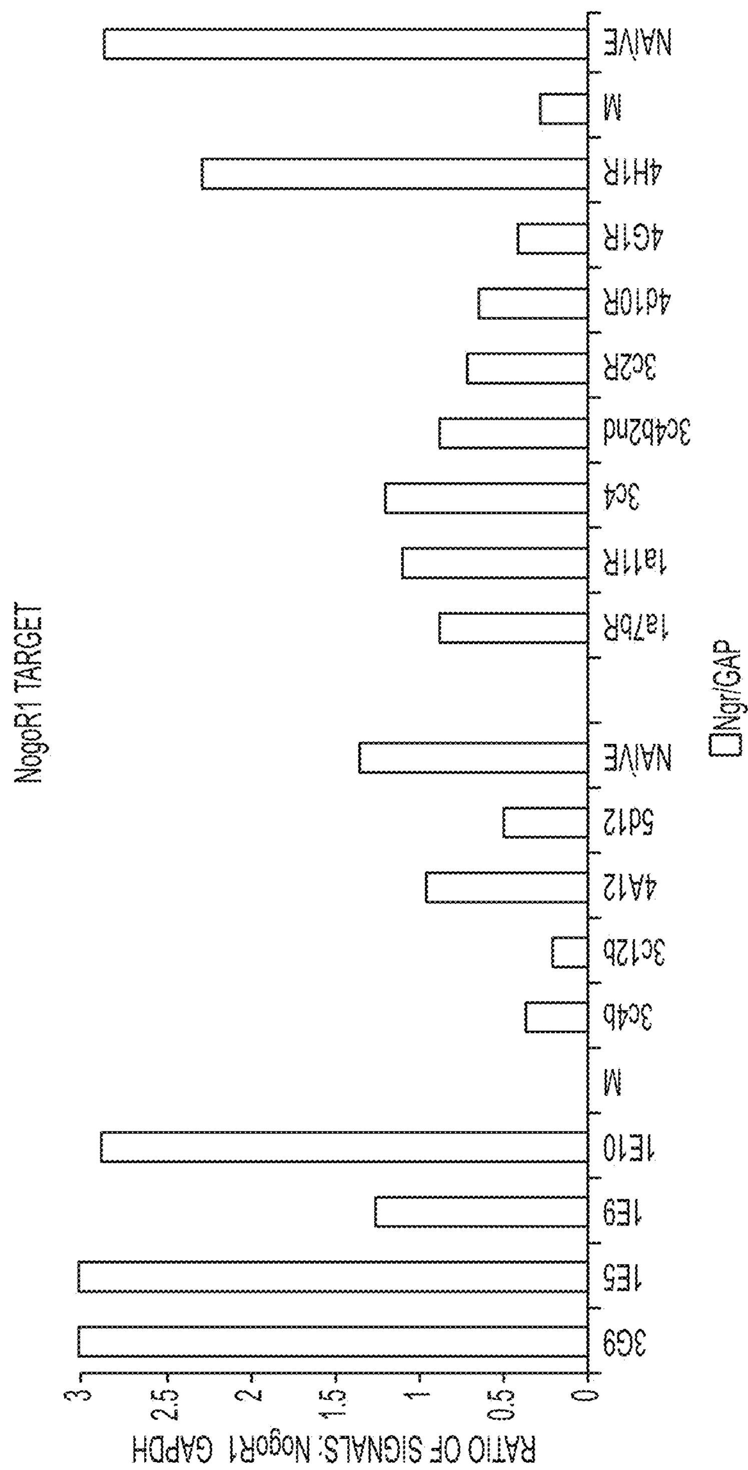
FIG. 22 shows a summary of NgR expression in cloned NeuroScreen cells transduced with LV (clone #309, 1E5 1E9 1E10), LV-NgR RNAi or naïve cells. NgR and GAPDH signals on western blot results were quantified by densitometry scanning.

About 20 cloned cell lines were analyzed for NgR expression by Western blot using 7E11 monoclonal antibody. A typical western blot results is shown in FIG. 21. GAPDH was used as control for loading normalization. The NgR expression in all clones was quantified by densitometry scanning of the NgR bands on the western blot and normalized to GAPDH levels. The ratio of NgR vs GAPDH was used to measure NgR expression levels. Of the 12 clones screened, 11 of them decreased NgR expression (using the lowest NgR expressing clone in LV-GFP transduced cells, 1E9, as reference). In contrast, all 4 LV-GFP transduced clones have comparable NgR levels as the naive NeuroScreen cells. FIG. 22. These results demonstrate that stable cell lines were established with reduced NgR expression.

EXAMPLE 27

Functional Analysis of LV-NGR RNAi Cells

Figure 23:
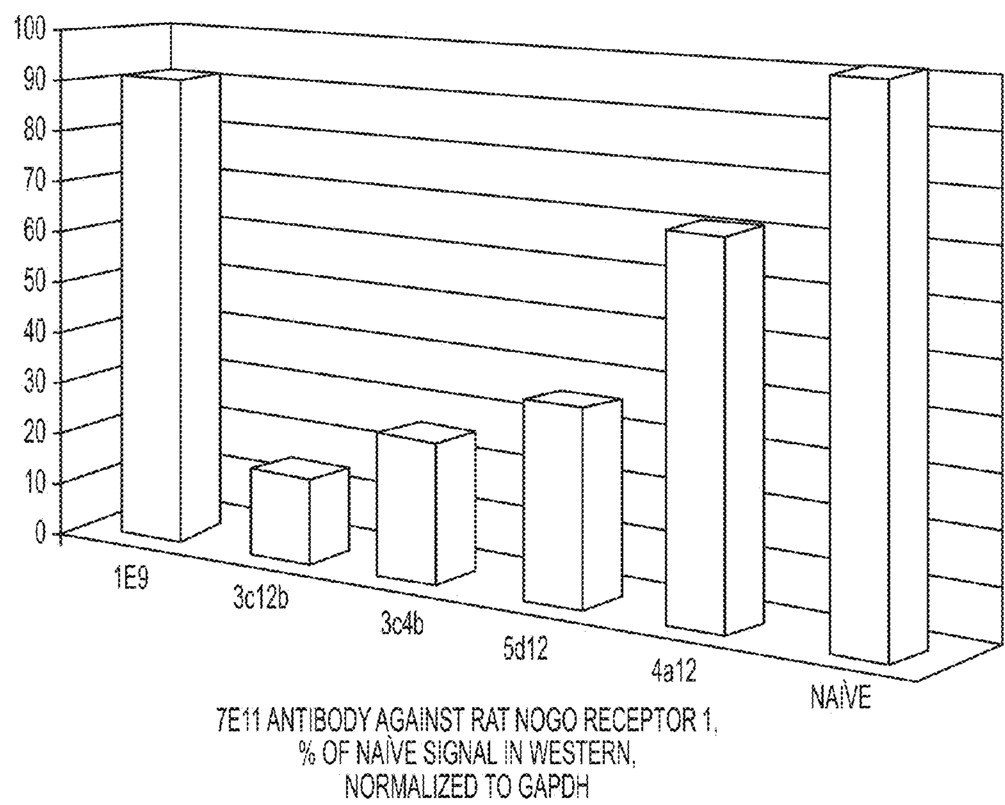
FIG. 23 shows four NeuroScreen cell clones that were established with different levels of NgR knockdown. NgR expression is shown as the percentage of the NgR:GAPDH signals ratio in naïve NeuroScreen cells.

We selected four clones from LV-NgR RNAi transduced cells for function analyses. Using the NgR levels of naive NeuroScreen cells as reference, the NgR levels of these four clones are approximately 10% for 3c12b, 20% for 3c4b, 30% for 5d12 and 60% for 4a12 of the naive cells, respectively (FIG. 23).

EXAMPLE 28

Mutations of Monoclonal Anti-NgR1 Antibody, 1D9 Allow Recognition of Human NgR1

By computer modeling it was shown that mutations in the 1D9 antibody allow recognition of human NgR1. N56 of the 1D9 heavy chain, via computer modeling, can be mutated to serine, glutamic acid, aspartic acid, or glutamine to interact with R78 of the human NgR1. In addition, R33 of the light chain can be mutated via computer modeling to alanine or serine to avoid the electrostatic and steric clashes with R95 of human NgR1.

EXAMPLE 29

Figure 24A:
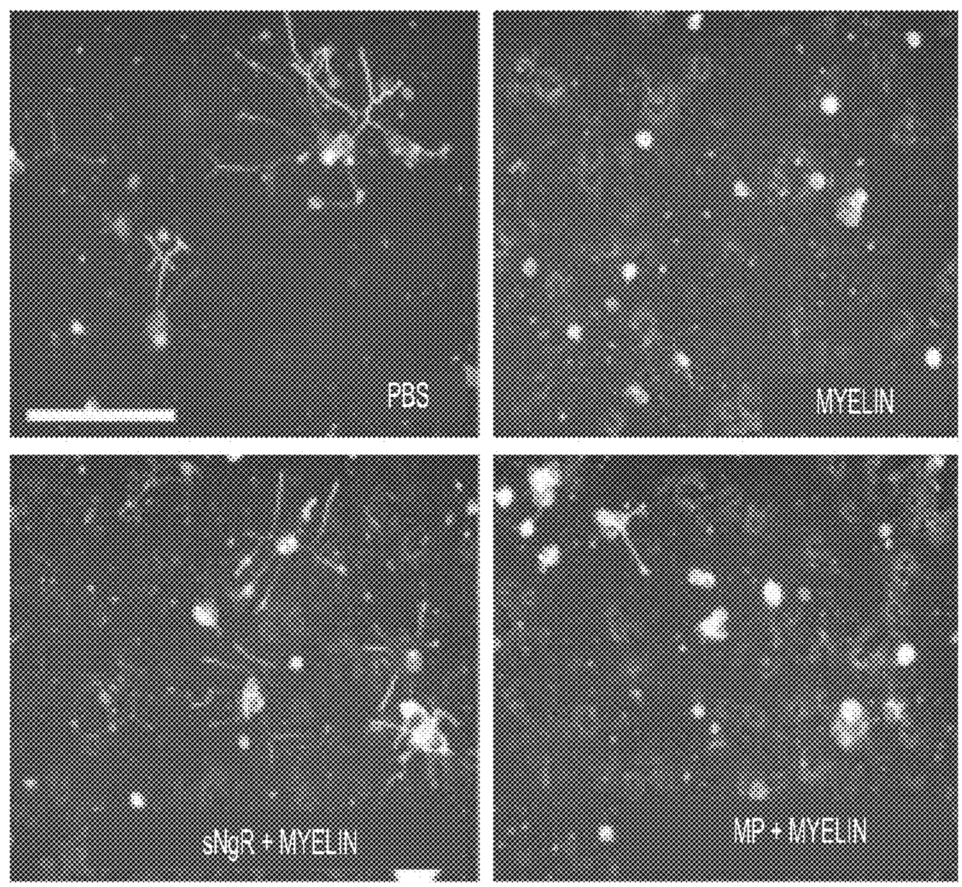
FIGS. 24A-B show the effect of ectodomain of the rat NgR1 (27-310) fused to a rat IgG [NgR(310)ecto-Fc] and methylprednisolone (MP) on myelin-induced inhibition of neurite outgrowth in chick dorsal root ganglia (DRGs) in vitro. (A) Dissociated embryonic day 13 chick DRG neurons were plated on phosphate-buffered saline (PBS) or myelin (400 ng/well) in the presence of NgR(310)ecto-Fc or MP. (B) Quantification of neurite outgrowth per cell (η-3) expressed as a percentage of PBS control±SEM (η-3). Scale bar, 200 μm. P<0/05 compared with PBS control.
Figure 24B:
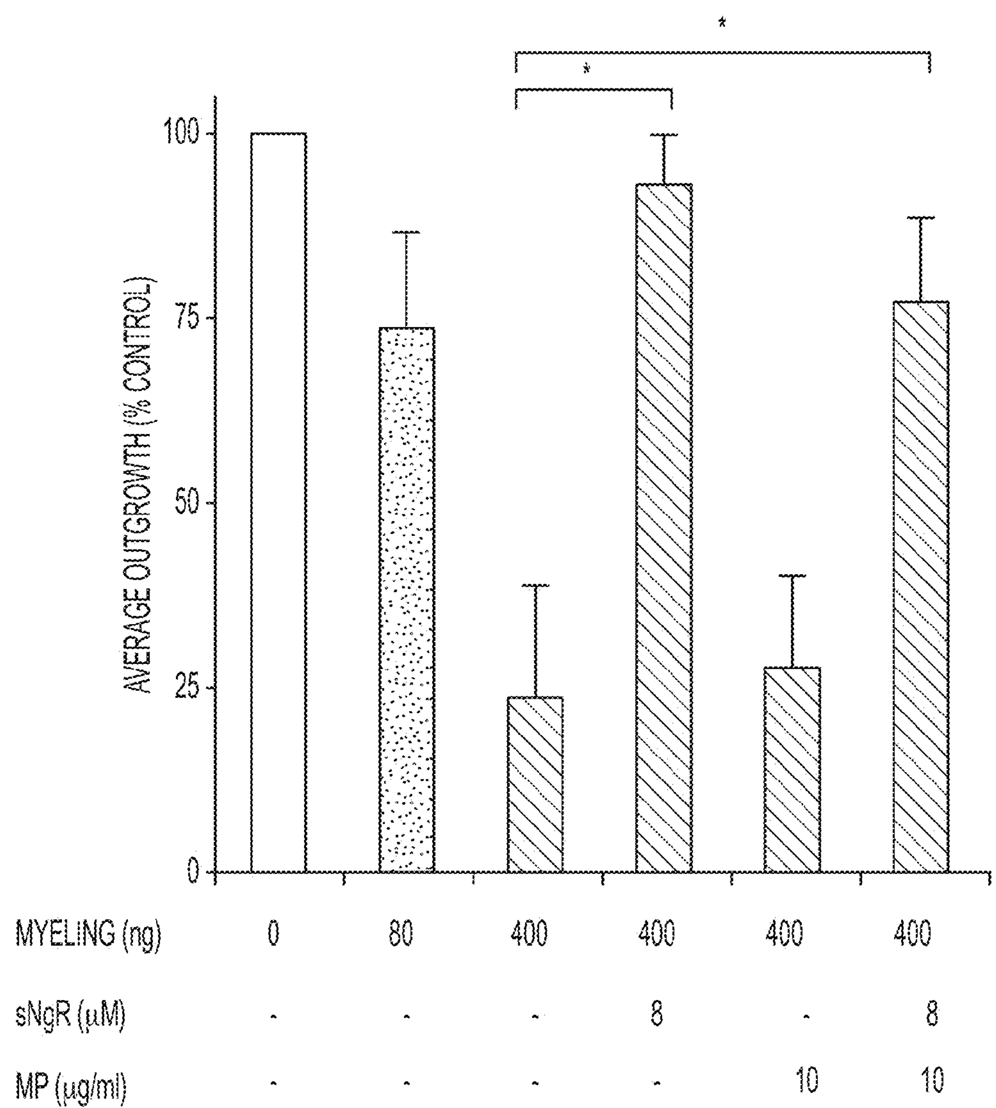

Ecto-Domain of the Rat NgR1 (27-310) Fused to a Rat IgG but not Methylprednisolone Reversed the Neurite Outgrowth Inhibitory Effect of Myelin Dorsal Root Ganglion Cells In investigating combined treatment with methyprednisolone (MP) and NgR(310)ecto-Fc for spinal cord injury (SCI), we sought to verify that these reagents have independent mechanisms of action. Briefly, myelin was dried overnight in poly-L-lysine-precoated plates (Becton Dickinson, Bedford, Mass., USA) at 80 or 400 ng/well (2.5 and 12.7 ng/mm$^2$, respectively). Wells were then coated with 10 g/ml laminin (Calbiochem, La Jolla, Calif., USA) for 1 hour at foom temperature (22-24 C). Embryonic day 13 chick dorsal root ganglion neurons were dissociated and plated for 6-8 hours as previously described (GrandPre et al., 2000; Fournier et al., 2001). Neurons were treated with 8 μM NgR(310)ecto-Fc in the presence or absence of 10 μg/nl MP (Pharmacia, Kalamazoo, Mich., USA) for the entire outgrowth period. Neurons were then fixed and stained with βIII tubulin antibody (Covance, Princeton, N.J., USA) and neurite outgrowth was quantified using an automated cellular imaging and analysis system (Axon Instrument, Union City, Calif.; USA). Neurite outgrowth per cell was normalized to the average of duplicate control wells for each experiment (n=3). The activity of NgR (310)ecto-Fc is based on its ability to reverse the inhibition of axon growth by myelin. FIGS. 24 A-B. In contrast, MP alone had no effect on neurite outgrowth from dorsal root ganglion neurons on a myelin substrate and the presence of MP did not alter axon growth stimulation by NgR(310)ecto-Fc. These data indicate that MP does not directly influence myelin-induced neurite outgrowth inhibition and that MP and NgR (310)ecto-Fc have independent actions. These in vitro data support the hypothesis that MP and NgR(310)ecto-Fc will enhance SCI recovery in a sequentially effective manner.

EXAMPLE 30

Figure 25A:
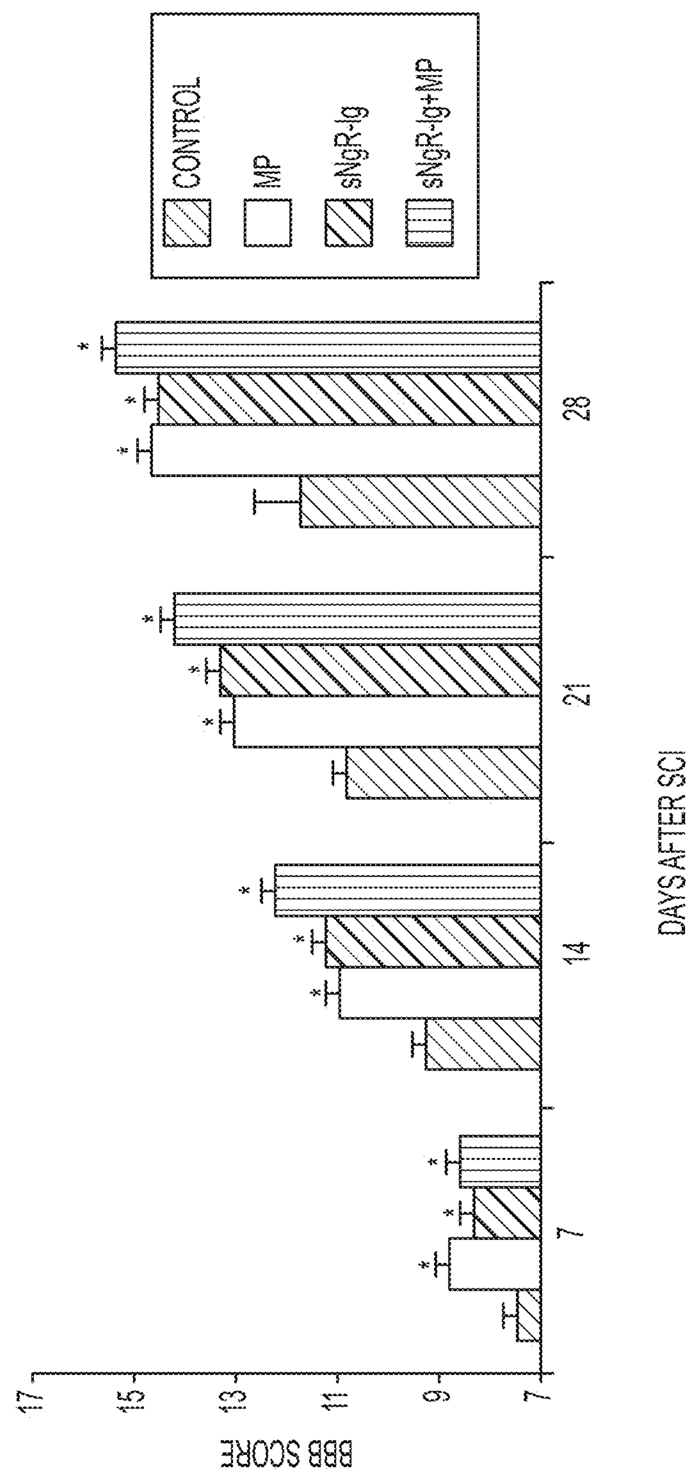
FIGS. 25A-E show the effect of ecto-domain of the rat NgR1 (27-310) fused to a rat IgG [NgR(310)ecto-Fc] and methylprednisolone (MP) on functional recovery after spinal cord injury (SCI). (A) BBB score was recorded weekly for 4 weeks. (B) BBB score in MP-treated rats 2 days after SI. (C) BBB scores normalized to day 2 for individual animals. (D) Frequency of consistent plantar stepping and hindlimb-forelimb coordination, illustrating the proportion of rats in each group that attained a score of 14 or higher 3 and 4 weeks after SCI. (E) Mean stride length in NgR(310)ecto-Fc- and MP+NgR(310)ecto-Fc-treated groups compared with controls.
Figure 25B:
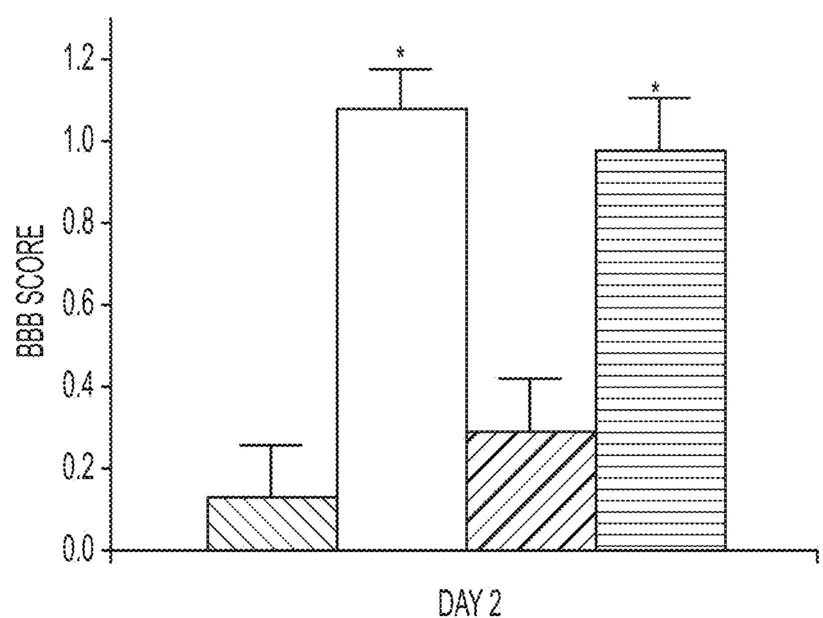
Figure 25C:
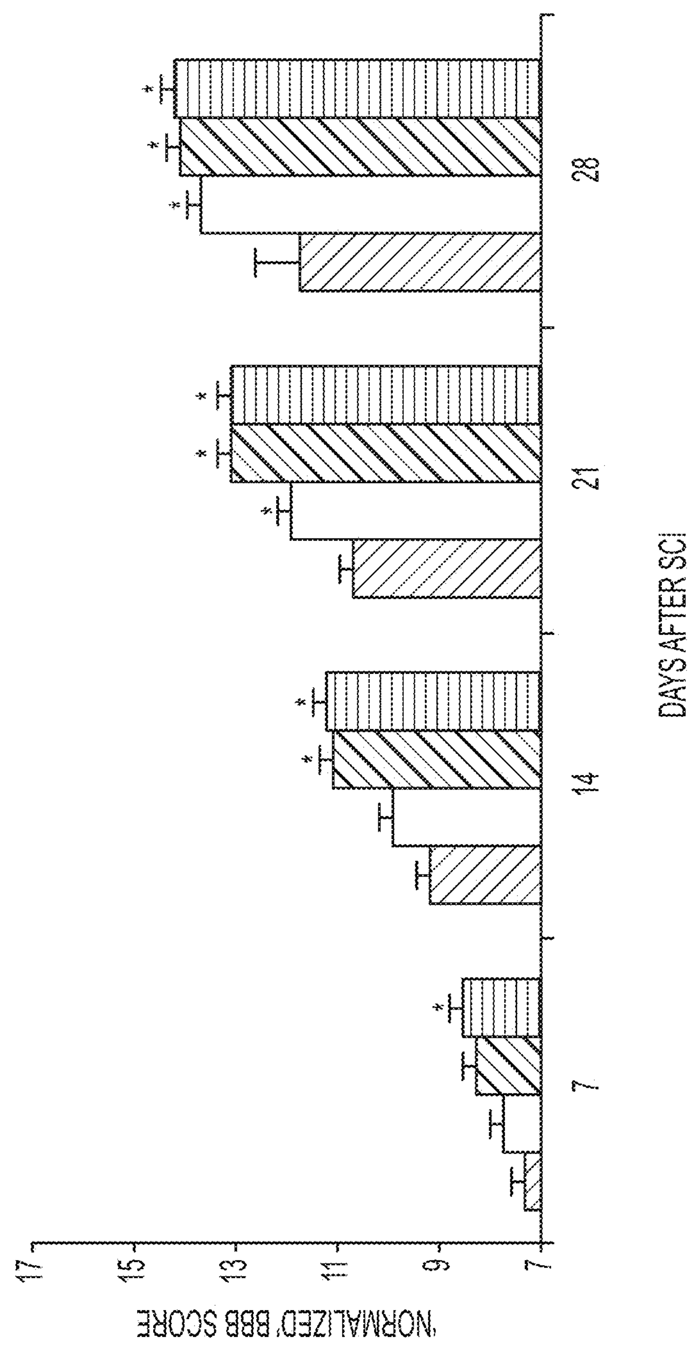

Ecto-Domain of the Rat NgR (27-310) Fused to a Rat IgG and Methylprednisolone Treatment Had a Temporally Distinct Effect on Functional Recovery after Spinal Cord Transection Both MP and NgR(310)ecto-Fc treatments had a temporally distinct effect on functional recovery after spinal cord transection. Briefly, female Long Evans rats (7 weels old; Charles River, Wilmington, Mass., USA) were anesthetized using 25 mg/kg midazolam i.p. (Abott Laboratories, Chicago, Ill., USA) and 2-3% fluothane (Baxter, Deerfield, Ill., USA) in $O_2$ and a dorsal laminectomy performed at spinal level T6 and T7. General anesthesia wa maintained at 1.5-2% fluothane in $O_2$ A dorsal hemisection was performed completely interrupting the main dorsomedial and the mino dorsplateral corticospinal tract (CST) components. A microscapel was used to sterotaxically transect the cord at a depth of 1.8 mm from the surface of the cord. Immediately after CST transection, an intrathecal catheter was inserted into the subarachnoid space at T7 and connected to a primed mini-osmotic pump inserted into the subcutaneous space. The mini-osmotic pumps delivered rat IgG isotype control protein or phosphate-buffered saline (PBS) (5 mg/ml, n=8) or NgR (310)ecto-Fc (50 μM, n=19) at a rate of 0.25 μL/h. A cohort of NgR(310)ecto-Fc treated rats (n=8) were also treated with MP (Pharmacia; 30 mg/kg iv) and a separatecohort treated with MP alone (30 mg/kg iv) immediately after injury and again 4 and 8 hours later. Functional recovery was assessed using the BBB openfield scoring method (Basso et al., *J. Neurotrauma* 12:1-21 (1995)) the following day and weekly thereafter. Control animals recovered hindlimb function over the course of the study reaching a mean BBB score of 12±0.87 after 4 weeks. Mean BBB scores for treated groups at the same time-point were: MP, 14.9±0.23; NgR(310)ecto-Fc, 14.8±0.24 and NgR(310)ecto-Fc plus MP, 15.63±0.18. All treatment groups showed improved BBB scores compared with controls over the course of the study. P<0/05 vs control, two-way repeated measure ANOVA with Tukey's posthoc test. (FIG. 25A). A statistically significant increase in BBB score was observed in MP– and MP plus NgR(310)ecto-Fc-treated rats the day after surgery compared with control animals or animals treated with NgR(310)ecto-Fc alone. BBB score was significantly improved in MP-treated rats 2 days after SCI. P<0/05 vs control, two-way repeated measure ANOVA with Tukey's posthoc test. (FIG. 25B). This observation indicated an early effect of MP treatment on recovery. Given this very early effect of MP, BBB scores were normalized to day 2 to subtract out this early effect of MP (FIG. 25C) thus illustrating the much later onset of effect of NgR(310) ecto-Fc. BBB scores normalized to day 2 for individual animals illustrate a significant improvement in functional recovery in NgR(310)ecto-Fc-treated rats±MP 2, 3 and 4 weeks after SCI. P<0/05 vs control, two-way repeated measure ANOVA with Tukey's posthoc test. (FIG. 25C). In combining treatment group normalized BBB scores abrogated the enhancing effect of MP on NgR(310)(ecto)-Fc treatment illustrating that (i) in the combined treatment group the effect of MP occurred early after SCI and (ii) by subtracting out this effect the rate and extent of functional recovery in the combined treatment group and the NgR(310)ecto-Fc group were identical and more pronounced than MP treatment alone.

Figure 25D:
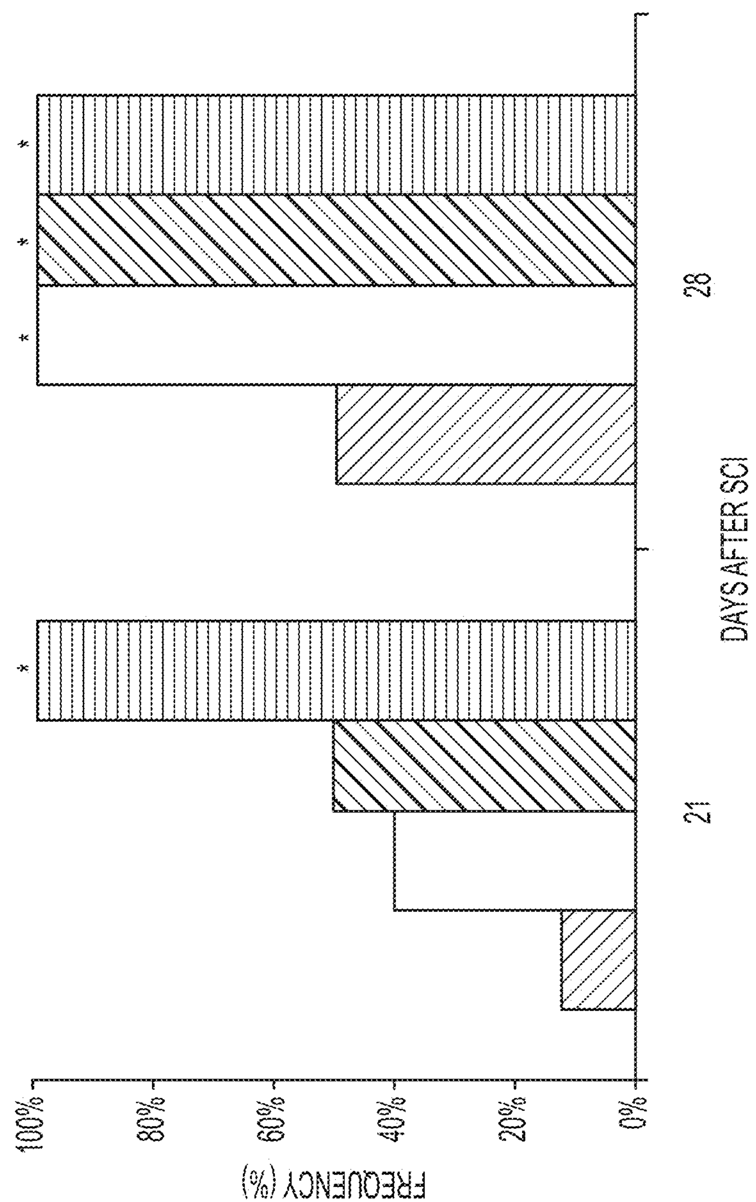
Figure 25E:
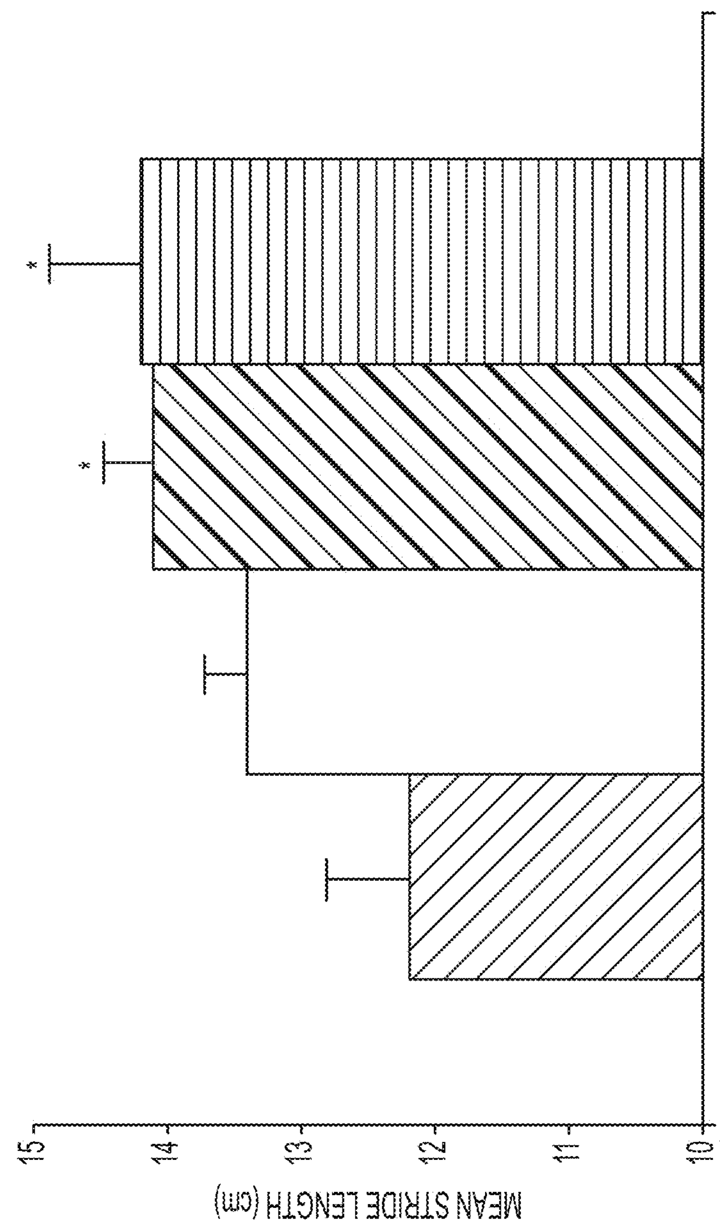

A discriminating point on the BBB score is a score of 14, corresponding to consistent weight supported planter steps and consistent hindlimb-forelimb coordination. Frequency of consistent planter stepping and hindlimb-forelimb coordination, illustrating the proportion of rats in each group that attained a score of 14 or higher 3 and 4 weeks after SCI. Accordingly, results were expressed as the frequency with which rats attained a score of 14 or greater; 50% of control rats attained a score of 14 or greater by 4 weeks after injury (FIG. 25D). Combined treatment with NgR(310)ecto-Fc and MP significantly improved the rate of functional recovery. P<0/05 vs control Fischer exact test. All rats (100%) treated with NgR(310)ecto-Fc or MP or combined therapy demonstrated consistent plantar stepping and coordinated movement by 4 weeks. Combination therapy increased the rate of recovery of coordinated function as a significantly higher proportion of this treatment group reached a score of 14 or greater by 3 weeks compared with controls or either NgR (310)ecto-Fc or MP treatment alone (FIG. 25D). Improved functional recovery was also demonstrated as significantly improved mean stride length in NgR(310)ecto-Fc and NgR (310)ecto-Fc plus MP-treated groups compared with controls (FIG. 25E). MP treatment alone did not significantly improve stride length measured 4 weeks after SCI. P<0/05, one-way ANOVA with Dunnett's posthoc test.

EXAMPLE 31

Ecto-Domain of the Rat NgR1 (27-310) Fused to a Rat IgG and Methylprednisolone Treatment Enhanced Axonal Plasticity/Regeneration after Spinal Cord Transection Treatment with NgR(310)ecto-Fc or combined treatment with MP and NgR(310)ecto-Fc enhanced axonal plasticity/regeneration after spinal cord transection. Briefly, for histological tracing of the CSTs, 2 weeks after CST transection animals were re-anesthetized and an incision made in the scalp. The area around the skin incision was injected with a local anesthetic, the left sensorimotor cortex exposed via a craniotomy and 7 μL 10% biotin dextran amine (BDA; 10,000 MW; Molecular Probes, Eugene, Oreg., USA) in PBS injected using a nanoliter injector and micro4 controller at 12 points 0-3.5 mm posterior to Bregma and 0-25 mm lateral to the midline at a depth of 1 mm below the surface of the cortex. In some instances, the CST was labeled bilaterally using the same procedure.

At 28 days after CST transection, the rats were anesthetized with inactin (100-110 mg/kg i.p.) and transcardially perfused with heparinized saline (100 ml, 10 iu heparin) followed by 4% paraformaldehyde (150 ml). Spinal cords were removed, postfixed in 4% paraformaldehyde and then impregnated with 30% sucrose for 48 hours; 25 mm lengths of spinal cord, 10 mm rostral and 15 mm caudal to the transection site, were embedded in optimal cutting temperature compound (OCT) with transverse segments of cord taken 10-15 mm rostral and 15-20 mm caudal to the lesion.

Frozen sections (50 μm) were serially cut and stained with strepavidin-conjugated AlexaFluor-594 (1:200; Molecular Probes) to visualize labeled CST axons. Axon counts were performed on transverse sections taken 10 and 15 mm caudal to the transection site. All measurements were performed blind. Every eighth section, i.e., sections 400 μm apart, was counted for each animal at each level of the cord and the values were expressed as mean number of axons per section.

Figure 26A:
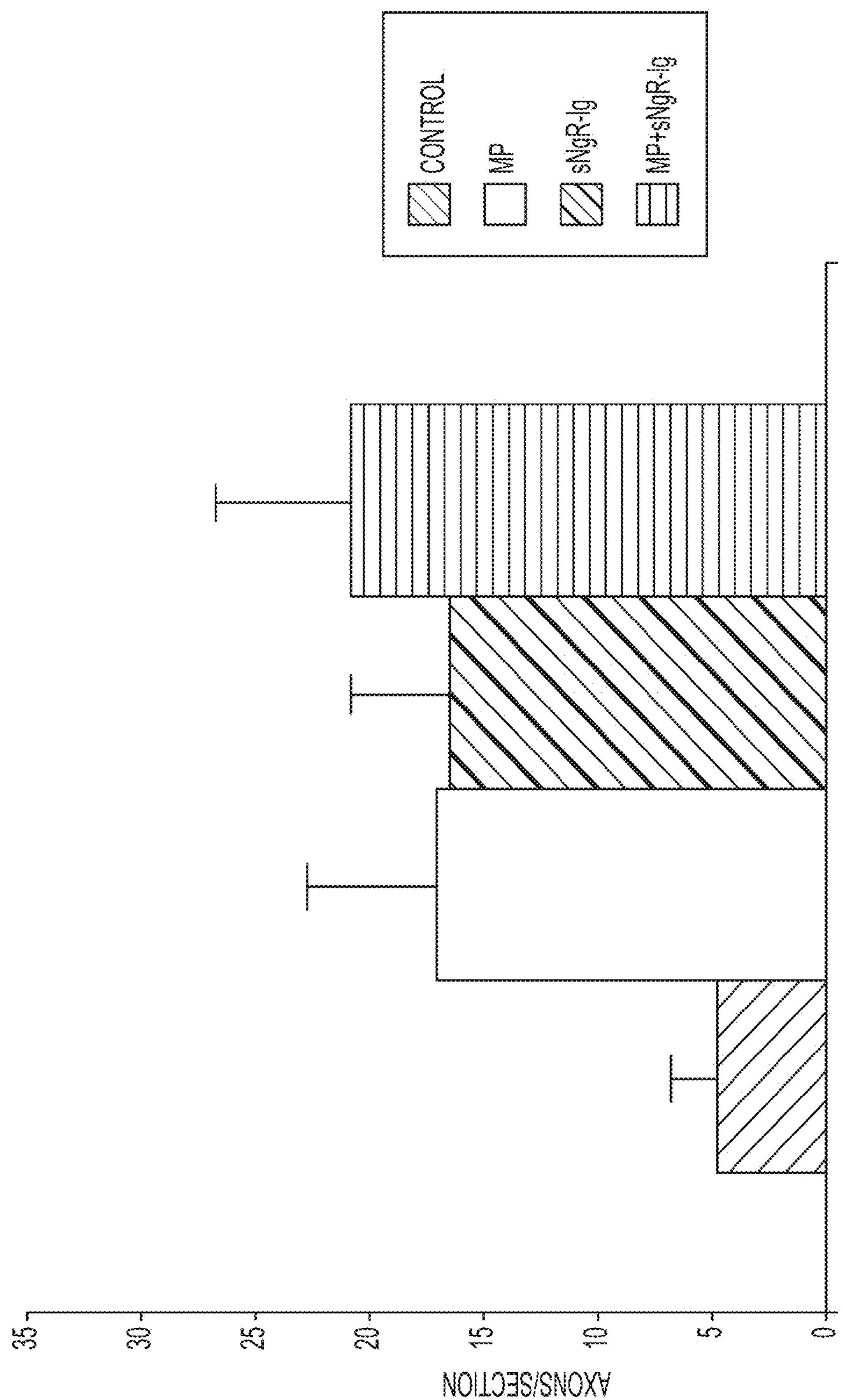
FIGS. 26A-B show the effect of ecto-domain of the rat NgR1 (27-310) fused to a rat IgG [NgR(310)ecto-Fc] and methylprednisolone (MP) treatment on axon number caudal to the spinal cord lesion.
Figure 26B:
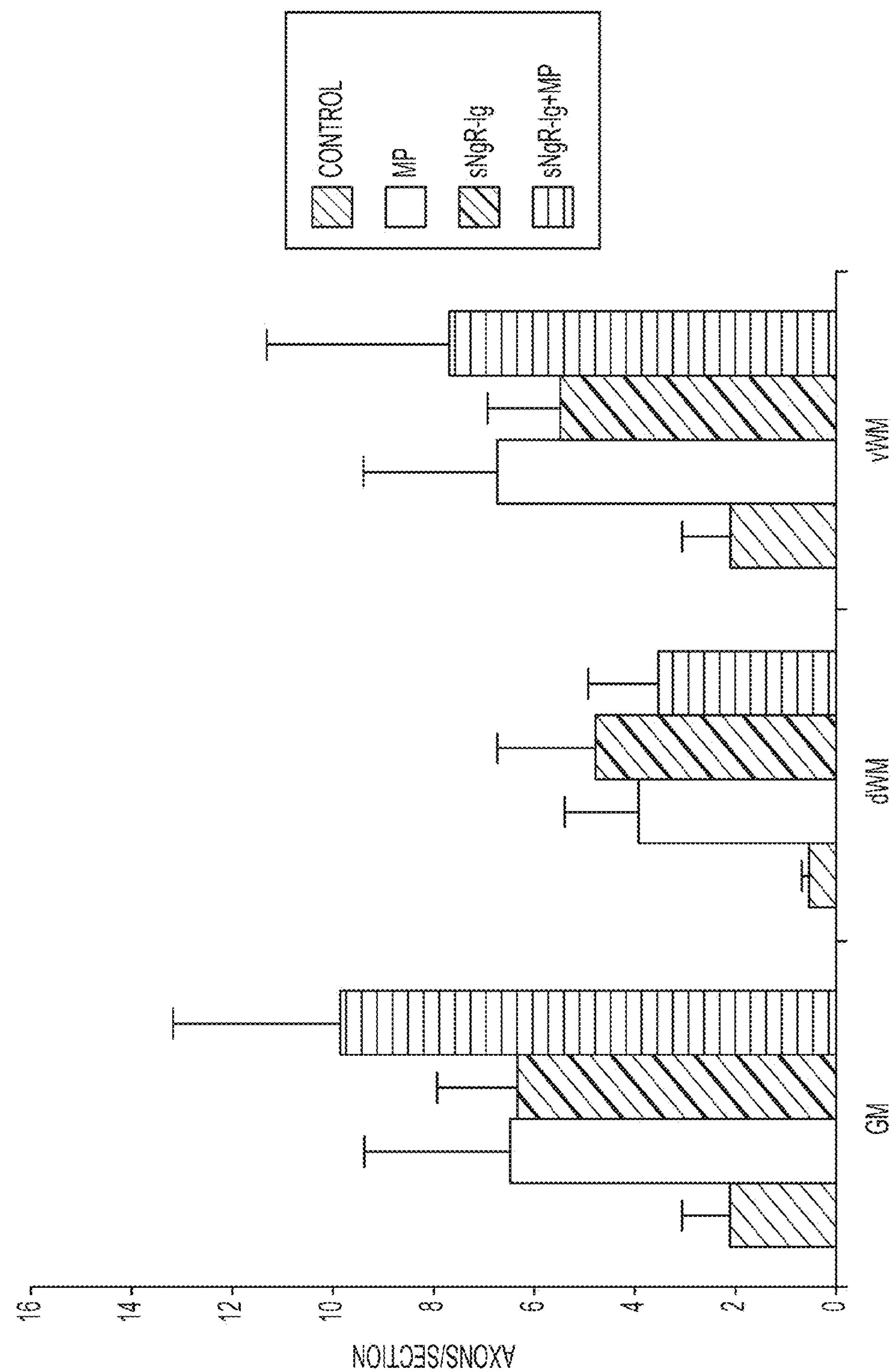

Treatment with NgR(310)ecto-Fc or combined treatment with MP and NgR(310)ecto-Fc resulted in significantly greater numbers of biotin dextran amine (BDA)-labeled axons counted 15 mm caudal to the injury site (FIG. 26A). BDA-labeled axons appeared to sprout from both the dorsal columns into the dorsal horn gray matter and the spared ventral CST, projecting into the ventral gray matter. Axon counts in discrete regions of the cord revealed the largest increase in axon number in the gray matter. The largest increase in axon numbers was observed in the gray matter (GM) compared with ventral white matter (vWM) and dorsal white matter (dWM) (FIG. 26B). P<0/05, one-way ANOVA with Dunnett's posthoc test. These data suggest that treatment with NgR(310)ecto-Fc with or without MP promotes plasticity in the spinal card after injury.

EXAMPLE 32

Figure 27:
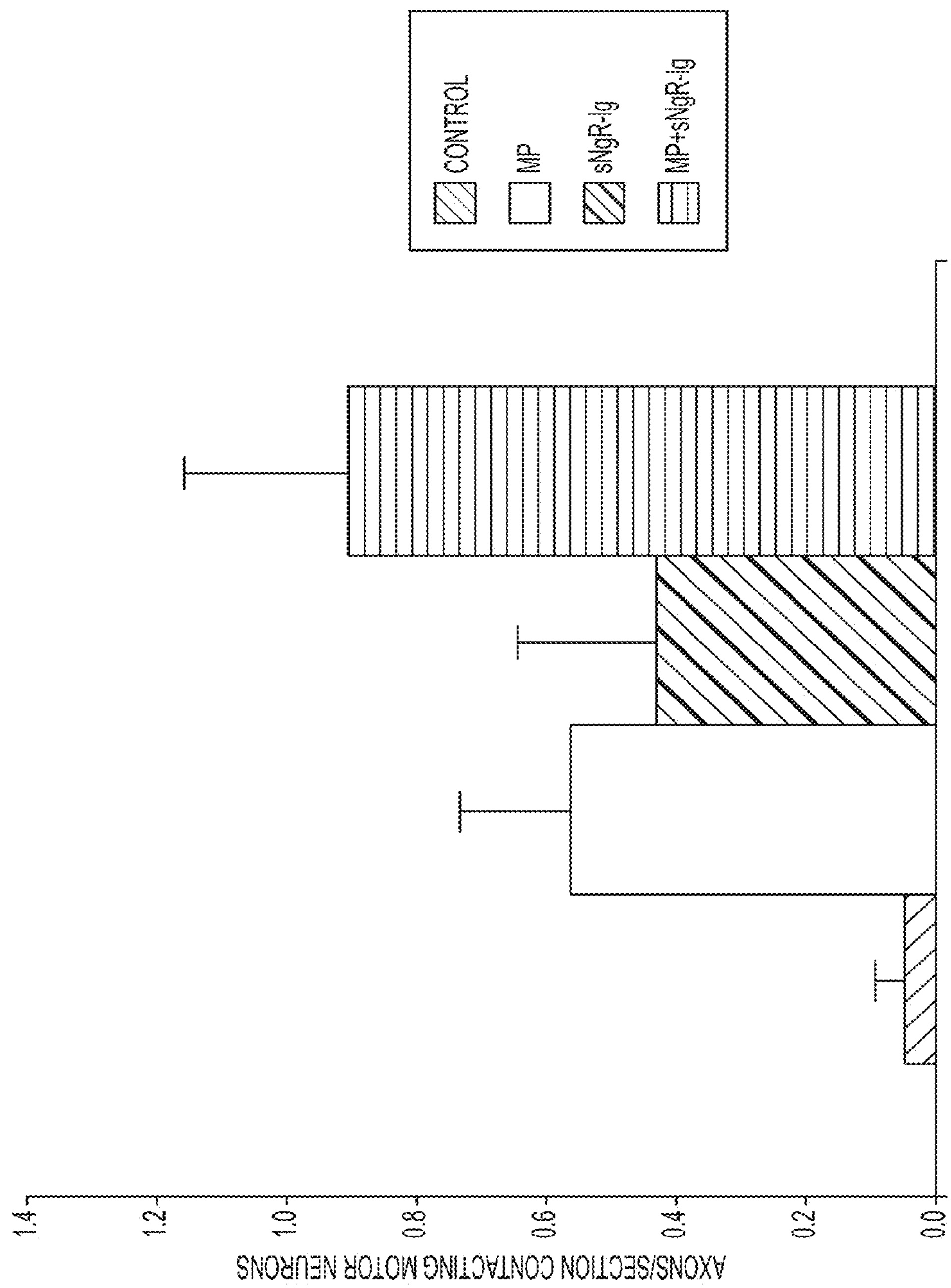
FIG. 27 shows the effect of ecto-domain of the rat NgR1 (27-310) fused to a rat IgG [NgR(310)ecto-Fc] and methylprednisolone (MP) treatment on the number of biotin dextran amine (BDA)-labeled axons contacting motor neurons in the ventral horn.

Combined Treatment with Ecto-Domain of the Rat NgR1 (27-310) Fused to a Rat IgG and Methylprednisolone Increased the Number of Axonal Connections Between Biotin Dextran Amine-Labeled Corticospinal Tract Fibers and Lumbar Motor Neurons Anti-vesicular glutamate transporter 1 (vGLUT1) antibody (dilution 1:2500) was used to stain for neuronal cell bodies and α- and γ-motor neurons in lamina 9 were identified by their size and morphology. The number of axons contacting α- or γ-motor neurons was significantly increased in the MP+NgR(310)ecto-Fc-treated group compared with control animals, with the most marked and significant effect observed in animals receiving combined treatment with NgR(310) ecto-Fc and MP (FIG. 27). P<0/05, one-way ANOVA with Dunnett's posthoc test.

Biological Deposits

Hybridomas HB 7E11 (ATCC® accession No. PTA-4587), HB 1H2 (ATCC® accession No. PTA-4584), HB 3G5 (ATCC® accession No. PTA-4586), HB 5B10 (ATCC® accession No. PTA-4588) and HB 2F7 (ATCC® accession No. PTA-4585) were deposited with the American Type Culture Collection ("ATCC®"), 10801 University Boulevard, Manassas, Va. 20110-2209, USA, on Aug. 9, 2002.

As those skilled in the art will appreciate, numerous changes and modifications may be made to the preferred embodiments of the invention without departing from the spirit of the invention. It is intended that all such variations fall within the scope of the invention.

It is claimed that:

1. A method of treating a central nervous system (CNS) disease, disorder, or injury in a mammal selected from the group comprising stroke, spinal cord injury, optic neuritis, and glaucoma, comprising administering to a mammal in need of treatment an effective amount of an agent comprising a NogoR polypeptide variant comprising:

a sNogoR310 polypeptide, comprising the amino acid sequence of residues 27-310 of SEQ ID NO: 58; and an antibody fragment, crystallizable (Fc):

wherein the Fc is joined to the sNogoR310 c-terminus, wherein the NogoR variant inhibits neurite outgrowth inhibition.

2. The method of claim 1 wherein the subject receives a NogoR polypeptide variant in combination with another therapy.

3. The method of claim 1, wherein the agent comprises a dimeric peptide comprising two of the NogoR variants.

4. A method of enhancing neurite outgrowth comprising administering to a mammal in need of treatment an effective amount of an agent comprising a NogoR polypeptide variant comprising:

a sNogoR310 polypeptide, comprising the amino acid sequence of residues 27-310 of SEQ ID NO: 58: and an antibody fragment, crystallizable (Fc);

wherein the Fc is joined to the sNogoR310 c-terminus, wherein the NogoR variant inhibits neurite outgrowth inhibition.

5. The method of claim 1, wherein the CNS disease, disorder, or injury is a spinal cord injury.

* * * * *

UNITED STATES PATENT AND TRADEMARK OFFICE

CERTIFICATE OF CORRECTION

PATENT NO. : 9,228,015 B2
APPLICATION NO. : 14/146345
DATED : January 5, 2016
INVENTOR(S) : Daniel H. S. Lee et al.

It is certified that error appears in the above-identified patent and that said Letters Patent is hereby corrected as shown below:

Title page

Item (71), please correct the Applicant to read: -- Biogen MA, Inc. --.

Item (73), please correct the Assignee to read: -- Biogen MA, Inc. --.

Signed and Sealed this
Nineteenth Day of April, 2016

Michelle K. Lee
*Director of the United States Patent and Trademark Office*

```
                              SEQUENCE LISTING


<160> NUMBER OF SEQ ID NOS: 89

<210> SEQ ID NO 1
<211> LENGTH: 16
<212> TYPE: PRT
<213> ORGANISM: Rattus

<400> SEQUENCE: 1

Leu Asp Leu Ser Asp Asn Ala Gln Leu Arg Val Val Asp Pro Thr Thr
1               5                   10                  15


<210> SEQ ID NO 2
<211> LENGTH: 16
<212> TYPE: PRT
<213> ORGANISM: Homo sapiens

<400> SEQUENCE: 2

Leu Asp Leu Ser Asp Asn Ala Gln Leu Arg Ser Val Asp Pro Ala Thr
1               5                   10                  15


<210> SEQ ID NO 3
<211> LENGTH: 35
<212> TYPE: PRT
<213> ORGANISM: Rattus

<400> SEQUENCE: 3

Ala Val Ala Ser Gly Pro Phe Arg Pro Phe Gln Thr Asn Gln Leu Thr
1               5                   10                  15
```

```
Asp Glu Glu Leu Leu Gly Leu Pro Lys Cys Cys Gln Pro Asp Ala Ala
            20                  25                  30

Asp Lys Ala
        35


<210> SEQ ID NO 4
<211> LENGTH: 35
<212> TYPE: PRT
<213> ORGANISM: Homo sapiens

<400> SEQUENCE: 4

Ala Val Ala Thr Gly Pro Tyr His Pro Ile Trp Thr Gly Arg Ala Thr
1               5                   10                  15

Asp Glu Glu Pro Leu Gly Leu Pro Lys Cys Cys Gln Pro Asp Ala Ala
            20                  25                  30

Asp Lys Ala
        35


<210> SEQ ID NO 5
<211> LENGTH: 10
<212> TYPE: PRT
<213> ORGANISM: Mus musculus

<400> SEQUENCE: 5

Cys Arg Leu Gly Gln Ala Gly Ser Gly Ala
1               5                   10


<210> SEQ ID NO 6
<211> LENGTH: 344
<212> TYPE: PRT
<213> ORGANISM: Homo sapiens

<400> SEQUENCE: 6

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190
```

```
Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala
            340


<210> SEQ ID NO 7
<211> LENGTH: 310
<212> TYPE: PRT
<213> ORGANISM: Homo sapiens

<400> SEQUENCE: 7

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220
```

```
Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala
305                 310


<210> SEQ ID NO 8
<211> LENGTH: 344
<212> TYPE: PRT
<213> ORGANISM: Rattus

<400> SEQUENCE: 8

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
```

```
        275                 280                 285

Leu Pro Gln Arg Leu Ala Gly Arg Asp Leu Lys Arg Leu Ala Thr Ser
    290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala
            340


<210> SEQ ID NO 9
<211> LENGTH: 310
<212> TYPE: PRT
<213> ORGANISM: Rattus

<400> SEQUENCE: 9

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
    290                 295                 300
```

Asp Leu Glu Gly Cys Ala
305 310

<210> SEQ ID NO 10
<211> LENGTH: 16
<212> TYPE: PRT
<213> ORGANISM: Rattus

<400> SEQUENCE: 10

Leu Asp Leu Ser Asp Asn Ala Gln Leu Arg Val Val Asp Pro Thr Thr
1 5 10 15

<210> SEQ ID NO 11
<211> LENGTH: 19
<212> TYPE: PRT
<213> ORGANISM: Rattus

<400> SEQUENCE: 11

Arg Val His Pro His Ala Phe Arg Asp Leu Gly Arg Leu Met Thr Leu
1 5 10 15

Tyr Leu Phe

<210> SEQ ID NO 12
<211> LENGTH: 34
<212> TYPE: DNA
<213> ORGANISM: Artificial Sequence
<220> FEATURE:
<223> OTHER INFORMATION: Synthetic primer for light chain sequence

<400> SEQUENCE: 12
tgaggagacg gtgaccgtgg tcccttggcc ccag 34

<210> SEQ ID NO 13
<211> LENGTH: 37
<212> TYPE: DNA
<213> ORGANISM: Artificial Sequence
<220> FEATURE:
<223> OTHER INFORMATION: Synthetic primer for heavy chain sequence

<400> SEQUENCE: 13
ggggatatcc accatgaagt tgcctgttag gctgttg 37

<210> SEQ ID NO 14
<211> LENGTH: 40
<212> TYPE: DNA
<213> ORGANISM: Artificial Sequence
<220> FEATURE:
<223> OTHER INFORMATION: Synthetic primer for heavy chain sequence
<220> FEATURE:
<221> NAME/KEY: misc_feature
<222> LOCATION: (20)..(20)
<223> OTHER INFORMATION: K is G or T
<220> FEATURE:
<221> NAME/KEY: misc_feature
<222> LOCATION: (25)..(25)
<223> OTHER INFORMATION: W is A or T
<220> FEATURE:
<221> NAME/KEY: misc_feature
<222> LOCATION: (32)..(32)
<223> OTHER INFORMATION: Y is T or C
<220> FEATURE:
<221> NAME/KEY: misc_feature
<222> LOCATION: (34)..(34)
<223> OTHER INFORMATION: Y is T or C
<220> FEATURE:
<221> NAME/KEY: misc_feature
<222> LOCATION: (37)..(37)
<223> OTHER INFORMATION: K is G or T

<400> SEQUENCE: 14

```
ggggatatcc accatgaggk ccccwgctca gytyctkgga                           40


<210> SEQ ID NO 15
<211> LENGTH: 144
<212> TYPE: PRT
<213> ORGANISM: Artificial Sequence
<220> FEATURE:
<223> OTHER INFORMATION: 7E11 light chain

<400> SEQUENCE: 15

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Asp Ala Glu Asp Leu Gly Val Tyr Phe Cys
            100                 105                 110

Ser Gln Ser Thr His Val Pro Phe Thr Phe Gly Gly Gly Thr Lys Leu
        115                 120                 125

Glu Ile Lys Arg Ala Asp Ala Ala Pro Thr Val Ser Ile Ser His His
    130                 135                 140


<210> SEQ ID NO 16
<211> LENGTH: 144
<212> TYPE: PRT
<213> ORGANISM: Artificial Sequence
<220> FEATURE:
<223> OTHER INFORMATION: 5B10 light chain

<400> SEQUENCE: 16

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Tyr Thr Tyr Leu His Trp Tyr Leu Gln Arg Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Asp Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val Ser Ile Ser His His
    130                 135                 140
```

```
<210> SEQ ID NO 17
<211> LENGTH: 116
<212> TYPE: PRT
<213> ORGANISM: Artificial Sequence
<220> FEATURE:
<223> OTHER INFORMATION: 7E11 heavy chain

<400> SEQUENCE: 17

Val Gln Leu Gln Glu Ser Gly Ala Glu Leu Val Met Pro Gly Ala Ser
1               5                   10                  15

Val Lys Met Ser Cys Lys Ala Ser Gly Tyr Thr Phe Thr Asp Tyr Trp
            20                  25                  30

Met His Trp Val Lys Gln Arg Pro Gly Gln Gly Leu Glu Trp Ile Gly
        35                  40                  45

Ala Ile Asp Pro Ser Asp Ser Tyr Ser Ser Tyr Asn Gln Asn Phe Lys
    50                  55                  60

Gly Lys Ala Thr Leu Thr Val Asp Gly Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Arg Ile Thr Glu Ala Gly Ala Trp Phe Ala Tyr Trp Gly Gln Gly
            100                 105                 110

Thr Thr Val Thr
        115


<210> SEQ ID NO 18
<211> LENGTH: 114
<212> TYPE: PRT
<213> ORGANISM: Artificial Sequence
<220> FEATURE:
<223> OTHER INFORMATION: 5B10 heavy chain
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Leu Gln Xaa Ser Gly Ala Glu Ile Val Met Pro Gly Thr Ala Val Thr
1               5                   10                  15

Met Ser Cys Lys Ala Ser Gly Tyr Thr Phe Thr Asp Phe Trp Met His
            20                  25                  30

Trp Val Lys Gln Arg Pro Gly Gln Gly Leu Glu Trp Ile Gly Ala Ile
        35                  40                  45

Asp Pro Ser Asp Ser Tyr Ser Arg Ile Asn Gln Lys Phe Lys Gly Lys
    50                  55                  60

Ala Thr Leu Thr Val Asp Glu Ser Ser Ser Thr Ala Tyr Met Gln Leu
65                  70                  75                  80

Ser Ser Leu Thr Ser Glu Asp Ser Ala Val Tyr Tyr Cys Ala Arg Arg
                85                  90                  95

Ile Thr Glu Ala Gly Ala Trp Phe Ala Tyr Trp Gly Gln Gly Thr Thr
            100                 105                 110

Val Thr


<210> SEQ ID NO 19
<211> LENGTH: 12
<212> TYPE: PRT
<213> ORGANISM: Artificial Sequence
<220> FEATURE:
<223> OTHER INFORMATION: Heavy chain CDR1 of 14D5

<400> SEQUENCE: 19
```

Gly Phe Ser Leu Ser Thr Ser Gly Gly Ser Val Gly
1 5 10

<210> SEQ ID NO 20
<211> LENGTH: 16
<212> TYPE: PRT
<213> ORGANISM: Artificial Sequence
<220> FEATURE:
<223> OTHER INFORMATION: Heavy chain CDR2 of 14D5

<400> SEQUENCE: 20

Leu Ile Tyr Ser Asn Asp Thr Lys Tyr Tyr Ser Thr Ser Leu Lys Thr
1 5 10 15

<210> SEQ ID NO 21
<211> LENGTH: 10
<212> TYPE: PRT
<213> ORGANISM: Artificial Sequence
<220> FEATURE:
<223> OTHER INFORMATION: Heavy chain CDR3 of 14D5

<400> SEQUENCE: 21

Ser Arg Phe Trp Thr Gly Glu Tyr Asp Val
1 5 10

<210> SEQ ID NO 22
<211> LENGTH: 11
<212> TYPE: PRT
<213> ORGANISM: Artificial Sequence
<220> FEATURE:
<223> OTHER INFORMATION: Light chain CDR1 of 14D5

<400> SEQUENCE: 22

Arg Ala Ser Gln Asn Ile Ala Ile Thr Leu Asn
1 5 10

<210> SEQ ID NO 23
<211> LENGTH: 7
<212> TYPE: PRT
<213> ORGANISM: Artificial Sequence
<220> FEATURE:
<223> OTHER INFORMATION: Light chain CDR2 of 14D5

<400> SEQUENCE: 23

Leu Ala Ser Ser Leu Gln Ser
1 5

<210> SEQ ID NO 24
<211> LENGTH: 8
<212> TYPE: PRT
<213> ORGANISM: Artificial Sequence
<220> FEATURE:
<223> OTHER INFORMATION: Light chain CDR3 of 14D5

<400> SEQUENCE: 24

Gln Gln Tyr Asp Asn Tyr Pro Leu
1 5

<210> SEQ ID NO 25
<211> LENGTH: 22
<212> TYPE: DNA
<213> ORGANISM: Artificial Sequence
<220> FEATURE:
<223> OTHER INFORMATION: Synthetic primer for light chain sequence
<220> FEATURE:
<221> NAME/KEY: misc_feature
<222> LOCATION: (5)..(5)

<223> OTHER INFORMATION: S is G or C
<220> FEATURE:
<221> NAME/KEY: misc_feature
<222> LOCATION: (6)..(6)
<223> OTHER INFORMATION: M is A or C
<220> FEATURE:
<221> NAME/KEY: misc_feature
<222> LOCATION: (8)..(8)
<223> OTHER INFORMATION: R is G or A
<220> FEATURE:
<221> NAME/KEY: misc_feature
<222> LOCATION: (15)..(15)
<223> OTHER INFORMATION: S is G or C
<220> FEATURE:
<221> NAME/KEY: misc_feature
<222> LOCATION: (20)..(20)
<223> OTHER INFORMATION: W is A or T

<400> SEQUENCE: 25
aggtsmarct gcagsagtcw gg 22

<210> SEQ ID NO 26
<211> LENGTH: 22
<212> TYPE: PRT
<213> ORGANISM: Rattus

<400> SEQUENCE: 26

Ala Ala Ala Phe Thr Gly Leu Thr Leu Leu Glu Gln Leu Asp Leu Ser
1 5 10 15

Asp Asn Ala Gln Leu Arg
20

<210> SEQ ID NO 27
<211> LENGTH: 10
<212> TYPE: PRT
<213> ORGANISM: Homo Sapiens
<220> FEATURE:
<221> NAME/KEY: misc_feature
<223> OTHER INFORMATION: sequence also found in Rattus

<400> SEQUENCE: 27

Leu Asp Leu Ser Asp Asn Ala Gln Leu Arg
1 5 10

<210> SEQ ID NO 28
<211> LENGTH: 6
<212> TYPE: PRT
<213> ORGANISM: Artificial Sequence
<220> FEATURE:
<223> OTHER INFORMATION: Mutant NgR1 aa 120-125

<400> SEQUENCE: 28

Val Val Asp Pro Thr Thr
1 5

<210> SEQ ID NO 29
<211> LENGTH: 10
<212> TYPE: PRT
<213> ORGANISM: Artificial Sequence
<220> FEATURE:
<223> OTHER INFORMATION: Mutant NgR1

<400> SEQUENCE: 29

Leu Asp Leu Ser Asp Asp Ala Glu Leu Arg
1 5 10

<210> SEQ ID NO 30
<211> LENGTH: 11

```
<212> TYPE: PRT
<213> ORGANISM: Artificial Sequence
<220> FEATURE:
<223> OTHER INFORMATION: Mutant NgR1

<400> SEQUENCE: 30

Leu Asp Leu Ala Ser Asp Asn Ala Gln Leu Arg
1               5                   10


<210> SEQ ID NO 31
<211> LENGTH: 11
<212> TYPE: PRT
<213> ORGANISM: Artificial Sequence
<220> FEATURE:
<223> OTHER INFORMATION: Mutant NgR1

<400> SEQUENCE: 31

Leu Asp Leu Ala Ser Asp Asp Ala Glu Leu Arg
1               5                   10


<210> SEQ ID NO 32
<211> LENGTH: 11
<212> TYPE: PRT
<213> ORGANISM: Artificial Sequence
<220> FEATURE:
<223> OTHER INFORMATION: Mutant NgR1

<400> SEQUENCE: 32

Leu Asp Ala Leu Ser Asp Asn Ala Gln Leu Arg
1               5                   10


<210> SEQ ID NO 33
<211> LENGTH: 11
<212> TYPE: PRT
<213> ORGANISM: Artificial Sequence
<220> FEATURE:
<223> OTHER INFORMATION: Mutant NgR1

<400> SEQUENCE: 33

Leu Asp Ala Leu Ser Asp Asp Ala Glu Leu Arg
1               5                   10


<210> SEQ ID NO 34
<211> LENGTH: 11
<212> TYPE: PRT
<213> ORGANISM: Artificial Sequence
<220> FEATURE:
<223> OTHER INFORMATION: Mutant NgR1

<400> SEQUENCE: 34

Leu Asp Leu Ser Ser Asp Asn Ala Gln Leu Arg
1               5                   10


<210> SEQ ID NO 35
<211> LENGTH: 11
<212> TYPE: PRT
<213> ORGANISM: Artificial Sequence
<220> FEATURE:
<223> OTHER INFORMATION: Mutant NgR1

<400> SEQUENCE: 35

Leu Asp Leu Ser Ser Asp Glu Ala Glu Leu Arg
1               5                   10


<210> SEQ ID NO 36
<211> LENGTH: 12
<212> TYPE: PRT
```

<213> ORGANISM: Homo Sapiens
<220> FEATURE:
<221> NAME/KEY: misc_feature
<223> OTHER INFORMATION: sequence also found in Rattus

<400> SEQUENCE: 36

Asp Asn Ala Gln Leu Arg Val Val Asp Pro Thr Thr
1 5 10

<210> SEQ ID NO 37
<211> LENGTH: 6
<212> TYPE: PRT
<213> ORGANISM: Homo Sapiens
<220> FEATURE:
<221> NAME/KEY: misc_feature
<223> OTHER INFORMATION: sequence also found in Rattus

<400> SEQUENCE: 37

Asp Asn Ala Gln Leu Arg
1 5

<210> SEQ ID NO 38
<211> LENGTH: 10
<212> TYPE: PRT
<213> ORGANISM: Mus musculus

<400> SEQUENCE: 38

Leu Asp Leu Ser Asp Asn Ala Gln Leu His
1 5 10

<210> SEQ ID NO 39
<211> LENGTH: 10
<212> TYPE: PRT
<213> ORGANISM: Homo Sapiens
<220> FEATURE:
<221> NAME/KEY: misc_feature
<223> OTHER INFORMATION: sequence also found in Rattus

<400> SEQUENCE: 39

Leu Asp Leu Gly Asp Asn Arg His Leu Arg
1 5 10

<210> SEQ ID NO 40
<211> LENGTH: 10
<212> TYPE: PRT
<213> ORGANISM: Homo Sapiens
<220> FEATURE:
<221> NAME/KEY: misc_feature
<223> OTHER INFORMATION: sequence also found in Rattus
<220> FEATURE:
<221> NAME/KEY: misc_feature
<223> OTHER INFORMATION: sequence also found in Mus musculus

<400> SEQUENCE: 40

Leu Asp Leu Gly Asp Asn Arg Gln Leu Arg
1 5 10

<210> SEQ ID NO 41
<211> LENGTH: 16
<212> TYPE: PRT
<213> ORGANISM: Artificial Sequence
<220> FEATURE:
<223> OTHER INFORMATION: Synthetic mutant L110A peptide

<400> SEQUENCE: 41

Ala Asp Leu Ser Asp Asn Ala Gln Leu Arg Val Val Asp Pro Thr Thr
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic mutant D111A peptide

<400> SEQUENCE: 42

Leu Ala Leu Ser Asp Asn Ala Gln Leu Arg Val Val Asp Pro Thr Thr
1 5 10 15

<210> SEQ ID NO 43
<211> LENGTH: 16
<212> TYPE: PRT
<213> ORGANISM: Artificial Sequence
<220> FEATURE:
<223> OTHER INFORMATION: Synthetic mutant Q117A peptide

<400> SEQUENCE: 43

Leu Asp Leu Ser Asp Asn Ala Ala Leu Arg Val Val Asp Pro Thr Thr
1 5 10 15

<210> SEQ ID NO 44
<211> LENGTH: 16
<212> TYPE: PRT
<213> ORGANISM: Artificial Sequence
<220> FEATURE:
<223> OTHER INFORMATION: Synthetic mutant R119H peptide

<400> SEQUENCE: 44

Leu Asp Leu Ser Asp Asn Ala Gln Leu His Val Val Asp Pro Thr Thr
1 5 10 15

<210> SEQ ID NO 45
<211> LENGTH: 16
<212> TYPE: PRT
<213> ORGANISM: Artificial Sequence
<220> FEATURE:
<223> OTHER INFORMATION: Synthetic mutant R119A peptide

<400> SEQUENCE: 45

Leu Asp Leu Ser Asp Asn Ala Gln Leu Ala Val Val Asp Pro Thr Thr
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: Synthetic mutant R119A peptide

<400> SEQUENCE: 46

Leu Asp Leu Ser Asp Asn Ala Gln Leu Ala Val Val Asp Pro Thr Thr
1 5 10 15

<210> SEQ ID NO 47
<211> LENGTH: 16
<212> TYPE: PRT
<213> ORGANISM: Homo sapiens

<400> SEQUENCE: 47

Leu Asp Leu Ser Asp Asn Ala Gln Leu Arg Ser Val Asp Pro Thr Thr
1 5 10 15

<210> SEQ ID NO 48
<211> LENGTH: 19

<212> TYPE: PRT
<213> ORGANISM: Homo sapiens

<400> SEQUENCE: 48

```
His Val His Pro His Ala Phe Arg Asp Leu Gly Arg Leu Met Thr Leu
1               5                   10                  15

Tyr Leu Phe
```

<210> SEQ ID NO 49
<211> LENGTH: 473
<212> TYPE: PRT
<213> ORGANISM: Homo sapiens

<400> SEQUENCE: 49

```
Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
```

```
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470


<210> SEQ ID NO 50
<211> LENGTH: 473
<212> TYPE: PRT
<213> ORGANISM: Rattus

<400> SEQUENCE: 50

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser His Val Pro Ala Ala Ser Phe Gln Ser Cys
65                  70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220
```

```
Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Asp Arg Asp Leu Lys Arg Leu Ala Ala Ser
    290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470


<210> SEQ ID NO 51
<211> LENGTH: 473
<212> TYPE: PRT
<213> ORGANISM: Mus musculus

<400> SEQUENCE: 51

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser His Val Pro Ala Ala Ser Phe Gln Ser Cys
65                  70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125
```

```
Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Asp Arg Asp Leu Lys Arg Leu Ala Ala Ser
    290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470
```

<210> SEQ ID NO 52
<211> LENGTH: 18
<212> TYPE: RNA
<213> ORGANISM: Artificial Sequence
<220> FEATURE:
<223> OTHER INFORMATION: Synthetic siRNA or shRNA sequence

<400> SEQUENCE: 52

```
cuacuucucc cgcaggcg                                                18
```

<210> SEQ ID NO 53
<211> LENGTH: 19
<212> TYPE: DNA
<213> ORGANISM: Artificial Sequence
<220> FEATURE:
<223> OTHER INFORMATION: Synthetic polynucleotide sequence complementary to siRNA or shRNA

<400> SEQUENCE: 53
gatgaagagg gcgtccgct 19

<210> SEQ ID NO 54
<211> LENGTH: 19
<212> TYPE: RNA
<213> ORGANISM: Artificial Sequence
<220> FEATURE:
<223> OTHER INFORMATION: Synthetic siRNA or shRNA sequence

<400> SEQUENCE: 54
cccggaccga cgucuucaa 19

<210> SEQ ID NO 55
<211> LENGTH: 19
<212> TYPE: DNA
<213> ORGANISM: Artificial Sequence
<220> FEATURE:
<223> OTHER INFORMATION: Synthetic polynucleotide sequence complementary to siRNA or shRNA

<400> SEQUENCE: 55
gggcctggct gcagaagtt 19

<210> SEQ ID NO 56
<211> LENGTH: 19
<212> TYPE: RNA
<213> ORGANISM: Artificial Sequence
<220> FEATURE:
<223> OTHER INFORMATION: Synthetic siRNA or shRNA sequence

<400> SEQUENCE: 56
cugaccacug agucuuccg 19

<210> SEQ ID NO 57
<211> LENGTH: 21
<212> TYPE: DNA
<213> ORGANISM: Artificial Sequence
<220> FEATURE:
<223> OTHER INFORMATION: Synthetic polynucleotide sequence complementary to siRNA or shRNA

<400> SEQUENCE: 57
gactggtgac tcagagaagg c 21

<210> SEQ ID NO 58
<211> LENGTH: 310
<212> TYPE: PRT
<213> ORGANISM: Artificial Sequence
<220> FEATURE:
<223> OTHER INFORMATION: Human NgR1 mutant

<400> SEQUENCE: 58

```
Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30
```

```
Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Ala Ala
305                 310
```

<210> SEQ ID NO 59
<211> LENGTH: 310
<212> TYPE: PRT
<213> ORGANISM: Artificial Sequence
<220> FEATURE:
<223> OTHER INFORMATION: Human NgR1 mutant

<400> SEQUENCE: 59

```
Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80
```

```
Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Ala Ala
305                 310


<210> SEQ ID NO 60
<211> LENGTH: 420
<212> TYPE: PRT
<213> ORGANISM: Homo sapiens

<400> SEQUENCE: 60

Met Leu Pro Gly Leu Arg Arg Leu Leu Gln Ala Pro Ala Ser Ala Cys
1               5                   10                  15

Leu Leu Leu Met Leu Leu Ala Leu Pro Leu Ala Ala Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Thr Leu Arg Pro Gly Thr Phe
65                  70                  75                  80

Gly Ser Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
    130                 135                 140
```

```
Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190

Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe Arg
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ser Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Ala Leu Arg Glu
    290                 295                 300

Ala Asp Phe Gln Ala Cys Pro Pro Ala Ala Pro Thr Arg Pro Gly Ser
305                 310                 315                 320

Arg Ala Arg Gly Asn Ser Ser Ser Asn His Leu Tyr Gly Val Ala Glu
                325                 330                 335

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Met
    370                 375                 380

Cys Pro Gly Ala Ala Cys Gln Ala Pro Pro Asp Ser Arg Gly Pro Ala
385                 390                 395                 400

Leu Ser Ala Gly Leu Pro Ser Pro Leu Leu Cys Leu Leu Leu Leu Val
                405                 410                 415

Pro His His Leu
            420


<210> SEQ ID NO 61
<211> LENGTH: 420
<212> TYPE: PRT
<213> ORGANISM: Mus musculus

<400> SEQUENCE: 61

Met Leu Pro Gly Leu Arg Arg Leu Leu Gln Gly Pro Ala Ser Ala Cys
1               5                   10                  15

Leu Leu Leu Thr Leu Leu Ala Leu Pro Ser Val Thr Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Ser Leu Arg Pro Gly Thr Phe
65                  70                  75                  80

Gly Pro Asn Leu Leu Thr Leu Trp Leu Phe Ser Asn Asn Leu Ser Thr
```

```
                85                  90                  95

Ile His Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
    130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190

Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe His
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ala Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Ala Leu Arg Asp
    290                 295                 300

Ser Asp Phe Gln Ala Cys Pro Pro Pro Thr Pro Thr Arg Pro Gly Ser
305                 310                 315                 320

Arg Ala Arg Gly Asn Ser Ser Ser Asn His Leu Tyr Gly Val Ala Glu
                325                 330                 335

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Thr
    370                 375                 380

Cys Pro Gly Ala Ala Cys Gln Ala Pro Ala Asp Ser Arg Gly Pro Ala
385                 390                 395                 400

Leu Ser Ala Gly Leu Arg Thr Pro Leu Leu Cys Leu Leu Pro Leu Ala
                405                 410                 415

Leu His His Leu
            420


<210> SEQ ID NO 62
<211> LENGTH: 441
<212> TYPE: PRT
<213> ORGANISM: Homo sapiens

<400> SEQUENCE: 62

Met Leu Arg Lys Gly Cys Cys Val Glu Leu Leu Leu Leu Leu Val Ala
1               5                   10                  15

Ala Glu Leu Pro Leu Gly Gly Gly Cys Pro Arg Asp Cys Val Cys Tyr
            20                  25                  30
```

```
Pro Ala Pro Met Thr Val Ser Cys Gln Ala His Asn Phe Ala Ala Ile
        35                  40                  45

Pro Glu Gly Ile Pro Val Asp Ser Glu Arg Val Phe Leu Gln Asn Asn
    50                  55                  60

Arg Ile Gly Leu Leu Gln Pro Gly His Phe Ser Pro Ala Met Val Thr
65                  70                  75                  80

Leu Trp Ile Tyr Ser Asn Asn Ile Thr Tyr Ile His Pro Ser Thr Phe
                85                  90                  95

Glu Gly Phe Val His Leu Glu Glu Leu Asp Leu Gly Asp Asn Arg Gln
            100                 105                 110

Leu Arg Thr Leu Ala Pro Glu Thr Phe Gln Gly Leu Val Lys Leu His
        115                 120                 125

Ala Leu Tyr Leu Tyr Lys Cys Gly Leu Ser Ala Leu Pro Ala Gly Val
    130                 135                 140

Phe Gly Gly Leu His Ser Leu Gln Tyr Leu Tyr Leu Gln Asp Asn His
145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Pro Gly Thr
            180                 185                 190

Phe Arg Gly Leu Val Asn Leu Asp Arg Leu Leu Leu His Glu Asn Gln
        195                 200                 205

Leu Gln Trp Val His His Lys Ala Phe His Asp Leu Arg Arg Leu Thr
    210                 215                 220

Thr Leu Phe Leu Phe Asn Asn Ser Leu Ser Glu Leu Gln Gly Glu Cys
225                 230                 235                 240

Leu Ala Pro Leu Gly Ala Leu Glu Phe Leu Arg Leu Asn Gly Asn Pro
                245                 250                 255

Trp Asp Cys Gly Cys Arg Ala Arg Ser Leu Trp Glu Trp Leu Gln Arg
            260                 265                 270

Phe Arg Gly Ser Ser Ser Ala Val Pro Cys Val Ser Pro Gly Leu Arg
        275                 280                 285

His Gly Gln Asp Leu Lys Leu Leu Arg Ala Glu Asp Phe Arg Asn Cys
    290                 295                 300

Thr Gly Pro Ala Ser Pro His Gln Ile Lys Ser His Thr Leu Thr Thr
305                 310                 315                 320

Thr Asp Arg Ala Ala Arg Lys Glu His His Ser Pro His Gly Pro Thr
                325                 330                 335

Arg Ser Lys Gly His Pro His Gly Pro Arg Pro Gly His Arg Lys Pro
            340                 345                 350

Gly Lys Asn Cys Thr Asn Pro Arg Asn Arg Asn Gln Ile Ser Lys Ala
        355                 360                 365

Gly Ala Gly Lys Gln Ala Pro Glu Leu Pro Asp Tyr Ala Pro Asp Tyr
    370                 375                 380

Gln His Lys Phe Ser Phe Asp Ile Met Pro Thr Ala Arg Pro Lys Arg
385                 390                 395                 400

Lys Gly Lys Cys Ala Arg Arg Thr Pro Ile Arg Ala Pro Ser Gly Val
                405                 410                 415

Gln Gln Ala Ser Ser Ala Ser Ser Leu Gly Ala Ser Leu Leu Ala Trp
            420                 425                 430

Thr Leu Gly Leu Ala Val Thr Leu Arg
        435                 440
```

```
<210> SEQ ID NO 63
<211> LENGTH: 445
<212> TYPE: PRT
<213> ORGANISM: Mus musculus

<400> SEQUENCE: 63

Met Leu Arg Lys Gly Cys Cys Val Glu Leu Leu Leu Leu Leu Leu Ala
1               5                   10                  15

Gly Glu Leu Pro Leu Gly Gly Gly Cys Pro Arg Asp Cys Val Cys Tyr
            20                  25                  30

Pro Ala Pro Met Thr Val Ser Cys Gln Ala His Asn Phe Ala Ala Ile
        35                  40                  45

Pro Glu Gly Ile Pro Glu Asp Ser Glu Arg Ile Phe Leu Gln Asn Asn
    50                  55                  60

Arg Ile Thr Phe Leu Gln Gln Gly His Phe Ser Pro Ala Met Val Thr
65                  70                  75                  80

Leu Trp Ile Tyr Ser Asn Asn Ile Thr Phe Ile Ala Pro Asn Thr Phe
                85                  90                  95

Glu Gly Phe Val His Leu Glu Glu Leu Asp Leu Gly Asp Asn Arg Gln
            100                 105                 110

Leu Arg Thr Leu Ala Pro Glu Thr Phe Gln Gly Leu Val Lys Leu His
        115                 120                 125

Ala Leu Tyr Leu Tyr Lys Cys Gly Leu Ser Ala Leu Pro Ala Gly Ile
    130                 135                 140

Phe Gly Gly Leu His Ser Leu Gln Tyr Leu Tyr Leu Gln Asp Asn His
145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Gln Gly Ile
            180                 185                 190

Phe Arg Gly Leu Val Asn Leu Asp Arg Leu Leu Leu His Glu Asn Gln
        195                 200                 205

Leu Gln Trp Val His His Lys Ala Phe His Asp Leu His Arg Leu Thr
    210                 215                 220

Thr Leu Phe Leu Phe Asn Asn Ser Leu Thr Glu Leu Gln Gly Asp Cys
225                 230                 235                 240

Leu Ala Pro Leu Val Ala Leu Glu Phe Leu Arg Leu Asn Gly Asn Ala
                245                 250                 255

Trp Asp Cys Gly Cys Arg Ala Arg Ser Leu Trp Glu Trp Leu Arg Arg
            260                 265                 270

Phe Arg Gly Ser Ser Ser Ala Val Pro Cys Ala Thr Pro Glu Leu Arg
        275                 280                 285

Gln Gly Gln Asp Leu Lys Leu Leu Arg Val Glu Asp Phe Arg Asn Cys
    290                 295                 300

Thr Gly Pro Val Ser Pro His Gln Ile Lys Ser His Thr Leu Thr Thr
305                 310                 315                 320

Ser Asp Arg Ala Ala Arg Lys Glu His His Pro Ser His Gly Ala Ser
                325                 330                 335

Arg Asp Lys Gly His Pro His Gly His Pro Pro Gly Ser Arg Ser Gly
            340                 345                 350

Tyr Lys Lys Ala Gly Lys Asn Cys Thr Ser His Arg Asn Arg Asn Gln
        355                 360                 365

Ile Ser Lys Val Ser Ser Gly Lys Glu Leu Thr Glu Leu Gln Asp Tyr
    370                 375                 380
```

```
Ala Pro Asp Tyr Gln His Lys Phe Ser Phe Asp Ile Met Pro Thr Ala
385                 390                 395                 400

Arg Pro Lys Arg Lys Gly Lys Cys Ala Arg Arg Thr Pro Ile Arg Ala
                405                 410                 415

Pro Ser Gly Val Gln Gln Ala Ser Ser Gly Thr Ala Leu Gly Ala Pro
            420                 425                 430

Leu Leu Ala Trp Ile Leu Gly Leu Ala Val Thr Leu Arg
        435                 440                 445


<210> SEQ ID NO 64
<211> LENGTH: 344
<212> TYPE: PRT
<213> ORGANISM: Artificial Sequence
<220> FEATURE:
<223> OTHER INFORMATION: Human NgR1 mutant

<400> SEQUENCE: 64

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Ala Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300
```

Asp Leu Gln Gly Ala Ala Val Ala Thr Gly Pro Tyr His Pro Ile Trp
305 310 315 320

Thr Gly Arg Ala Thr Asp Glu Glu Pro Leu Gly Leu Pro Lys Cys Cys
325 330 335

Gln Pro Asp Ala Ala Asp Lys Ala
340

<210> SEQ ID NO 65
<211> LENGTH: 15
<212> TYPE: PRT
<213> ORGANISM: Artificial Sequence
<220> FEATURE:
<223> OTHER INFORMATION: Synthetic linker

<400> SEQUENCE: 65

Gly Gly Gly Gly Ser Gly Gly Gly Gly Ser Gly Gly Gly Gly Ser
1 5 10 15

<210> SEQ ID NO 66
<211> LENGTH: 10
<212> TYPE: PRT
<213> ORGANISM: Artificial Sequence
<220> FEATURE:
<223> OTHER INFORMATION: Synthetic linker

<400> SEQUENCE: 66

Gly Gly Gly Gly Ser Gly Gly Gly Gly Ser
1 5 10

<210> SEQ ID NO 67
<211> LENGTH: 15
<212> TYPE: PRT
<213> ORGANISM: Artificial Sequence
<220> FEATURE:
<223> OTHER INFORMATION: Synthetic linker

<400> SEQUENCE: 67

Glu Ser Gly Arg Ser Gly Gly Gly Gly Ser Gly Gly Gly Gly Ser
1 5 10 15

<210> SEQ ID NO 68
<211> LENGTH: 14
<212> TYPE: PRT
<213> ORGANISM: Artificial Sequence
<220> FEATURE:
<223> OTHER INFORMATION: Synthetic linker

<400> SEQUENCE: 68

Glu Gly Lys Ser Ser Gly Ser Gly Ser Glu Ser Lys Ser Thr
1 5 10

<210> SEQ ID NO 69
<211> LENGTH: 15
<212> TYPE: PRT
<213> ORGANISM: Artificial Sequence
<220> FEATURE:
<223> OTHER INFORMATION: Synthetic linker

<400> SEQUENCE: 69

Glu Gly Lys Ser Ser Gly Ser Gly Ser Glu Ser Lys Ser Thr Gln
1 5 10 15

<210> SEQ ID NO 70
<211> LENGTH: 14
<212> TYPE: PRT
<213> ORGANISM: Artificial Sequence
<220> FEATURE:
<223> OTHER INFORMATION: Synthetic linker

<400> SEQUENCE: 70

Glu Gly Lys Ser Ser Gly Ser Gly Ser Glu Ser Lys Val Asp
1 5 10

<210> SEQ ID NO 71
<211> LENGTH: 14
<212> TYPE: PRT
<213> ORGANISM: Artificial Sequence
<220> FEATURE:
<223> OTHER INFORMATION: Synthetic linker

<400> SEQUENCE: 71

Gly Ser Thr Ser Gly Ser Gly Lys Ser Ser Glu Gly Lys Gly
1 5 10

<210> SEQ ID NO 72
<211> LENGTH: 18
<212> TYPE: PRT
<213> ORGANISM: Artificial Sequence
<220> FEATURE:
<223> OTHER INFORMATION: Synthetic linker

<400> SEQUENCE: 72

Lys Glu Ser Gly Ser Val Ser Ser Glu Gln Leu Ala Gln Phe Arg Ser
1 5 10 15

Leu Asp

<210> SEQ ID NO 73
<211> LENGTH: 16
<212> TYPE: PRT
<213> ORGANISM: Artificial Sequence
<220> FEATURE:
<223> OTHER INFORMATION: Synthetic primer

<400> SEQUENCE: 73

Glu Ser Gly Ser Val Ser Ser Glu Glu Leu Ala Phe Arg Ser Leu Asp
1 5 10 15

<210> SEQ ID NO 74
<211> LENGTH: 8
<212> TYPE: PRT
<213> ORGANISM: Artificial Sequence
<220> FEATURE:
<223> OTHER INFORMATION: Synthetic FLAG epitope

<400> SEQUENCE: 74

Asp Tyr Lys Asp Asp Asp Asp Lys
1 5

<210> SEQ ID NO 75
<211> LENGTH: 8
<212> TYPE: PRT
<213> ORGANISM: Artificial Sequence
<220> FEATURE:
<223> OTHER INFORMATION: Synthetic FLAG epitope

<400> SEQUENCE: 75

Asp Tyr Lys Asp Glu Asp Asp Lys
1 5

<210> SEQ ID NO 76
<211> LENGTH: 9
<212> TYPE: PRT

<213> ORGANISM: Artificial Sequence
<220> FEATURE:
<223> OTHER INFORMATION: Synthetic Strep epitope

<400> SEQUENCE: 76

Ala Trp Arg His Pro Gln Phe Gly Gly
1               5

<210> SEQ ID NO 77
<211> LENGTH: 11
<212> TYPE: PRT
<213> ORGANISM: Artificial Sequence
<220> FEATURE:
<223> OTHER INFORMATION: Synthetic VSV-G epitope

<400> SEQUENCE: 77

Tyr Thr Asp Ile Glu Met Asn Arg Leu Gly Lys
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Synthetic poly-His epitope

<400> SEQUENCE: 78

His His His His His His
1               5

<210> SEQ ID NO 79
<211> LENGTH: 13
<212> TYPE: PRT
<213> ORGANISM: Influenza Virus

<400> SEQUENCE: 79

Tyr Pro Tyr Asp Val Pro Asp Tyr Ala Ile Glu Gly Arg
1               5                   10

<210> SEQ ID NO 80
<211> LENGTH: 11
<212> TYPE: PRT
<213> ORGANISM: Homo sapiens

<400> SEQUENCE: 80

Glu Gln Lys Leu Leu Ser Glu Glu Asp Leu Asn
1               5                   10

<210> SEQ ID NO 81
<211> LENGTH: 1719
<212> TYPE: DNA
<213> ORGANISM: Homo sapiens

<400> SEQUENCE: 81
agcccagcca gagccgggcg gagcggagcg cgccgagcct cgtcccgcgg ccgggccggg      60
gccgggccgt agcggcggcg cctggatgcg gacccggccg cggggagacg ggcgcccgcc     120
ccgaaacgac tttcagtccc cgacgcgccc cgcccaaccc ctacgatgaa gagggcgtcc     180
gctggaggga gccggctgct ggcatgggtg ctgtggctgc aggcctggca ggtggcagcc     240
ccatgcccag gtgcctgcgt atgctacaat gagcccaagg tgacgacaag ctgcccccag     300
cagggcctgc aggctgtgcc cgtgggcatc cctgctgcca gccagcgcat cttcctgcac     360
ggcaaccgca tctcgcatgt gccagctgcc agcttccgtg cctgccgcaa cctcaccatc     420

```
ctgtggctgc actcgaatgt gctggcccga attgatgcgg ctgccttcac tggcctggcc    480

ctcctggagc agctggacct cagcgataat gcacagctcc ggtctgtgga ccctgccaca    540

ttccacggcc tgggccgcct acacacgctg cacctggacc gctgcggcct gcaggagctg    600

ggcccggggc tgttccgcgg cctggctgcc ctgcagtacc tctacctgca ggacaacgcg    660

ctgcaggcac tgcctgatga caccttccgc gacctgggca acctcacaca cctcttcctg    720

cacggcaacc gcatctccag cgtgcccgag cgcgccttcc gtgggctgca cagcctcgac    780

cgtctcctac tgcaccagaa ccgcgtggcc catgtgcacc cgcatgcctt ccgtgacctt    840

ggccgcctca tgacactcta tctgtttgcc aacaatctat cagcgctgcc cactgaggcc    900

ctggcccccc tgcgtgccct gcagtacctg aggctcaacg acaacccctg ggtgtgtgac    960

tgccgggcac gcccactctg ggcctggctg cagaagttcc gcggctcctc ctccgaggtg   1020

ccctgcagcc tcccgcaacg cctggctggc cgtgacctca aacgcctagc tgccaatgac   1080

ctgcagggct gcgctgtggc caccggccct taccatccca tctggaccgg cagggccacc   1140

gatgaggagc cgctggggct tcccaagtgc tgccagccag atgccgctga caaggcctca   1200

gtactggagc ctggaagacc agcttcggca ggcaatgcgc tgaagggacg cgtgccgccc   1260

ggtgacagcc cgccgggcaa cggctctggc ccacggcaca tcaatgactc accctttggg   1320

actctgcctg gctctgctga gcccccgctc actgcagtgc ggcccgaggg ctccgagcca   1380

ccagggttcc ccacctcggg ccctcgccgg aggccaggct gttcacgcaa gaaccgcacc   1440

cgcagccact gccgtctggg ccaggcaggc agcgggggtg gcgggactgg tgactcagaa   1500

ggctcaggtg ccctacccag cctcacctgc agcctcaccc ccctgggcct ggcgctggtg   1560

ctgtggacag tgcttgggcc ctgctgaccc ccagcggaca caagagcgtg ctcagcagcc   1620

aggtgtgtgt acatacgggg tctctctcca cgccgccaag ccagccgggc ggccgacccg   1680

tggggcaggc caggccaggt cctccctgat ggacgcctg                          1719
```

```
<210> SEQ ID NO 82
<211> LENGTH: 1422
<212> TYPE: DNA
<213> ORGANISM: Rattus

<400> SEQUENCE: 82

atgaagaggg cgtcctccgg aggaagccgg ctgccgacat gggtgttatg gctacaggcc     60

tggagggtag caacgccctg ccctggtgcc tgtgtgtgct acaatgagcc caaggtcaca    120

acaagccgcc cccagcaggg cctgcaggct gtacccgctg gcatcccagc ctccagccag    180

agaatcttcc tgcacggcaa ccgaatctct tacgtgccag ccgccagctt ccagtcatgc    240

cggaatctca ccatcctgtg gctgcactca aatgcgctgg ccgggattga tgccgcggcc    300

ttcactggtc tgaccctcct ggagcaacta gatcttagtg acaatgcaca gctccgtgtc    360

gtggacccca ccacgttccg tggcctgggc cacctgcaca cgctgcacct agaccgatgc    420

ggcctgcagg agctggggcc tggcctattc cgtgggctgg cagctctgca gtacctctac    480

ctacaagaca acaacctgca ggcacttccc gacaacacct tccgagacct gggcaacctc    540

acgcatctct ttctgcatgg caaccgtatc cccagtgttc ctgagcacgc tttccgtggc    600

ttgcacagtc ttgaccgtct cctcttgcac cagaaccatg tggctcgtgt gcacccacat    660

gccttccggg accttggccg actcatgacc ctctacctgt ttgccaacaa cctctccatg    720

ctccccgcag aggtcctagt gcccctgagg tctctgcagt acctgcgact caatgacaac    780

ccctgggtgt gtgactgcag ggcacgtccg ctctgggcct ggctgcagaa gttccgaggt    840
```

```
tcctcatccg gggtgcccag caacctaccc caacgcctgg caggccgtga tctgaagcgc    900
ctggctacca gtgacttaga gggttgtgct gtggcttcgg ggcccttccg tcccttccag    960
accaatcagc tcactgatga ggagctgctg ggcctcccca agtgctgcca gccggatgct   1020
gcagacaagg cctcagtact ggaacccggg aggccggcgt ctgttggaaa tgcactcaag   1080
ggacgtgtgc ctcccggtga cactccacca ggcaatggct caggcccacg gcacatcaat   1140
gactctccat ttgggacttt gcccggctct gcagagcccc cactgactgc cctgcggcct   1200
gggggttccg agcccccggg actgcccacc acgggccccc gcaggaggcc aggttgttcc   1260
agaaagaacc gcacccgtag ccactgccgt ctgggccagg caggaagtgg gagcagtgga   1320
actggggatg cagaaggttc gggggccctg cctgccctgg cctgcagcct tgctcctctg   1380
ggccttgcac tggtactttg gacagtgctt gggccctgct ga                      1422

<210> SEQ ID NO 83
<211> LENGTH: 1892
<212> TYPE: DNA
<213> ORGANISM: Mus musculus

<400> SEQUENCE: 83

agccgcagcc cgcgagccca gcccggcccg gtagagcgga gcgccggagc ctcgtcccgc     60
ggccgggccg ggaccgggcc ggagcagcgg cgcctggatg cggacccggc cgcgcgcaga    120
cgggcgcccg ccccgaagcc gcttccagtg cccgacgcgc cccgctcgac cccgaagatg    180
aagagggcgt cctccggagg aagcaggctg ctggcatggg tgttatggct acaggcctgg    240
agggtagcaa caccatgccc tggtgcttgt gtgtgctaca atgagcccaa ggtaacaaca    300
agctgccccc agcagggtct gcaggctgtg cccactggca tcccagcctc tagccagcga    360
atcttcctgc atggcaaccg aatctctcac gtgccagctg cgagcttcca gtcatgccga    420
aatctcacta tcctgtggct gcactctaat gcgctggctc ggatcgatgc tgctgccttc    480
actggtctga ccctcctgga gcaactagat cttagtgata atgcacagct tcatgtcgtg    540
gaccctacca cgttccacgg cctgggccac ctgcacacac tgcacctaga ccgatgtggc    600
ctgcgggagc tgggtcccgg cctattccgt ggactagcag ctctgcagta cctctaccta    660
caagacaaca atctgcaggc actccctgac aacacctttc gagacctggg caacctcacg    720
catctctttc tgcatggcaa ccgtatcccc agtgtgcctg agcacgcttt ccgtggcctg    780
cacagtcttg accgcctcct cttgcaccag aaccatgtgg ctcgtgtgca cccacatgcc    840
ttccgggacc ttggccgcct catgaccctc tacctgtttg ccaacaacct ctccatgctg    900
cctgcagagg tcctaatgcc cctgaggtct ctgcagtacc tgcgactcaa tgacaacccc    960
tgggtgtgtg actgccgggc acgtccactc tgggcctggc tgcagaagtt ccgaggttcc   1020
tcatcagagg tgccctgcaa cctgccccaa cgcctggcag accgtgatct taagcgcctc   1080
gctgccagtg acctagaggg ctgtgctgtg gcttcaggac ccttccgtcc catccagacc   1140
agtcagctca ctgatgagga gctgctgagc ctccccaagt gctgccagcc agatgctgca   1200
gacaaagcct cagtactgga acccgggagg ccagcttctg ccggaaacgc cctcaaggga   1260
cgtgtgcctc ccggtgacac tccaccaggc aatggctcag gccctcggca catcaatgac   1320
tctccatttg gaactttgcc cagctctgca gagcccccac tgactgccct gcggcctggg   1380
ggttccgagc caccaggact tcccaccact ggtccccgca ggaggccagg ttgttcccgg   1440
aagaatcgca cccgcagcca ctgccgtctg ggccaggcgg gaagtggggc cagtggaaca   1500
```

```
ggggacgcag agggttcagg ggctctgcct gctctggcct gcagccttgc tcctctgggc   1560
cttgcactgg tactttggac agtgcttggg ccctgctgac cagccaccag ccaccaggtg   1620
tgtgtacata tggggtctcc ctccacgccg ccagccagag ccagggacag gctctgaggg   1680
gcaggccagg ccctccctga cagatgcctc cccaccagcc cacccccatc tccaccccat   1740
catgtttaca gggttccggg ggtggcgttt gttccagaac gccacctccc acccggatcg   1800
cggtatatag agatatgaat tttattttac ttgtgtaaaa tatcggatga cgtggaataa   1860
agagctcttt tcttaaaaaa aaaaaaaaaa aa                                 1892
```

<210> SEQ ID NO 84
<211> LENGTH: 1263
<212> TYPE: DNA
<213> ORGANISM: Homo sapiens

<400> SEQUENCE: 84

```
atgctgcccg ggctcaggcg cctgctgcaa gctcccgcct cggcctgcct cctgctgatg     60
ctcctggccc tgcccctggc ggcccccagc tgccccatgc tctgcacctg ctactcatcc    120
ccgcccaccg tgagctgcca ggccaacaac ttctcctctg tgccgctgtc cctgccaccc    180
agcactcagc gactcttcct gcagaacaac ctcatccgca cgctgcggcc aggcaccttt    240
gggtccaacc tgctcaccct gtggctcttc tccaacaacc tctccaccat ctacccgggc    300
actttccgcc acttgcaagc cctggaggag ctggacctcg gtgacaaccg gcacctgcgc    360
tcgctggagc ccgacacctt ccagggcctg gagcggctgc agtcgctgca tttgtaccgc    420
tgccagctca gcagcctgcc cggcaacatc ttccgaggcc tggtcagcct gcagtacctc    480
tacctccagg agaacagcct gctccaccta caggatgact tgttcgcgga cctggccaac    540
ctgagccacc tcttcctcca cgggaaccgc ctgcggctgc tcacagagca cgtgtttcgc    600
ggcctgggca gcctggaccg gctgctgctg cacgggaacc ggctgcaggg cgtgcaccgc    660
gcggccttcc gcggcctcag ccgcctcacc atcctctacc tgttcaacaa cagcctggcc    720
tcgctgcccg gcgaggcgct cgccgacctg ccctcgctcg agttcctgcg gctcaacgct    780
aacccctggg cgtgcgactg ccgcgcgcgg ccgctctggg cctggttcca gcgcgcgcgc    840
gtgtccagct ccgacgtgac ctgcgccacc cccccggagc gccagggccg agacctgcgc    900
gcgctccgcg aggccgactt ccaggcgtgt ccgcccgcgg cacccacgcg gccgggcagc    960
cgcgcccgcg gcaacagctc ctccaaccac ctgtacgggg tggccgaggc cggggcgccc   1020
ccagccgatc cctccaccct ctaccgagat ctgcctgccg aagactcgcg ggggcgccag   1080
ggcggggacg cgcctactga ggacgactac tggggggcct acgggggtga ggaccagcga   1140
ggggagcaga tgtgccccgg cgctgcctgc caggcgcccc cggactcccg aggccctgcg   1200
ctctcggccg ggctccccag ccctctgctt tgcctcctgc tcctggtgcc ccaccacctc   1260
tga                                                                 1263
```

<210> SEQ ID NO 85
<211> LENGTH: 1263
<212> TYPE: DNA
<213> ORGANISM: Mus musculus

<400> SEQUENCE: 85

```
atgctgcccg ggctccggcg cctgctgcaa ggtcctgcct cagcctgcct actgctgaca     60
ctcctggccc ttccttccgt gacccccagc tgtcctatgc tctgcacctg ctactcctcc    120
ccgcccaccg tgagctgcca ggccaacaac ttctcctcag tgccgctgtc cttgccaccc    180
```

```
agtacacaga gactcttctt gcagaacaac ctcatccgct cactgcggcc aggcaccttt    240

gggcccaacc tgctcaccct gtggctcttc tccaacaacc tctccaccat ccaccctggc    300

accttccgcc acctgcaggc cctagaagaa ctggacctcg gtgacaaccg gcacctgcgc    360

tccctggagc ccgacacctt ccagggtctg gagaggctgc agtcactaca cctgtatcgt    420

tgccagctca gcagcctgcc tggcaacatt ttccgaggct tggtcagcct acagtacctc    480

tacctccagg agaacagcct gctccatcta caggatgact tgttcgcgga cctggccaac    540

ctgagccacc tcttcctcca cgggaaccgc ctgcggctgc tcacggagca cgtgttccgc    600

ggcttgggca gcctggaccg gctgttgctg cacgggaacc ggctgcaggg cgtgcaccgc    660

gcggctttcc acggcctcag ccgcctcacc atcctctacc tgttcaacaa cagcctggcc    720

tcgctgccgg gagaggcgct ggccgacctg ccggcgctcg agttcctgcg gctcaacgcc    780

aacccctggg cgtgcgactg ccgcgctcgg ccgctctggg cttggttcca gcgcgcgcgg    840

gtgtccagct ccgacgtgac ctgcgccacc ccgcccgagc gccagggccg ggacctgcgc    900

gcgctgcgcg actccgattt ccaagcgtgc ccgccgccca cgcccacgcg gccgggcagc    960

cgcgcccgcg gcaacagctc ttccaaccac ctgtacggcg tggccgaggc tggcgctccc   1020

cccgcagacc cgtccacgct ctaccgagat ctgcccgccg aggactcgcg ggggcgccag   1080

ggcggggacg cgcccaccga ggacgactac tgggggggct acggcggcga ggatcagcgg   1140

ggcgagcaga cgtgtcccgg ggccgcgtgc caggcgcccg cagactcgcg tggccccgcg   1200

ctctcggccg ggctgcgcac ccctctgctc tgcctcttgc ccctggcgct ccatcacctc   1260

tga                                                                 1263
```

<210> SEQ ID NO 86
<211> LENGTH: 1326
<212> TYPE: DNA
<213> ORGANISM: Homo sapiens

<400> SEQUENCE: 86

```
atgcttcgca aagggtgctg tgtggagttg ctgctgctgt tggtagctgc ggagctgccc     60

ctgggtggtg gctgcccacg ggactgtgtg tgctacccgg cgcccatgac ggtcagctgc    120

caggcgcaca actttgcagc catcccggag ggcatccccg tggacagcga gcgcgtcttc    180

ctgcagaaca accgcatcgg cctcctccag cccggccact tcagccccgc catggtcacc    240

ctgtggatct actcgaacaa catcacctac atccacccca gcaccttcga gggcttcgtg    300

cacctggagg agctggacct cggcgacaac cggcagctgc ggacgctggc acccgagacc    360

ttccagggcc tggtgaagct tcacgccctc tacctctaca agtgtgggct cagcgccttg    420

ccggccggcg tctttggcgg cctgcacagc ctgcagtacc tctacctgca ggacaaccac    480

atcgagtacc tccaggacga catcttcgtg gacctggtca acctcagcca cctgtttctc    540

cacggcaaca agctgtggag tctgggcccg ggcaccttcc ggggcctggt gaacctggac    600

cgtcttttgc tgcacgagaa ccagctgcag tgggtccacc acaaggcatt ccacgacctc    660

cgcaggctga ccaccctctt cctcttcaac aacagcctct cggagctgca gggtgagtgc    720

ctggccccgc tgggggccct ggagttcctc cgcctcaatg gcaacccctg ggactgtggt    780

tgtcgcgcgc gctccctgtg ggaatggctg cagaggttcc ggggctccag ctccgctgtc    840

ccctgtgtgt cccctgggct gcggcacggc caggacctga agctgctgag ggccgaggac    900

ttccggaact gcacgggacc agcgtccccg caccagatca agtcacacac gctcaccacc    960
```

```
accgacaggg ccgcccgcaa ggaacaccac tcaccccacg gccccaccag gagcaagggc   1020

cacccgcacg gcccccggcc cggccacagg aagccgggga agaactgcac caaccccagg   1080

aaccgcaatc agatctctaa ggcgggcgcc gggaaacagg cccccgagct gccagactat   1140

gccccagact accagcacaa gttcagtttt gacatcatgc ctacggcccg gcccaagagg   1200

aagggcaagt gtgcccgcag gacccccatc cgtgccccca gcggggtgca gcaggcctcc   1260

tcggccagtt ccctgggggc ctccctcctg gcctggacac tggggctggc ggtcactctc   1320

cgctga                                                              1326
```

```
<210> SEQ ID NO 87
<211> LENGTH: 1338
<212> TYPE: DNA
<213> ORGANISM: Mus musculus

<400> SEQUENCE: 87

atgcttcgca aagggtgctg tgtggaattg ctgctgttgc tgctcgctgg agagctacct     60

ctgggtggtg gttgtcctcg agactgtgtg tgctaccctg cgcccatgac tgtcagctgc    120

caggcacaca actttgctgc catcccggag ggcatcccag aggacagtga gcgcatcttc    180

ctgcagaaca atcgcatcac cttcctccag cagggccact tcagccccgc catggtcacc    240

ctctggatct actccaacaa catcactttc attgctccca acaccttcga gggctttgtg    300

catctggagg agctagacct tggagacaac cgacagctgc gaacgctggc acccgagacc    360

ttccaaggcc tggtgaagct tcacgccctc tacctctata agtgtggact gagcgccctg    420

cccgcaggca tctttggtgg cctgcacagc ctgcagtatc tctacttgca ggacaaccat    480

atcgagtacc tccaagatga catctttgtg gacctggtca atctcagtca cttgtttctc    540

catggtaaca agctatggag cctgggccaa ggcatcttcc ggggcctggt gaacctggac    600

cggttgctgc tgcatgagaa ccagctacag tgggttcacc acaaggcttt ccatgacctc    660

cacaggctaa ccaccctctt tctcttcaac aacagcctca ctgagctgca gggtgactgt    720

ctggcccccc tggtggcctt ggagttcctt cgcctcaatg ggaatgcttg ggactgtggc    780

tgccgggcac gttccctgtg ggaatggctg cgaaggttcc gtggctctag ctctgctgtc    840

ccctgcgcga cccccgagct gcggcaaggc caggatctga agctgctgag ggtggaggac    900

ttccggaact gcacaggacc agtgtctcct caccagatca agtctcacac gcttaccacc    960

tctgacaggg ctgcccgcaa ggagcaccat ccgtcccatg ggcctccagg ggacaaaggc   1020

cacccacatg gccatccgcc tggctccagg tcaggttaca agaaggcagg caagaactgc   1080

accagccaca ggaaccggaa ccagatctct aaggtgagct ctgggaaaga gcttaccgaa   1140

ctgcaggact atgcccccga ctatcagcac aagttcagct ttgacatcat gcccaccgca   1200

cgacccaaga ggaagggcaa gtgtgctcgc aggaccccca tccgtgcccc cagtggggtg   1260

cagcaggcat cctcaggcac ggcccttggg gccccactcc tggcctggat actggggctg   1320

gcagtcactc tccgctga                                                 1338
```

```
<210> SEQ ID NO 88
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of an siRNA molecule
<220> FEATURE:
<221> NAME/KEY: misc_feature
<222> LOCATION: (1)..(200)
```

-continued

```
<223> OTHER INFORMATION: n is a, c, g, t, or u
<220> FEATURE:
<221> NAME/KEY: misc_feature
<222> LOCATION: (2)..(200)
<223> OTHER INFORMATION: nucleotide may be missing

<400> SEQUENCE: 88

nnnnnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn                                                 200


<210> SEQ ID NO 89
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of an siRNA molecule
<220> FEATURE:
<221> NAME/KEY: misc_feature
<222> LOCATION: (1)..(200)
<223> OTHER INFORMATION: n is a, c, g, t, or u
<220> FEATURE:
<221> NAME/KEY: misc_feature
<222> LOCATION: (2)..(200)
<223> OTHER INFORMATION: nucleotide may be missing

<400> SEQUENCE: 89

nnnnnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn                                                 200
```